(12) United States Patent
Witman et al.

(10) Patent No.: US 8,309,691 B2
(45) Date of Patent: Nov. 13, 2012

(54) CHLAMYDOMONAS INTRAFLAGELLAR TRANSPORT 88 (IFT-88)

(75) Inventors: George B. Witman, Grafton, MA (US); Gregory J. Pazour, Framingham, MA (US); Joel L. Rosenbaum, Branford, CT (US); Douglas G. Cole, Moscow, ID (US)

(73) Assignees: University of Massachusetts, Shrewsbury, MA (US); Yale University, New Haven, CT (US)

( * ) Notice: Subject to any disclaimer, the term of this patent is extended or adjusted under 35 U.S.C. 154(b) by 0 days.

(21) Appl. No.: 13/188,621

(22) Filed: Jul. 22, 2011

(65) Prior Publication Data

US 2012/0046448 A1 Feb. 23, 2012

Related U.S. Application Data

(60) Division of application No. 12/481,536, filed on Jun. 9, 2009, now Pat. No. 7,985,583, which is a division of application No. 10/839,016, filed on May 5, 2004, now Pat. No. 7,553,674, which is a continuation of application No. 09/866,582, filed on May 24, 2001, now abandoned.

(60) Provisional application No. 60/206,923, filed on May 24, 2000.

(51) Int. Cl.
*C07K 16/00* (2006.01)
(52) U.S. Cl. ............. 530/387.9; 530/388.1; 530/388.15; 530/388.2; 530/389.1
(58) Field of Classification Search .................. None
See application file for complete search history.

(56) References Cited

FOREIGN PATENT DOCUMENTS
WO WO 00/18909 6/2000

OTHER PUBLICATIONS

Campbell, "Monoclonal Antibody Technology," *Elsevier Science Publishing Company, Inc.*, pp. 1-32; 1984.
Asamizu et al., "A large scale structural analysis of cDNAs in a unicellular green alga, *Chlamydomonas reinhardtii*. I. Generation of 3433 non-redundant expressed sequence tags," DNA Res. 6(6):369-373 (1999).
Asamizu et al., "Generation of expressed sequence tags from low-$CO_2$ and high-$CO_2$ adapted cells of *Chlamydomonas reinhardtii*," DNA Research 7(5):305-307 (2000).
Badano et al., "The Ciliopathies: An emerging class of human genetic disorders," Annu. Rev. Genomics Hum. Genet. 7:125-148 (2006).
Baker et al., "IFT20 links kinesin II with a mammalian intraflagellar transport complex that is conserved in motile flagella and sensory cilia," J. Biol. Chem. 278(36):34211-34218 (2003), Epub. Jun. 23, 2003.
Beales et al., "IFT80, which encodes a conserved intraflagellar transport protein, is mutated in Jeune asphyxiating thoracic dystrophy," Nature Genetics 39(6):727-729 (2007).
Cole et al., "*Chlamydomonas* kinesin-II-dependent intraflagellar transport (IFT): IFT particles contain proteins required for ciliary assembly in *Caenorhabditis elegans* sensory neurons," J. Cell Biol. 141(4):993-1008 (1998).
Davis et al., *Microbiology*, Third Edition, Harper and Row, 1980, p. 267.
Follit et al., "The intraflagellar transport protein IFT20 is associated with the Golgi complex and is required for cilia assembly," Mol. Biol. Cell. 17(9):3781-3792 (2006), Epub. Jun. 14, 2006.
GenBank Accession No. AF298884.1, *Chlamydomonas* IFT-88 Sequence, Dec. 4, 2000.
Grossman et al., (Accession No. BE352290, Jul. 18, 2000).
Hildebrandt and Otto, "Cilia and centrosomes: A unifying pathogenic concept for cystic kidney disease?" Nat. Rev. Genet. 6(12):928-940 (2005).
Hou et al., "Functional analysis of an individual IFT protein: IFT46 is required for transport of outer dynein arms into flagella," J. Cell Biology 176(5):653-665 (2007).
Jurczyk et al., "Pericentrin forms a complex with intraflagellar transport proteins and polycystin-2 and is required for primary cilia assembly ," J. Cell. Biol. 166(5):637-643 (2004).
Kozminski et al., "A motility in the eukaryotic flagellum unrelated to flagellar beating," Proc. Natl. Acad. Sci. USA, 90:5519-5523 (1993).
Kozminski et al., "The *Chlamydomonas* kinesin-like protein FLA10 is involved in motility associated with the flagellar membrane," The Journal of Cell Biology 131(6)(1):1517-1527 (1995).
Lewin, *Genes IV*, Oxford University Press, 1990, p. 810.
Lucker et al., "Characterization of the intraflagellar transport complex B core: direct interaction of the IFT81 and IFT74/72 subunits," J. Biol. Chem. 280(30):27688-27696 (2005), Epub. Jun. 13, 2005.
Marshall, "Human cilia proteome contains homolog of zebrafish polycystic kidney disease gene qilin," Curr Biol. 14(21):R913-4 (2004).
Moyer et al., "Candidate gene associated with a mutation causing recessive polycystic kidney disease in mice," Science 264:1329-1333 (1994).
Murcia et al., "The Oak Ridge Polycystic Kidney (orpk) disease gene is required for left-right axis determination," Development 127:2347-2355 (2000).
Ostrowski et al., "A proteomic analysis of human cilia: identification of novel components," Mol. Cell Proteomics. 1(6):451-65 (2002).
Pan et al., "Cilium-generated signaling and cilia-related disorders," Lab Invest. 85(4):452-463 (2005).
Pazour et al., "A dynein light chair is essential for the retrograde particle movement of intraflagellar transport (IFT)," The Journal of Cell Biology 141(4):979-992 (1998).

(Continued)

*Primary Examiner* — Patricia A Duffy
(74) *Attorney, Agent, or Firm* — Fish & Richardson P.C.

(57) ABSTRACT

The invention relates to various intraflagellar transport (IFT) polypeptides and the nucleic acids that encode them. The new IFT particle polypeptides and nucleic acids can be used in a variety of diagnostic, screening, and therapeutic methods.

9 Claims, 5 Drawing Sheets

OTHER PUBLICATIONS

Pazour et al., "*Chlamydomonas* IFT88 and its mouse homologue, polycystic kidney disease gene Tg737, are required for assembly of cilia and flagella," The Journal of Cell Biology 151(3):709-718 (2000).

Pazour et al., "The DHC1b (DHC2) isoform of cytoplasmic dynein is required for flagellar assembly," The Journal of Cell Biology 144(3):473-481 (1999).

Piperno et al., "Inner dynein arms but not outer dynein arms require the activity of kinesin homologue protein KHP1$^{FLA10}$ to reach the distal part of flagella in *Chlamydomonas*," The Journal of Cell Biology 133(2):371-379 (1996).

Piperno et al., "Transport of a novel complex in the cytoplasmic matrix of *Chlamydomonas flagella*," Proc. Natl. Acad. Sci. USA 94:4457-4462 (1997).

Sambrook et al., *Molecular Cloning: A Laboratory Manual*, Second Edition, Cold Spring Harbor Laboratory Press, 1989, pp. 16.1-16.81.

Schrick et al., "Characterization of the human homologue of the mouse Tg737 candidate polycystic kidney disease gene," Human Molecular Genetics 4(4):559-567 (1995).

Walther et al., "The *Chlamydomonas* FLA10 gene encodes a novel kinesin-homologous protein," The Journal of Cell Biology 126(1):175-188 (1994).

Yin et al., "Cloning and characterization of the human IFT20 gene," Mol. Biol. Rep. 30(4):255-260 (2003).

SEQUENCE LISTING

<160> NUMBER OF SEQ ID NOS: 50

<210> SEQ ID NO 1
<211> LENGTH: 877
<212> TYPE: DNA
<213> ORGANISM: Chlamydomonas reinhardtii
<220> FEATURE:
<221> NAME/KEY: CDS
<222> LOCATION: (114)...(518)

<400> SEQUENCE: 1

```
caccgctgcc gctgaacaga aagtctgcgc agactcgtct tcttgccaag ttcttgccaa      60
aaccagcagg cctagaggtt gccttaacct aaatatacaa aacacagagc atc atg       116
                                                          Met
                                                          1 gac gcg gta gat aga gga gtc tac ttt gac gag gac ttt cat gtc cgc      164
Asp Ala Val Asp Arg Gly Val Tyr Phe Asp Glu Asp Phe His Val Arg
      5                  10                  15 att ctt gat gtt gac aag tac aat gct tca aag tcg ctc cag gac aac      212
Ile Leu Asp Val Asp Lys Tyr Asn Ala Ser Lys Ser Leu Gln Asp Asn
 20                  25                  30 aca aat gtg ttc att aac aac atc caa aat atg caa ggc ctc gtg gac      260
Thr Asn Val Phe Ile Asn Asn Ile Gln Asn Met Gln Gly Leu Val Asp
     35                  40                  45 aag tac gtg tcc gcc atc gac cag cag gtc gag cgg cta gaa gct gaa      308
Lys Tyr Val Ser Ala Ile Asp Gln Gln Val Glu Arg Leu Glu Ala Glu
 50                  55                  60                  65 aag ctg aag gcc att ggc ctg cgg aac cgg gtg gct gcg ctg agc gag      356
Lys Leu Lys Ala Ile Gly Leu Arg Asn Arg Val Ala Ala Leu Ser Glu
                 70                  75                  80 gag cgg aaa cgt aaa caa aag gag cag gag cgc atg cta gcg gag aag      404
Glu Arg Lys Arg Lys Gln Lys Glu Gln Glu Arg Met Leu Ala Glu Lys
             85                  90                  95 cag gag gag ctt gag agg ctc caa atg gag gag cag tcg ctg atc aag      452
Gln Glu Glu Leu Glu Arg Leu Gln Met Glu Glu Gln Ser Leu Ile Lys
            100                 105                 110 gtg aag ggc gag cag gag ctc atg att cag aag ctg tcg gac agc agc      500
Val Lys Gly Glu Gln Glu Leu Met Ile Gln Lys Leu Ser Asp Ser Ser
            115                 120                 125 agc ggg gcg gca tac gtg taaacggtgt tcggacgtca tgcgtgcaaa              548
Ser Gly Ala Ala Tyr Val
130                 135 ggtagtttgc tctgtgaggg ttggctgagg cggcggaggc tgctattgag gctgcagcat     608
gcggtctggt ggcagatgta cataacggta tggggtgttg cgacagaac gaaacggcga      668 gggtgcgcaa atgtcgtgca gaagcgacgc tacagcatcc atggtacgta gaggcttact     728
gggtgtcagt gcgtcgtccg ccactgggga cacacttgca gcgaggagcg ccattgtttg     788
gcccacggat tgcgtcaagg acttgaacgg cgccagtgaa ggcggggaat ggaatgtaaa     848
caaacgactc gaaaaaaaaa aaaaaaaaa                                       877
```

<210> SEQ ID NO 2
<211> LENGTH: 135
<212> TYPE: PRT
<213> ORGANISM: Chlamydomonas reinhardtii -continued

<400> SEQUENCE: 2

Met Asp Ala Val Asp Arg Gly Val Tyr Phe Asp Glu Asp Phe His Val
1               5                   10                  15

Arg Ile Leu Asp Val Asp Lys Tyr Asn Ala Ser Lys Ser Leu Gln Asp
            20                  25                  30

Asn Thr Asn Val Phe Ile Asn Asn Ile Gln Asn Met Gln Gly Leu Val
        35                  40                  45

Asp Lys Tyr Val Ser Ala Ile Asp Gln Gln Val Glu Arg Leu Glu Ala
    50                  55                  60

Glu Lys Leu Lys Ala Ile Gly Leu Arg Asn Arg Val Ala Ala Leu Ser
65                  70                  75                  80

Glu Glu Arg Lys Arg Lys Gln Lys Gln Glu Arg Met Leu Ala Glu
                85                  90                  95

Lys Gln Glu Glu Leu Glu Arg Leu Gln Met Glu Gln Ser Leu Ile
            100                 105                 110

Lys Val Lys Gly Glu Gln Glu Leu Met Ile Gln Lys Leu Ser Asp Ser
        115                 120                 125

Ser Ser Gly Ala Ala Tyr Val
    130                 135

<210> SEQ ID NO 3
<211> LENGTH: 615
<212> TYPE: DNA
<213> ORGANISM: Chlamydomonas reinhardtii
<220> FEATURE:
<221> NAME/KEY: CDS
<222> LOCATION: (1)...(612)

<400> SEQUENCE: 3 atg gtg aag aaa gaa gtg aag ccc atc gat atc acc gca acg cta aga      48
Met Val Lys Lys Glu Val Lys Pro Ile Asp Ile Thr Ala Thr Leu Arg
1               5                   10                  15 tgc aaa gta gca gta gtc ggc gaa gcg act gtc ggc aag agc gcg ctc      96
Cys Lys Val Ala Val Val Gly Glu Ala Thr Val Gly Lys Ser Ala Leu
            20                  25                  30 atc tct atg ttc acg agt aaa ggc agc aag ttt cta aag gac tat gcg    144
Ile Ser Met Phe Thr Ser Lys Gly Ser Lys Phe Leu Lys Asp Tyr Ala
        35                  40                  45 atg acg agt ggg gtg gag gtg gtg gta gcc ccg gtg acc att ccg gac    192
Met Thr Ser Gly Val Glu Val Val Val Ala Pro Val Thr Ile Pro Asp
    50                  55                  60 acg acg gtc tcg gtg gag ctc ttt ctg ctg gac acg gcg ggg agc gac    240
Thr Thr Val Ser Val Glu Leu Phe Leu Leu Asp Thr Ala Gly Ser Asp
65                  70                  75                  80 ctg tac aag gag cag ata tcg cag tac tgg aac ggc gta tac tac gcc    288
Leu Tyr Lys Glu Gln Ile Ser Gln Tyr Trp Asn Gly Val Tyr Tyr Ala
                85                  90                  95 att ctc gtg ttc gat gtg agc tct atg gag tcc ttc gag tcg tgc aag    336
Ile Leu Val Phe Asp Val Ser Ser Met Glu Ser Phe Glu Ser Cys Lys
            100                 105                 110 gcg tgg ttt gag ctg ctc aaa tcg gcg cgt ccc gac cgc gag cgg ccg    384
Ala Trp Phe Glu Leu Leu Lys Ser Ala Arg Pro Asp Arg Glu Arg Pro
        115                 120                 125 ctg cgc gcc gtg ctg gtg gcg aac aag acg gac ctt ccg ccg cag cgg    432
Leu Arg Ala Val Leu Val Ala Asn Lys Thr Asp Leu Pro Pro Gln Arg
    130                 135                 140 cac cag gtg cgg ctg gac atg gcg cag gac tgg gcc acc acc aac acc    480
His Gln Val Arg Leu Asp Met Ala Gln Asp Trp Ala Thr Thr Asn Thr
145                 150                 155                 160

```
ctc gac ttc ttc gac gtg tcc gcg aac ccg ccc ggc aag gac gcg gat      528
Leu Asp Phe Phe Asp Val Ser Ala Asn Pro Pro Gly Lys Asp Ala Asp
            165                 170                 175 gcg ccg ttc ctg tcc atc gcc acc acc ttc tac cgc aac tac gag gac      576
Ala Pro Phe Leu Ser Ile Ala Thr Thr Phe Tyr Arg Asn Tyr Glu Asp
            180                 185                 190 aag gtg gcg gcc ttc cag gac gct tgc cgc aac tac tga                  615
Lys Val Ala Ala Phe Gln Asp Ala Cys Arg Asn Tyr
            195                 200
```

<210> SEQ ID NO 4
<211> LENGTH: 204
<212> TYPE: PRT
<213> ORGANISM: Chlamydomonas reinhardtii

<400> SEQUENCE: 4

```
Met Val Lys Lys Glu Val Lys Pro Ile Asp Ile Thr Ala Thr Leu Arg
 1               5                  10                  15

Cys Lys Val Ala Val Gly Glu Ala Thr Val Gly Lys Ser Ala Leu
            20                  25                  30

Ile Ser Met Phe Thr Ser Lys Gly Ser Lys Phe Leu Lys Asp Tyr Ala
            35                  40                  45

Met Thr Ser Gly Val Glu Val Val Ala Pro Val Thr Ile Pro Asp
    50                  55                  60

Thr Thr Val Ser Val Glu Leu Phe Leu Leu Asp Thr Ala Gly Ser Asp
65                  70                  75                  80

Leu Tyr Lys Glu Gln Ile Ser Gln Tyr Trp Asn Gly Val Tyr Tyr Ala
                85                  90                  95

Ile Leu Val Phe Asp Val Ser Ser Met Glu Ser Phe Glu Ser Cys Lys
            100                 105                 110

Ala Trp Phe Glu Leu Leu Lys Ser Ala Arg Pro Asp Arg Glu Arg Pro
            115                 120                 125

Leu Arg Ala Val Leu Val Ala Asn Lys Thr Asp Leu Pro Pro Gln Arg
            130                 135                 140

His Gln Val Arg Leu Asp Met Ala Gln Asp Trp Ala Thr Thr Asn Thr
145                 150                 155                 160

Leu Asp Phe Phe Asp Val Ser Ala Asn Pro Pro Gly Lys Asp Ala Asp
            165                 170                 175

Ala Pro Phe Leu Ser Ile Ala Thr Thr Phe Tyr Arg Asn Tyr Glu Asp
            180                 185                 190

Lys Val Ala Ala Phe Gln Asp Ala Cys Arg Asn Tyr
            195                 200
```

<210> SEQ ID NO 5
<211> LENGTH: 1035
<212> TYPE: DNA
<213> ORGANISM: Chlamydomonas reinhardtii
<220> FEATURE:
<221> NAME/KEY: CDS
<222> LOCATION: (1)...(1032)

<400> SEQUENCE: 5

```
atg gat gac tct atg gac tac cct gac cgc gac ggg gac gac ctg gac      48
Met Asp Asp Ser Met Asp Tyr Pro Asp Arg Asp Gly Asp Asp Leu Asp
 1               5                  10                  15 cag ttc cag ggc acc gcg cgc tcg cag gtc gtg cag aac cag ccg cac      96
Gln Phe Gln Gly Thr Ala Arg Ser Gln Val Val Gln Asn Gln Pro His
            20                  25                  30 gac gag gag gtg aac ctg agt gag tcg gag agc ttc gcg gga gcg gat     144
Asp Glu Glu Val Asn Leu Ser Glu Ser Glu Ser Phe Ala Gly Ala Asp
```

|  |  |  |  |  |  |  |  |  |  |  |  |  |  |  |  |
|---|---|---|---|---|---|---|---|---|---|---|---|---|---|---|---|
|  |  | 35 |  |  |  |  | 40 |  |  |  |  | 45 |  |  |  |

```
gag cct cca gct gcg cct aga gat gcg tcg ctc ata gag tca cac gac     192
Glu Pro Pro Ala Ala Pro Arg Asp Ala Ser Leu Ile Glu Ser His Asp
     50                  55                  60 atg gac gag ggg cca gct gct cca gcg cgg aca ctc tca cca acg ggc     240
Met Asp Glu Gly Pro Ala Ala Pro Ala Arg Thr Leu Ser Pro Thr Gly
 65                  70                  75                  80 tat gag gct gga aag cac gca cct ggc ggc atc gcc aac tcg gac gag     288
Tyr Glu Ala Gly Lys His Ala Pro Gly Gly Ile Ala Asn Ser Asp Glu
                 85                  90                  95 gca ccg ccg ggt gct tac aac gca cag gag tac aag cac ctg aac gtg     336
Ala Pro Pro Gly Ala Tyr Asn Ala Gln Glu Tyr Lys His Leu Asn Val
            100                 105                 110 ggc gag gac gtg cgc gag ctg ttc tcc tac atc ggc cgc tac aag ccg     384
Gly Glu Asp Val Arg Glu Leu Phe Ser Tyr Ile Gly Arg Tyr Lys Pro
        115                 120                 125 cag acg gtg gag ctg gac acg cgc atc aag ccc ttc atc cct gac tac     432
Gln Thr Val Glu Leu Asp Thr Arg Ile Lys Pro Phe Ile Pro Asp Tyr
    130                 135                 140 atc ccc gcg gtg ggc ggc atc gac gag ttc atc aag gtg ccg cga ccc     480
Ile Pro Ala Val Gly Gly Ile Asp Glu Phe Ile Lys Val Pro Arg Pro
145                 150                 155                 160 gac acc aag ccc gac tac ctg ggg ctc aag gtt ctg gac gag ccg gcc     528
Asp Thr Lys Pro Asp Tyr Leu Gly Leu Lys Val Leu Asp Glu Pro Ala
                165                 170                 175 gcc aag cag tcg gac ccc acg gtg ctg acg ctg cag ctg cgg cag ctg     576
Ala Lys Gln Ser Asp Pro Thr Val Leu Thr Leu Gln Leu Arg Gln Leu
            180                 185                 190 tcc aag gag gcg ccg ggc gcc aag gcc gac atg gtg ggg cgg ctg gag     624
Ser Lys Glu Ala Pro Gly Ala Lys Ala Asp Met Val Gly Arg Leu Glu
        195                 200                 205 cac acc gac gag aac aag gcc aag aag atc cag cag tgg atc gcc tcc     672
His Thr Asp Glu Asn Lys Ala Lys Lys Ile Gln Gln Trp Ile Ala Ser
    210                 215                 220 atc aac gac atc cac aag gcc aag ccg gcc gcc acc gtc aac tac agc     720
Ile Asn Asp Ile His Lys Ala Lys Pro Ala Ala Thr Val Asn Tyr Ser
225                 230                 235                 240 aag cgc atg cca gag atc gag gcg ctg atg cag gag tgg ccg ccg gag     768
Lys Arg Met Pro Glu Ile Glu Ala Leu Met Gln Glu Trp Pro Pro Glu
                245                 250                 255 gtg gag acc ttc ctc aag acc atg cac atg ccg tcc ggc gat gtg gag     816
Val Glu Thr Phe Leu Lys Thr Met His Met Pro Ser Gly Asp Val Glu
            260                 265                 270 ctg gac atc aag acc tac gcc cgg ctg gtg tgc acg ctg ctg gac att     864
Leu Asp Ile Lys Thr Tyr Ala Arg Leu Val Cys Thr Leu Leu Asp Ile
        275                 280                 285 ccc gtg tac gac gac ccc gtg gag agc ctg cac gtg ctg ttc aca ctg     912
Pro Val Tyr Asp Asp Pro Val Glu Ser Leu His Val Leu Phe Thr Leu
    290                 295                 300 tac ctg gag ttc aag aac aac ccc atc ttc agg cag cac atg gag atg     960
Tyr Leu Glu Phe Lys Asn Asn Pro Ile Phe Arg Gln His Met Glu Met
305                 310                 315                 320 gag aac aag ctg gac ggc atg tcg ggc ggc ggc ggc atg atg ggc        1008
Glu Asn Lys Leu Asp Gly Met Ser Gly Gly Gly Gly Met Met Gly
                325                 330                 335 ggc ggc gcg gat gtg ctg ggc ttg tga                               1035
Gly Gly Ala Asp Val Leu Gly Leu
            340
```

<210> SEQ ID NO 6

<211> LENGTH: 344
<212> TYPE: PRT
<213> ORGANISM: Chlamydomonas reinhardtii

<400> SEQUENCE: 6

| | | | | | | | | | | | | | | |
|---|---|---|---|---|---|---|---|---|---|---|---|---|---|---|
| Met | Asp | Asp | Ser | Met | Asp | Tyr | Pro | Asp | Arg | Asp | Gly | Asp | Leu | Asp |
| 1 | | | | 5 | | | | | 10 | | | | | 15 |
| Gln | Phe | Gln | Gly | Thr | Ala | Arg | Ser | Gln | Val | Val | Gln | Asn | Gln | Pro | His |
| | | | 20 | | | | | 25 | | | | | 30 | | |
| Asp | Glu | Glu | Val | Asn | Leu | Ser | Glu | Ser | Glu | Ser | Phe | Ala | Gly | Ala | Asp |
| | | 35 | | | | | 40 | | | | | 45 | | | |
| Glu | Pro | Pro | Ala | Ala | Pro | Arg | Asp | Ala | Ser | Leu | Ile | Glu | Ser | His | Asp |
| 50 | | | | | 55 | | | | | 60 | | | | | |
| Met | Asp | Glu | Gly | Pro | Ala | Ala | Pro | Ala | Arg | Thr | Leu | Ser | Pro | Thr | Gly |
| 65 | | | | 70 | | | | | 75 | | | | | 80 | |
| Tyr | Glu | Ala | Gly | Lys | His | Ala | Pro | Gly | Gly | Ile | Ala | Asn | Ser | Asp | Glu |
| | | | | 85 | | | | | 90 | | | | | 95 | |
| Ala | Pro | Pro | Gly | Ala | Tyr | Asn | Ala | Gln | Glu | Tyr | Lys | His | Leu | Asn | Val |
| | | | 100 | | | | | 105 | | | | | 110 | | |
| Gly | Glu | Asp | Val | Arg | Glu | Leu | Phe | Ser | Tyr | Ile | Gly | Arg | Tyr | Lys | Pro |
| | | | 115 | | | | | 120 | | | | | 125 | | |
| Gln | Thr | Val | Glu | Leu | Asp | Thr | Arg | Ile | Lys | Pro | Phe | Ile | Pro | Asp | Tyr |
| | 130 | | | | | 135 | | | | | 140 | | | | |
| Ile | Pro | Ala | Val | Gly | Gly | Ile | Asp | Glu | Phe | Ile | Lys | Val | Pro | Arg | Pro |
| 145 | | | | | 150 | | | | | 155 | | | | | 160 |
| Asp | Thr | Lys | Pro | Asp | Tyr | Leu | Gly | Leu | Lys | Val | Leu | Asp | Glu | Pro | Ala |
| | | | | 165 | | | | | 170 | | | | | 175 | |
| Ala | Lys | Gln | Ser | Asp | Pro | Thr | Val | Leu | Thr | Leu | Gln | Leu | Arg | Gln | Leu |
| | | | 180 | | | | | 185 | | | | | 190 | | |
| Ser | Lys | Glu | Ala | Pro | Gly | Ala | Lys | Ala | Asp | Met | Val | Gly | Arg | Leu | Glu |
| | | | 195 | | | | | 200 | | | | | 205 | | |
| His | Thr | Asp | Glu | Asn | Lys | Ala | Lys | Lys | Ile | Gln | Gln | Trp | Ile | Ala | Ser |
| | 210 | | | | | 215 | | | | | 220 | | | | |
| Ile | Asn | Asp | Ile | His | Lys | Ala | Lys | Pro | Ala | Ala | Thr | Val | Asn | Tyr | Ser |
| 225 | | | | | 230 | | | | | 235 | | | | | 240 |
| Lys | Arg | Met | Pro | Glu | Ile | Glu | Ala | Leu | Met | Gln | Glu | Trp | Pro | Pro | Glu |
| | | | | 245 | | | | | 250 | | | | | 255 | |
| Val | Glu | Thr | Phe | Leu | Lys | Thr | Met | His | Met | Pro | Ser | Gly | Asp | Val | Glu |
| | | | 260 | | | | | 265 | | | | | 270 | | |
| Leu | Asp | Ile | Lys | Thr | Tyr | Ala | Arg | Leu | Val | Cys | Thr | Leu | Leu | Asp | Ile |
| | | 275 | | | | | 280 | | | | | 285 | | | |
| Pro | Val | Tyr | Asp | Asp | Pro | Val | Glu | Ser | Leu | His | Val | Leu | Phe | Thr | Leu |
| | 290 | | | | | 295 | | | | | 300 | | | | |
| Tyr | Leu | Glu | Phe | Lys | Asn | Asn | Pro | Ile | Phe | Arg | Gln | His | Met | Glu | Met |
| 305 | | | | | 310 | | | | | 315 | | | | | 320 |
| Glu | Asn | Lys | Leu | Asp | Gly | Met | Ser | Gly | Gly | Gly | Gly | Met | Met | Gly |
| | | | | 325 | | | | | 330 | | | | | 335 | |
| Gly | Gly | Ala | Asp | Val | Leu | Gly | Leu |
| | | | 340 | | | | |

<210> SEQ ID NO 7
<211> LENGTH: 2362
<212> TYPE: DNA
<213> ORGANISM: Chlamydomonas reinhardtii
<220> FEATURE:
<221> NAME/KEY: CDS
<222> LOCATION: (92)...(1453)

<400> SEQUENCE: 7

```
ctaatggcat gcagtaaggc actggtatag aaaccgttcc caccgccgcg cccagccccg      60
cgtcctgtga gctgagagct acttaacagc c atg gag gag ccg ggc gcg gag        112
                                   Met Glu Glu Pro Gly Ala Glu
                                     1               5 gag gtt cgg att ctc ttc agc aca gcg aag ggg gaa tcc cat acg cac        160
Glu Val Arg Ile Leu Phe Ser Thr Ala Lys Gly Glu Ser His Thr His
         10                  15                  20 aag gca ggc ttc aag cag cta ttt cga cga ttg cgt tca act tat cgt        208
Lys Ala Gly Phe Lys Gln Leu Phe Arg Arg Leu Arg Ser Thr Tyr Arg
 25                  30                  35 cca gac aaa gta gat aag gat gac ttc acg ctg gac acg ctg cgg tca        256
Pro Asp Lys Val Asp Lys Asp Asp Phe Thr Leu Asp Thr Leu Arg Ser
 40                  45                  50                  55 gcg cac atc ctt gtg ctc ggt ggc ccg aag gag aag ttc acc gcg cct        304
Ala His Ile Leu Val Leu Gly Gly Pro Lys Glu Lys Phe Thr Ala Pro
                 60                  65                  70 gag gtg gac atg ctc aaa aag ttc gtg aag aat ggt ggc tcc atc ctc        352
Glu Val Asp Met Leu Lys Lys Phe Val Lys Asn Gly Gly Ser Ile Leu
             75                  80                  85 att cta atg tcg gag ggc ggc gag gag aag gcg ggc act aac atc aac        400
Ile Leu Met Ser Glu Gly Gly Glu Glu Lys Ala Gly Thr Asn Ile Asn
         90                  95                 100 tac ttc ctc gag cag ttt ggc atg tcg gtg aac aac gac gcc gtg gtc        448
Tyr Phe Leu Glu Gln Phe Gly Met Ser Val Asn Asn Asp Ala Val Val
    105                 110                 115 cgc acc acg cac tac aag tac ctg cac ccc aag gag gtg ctc atc tcg        496
Arg Thr Thr His Tyr Lys Tyr Leu His Pro Lys Glu Val Leu Ile Ser
120                 125                 130                 135 gac ggc atc ctc aac cgg gcg gtg atc acg ggc gcg ggg aag tcg ctg        544
Asp Gly Ile Leu Asn Arg Ala Val Ile Thr Gly Ala Gly Lys Ser Leu
                140                 145                 150 aac agc aac gac gac gac gag ttc cgc gtg tcg cgg ggg ccg cag gct        592
Asn Ser Asn Asp Asp Asp Glu Phe Arg Val Ser Arg Gly Pro Gln Ala
            155                 160                 165 ttt gat ggc acg ggc ctg gag tac gtc ttc ccc ttc ggt gcc acg ctc        640
Phe Asp Gly Thr Gly Leu Glu Tyr Val Phe Pro Phe Gly Ala Thr Leu
        170                 175                 180 tca gtg cag aag ccc gcg gtg ccc gtc ttg tcc agc ggc aaa atc gcg        688
Ser Val Gln Lys Pro Ala Val Pro Val Leu Ser Ser Gly Lys Ile Ala
    185                 190                 195 tac ccc atg aac cgg cca gtg ggt gcg gta tgg gcg cag ccc ggc tac        736
Tyr Pro Met Asn Arg Pro Val Gly Ala Val Trp Ala Gln Pro Gly Tyr
200                 205                 210                 215 ggc cgc atc gcc gtg ctg ggc tcg tgc gcc atg ttt gac gac aag tgg        784
Gly Arg Ile Ala Val Leu Gly Ser Cys Ala Met Phe Asp Asp Lys Trp
                220                 225                 230 ctg gac aag gag gag aac tcc aaa atc atg gac ttc ttc aag ttc            832
Leu Asp Lys Glu Glu Asn Ser Lys Ile Met Asp Phe Phe Lys Phe
            235                 240                 245 ctc gag ccg cat tcc aaa atc caa ctc aac gac att gac gcg gag gag        880
Leu Glu Pro His Ser Lys Ile Gln Leu Asn Asp Ile Asp Ala Glu Glu
        250                 255                 260 ccg gac gtg agc gac ctg aag ctg ctg ccc gac aca gcc agt ctg gca        928
Pro Asp Val Ser Asp Leu Lys Leu Leu Pro Asp Thr Ala Ser Leu Ala
    265                 270                 275 gac aag ctg aag ggc tgc ctc cag gag atc gac gac gtg ccg cgc gac        976
Asp Lys Leu Lys Gly Cys Leu Gln Glu Ile Asp Asp Val Pro Arg Asp
280                 285                 290                 295
```

| | | | | | | | | | | | | | | |
|---|---|---|---|---|---|---|---|---|---|---|---|---|---|---|
| tgg | acc | tcg | ctg | ttc | gac | gac | tcg | ctg | ttc | aag | ttc | gac | acc | ggc | ctc | 1024 |
| Trp | Thr | Ser | Leu | Phe | Asp | Asp | Ser | Leu | Phe | Lys | Phe | Asp | Thr | Gly | Leu |
| | | | 300 | | | | | 305 | | | | | 310 | | |

```
tgg acc tcg ctg ttc gac gac tcg ctg ttc aag ttc gac acc ggc ctc      1024
Trp Thr Ser Leu Phe Asp Asp Ser Leu Phe Lys Phe Asp Thr Gly Leu
            300                 305                 310 atc cct gag gcc gtg tcg ctg tac gag aag ctg ggc gtg aag aag ggg      1072
Ile Pro Glu Ala Val Ser Leu Tyr Glu Lys Leu Gly Val Lys Lys Gly
            315                 320                 325 cag ctg aac ctc atc ccg ccc tcc ttc gag acg cca ctg ccg ccg ctg      1120
Gln Leu Asn Leu Ile Pro Pro Ser Phe Glu Thr Pro Leu Pro Pro Leu
            330                 335                 340 cag ccc gcc gtg ttc ccg ccc acc atc cgt gag ccg ccg ccg gcg          1168
Gln Pro Ala Val Phe Pro Pro Thr Ile Arg Glu Pro Pro Pro Ala
345                 350                 355 ctg gag ctg ttc gac ctg gat gag agc ttt gcc agc gag acg aac cgg      1216
Leu Glu Leu Phe Asp Leu Asp Glu Ser Phe Ala Ser Glu Thr Asn Arg
360                 365                 370                 375 ctg gcc tcg ctc acc aac aag tgc cac ggc gag gag gac ctg gag tac      1264
Leu Ala Ser Leu Thr Asn Lys Cys His Gly Glu Glu Asp Leu Glu Tyr
            380                 385                 390 tac atc atg gag gcg ggc cac atc ctg ggc ctc aag ctg cag gag aac      1312
Tyr Ile Met Glu Ala Gly His Ile Leu Gly Leu Lys Leu Gln Glu Asn
            395                 400                 405 gcc aac gcc aag cac gtg ctg tcg gag gtg ttc cgc cgc atc gcg cag      1360
Ala Asn Ala Lys His Val Leu Ser Glu Val Phe Arg Arg Ile Ala Gln
            410                 415                 420 tac aag atg ggc agc ctg ggc ctg ggc cag acg ctg gac tcc atg ggc      1408
Tyr Lys Met Gly Ser Leu Gly Leu Gly Gln Thr Leu Asp Ser Met Gly
            425                 430                 435 cag acc ctg ccc gcg gcc aac cag ttc ggc gac cag ttc gag ctg          1453
Gln Thr Leu Pro Ala Ala Asn Gln Phe Gly Asp Gln Phe Glu Leu
440                 445                 450 taaggagcag cgagctacag gccgagcaac tgcgtggcag gcggcagggc gggcgctggc    1513
tgcggcggag gccgaggcgg gggcggctgg cctgggaatg ctgctggcag cggatgtgga    1573
aacgtggggc gccgcagctg ctggagctga ggcggttcgg ggctggctgc tggcgtgctg    1633
gcagcaggat gtgcgcttgt gctgatgcgg tcagcggagc agcgggcatg ctgggctgct    1693
gaacagagcc acgcgggagg gtgtgcggcg cgccaacggc agcagcatgc tgcacgcggg    1753
gttgtgccct ggcggcgaaa agctgggcat tcaccggtgc ctcctctgaa aggcggctgg    1813
gcttggcacc gcgtgtgccg cttgcggtgt gctgggtgta ctggtttcac gcgttctcca    1873
gtctgatgag aggagccttt atcggattga caatggtcca tggtgaacga tggattatgg    1933
atatcggagt gcacagaggc tgacaagata acgttacagt ccaggagata tgtggtggta    1993
gctgcagcaa ctacaagatg gcgtcagtca gacccgacct gttttgagtg ctgcaggctg    2053
acacgcatgc tgacagaaca gacgccgctg caattgcggt tgatattta gccagaaggc     2113 aatatgtggg tgtatgcggg gggtggcatg aggcgcgcga gtggaggagt acagggctgc    2173
gtcgggcgtg cgcgtctgcg gttgcaacag tgagctgtgt tgggtgtgca aggtggtggg    2233
cgtgtgcatg gagccgtgtg gagcagtgtt cccgtggcgc tcaagcggcc cagcattcac    2293
taagctcacg tgtaaaactc attgcggctg aaaaaaaaaa aaaaaaaaa aaaaaaaaa      2353 aaaaaaaaa                                                             2362
```

<210> SEQ ID NO 8
<211> LENGTH: 454
<212> TYPE: PRT
<213> ORGANISM: Chlamydomonas reinhardtii
<400> SEQUENCE: 8

-continued

```
Met Glu Glu Pro Gly Ala Glu Val Arg Ile Leu Phe Ser Thr Ala
 1               5                  10                 15

Lys Gly Glu Ser His Thr His Lys Ala Gly Phe Lys Gln Leu Phe Arg
            20                  25                  30

Arg Leu Arg Ser Thr Tyr Arg Pro Asp Lys Val Asp Lys Asp Phe
        35                  40                  45

Thr Leu Asp Thr Leu Arg Ser Ala His Ile Leu Val Leu Gly Gly Pro
    50                  55                  60

Lys Glu Lys Phe Thr Ala Pro Glu Val Asp Met Leu Lys Lys Phe Val
 65              70                  75                  80

Lys Asn Gly Gly Ser Ile Leu Ile Leu Met Ser Glu Gly Gly Glu Glu
                85                  90                  95

Lys Ala Gly Thr Asn Ile Asn Tyr Phe Leu Glu Gln Phe Gly Met Ser
            100                 105                 110

Val Asn Asn Asp Ala Val Val Arg Thr Thr His Tyr Lys Tyr Leu His
            115                 120                 125

Pro Lys Glu Val Leu Ile Ser Asp Gly Ile Leu Asn Arg Ala Val Ile
        130                 135                 140

Thr Gly Ala Gly Lys Ser Leu Asn Ser Asn Asp Asp Glu Phe Arg
145                 150                 155                 160

Val Ser Arg Gly Pro Gln Ala Phe Asp Gly Thr Gly Leu Glu Tyr Val
            165                 170                 175

Phe Pro Phe Gly Ala Thr Leu Ser Val Gln Lys Pro Ala Val Pro Val
            180                 185                 190

Leu Ser Ser Gly Lys Ile Ala Tyr Pro Met Asn Arg Pro Val Gly Ala
        195                 200                 205

Val Trp Ala Gln Pro Gly Tyr Gly Arg Ile Ala Val Leu Gly Ser Cys
    210                 215                 220

Ala Met Phe Asp Asp Lys Trp Leu Asp Lys Glu Glu Asn Ser Lys Ile
225                 230                 235                 240

Met Asp Phe Phe Phe Lys Phe Leu Glu Pro His Ser Lys Ile Gln Leu
            245                 250                 255

Asn Asp Ile Asp Ala Glu Glu Pro Asp Val Ser Asp Leu Lys Leu Leu
        260                 265                 270

Pro Asp Thr Ala Ser Leu Ala Asp Lys Leu Lys Gly Cys Leu Gln Glu
    275                 280                 285

Ile Asp Asp Val Pro Arg Asp Trp Thr Ser Leu Phe Asp Asp Ser Leu
    290                 295                 300

Phe Lys Phe Asp Thr Gly Leu Ile Pro Glu Ala Val Ser Leu Tyr Glu
305                 310                 315                 320

Lys Leu Gly Val Lys Lys Gly Gln Leu Asn Leu Ile Pro Pro Ser Phe
            325                 330                 335

Glu Thr Pro Leu Pro Pro Leu Gln Pro Ala Val Phe Pro Pro Thr Ile
            340                 345                 350

Arg Glu Pro Pro Pro Ala Leu Glu Leu Phe Asp Leu Asp Glu Ser
        355                 360                 365

Phe Ala Ser Glu Thr Asn Arg Leu Ala Ser Leu Thr Asn Lys Cys His
    370                 375                 380

Gly Glu Glu Asp Leu Glu Tyr Tyr Ile Met Glu Ala Gly His Ile Leu
385                 390                 395                 400

Gly Leu Lys Leu Gln Glu Asn Ala Asn Ala Lys His Val Leu Ser Glu
            405                 410                 415

Val Phe Arg Arg Ile Ala Gln Tyr Lys Met Gly Ser Leu Gly Leu Gly
```

```
                     420              425              430
Gln Thr Leu Asp Ser Met Gly Gln Thr Leu Pro Ala Ala Asn Gln Phe
        435                  440                  445

Gly Asp Gln Phe Glu Leu
    450

<210> SEQ ID NO 9
<211> LENGTH: 1902
<212> TYPE: DNA
<213> ORGANISM: Chlamydomonas reinhardtii
<220> FEATURE:
<221> NAME/KEY: CDS
<222> LOCATION: (86)...(1492)

<400> SEQUENCE: 9
gtcttgggaa cccagcgagc cgcgctcctt gccacatgtc ctgctagctt ctggtttaca     60
ccgtagattc atttaagcga gagac atg agc agc aag cgg ggt ggg cgg tca    112
                              Met Ser Ser Lys Arg Gly Gly Arg Ser
                                1               5 tcc tta gca aag gcg ccc gaa gag gcg gta aat ggc gag gca ttt gcg    160
Ser Leu Ala Lys Ala Pro Glu Glu Ala Val Asn Gly Glu Ala Phe Ala
 10              15                  20                  25 cct gag gca tct ccc cct cca ccc ggc gac gat gga gat gct ggt ggg    208
Pro Glu Ala Ser Pro Pro Pro Pro Gly Asp Asp Gly Asp Ala Gly Gly
             30                  35                  40 gag gac ggt ggc gcg cct gcg ccc cct ccg ccc ccg gct aca aag ggc    256
Glu Asp Gly Gly Ala Pro Ala Pro Pro Pro Pro Ala Thr Lys Gly
         45                  50                  55 ggt cca gta gct gta gga agg tcg ctg gag ata caa aca acg ccg gac    304
Gly Pro Val Ala Val Gly Arg Ser Leu Glu Ile Gln Thr Thr Pro Asp
     60                  65                  70 gtg tgc atg gaa atg ctg gcc gac aag ctg aag ctg cta aac tac gag    352
Val Cys Met Glu Met Leu Ala Asp Lys Leu Lys Leu Leu Asn Tyr Glu
 75                  80                  85 gcg gat ttc tgc agg aag aag aag ccc tac cgg aaa ccc ctc tcg cgg    400
Ala Asp Phe Cys Arg Lys Lys Lys Pro Tyr Arg Lys Pro Leu Ser Arg
 90                  95                 100                 105 ctc tat ttt gcg gtg ccg ctc gca aac tcg agc gag cag ttc ttc tac    448
Leu Tyr Phe Ala Val Pro Leu Ala Asn Ser Ser Glu Gln Phe Phe Tyr
             110                 115                 120 ttt acc agt ctg gcg acc tgg ctg ctg ggc ctg gct ggc gtg gag ctg    496
Phe Thr Ser Leu Ala Thr Trp Leu Leu Gly Leu Ala Gly Val Glu Leu
         125                 130                 135 ccc gct ccc aag gag ttt gat gac ccg aac ttg acg tgc cag aac atc    544
Pro Ala Pro Lys Glu Phe Asp Asp Pro Asn Leu Thr Cys Gln Asn Ile
     140                 145                 150 ctg ggt gcg gtg aag aag ctg ggc ttt gcg ccg ccc agc tac cac cct    592
Leu Gly Ala Val Lys Lys Leu Gly Phe Ala Pro Pro Ser Tyr His Pro
 155                 160                 165 acc aag ctc aca gtg ggc aac ggc aag gag gtg gtg ggt gtg ctg gac    640
Thr Lys Leu Thr Val Gly Asn Gly Lys Glu Val Val Gly Val Leu Asp
170                 175                 180                 185 ggg ctg gtg gac ttc gtg ctg gag cgg cgg cac cac aag tac agc cgg    688
Gly Leu Val Asp Phe Val Leu Glu Arg Arg His His Lys Tyr Ser Arg
             190                 195                 200 ccc gcg tac gga aat gat ggg caa ccg gag gag ggc gtg caa ctg gac    736
Pro Ala Tyr Gly Asn Asp Gly Gln Pro Glu Glu Gly Val Gln Leu Asp
         205                 210                 215 gat gag gcg gag gct gcc gcg atg gag ggt gcg gat gag ctg gcg atg    784
Asp Glu Ala Glu Ala Ala Ala Met Glu Gly Ala Asp Glu Leu Ala Met
     220                 225                 230
```

| | | |
|---|---|---|
| cca gcc cag aac cag gcg gat gac gat gag gag gag gag ggc gta tac<br>Pro Ala Gln Asn Gln Ala Asp Asp Asp Glu Glu Glu Glu Gly Val Tyr<br>235 240 245 | | 832 |
| gtg gac ccg ggg cgc ggt gac gcc gcg ggc cca ggg aca ggg gca tcc<br>Val Asp Pro Gly Arg Gly Asp Ala Ala Gly Pro Gly Thr Gly Ala Ser<br>250 255 260 265 | | 880 |
| gcg gcg atg gac gcg gag aag gcg gtg ctt gtg tcc aag gtg gac ccc<br>Ala Ala Met Asp Ala Glu Lys Ala Val Leu Val Ser Lys Val Asp Pro<br>270 275 280 | | 928 |
| acg ctc tgg aag atc gag ctg gag cgc gtg gcg ccg aag ctg cgt atc<br>Thr Leu Trp Lys Ile Glu Leu Glu Arg Val Ala Pro Lys Leu Arg Ile<br>285 290 295 | | 976 |
| acc atc gcc gcc gac tcg aag gac tgg cgc tca cat ctg gat gag gcg<br>Thr Ile Ala Ala Asp Ser Lys Asp Trp Arg Ser His Leu Asp Glu Ala<br>300 305 310 | | 1024 |
| cac cag cac aag gag gtg atc agc aag gcc tgg ccc gac agc aag acg<br>His Gln His Lys Glu Val Ile Ser Lys Ala Trp Pro Asp Ser Lys Thr<br>315 320 325 | | 1072 |
| tcg ctg gag cgc ctg cgt gcg gac ctg aac ggc acg ctg gag aag ctg<br>Ser Leu Glu Arg Leu Arg Ala Asp Leu Asn Gly Thr Leu Glu Lys Leu<br>330 335 340 345 | | 1120 |
| cag acg cgt gag aag ttc ctc aac gag cag ttt gag agc ctc atg cag<br>Gln Thr Arg Glu Lys Phe Leu Asn Glu Gln Phe Glu Ser Leu Met Gln<br>350 355 360 | | 1168 |
| cag tac cgc gcc gcc cgc acc acg ttc acg gac gtg cag gag aca tac<br>Gln Tyr Arg Ala Ala Arg Thr Thr Phe Thr Asp Val Gln Glu Thr Tyr<br>365 370 375 | | 1216 |
| aac cgc aag acg gag gcg gtg gcg gac cgg aac cag gag atg cac cgc<br>Asn Arg Lys Thr Glu Ala Val Ala Asp Arg Asn Gln Glu Met His Arg<br>380 385 390 | | 1264 |
| atc ggc gag acg ctg gag gag gtg aag gcc atg atg gac gag aag ggc<br>Ile Gly Glu Thr Leu Glu Glu Val Lys Ala Met Met Asp Glu Lys Gly<br>395 400 405 | | 1312 |
| agc aac atc gcg gac gcc acg cct gtg gct cgc atc aag acc gcc atc<br>Ser Asn Ile Ala Asp Ala Thr Pro Val Ala Arg Ile Lys Thr Ala Ile<br>410 415 420 425 | | 1360 |
| aag cag ctt aac aag gag ctg cac gac atg gag gtg cgc atc ggc gtg<br>Lys Gln Leu Asn Lys Glu Leu His Asp Met Glu Val Arg Ile Gly Val<br>430 435 440 | | 1408 |
| gtt agc cac acg ctg ctg cag cta tcg ctg cgc aac aag cga ttg ctg<br>Val Ser His Thr Leu Leu Gln Leu Ser Leu Arg Asn Lys Arg Leu Leu<br>445 450 455 | | 1456 |
| cag gcg cag gcg gct ctc agt gac gag gag gag gac tagctagatc<br>Gln Ala Gln Ala Ala Leu Ser Asp Glu Glu Glu Asp<br>460 465 | | 1502 |
| agcgagtgac agagggcatg tgtgcgtacc gtgtgcgcgg gtacagccgt gggatggaag | | 1562 |
| aggtgatgtg gcgggttgcg gacccagcat tcggtagacc agatcactta taggtacaga | | 1622 |
| aagacggcta tattgttggg ggcggcgcac cctggctatg tatatacaag ccgtagcgca | | 1682 |
| gagccgctgc aaatgcggtg ctgtgcctgt gctcccgtgg gtgtgcggcg ttccggtcaa | | 1742 |
| gttcatataa gctgttgtga cttgtgaggc aggcatggca tatggacagg gcatccctgc | | 1802 |
| aaggaaagca ggcagcggta tccttgtggc gatgggtcaa gcagtgatgg aggggcgaag | | 1862 |
| cgagttgcgg gcctgtaagc acaggggttgc caaaaaaaaa | | 1902 |

<210> SEQ ID NO 10
<211> LENGTH: 469
<212> TYPE: PRT
<213> ORGANISM: Chlamydomonas reinhardtii

<400> SEQUENCE: 10

Met Ser Ser Lys Arg Gly Gly Arg Ser Leu Ala Lys Ala Pro Glu
1               5                   10                  15

Glu Ala Val Asn Gly Glu Ala Phe Ala Pro Glu Ala Ser Pro Pro
            20                  25                  30

Pro Gly Asp Asp Gly Asp Ala Gly Glu Asp Gly Gly Ala Pro Ala
        35                  40                  45

Pro Pro Pro Pro Ala Thr Lys Gly Gly Pro Val Ala Val Gly Arg
    50                  55                  60

Ser Leu Glu Ile Gln Thr Thr Pro Asp Val Cys Met Glu Met Leu Ala
65                  70                  75                  80

Asp Lys Leu Lys Leu Leu Asn Tyr Glu Ala Asp Phe Cys Arg Lys Lys
                85                  90                  95

Lys Pro Tyr Arg Lys Pro Leu Ser Arg Leu Tyr Phe Ala Val Pro Leu
                100                 105                 110

Ala Asn Ser Ser Glu Gln Phe Phe Tyr Phe Thr Ser Leu Ala Thr Trp
            115                 120                 125

Leu Leu Gly Leu Ala Gly Val Glu Leu Pro Ala Pro Lys Glu Phe Asp
130                 135                 140

Asp Pro Asn Leu Thr Cys Gln Asn Ile Leu Gly Ala Val Lys Lys Leu
145                 150                 155                 160

Gly Phe Ala Pro Pro Ser Tyr His Pro Thr Lys Leu Thr Val Gly Asn
                165                 170                 175

Gly Lys Glu Val Val Gly Val Leu Asp Gly Leu Val Asp Phe Val Leu
            180                 185                 190

Glu Arg Arg His His Lys Tyr Ser Arg Pro Ala Tyr Gly Asn Asp Gly
            195                 200                 205

Gln Pro Glu Glu Gly Val Gln Leu Asp Glu Ala Glu Ala Ala Ala
        210                 215                 220

Met Glu Gly Ala Asp Glu Leu Ala Met Pro Ala Gln Asn Gln Ala Asp
225                 230                 235                 240

Asp Asp Glu Glu Glu Gly Val Tyr Val Asp Pro Gly Arg Gly Asp
                245                 250                 255

Ala Ala Gly Pro Gly Thr Gly Ala Ser Ala Ala Met Asp Ala Glu Lys
                260                 265                 270

Ala Val Leu Val Ser Lys Val Asp Pro Thr Leu Trp Lys Ile Glu Leu
            275                 280                 285

Glu Arg Val Ala Pro Lys Leu Arg Ile Thr Ile Ala Ala Asp Ser Lys
            290                 295                 300

Asp Trp Arg Ser His Leu Asp Glu Ala His Gln His Lys Glu Val Ile
305                 310                 315                 320

Ser Lys Ala Trp Pro Asp Ser Lys Thr Ser Leu Glu Arg Leu Arg Ala
                325                 330                 335

Asp Leu Asn Gly Thr Leu Glu Lys Leu Gln Thr Arg Glu Lys Phe Leu
            340                 345                 350

Asn Glu Gln Phe Glu Ser Leu Met Gln Gln Tyr Arg Ala Ala Arg Thr
            355                 360                 365

Thr Phe Thr Asp Val Gln Glu Thr Tyr Asn Arg Lys Thr Glu Ala Val
370                 375                 380

Ala Asp Arg Asn Gln Glu Met His Arg Ile Gly Glu Thr Leu Glu Glu
385                 390                 395                 400

Val Lys Ala Met Met Asp Glu Lys Gly Ser Asn Ile Ala Asp Ala Thr
                405                 410                 415

```
Pro Val Ala Arg Ile Lys Thr Ala Ile Lys Gln Leu Asn Lys Glu Leu
        420                 425                 430

His Asp Met Glu Val Arg Ile Gly Val Val Ser His Thr Leu Leu Gln
        435                 440                 445

Leu Ser Leu Arg Asn Lys Arg Leu Leu Gln Ala Gln Ala Ala Leu Ser
        450                 455                 460

Asp Glu Glu Glu Asp
465

<210> SEQ ID NO 11
<211> LENGTH: 1559
<212> TYPE: DNA
<213> ORGANISM: Mus musculus
<220> FEATURE:
<221> NAME/KEY: CDS
<222> LOCATION: (59)...(1345)

<400> SEQUENCE: 11
gcgaaggctg cagagatcct ggccggagcc cagccgggcg ctgggggtct gagcaggg      58 atg gcc gcc gcg gcc gcg gtg atc ccg ccg tcg ggc ttg gac gat ggg     106
Met Ala Ala Ala Ala Ala Val Ile Pro Pro Ser Gly Leu Asp Asp Gly
 1               5                  10                  15 gtg tct cgg gct cgc ggg gaa ggc gca ggg gag gct gtg gtg gag cgc     154
Val Ser Arg Ala Arg Gly Glu Gly Ala Gly Glu Ala Val Val Glu Arg
             20                  25                  30 ggg cca gga gcg gcc tac cac atg ttc gtg gtg atg gaa gac tta gtg     202
Gly Pro Gly Ala Ala Tyr His Met Phe Val Val Met Glu Asp Leu Val
         35                  40                  45 gag aag ctg aag ctg ctc cgc tac gag gag gag cta ctc cga aag agc     250
Glu Lys Leu Lys Leu Leu Arg Tyr Glu Glu Glu Leu Leu Arg Lys Ser
     50                  55                  60 aat ctg aag ccc ccg tcc aga cac tac ttt gct ctg cct acc aac cca     298
Asn Leu Lys Pro Pro Ser Arg His Tyr Phe Ala Leu Pro Thr Asn Pro
 65                  70                  75                  80 ggc gag cag ttc tac atg ttt tgc act ctt gct gcg tgg ctg atc aac     346
Gly Glu Gln Phe Tyr Met Phe Cys Thr Leu Ala Ala Trp Leu Ile Asn
                 85                  90                  95 aaa act ggc cgt gcc ttt gag cag cct caa gaa tac gac gat ccc aat     394
Lys Thr Gly Arg Ala Phe Glu Gln Pro Gln Glu Tyr Asp Asp Pro Asn
            100                 105                 110 gca act ata tct aat ata ctc tct gag ctt cgc tct ttt ggg aga act     442
Ala Thr Ile Ser Asn Ile Leu Ser Glu Leu Arg Ser Phe Gly Arg Thr
        115                 120                 125 gca gat ttt cct cct tca aaa tta aag tct ggt tac gga gaa caa gtg     490
Ala Asp Phe Pro Pro Ser Lys Leu Lys Ser Gly Tyr Gly Glu Gln Val
    130                 135                 140 tgc tat gtt ctt gat tgc tta gct gaa gaa gct tta aaa tat att ggt     538
Cys Tyr Val Leu Asp Cys Leu Ala Glu Glu Ala Leu Lys Tyr Ile Gly
145                 150                 155                 160 ttc act tgg aaa agg cca tca tac cca gtg gaa gaa cta gaa gaa gaa     586
Phe Thr Trp Lys Arg Pro Ser Tyr Pro Val Glu Glu Leu Glu Glu Glu
                165                 170                 175 act gtt cca gaa gat gat gcc gag tta aca tta agt aaa gtg gat gaa     634
Thr Val Pro Glu Asp Asp Ala Glu Leu Thr Leu Ser Lys Val Asp Glu
            180                 185                 190 gaa ttt gtg gaa gag gag aca gat aat gaa gaa aac ttt att gat ctc     682
Glu Phe Val Glu Glu Glu Thr Asp Asn Glu Glu Asn Phe Ile Asp Leu
        195                 200                 205 aac gtt tta aag gcc cag acc tat cgc ttg gac aca aac gag tct gcc     730
Asn Val Leu Lys Ala Gln Thr Tyr Arg Leu Asp Thr Asn Glu Ser Ala
```

```
                 210                 215                 220
aaa caa gaa gat att ttg gaa tct acg aca gat gct gcg gaa tgg agc      778
Lys Gln Glu Asp Ile Leu Glu Ser Thr Thr Asp Ala Ala Glu Trp Ser
225                 230                 235                 240 cta gaa gtt gag cgt gta cta ccg cag ctg aaa gtc acg att agg act      826
Leu Glu Val Glu Arg Val Leu Pro Gln Leu Lys Val Thr Ile Arg Thr
                245                 250                 255 gac aat aag gat tgg agg atc cat gtt gac caa atg cac cag cac aaa      874
Asp Asn Lys Asp Trp Arg Ile His Val Asp Gln Met His Gln His Lys
            260                 265                 270 agt ggg att gaa tct gct ctg aag gag acc aag ggg ttt ttg gac aag      922
Ser Gly Ile Glu Ser Ala Leu Lys Glu Thr Lys Gly Phe Leu Asp Lys
        275                 280                 285 ctc cat aat gaa att agc agg act ctg gaa aag att ggc agc cga gaa      970
Leu His Asn Glu Ile Ser Arg Thr Leu Glu Lys Ile Gly Ser Arg Glu
    290                 295                 300 aag tac att aac aat caa ctt gag cac ttg gtt caa gaa tat cgt ggg     1018
Lys Tyr Ile Asn Asn Gln Leu Glu His Leu Val Gln Glu Tyr Arg Gly
305                 310                 315                 320 gcc caa gcc cag cta agt gag gca agg gag cgc tac cag cag ggc aat     1066
Ala Gln Ala Gln Leu Ser Glu Ala Arg Glu Arg Tyr Gln Gln Gly Asn
                325                 330                 335 ggc gga gta act gaa cgg acc aga ctc ctc tct gag gtt aca gaa gaa     1114
Gly Gly Val Thr Glu Arg Thr Arg Leu Leu Ser Glu Val Thr Glu Glu
            340                 345                 350 tta gaa aag gta aag caa gaa atg gaa gag aag ggc agc agc atg acg     1162
Leu Glu Lys Val Lys Gln Glu Met Glu Glu Lys Gly Ser Ser Met Thr
        355                 360                 365 gac ggc act cct ttg gtg aag att aag cag agc tta acc aag ctg aag     1210
Asp Gly Thr Pro Leu Val Lys Ile Lys Gln Ser Leu Thr Lys Leu Lys
    370                 375                 380 caa gaa act gtt cag atg gac att aga atc ggt gtg gtg gag cac acg     1258
Gln Glu Thr Val Gln Met Asp Ile Arg Ile Gly Val Val Glu His Thr
385                 390                 395                 400 cta ctt cag tca aaa ctc aag gag aag tgc aac atg acc agg gac atg     1306
Leu Leu Gln Ser Lys Leu Lys Glu Lys Cys Asn Met Thr Arg Asp Met
                405                 410                 415 cat gca gct gtc acc cca gag tca gca att ggc ttc tat taaacacgtg      1355
His Ala Ala Val Thr Pro Glu Ser Ala Ile Gly Phe Tyr
            420                 425 ggcttccatg cttctgatta tttcgttttt atatcaaatg attttttaat gttgcattga   1415
tttccaaaca caattatac ttcttcaagc atattcagtg ggtattttg cacatgtgtt     1475 aatatcatgg tgattatgat ggccaaagcc tgtacaatga atatagtatt taataaagta   1535
cttaaaatta aaaaaaaaaa aaaa                                          1559

<210> SEQ ID NO 12
<211> LENGTH: 429
<212> TYPE: PRT
<213> ORGANISM: Mus musculus

<400> SEQUENCE: 12

Met Ala Ala Ala Ala Val Ile Pro Pro Ser Gly Leu Asp Asp Gly
1               5                   10                  15

Val Ser Arg Ala Arg Gly Glu Gly Ala Gly Glu Ala Val Val Glu Arg
                20                  25                  30

Gly Pro Gly Ala Ala Tyr His Met Phe Val Val Met Glu Asp Leu Val
            35                  40                  45

Glu Lys Leu Lys Leu Leu Arg Tyr Glu Glu Glu Leu Leu Arg Lys Ser
```

```
                50                  55                  60
Asn Leu Lys Pro Pro Ser Arg His Tyr Phe Ala Leu Pro Thr Asn Pro
 65                  70                  75                  80

Gly Glu Gln Phe Tyr Met Phe Cys Thr Leu Ala Ala Trp Leu Ile Asn
                 85                  90                  95

Lys Thr Gly Arg Ala Phe Glu Gln Pro Gln Glu Tyr Asp Asp Pro Asn
            100                 105                 110

Ala Thr Ile Ser Asn Ile Leu Ser Glu Leu Arg Ser Phe Gly Arg Thr
        115                 120                 125

Ala Asp Phe Pro Pro Ser Lys Leu Lys Ser Gly Tyr Gly Glu Gln Val
130                 135                 140

Cys Tyr Val Leu Asp Cys Leu Ala Glu Ala Leu Lys Tyr Ile Gly
145                 150                 155                 160

Phe Thr Trp Lys Arg Pro Ser Tyr Pro Val Glu Leu Glu Glu
                165                 170                 175

Thr Val Pro Glu Asp Asp Ala Glu Leu Thr Leu Ser Lys Val Asp Glu
            180                 185                 190

Glu Phe Val Glu Glu Glu Thr Asp Asn Glu Glu Asn Phe Ile Asp Leu
        195                 200                 205

Asn Val Leu Lys Ala Gln Thr Tyr Arg Leu Asp Thr Asn Glu Ser Ala
    210                 215                 220

Lys Gln Glu Asp Ile Leu Glu Ser Thr Thr Asp Ala Ala Glu Trp Ser
225                 230                 235                 240

Leu Glu Val Glu Arg Val Leu Pro Gln Leu Lys Val Thr Ile Arg Thr
                245                 250                 255

Asp Asn Lys Asp Trp Arg Ile His Val Asp Gln Met His Gln His Lys
            260                 265                 270

Ser Gly Ile Glu Ser Ala Leu Lys Glu Thr Lys Gly Phe Leu Asp Lys
        275                 280                 285

Leu His Asn Glu Ile Ser Arg Thr Leu Glu Lys Ile Gly Ser Arg Glu
    290                 295                 300

Lys Tyr Ile Asn Asn Gln Leu Glu His Leu Val Gln Glu Tyr Arg Gly
305                 310                 315                 320

Ala Gln Ala Gln Leu Ser Glu Ala Arg Glu Arg Tyr Gln Gln Gly Asn
                325                 330                 335

Gly Gly Val Thr Glu Arg Thr Arg Leu Leu Ser Glu Val Thr Glu Glu
            340                 345                 350

Leu Glu Lys Val Lys Gln Glu Met Glu Glu Lys Gly Ser Ser Met Thr
        355                 360                 365

Asp Gly Thr Pro Leu Val Lys Ile Lys Gln Ser Leu Thr Lys Leu Lys
370                 375                 380

Gln Glu Thr Val Gln Met Asp Ile Arg Ile Gly Val Val Glu His Thr
                390                 395                 400

Leu Leu Gln Ser Lys Leu Lys Glu Lys Cys Asn Met Thr Arg Asp Met
            405                 410                 415

His Ala Ala Val Thr Pro Glu Ser Ala Ile Gly Phe Tyr
        420                 425

<210> SEQ ID NO 13
<211> LENGTH: 1954
<212> TYPE: DNA
<213> ORGANISM: Chlamydomonas reinhardtii
<220> FEATURE:
<221> NAME/KEY: CDS
<222> LOCATION: (1)...(1302)
```

<400> SEQUENCE: 13

```
gtg tac gtg atc cag cag gag ttc gcg gcg ctc aag gac cgc aac gag      48
Val Tyr Val Ile Gln Gln Glu Phe Ala Ala Leu Lys Asp Arg Asn Glu
 1               5                  10                  15 cag cag cgc aag cgc gtg gac gag gtg ctc acg gag cgc ctc aac ctc      96
Gln Gln Arg Lys Arg Val Asp Glu Val Leu Thr Glu Arg Leu Asn Leu
             20                  25                  30 gag tcc aag gcc aag cag gcc gag tcc aag atg tct gag atc cag gcg     144
Glu Ser Lys Ala Lys Gln Ala Glu Ser Lys Met Ser Glu Ile Gln Ala
         35                  40                  45 tcc atg gac cag cgc ctc aac tct atg ccg ccc agc cag cgc aac gaa     192
Ser Met Asp Gln Arg Leu Asn Ser Met Pro Pro Ser Gln Arg Asn Glu
     50                  55                  60 tac acc acg ctc gtg gcc gag cag cag cag ctg cag gcc gac agc aag     240
Tyr Thr Thr Leu Val Ala Glu Gln Gln Gln Leu Gln Ala Asp Ser Lys
 65                  70                  75                  80 cgc ttt gag gag gtg ctg gac gag ctg gac aag gcg ctg cag gcc agc     288
Arg Phe Glu Glu Val Leu Asp Glu Leu Asp Lys Ala Leu Gln Ala Ser
                 85                  90                  95 gag ggc gag ctg gcg cgc aac ccc ttc aag cag cgc agc ctg cag ctg     336
Glu Gly Glu Leu Ala Arg Asn Pro Phe Lys Gln Arg Ser Leu Gln Leu
            100                 105                 110 cag gag cag atc cgc gcg ctc acg ggg aag aag tac gag ctg acg gag     384
Gln Glu Gln Ile Arg Ala Leu Thr Gly Lys Lys Tyr Glu Leu Thr Glu
        115                 120                 125 gag gag cgg cag agc aag cgc tcg ccc gag gag ctg cgc gcc gac ctc     432
Glu Glu Arg Gln Ser Lys Arg Ser Pro Glu Glu Leu Arg Ala Asp Leu
    130                 135                 140 atg gcc aag atc aag cga gac aac acc gag gtg gag cag atg acg cag     480
Met Ala Lys Ile Lys Arg Asp Asn Thr Glu Val Glu Gln Met Thr Gln
145                 150                 155                 160 cag atc cgc gag ctt cag gac cag atc aag aag atg gag gag cgc gtc     528
Gln Ile Arg Glu Leu Gln Asp Gln Ile Lys Lys Met Glu Glu Arg Val
                165                 170                 175 aag agc ctg ggc ggc gcc acc agc ggc gcg gtg gcg gcg gag gaa aag     576
Lys Ser Leu Gly Gly Ala Thr Ser Gly Ala Val Ala Ala Glu Glu Lys
            180                 185                 190 gcc aac cgc gag aag ttt gag gag ctg ttg gcc aag gag cgc cac cta     624
Ala Asn Arg Glu Lys Phe Glu Glu Leu Leu Ala Lys Glu Arg His Leu
        195                 200                 205 aac aac ttt atg gac ggc ttc ccc agc cgc aag gcc gcc aag atg cag     672
Asn Asn Phe Met Asp Gly Phe Pro Ser Arg Lys Ala Ala Lys Met Gln
    210                 215                 220 gag aag cag cag aag gag gac ggc atc gtg ggc gtg ctg gag aag atg     720
Glu Lys Gln Gln Lys Glu Asp Gly Ile Val Gly Val Leu Glu Lys Met
225                 230                 235                 240 gtg aag atg cag ggc atc att ggc tcc aac ctg ccc agc cag aag aag     768
Val Lys Met Gln Gly Ile Ile Gly Ser Asn Leu Pro Ser Gln Lys Lys
                245                 250                 255 tac aag gaa atg cag gac gag ctc gag tac aag aag atg cag ctg gag     816
Tyr Lys Glu Met Gln Asp Glu Leu Glu Tyr Lys Lys Met Gln Leu Glu
            260                 265                 270 aac acg cag acc acg cag gag cgg ctc aag gag gag ctg acc atg cgg     864
Asn Thr Gln Thr Thr Gln Glu Arg Leu Lys Glu Glu Leu Thr Met Arg
        275                 280                 285 cgc aca gag ctg gag aag atc gat acg ctg gag gac aag atc aag ctg     912
Arg Thr Glu Leu Glu Lys Ile Asp Thr Leu Glu Asp Lys Ile Lys Leu
    290                 295                 300 gag ctg acg cag ctg gcg gag cgg cag gag gcc atg gag aag gag atg     960
Glu Leu Thr Gln Leu Ala Glu Arg Gln Glu Ala Met Glu Lys Glu Met
```

```
                305                 310                 315                 320
ggc gag ttc ggc agc gtc gag gac atc cag cgc aag gcc aac gcc gca       1008
Gly Glu Phe Gly Ser Val Glu Asp Ile Gln Arg Lys Ala Asn Ala Ala
                    325                 330                 335 cgc gag cgc atg ggg gcc tgc gca gtg tgc tgt ttg aag cgc aag gac       1056
Arg Glu Arg Met Gly Ala Cys Ala Val Cys Cys Leu Lys Arg Lys Asp
                340                 345                 350 ctg ctg cgc tcc atc gtg gcg gag cgc ggc ctc aag ttc cag gcc aag       1104
Leu Leu Arg Ser Ile Val Ala Glu Arg Gly Leu Lys Phe Gln Ala Lys
            355                 360                 365 cgc gcg cag ctg cag gac cac aac ctc cag gtg cag ctg gag aag atg       1152
Arg Ala Gln Leu Gln Asp His Asn Leu Gln Val Gln Leu Glu Lys Met
        370                 375                 380 gag gcc aag ctg aag aat ctg agc gcg ggc gta ttc gag atg gac gag       1200
Glu Ala Lys Leu Lys Asn Leu Ser Ala Gly Val Phe Glu Met Asp Glu
385                 390                 395                 400 ttc atc aag gcc aag gag agc gag acc aac tac cgc cag ctg gcc tcc       1248
Phe Ile Lys Ala Lys Glu Ser Glu Thr Asn Tyr Arg Gln Leu Ala Ser
                405                 410                 415 aac ata gcg gcg ctg gta gac gac ctc aac gtg cat gtc aag aag gcc       1296
Asn Ile Ala Ala Leu Val Asp Asp Leu Asn Val His Val Lys Lys Ala
            420                 425                 430 gtg gtg taagaaggag gcagtggtgt aagggtctc cggaggaggg cgcgtgccgt         1352
Val Val tgttggggtg ttggggcgc ggcgcgagaa gtacgtgcgt gtggcgttgt gcctttcagc      1412
aggctgcacg tgtagtacgg tagtcaaggt gaagggcggc ctgggcacag gaggatgctg     1472
acgccgtgac gggtgacgat gacaggccat cgcgagtttg atctctgctg tcgagtcatt    1532
gacttgggtt cctagacagg tcgggctaca agcccggagg ttgatggctc acctcgcagt    1592
gcgcggacag caggtgtggc gcatgcgcat gtgcctcagg agcgcggtgc ggaccaggga    1652
agatgcgatg ggagtaggct aggcctgtgt gagggcccctt gccgaagcgc acggccatt    1712 ccatggcctg gcccgaaggc agcgctcgtg gttggatact gaccagcggc gtcaagcggc    1772
gtacgatgtc agaagtggag ctaccgcccc tgcacaaggg gtgatgtaca tactgttatt    1832
taggagtccg ctgcttatag ctactggact gcagaagaag gaggctgcaa ggatctgatg    1892
gaggcgctgg tgtgtatgga tgacgctgta agagatgcac aagagaaaaa aaaaaaaaa    1952 aa                                                                    1954
```

<210> SEQ ID NO 14
<211> LENGTH: 434
<212> TYPE: PRT
<213> ORGANISM: Chlamydomonas reinhardtii

<400> SEQUENCE: 14

```
Val Tyr Val Ile Gln Gln Glu Phe Ala Ala Leu Lys Asp Arg Asn Glu
  1               5                  10                  15

Gln Gln Arg Lys Arg Val Asp Glu Val Leu Thr Glu Arg Leu Asn Leu
                20                  25                  30

Glu Ser Lys Ala Lys Gln Ala Glu Ser Lys Met Ser Glu Ile Gln Ala
            35                  40                  45

Ser Met Asp Gln Arg Leu Asn Ser Met Pro Pro Ser Gln Arg Asn Glu
        50                  55                  60

Tyr Thr Thr Leu Val Ala Glu Gln Gln Leu Gln Ala Asp Ser Lys
 65                  70                  75                  80

Arg Phe Glu Glu Val Leu Asp Glu Leu Asp Lys Ala Leu Gln Ala Ser
                85                  90                  95
```

Glu Gly Glu Leu Ala Arg Asn Pro Phe Lys Gln Arg Ser Leu Gln Leu
            100                 105                 110

Gln Glu Gln Ile Arg Ala Leu Thr Gly Lys Lys Tyr Glu Leu Thr Glu
            115                 120                 125

Glu Glu Arg Gln Ser Lys Arg Ser Pro Glu Glu Leu Arg Ala Asp Leu
130                 135                 140

Met Ala Lys Ile Lys Arg Asp Asn Thr Glu Val Glu Gln Met Thr Gln
145                 150                 155                 160

Gln Ile Arg Glu Leu Gln Asp Gln Ile Lys Lys Met Glu Glu Arg Val
            165                 170                 175

Lys Ser Leu Gly Gly Ala Thr Ser Gly Ala Val Ala Ala Glu Glu Lys
            180                 185                 190

Ala Asn Arg Glu Lys Phe Glu Glu Leu Leu Ala Lys Glu Arg His Leu
            195                 200                 205

Asn Asn Phe Met Asp Gly Phe Pro Ser Arg Lys Ala Ala Lys Met Gln
            210                 215                 220

Glu Lys Gln Gln Lys Glu Asp Gly Ile Val Gly Val Leu Glu Lys Met
225                 230                 235                 240

Val Lys Met Gln Gly Ile Ile Gly Ser Asn Leu Pro Ser Gln Lys Lys
            245                 250                 255

Tyr Lys Glu Met Gln Asp Glu Leu Glu Tyr Lys Lys Met Gln Leu Glu
            260                 265                 270

Asn Thr Gln Thr Thr Gln Glu Arg Leu Lys Glu Glu Leu Thr Met Arg
            275                 280                 285

Arg Thr Glu Leu Glu Lys Ile Asp Thr Leu Glu Asp Lys Ile Lys Leu
            290                 295                 300

Glu Leu Thr Gln Leu Ala Glu Arg Gln Glu Ala Met Glu Lys Glu Met
305                 310                 315                 320

Gly Glu Phe Gly Ser Val Glu Asp Ile Gln Arg Lys Ala Asn Ala Ala
            325                 330                 335

Arg Glu Arg Met Gly Ala Cys Ala Val Cys Cys Leu Lys Arg Lys Asp
            340                 345                 350

Leu Leu Arg Ser Ile Val Ala Glu Arg Gly Leu Lys Phe Gln Ala Lys
            355                 360                 365

Arg Ala Gln Leu Gln Asp His Asn Leu Gln Val Gln Leu Glu Lys Met
370                 375                 380

Glu Ala Lys Leu Lys Asn Leu Ser Ala Gly Val Phe Glu Met Asp Glu
385                 390                 395                 400

Phe Ile Lys Ala Lys Glu Ser Glu Thr Asn Tyr Arg Gln Leu Ala Ser
            405                 410                 415

Asn Ile Ala Ala Leu Val Asp Asp Leu Asn Val His Val Lys Lys Ala
            420                 425                 430

Val Val

<210> SEQ ID NO 15
<211> LENGTH: 3388
<212> TYPE: DNA
<213> ORGANISM: Chlamydomonas reinhardtii
<220> FEATURE:
<221> NAME/KEY: CDS
<222> LOCATION: (108)...(2453)

<400> SEQUENCE: 15
cggcaacttg acacttgagc tactcgaagg cagggccgtg tgcagagctc cttccccact      60
atccttcctt tgcgtaccat acttatcttg ctaacagcct atagaag atg agc tac      116

-continued

|  |  |  |  |  |  |  |  |  |  |  |  |  |  |  |  |
|---|---|---|---|---|---|---|---|---|---|---|---|---|---|---|---|
|  |  |  |  |  |  |  |  |  |  |  |  | Met | Ser | Tyr |  |
|  |  |  |  |  |  |  |  |  |  |  |  | 1 |  |  |  |

| ggg | ggc | acg | gag | gag | gat | gac | ctt | tat | gga | gga | tat | gat | gag | caa | tcg | 164 |
|-----|-----|-----|-----|-----|-----|-----|-----|-----|-----|-----|-----|-----|-----|-----|-----|-----|
| Gly | Gly | Thr | Glu | Glu | Asp | Asp | Leu | Tyr | Gly | Gly | Tyr | Asp | Glu | Gln | Ser |  |
|     | 5   |     |     |     | 10  |     |     |     |     | 15  |     |     |     |     |     |  |

| aac | ccg | ctt | gcg | ggc | tcg | ggt | ggt | gcc | gca | ttt | aag | gca | ctt | ggg | gcc | 212 |
| Asn | Pro | Leu | Ala | Gly | Ser | Gly | Gly | Ala | Ala | Phe | Lys | Ala | Leu | Gly | Ala |  |
| 20  |     |     |     |     | 25  |     |     |     |     | 30  |     |     |     |     | 35  |  |

| gat | gga | gct | cct | cca | ggc | acc | gcc | atg | atg | ggg | ccg | cct | ggc | acg | gcc | 260 |
| Asp | Gly | Ala | Pro | Pro | Gly | Thr | Ala | Met | Met | Gly | Pro | Pro | Gly | Thr | Ala |  |
|     |     |     | 40  |     |     |     |     | 45  |     |     |     |     | 50  |     |     |  |

| atg | aag | agc | ttc | gtg | cca | ggc | acg | gct | atg | cgg | ggc | ggc | acg | gcg | atg | 308 |
| Met | Lys | Ser | Phe | Val | Pro | Gly | Thr | Ala | Met | Arg | Gly | Gly | Thr | Ala | Met |  |
|     |     |     | 55  |     |     |     |     | 60  |     |     |     |     | 65  |     |     |  |

| cag | cag | gac | ccc | agc | ctg | gcg | cgg | cct | atg | acc | tcg | aac | cgg | ggt | gct | 356 |
| Gln | Gln | Asp | Pro | Ser | Leu | Ala | Arg | Pro | Met | Thr | Ser | Asn | Arg | Gly | Ala |  |
|     |     |     | 70  |     |     |     |     | 75  |     |     |     |     | 80  |     |     |  |

| ggc | ttc | acg | tcg | gcg | cct | aac | aag | aag | ttt | gac | ccc | ctc | aat | cgc | tca | 404 |
| Gly | Phe | Thr | Ser | Ala | Pro | Asn | Lys | Lys | Phe | Asp | Pro | Leu | Asn | Arg | Ser |  |
|     |     | 85  |     |     |     |     | 90  |     |     |     |     | 95  |     |     |     |  |

| atg | ggg | tcg | aca | ctg | ggc | tcg | tcg | ggg | ggt | ggc | gca | atg | ctg | gtg | gct | 452 |
| Met | Gly | Ser | Thr | Leu | Gly | Ser | Ser | Gly | Gly | Gly | Ala | Met | Leu | Val | Ala |  |
| 100 |     |     |     |     | 105 |     |     |     |     | 110 |     |     |     |     | 115 |  |

| cgc | aag | ggt | gac | acc | agc | ccg | gag | gag | cag | gcg | cgc | ggg | atg | gag | aag | 500 |
| Arg | Lys | Gly | Asp | Thr | Ser | Pro | Glu | Glu | Gln | Ala | Arg | Gly | Met | Glu | Lys |  |
|     |     |     |     | 120 |     |     |     |     | 125 |     |     |     |     | 130 |     |  |

| acg | gtg | cat | gag | ctg | ctt | gag | aag | agc | gcg | gcg | gac | gcg | gct | aag | aat | 548 |
| Thr | Val | His | Glu | Leu | Leu | Glu | Lys | Ser | Ala | Ala | Asp | Ala | Ala | Lys | Asn |  |
|     |     |     | 135 |     |     |     |     | 140 |     |     |     |     | 145 |     |     |  |

| gac | atc | aac | tcg | gcc | ctg | gag | aac | gcc | atg | gag | gcg | aag | aag | aat | gag | 596 |
| Asp | Ile | Asn | Ser | Ala | Leu | Glu | Asn | Ala | Met | Glu | Ala | Lys | Lys | Asn | Glu |  |
|     |     |     | 150 |     |     |     |     | 155 |     |     |     |     | 160 |     |     |  |

| cga | aag | ctg | tgc | cgc | ttc | cgg | gaa | cag | aac | aac | atg | gcg | gac | cag | atc | 644 |
| Arg | Lys | Leu | Cys | Arg | Phe | Arg | Glu | Gln | Asn | Asn | Met | Ala | Asp | Gln | Ile |  |
|     | 165 |     |     |     |     | 170 |     |     |     |     | 175 |     |     |     |     |  |

| aac | ctg | gag | ctg | atg | tac | gcc | gtg | gac | ttc | aac | ctg | gca | cac | atg | tac | 692 |
| Asn | Leu | Glu | Leu | Met | Tyr | Ala | Val | Asp | Phe | Asn | Leu | Ala | His | Met | Tyr |  |
| 180 |     |     |     |     | 185 |     |     |     |     | 190 |     |     |     |     | 195 |  |

| cac | atg | aac | aag | aac | tac | agc | gag | gcg | ctg | aac | ctg | tac | aca | gcc | atc | 740 |
| His | Met | Asn | Lys | Asn | Tyr | Ser | Glu | Ala | Leu | Asn | Leu | Tyr | Thr | Ala | Ile |  |
|     |     |     | 200 |     |     |     |     | 205 |     |     |     |     | 210 |     |     |  |

| gtg | cgc | aac | aag | aac | ttc | ccg | cag | tcg | ggt | tgg | ctg | cgc | gtc | aac | atg | 788 |
| Val | Arg | Asn | Lys | Asn | Phe | Pro | Gln | Ser | Gly | Trp | Leu | Arg | Val | Asn | Met |  |
|     |     |     | 215 |     |     |     |     | 220 |     |     |     |     | 225 |     |     |  |

| ggc | aac | atc | cac | ttc | gag | cag | aag | aag | tac | ccc | tcc | gcc | atc | aag | atg | 836 |
| Gly | Asn | Ile | His | Phe | Glu | Gln | Lys | Lys | Tyr | Pro | Ser | Ala | Ile | Lys | Met |  |
|     |     | 230 |     |     |     |     | 235 |     |     |     |     | 240 |     |     |     |  |

| tac | cgc | atg | gcg | ttg | gac | cag | atc | agc | gcc | acc | gcc | aag | gag | gtc | cgc | 884 |
| Tyr | Arg | Met | Ala | Leu | Asp | Gln | Ile | Ser | Ala | Thr | Ala | Lys | Glu | Val | Arg |  |
|     | 245 |     |     |     |     | 250 |     |     |     |     | 255 |     |     |     |     |  |

| ttc | aag | atc | atg | cgc | aac | atc | ggg | ctg | tcg | ttc | gtg | cgc | atg | ggc | cag | 932 |
| Phe | Lys | Ile | Met | Arg | Asn | Ile | Gly | Leu | Ser | Phe | Val | Arg | Met | Gly | Gln |  |
| 260 |     |     |     |     | 265 |     |     |     |     | 270 |     |     |     |     | 275 |  |

| tac | ccc | gac | gcg | ctg | cag | tcc | ttc | gcc | acg | gtc | atg | gac | aac | gtg | ccc | 980 |
| Tyr | Pro | Asp | Ala | Leu | Gln | Ser | Phe | Ala | Thr | Val | Met | Asp | Asn | Val | Pro |  |
|     |     |     | 280 |     |     |     |     | 285 |     |     |     |     | 290 |     |     |  |

| gac | cac | cag | acc | ggc | tac | aac | ctg | gtc | atg | tgc | aac | tac | gcg | ctg | agc | 1028 |
| Asp | His | Gln | Thr | Gly | Tyr | Asn | Leu | Val | Met | Cys | Asn | Tyr | Ala | Leu | Ser |  |
|     |     |     | 295 |     |     |     |     | 300 |     |     |     |     | 305 |     |     |  |

| gac | cgc | gag | ggc | atg | aag | aac | gcc | ttc | atc | aag | ctg | ctc | aag | gtg | agc | 1076 |

-continued

```
                Asp Arg Glu Gly Met Lys Asn Ala Phe Ile Lys Leu Leu Lys Val Ser
                        310                 315                 320 cca tcc agc gag atg gat gac gat gac gac gac gac ccc atg ggc gat      1124
Pro Ser Ser Glu Met Asp Asp Asp Asp Asp Asp Asp Pro Met Gly Asp
325                 330                 335 gac gac atg caa gtg atg acc atg gat gac ggg ctg aag gac gag atg      1172
Asp Asp Met Gln Val Met Thr Met Asp Asp Gly Leu Lys Asp Glu Met
340                 345                 350                 355 cgc aag cgc aac acc atc atc acg cgc ctc att gtc aag gcc gcg cag      1220
Arg Lys Arg Asn Thr Ile Ile Thr Arg Leu Ile Val Lys Ala Ala Gln
                360                 365                 370 ctc atc tcc gag aag gtg gat cgc gcc aac ggc ttt gag ggc ggc ttc      1268
Leu Ile Ser Glu Lys Val Asp Arg Ala Asn Gly Phe Glu Gly Gly Phe
        375                 380                 385 atg tgg tgc tgc gag cag ctg cgc gac gcg ggc tac acc aag ctg gcc      1316
Met Trp Cys Cys Glu Gln Leu Arg Asp Ala Gly Tyr Thr Lys Leu Ala
            390                 395                 400 aac gag gtg gag ctg gcc aag gcg acc cgg ttc atg ggg caa aag cag      1364
Asn Glu Val Glu Leu Ala Lys Ala Thr Arg Phe Met Gly Gln Lys Gln
405                 410                 415 ttt gac aaa gcc gtg ggc gtg ttc aag gac ttt gag aag aag gag ccg      1412
Phe Asp Lys Ala Val Gly Val Phe Lys Asp Phe Glu Lys Lys Glu Pro
420                 425                 430                 435 cgc gtc aag gcg cgc gcc gcc acc aac ctg gcg ttc ctg tac ttc ctg      1460
Arg Val Lys Ala Arg Ala Ala Thr Asn Leu Ala Phe Leu Tyr Phe Leu
                440                 445                 450 gag ggc gag acc gac cag gcc gac aag tac agc gag atg gcg ctc aag      1508
Glu Gly Glu Thr Asp Gln Ala Asp Lys Tyr Ser Glu Met Ala Leu Lys
        455                 460                 465 agc gac cgc tac aac gca cga gcc tac gtc aac aag gga tgc gtg ctg      1556
Ser Asp Arg Tyr Asn Ala Arg Ala Tyr Val Asn Lys Gly Cys Val Leu
            470                 475                 480 gtg gag cgc ggc gat ctg gag gga gcg cga agc ctg ttc aac gag gct      1604
Val Glu Arg Gly Asp Leu Glu Gly Ala Arg Ser Leu Phe Asn Glu Ala
485                 490                 495 gcc ggc atc gac ccc tac tgc gtg gag gcc atc tac aac ctg ggc ctg      1652
Ala Gly Ile Asp Pro Tyr Cys Val Glu Ala Ile Tyr Asn Leu Gly Leu
500                 505                 510                 515 gtg agc cag cgc ctg aac gag ctg ccg tac gcg ctg gcg gcg ttc aag      1700
Val Ser Gln Arg Leu Asn Glu Leu Pro Tyr Ala Leu Ala Ala Phe Lys
                520                 525                 530 aag ctg cac aac atg gtg ccc gac aac gtg gag gtc atc cac cag atc      1748
Lys Leu His Asn Met Val Pro Asp Asn Val Glu Val Ile His Gln Ile
        535                 540                 545 gcc acc acg tac gac atg atg ggc gac ttc aag aac gcg gtc aag tgg      1796
Ala Thr Thr Tyr Asp Met Met Gly Asp Phe Lys Asn Ala Val Lys Trp
            550                 555                 560 ttt gag ctg ctc acc tcg ctg gtc agc aac gac ccc ggc gtg ctg gcg      1844
Phe Glu Leu Leu Thr Ser Leu Val Ser Asn Asp Pro Gly Val Leu Ala
565                 570                 575 cga ctg gga gcc atc cac gcc agg ttc gac gac gag gcc aag gcg ctg      1892
Arg Leu Gly Ala Ile His Ala Arg Phe Asp Asp Glu Ala Lys Ala Leu
580                 585                 590                 595 cac tac tac cag gag tcg cac cgc gtg tac ccg gtg aac atg gac gtc      1940
His Tyr Tyr Gln Glu Ser His Arg Val Tyr Pro Val Asn Met Asp Val
                600                 605                 610 atc tcc tgg ctg ggc gcc tac cat gtc aaa tcg gag gtg tac gag aag      1988
Ile Ser Trp Leu Gly Ala Tyr His Val Lys Ser Glu Val Tyr Glu Lys
        615                 620                 625 gcc atg ccc ttc ttt gac ctg gcc tcc aag atc cag ccg cag gag gtc      2036
```

```
         Ala Met Pro Phe Phe Asp Leu Ala Ser Lys Ile Gln Pro Gln Glu Val
                 630                 635                 640 aag tgg gcg ctc atg gtg gcg tcc tgc tac cgc cgc acc aac aac ctg         2084
Lys Trp Ala Leu Met Val Ala Ser Cys Tyr Arg Arg Thr Asn Asn Leu
        645                 650                 655 ccc gcc gcg ctg ggc aag tac aag caa atc cac acg cag cac ccc gac         2132
Pro Ala Ala Leu Gly Lys Tyr Lys Gln Ile His Thr Gln His Pro Asp
660                 665                 670                 675 aac gtt gag tgc ctg cgc tac ctg gtg cac ctg tgc tcc gag ctg ggc         2180
Asn Val Glu Cys Leu Arg Tyr Leu Val His Leu Cys Ser Glu Leu Gly
                680                 685                 690 cgc cgc gcc gag gcc gcc gag tac atg acc aag ctc aaa aag gcg gag         2228
Arg Arg Ala Glu Ala Ala Glu Tyr Met Thr Lys Leu Lys Lys Ala Glu
            695                 700                 705 aag gcg gcg gtg ccc gag gca acg aca gcg gcg gcg ccc gcc gcg gcc         2276
Lys Ala Ala Val Pro Glu Ala Thr Thr Ala Ala Ala Pro Ala Ala Ala
        710                 715                 720 gca gct ggc agt ggc atg ggt ggc atg ggc ggc ctg gac gac gac att         2324
Ala Ala Gly Ser Gly Met Gly Gly Met Gly Gly Leu Asp Asp Asp Ile
    725                 730                 735 ggc agc agc gcg gtg tcg gcg cag aac cgc ggc aag aag atg ctg gtc         2372
Gly Ser Ser Ala Val Ser Ala Gln Asn Arg Gly Lys Lys Met Leu Val
740                 745                 750                 755 aaa gag cac atg ggt ggc ggc ggt ggc aag gac aac gac gac tgg gga         2420
Lys Glu His Met Gly Gly Gly Gly Lys Asp Asn Asp Asp Trp Gly
                760                 765                 770 aac gag cag ctt ggg gac gac ctg ctg ccc atg taaaccgcag tgctgccaca      2473
Asn Glu Gln Leu Gly Asp Asp Leu Leu Pro Met
            775                 780 gggcttggcg ggggcggggc gtcagcgcag ccagtggggc taccgccgcg gcctggcgga      2533
ggtggcggcg gcgcagctgg cggagccatg cgcgcccagg ccaggggct gtggggaggt       2593 gatggcgagg gcgaggacga cgaccaccta aaagcgctgg gctgggggt ggggttggtg       2653 ggcggccgca gcggggcgc gctgtctgcc ggcacggggc gcgtgaaggc cgatgtcagc      2713
cgcgccgcct ctcacccgga gttcggggcc gagcctgcgt ttggaaaggt gctgagcttt     2773
ggctcggctg ggacgtccag cgcactgcct gagctggcgt aaagccatta ccgctgatgc    2833
agcccgccat tcgtgtgtgt gcgtatatgt gtgtgaatgt atgtgtgtgc taggtaagca    2893
cgagatgcgt gtgcgtttgc tggttcgcgc tgcgccactt ttggctgcag gggtccccag    2953
gtcagtgtga agcccggccc gggcggaaat gggtgcatgg cagttgcggc gcatgcatgc    3013
ggaagtgagc gaagtgcaat aggctcctgc agggcatgga tgcgtaggaa cagggcttga    3073
atgatatcac tatgtggcgt tgacgggccc acaacttaca tgggagaggc acgccgaaag    3133
ggtgtgtgag gatcaggagc ttggacttgc cgtagtgctg tacatggtgc cagtctacgt    3193
gcgggcatag acacatacag gacctgtgct gctgcggagt ccgcatctgc aggaagtcgt    3253
gccgggtgtc acgagtgcgg acgatgcgga ttgtggagga gtacagatgg ggccatcgga    3313
catactggca cagtggcacc accggccccc tgcgacgcat gctcgcacga ccctgtaaag    3373
gtcgagccca aaaaa                                                      3388

<210> SEQ ID NO 16
<211> LENGTH: 782
<212> TYPE: PRT
<213> ORGANISM: Chlamydomonas reinhardtii

<400> SEQUENCE: 16

Met Ser Tyr Gly Gly Thr Glu Glu Asp Asp Leu Tyr Gly Gly Tyr Asp
```

```
                1               5              10              15
      Glu Gln Ser Asn Pro Leu Ala Gly Ser Gly Gly Ala Ala Phe Lys Ala
                        20                  25                  30

Leu Gly Ala Asp Gly Ala Pro Pro Gly Thr Ala Met Met Gly Pro Pro
                    35                  40                  45

Gly Thr Ala Met Lys Ser Phe Val Pro Gly Thr Ala Met Arg Gly Gly
               50                  55                  60

Thr Ala Met Gln Gln Asp Pro Ser Leu Ala Arg Pro Met Thr Ser Asn
       65                  70                  75                  80

Arg Gly Ala Gly Phe Thr Ser Ala Pro Asn Lys Lys Phe Asp Pro Leu
                            85                  90                  95

Asn Arg Ser Met Gly Ser Thr Leu Gly Ser Ser Gly Gly Ala Met
                       100                 105                 110

Leu Val Ala Arg Lys Gly Asp Thr Ser Pro Glu Gln Ala Arg Gly
                   115                 120                 125

Met Glu Lys Thr Val His Glu Leu Leu Glu Lys Ser Ala Ala Asp Ala
                   130                 135                 140

Ala Lys Asn Asp Ile Asn Ser Ala Leu Glu Asn Ala Met Glu Ala Lys
      145                 150                 155                 160

Lys Asn Glu Arg Lys Leu Cys Arg Phe Arg Glu Gln Asn Asn Met Ala
                       165                 170                 175

Asp Gln Ile Asn Leu Glu Leu Met Tyr Ala Val Asp Phe Asn Leu Ala
                   180                 185                 190

His Met Tyr His Met Asn Lys Asn Tyr Ser Glu Ala Leu Asn Leu Tyr
                   195                 200                 205

Thr Ala Ile Val Arg Asn Lys Asn Phe Pro Gln Ser Gly Trp Leu Arg
                   210                 215                 220

Val Asn Met Gly Asn Ile His Phe Glu Gln Lys Lys Tyr Pro Ser Ala
      225                 230                 235                 240

Ile Lys Met Tyr Arg Met Ala Leu Asp Gln Ile Ser Ala Thr Ala Lys
                       245                 250                 255

Glu Val Arg Phe Lys Ile Met Arg Asn Ile Gly Leu Ser Phe Val Arg
                   260                 265                 270

Met Gly Gln Tyr Pro Asp Ala Leu Gln Ser Phe Ala Thr Val Met Asp
               275                 280                 285

Asn Val Pro Asp His Gln Thr Gly Tyr Asn Leu Val Met Cys Asn Tyr
               290                 295                 300

Ala Leu Ser Asp Arg Glu Gly Met Lys Asn Ala Phe Ile Lys Leu Leu
      305                 310                 315                 320

Lys Val Ser Pro Ser Ser Glu Met Asp Asp Asp Asp Asp Pro
                       325                 330                 335

Met Gly Asp Asp Asp Met Gln Val Met Thr Met Asp Asp Gly Leu Lys
               340                 345                 350

Asp Glu Met Arg Lys Arg Asn Thr Ile Ile Thr Arg Leu Ile Val Lys
                   355                 360                 365

Ala Ala Gln Leu Ile Ser Glu Lys Val Asp Arg Ala Asn Gly Phe Glu
               370                 375                 380

Gly Gly Phe Met Trp Cys Cys Glu Gln Leu Arg Asp Ala Gly Tyr Thr
      385                 390                 395                 400

Lys Leu Ala Asn Glu Val Glu Leu Ala Lys Ala Thr Arg Phe Met Gly
                       405                 410                 415

Gln Lys Gln Phe Asp Lys Ala Val Gly Val Phe Lys Asp Phe Glu Lys
                   420                 425                 430
```

-continued

```
Lys Glu Pro Arg Val Lys Ala Arg Ala Ala Thr Asn Leu Ala Phe Leu
            435                 440                 445
Tyr Phe Leu Glu Gly Glu Thr Asp Gln Ala Asp Lys Tyr Ser Glu Met
450                 455                 460
Ala Leu Lys Ser Asp Arg Tyr Asn Ala Arg Ala Tyr Val Asn Lys Gly
465                 470                 475                 480
Cys Val Leu Val Glu Arg Gly Asp Leu Glu Gly Ala Arg Ser Leu Phe
                485                 490                 495
Asn Glu Ala Ala Gly Ile Asp Pro Tyr Cys Val Glu Ala Ile Tyr Asn
            500                 505                 510
Leu Gly Leu Val Ser Gln Arg Leu Asn Glu Leu Pro Tyr Ala Leu Ala
        515                 520                 525
Ala Phe Lys Lys Leu His Asn Met Val Pro Asp Asn Val Glu Val Ile
530                 535                 540
His Gln Ile Ala Thr Thr Tyr Asp Met Met Gly Asp Phe Lys Asn Ala
545                 550                 555                 560
Val Lys Trp Phe Glu Leu Leu Thr Ser Leu Val Ser Asn Asp Pro Gly
                565                 570                 575
Val Leu Ala Arg Leu Gly Ala Ile His Ala Arg Phe Ala Asp Glu Ala
            580                 585                 590
Lys Ala Leu His Tyr Tyr Gln Glu Ser His Arg Val Tyr Pro Val Asn
        595                 600                 605
Met Asp Val Ile Ser Trp Leu Gly Ala Tyr His Val Lys Ser Glu Val
610                 615                 620
Tyr Glu Lys Ala Met Pro Phe Phe Asp Leu Ala Ser Lys Ile Gln Pro
625                 630                 635                 640
Gln Glu Val Lys Trp Ala Leu Met Val Ala Ser Cys Tyr Arg Arg Thr
                645                 650                 655
Asn Asn Leu Pro Ala Ala Leu Gly Lys Tyr Lys Gln Ile His Thr Gln
            660                 665                 670
His Pro Asp Asn Val Glu Cys Leu Arg Tyr Leu Val His Leu Cys Ser
        675                 680                 685
Glu Leu Gly Arg Arg Ala Glu Ala Ala Glu Tyr Met Thr Lys Leu Lys
690                 695                 700
Lys Ala Glu Lys Ala Ala Val Pro Glu Ala Thr Thr Ala Ala Ala Pro
705                 710                 715                 720
Ala Ala Ala Ala Ala Gly Ser Gly Met Gly Gly Met Gly Gly Leu Asp
                725                 730                 735
Asp Asp Ile Gly Ser Ser Ala Val Ser Ala Gln Asn Arg Gly Lys Lys
            740                 745                 750
Met Leu Val Lys Glu His Met Gly Gly Gly Gly Lys Asp Asn Asp
        755                 760                 765
Asp Trp Gly Asn Glu Gln Leu Gly Asp Leu Leu Pro Met
770                 775                 780
```

<210> SEQ ID NO 17
<211> LENGTH: 2036
<212> TYPE: DNA
<213> ORGANISM: Chlamydomonas reinhardtii
<220> FEATURE:
<221> NAME/KEY: CDS
<222> LOCATION: (3)...(1517)

<400> SEQUENCE: 17

```
gg cac gag ggc cac ttc cgc cgc gcg ccg cac ttt gcg tac gcc aag      47
   His Glu Gly His Phe Arg Arg Ala Pro His Phe Ala Tyr Ala Lys
    1               5                  10                  15
```

-continued

| | | |
|---|---|---|
| gag acg ctg ctc aaa atg gac gac acc aag ggc ctg atc acg ctg tac<br>Glu Thr Leu Leu Lys Met Asp Asp Thr Lys Gly Leu Ile Thr Leu Tyr<br>              20                    25                 30 | 95 |
| gtg gag gct gag aag tgg gat gac gcc ttc ctg ctg ctg cac gcg cac<br>Val Glu Ala Glu Lys Trp Asp Asp Ala Phe Leu Leu Leu His Ala His<br>         35                    40                 45 | 143 |
| ccc gag tgc cgg cag gac gtg tac ctg ccc tac gcc aag tgg ctc agc<br>Pro Glu Cys Arg Gln Asp Val Tyr Leu Pro Tyr Ala Lys Trp Leu Ser<br>        50                    55                60 | 191 |
| aac cag gac cgc ttc gat gag gcg cgg ctg gcg tac cag gag ggc ggc<br>Asn Gln Asp Arg Phe Asp Glu Ala Arg Leu Ala Tyr Gln Glu Gly Gly<br>     65                    70                75 | 239 |
| ttt ccc agc ctg gcc acc cgc atc ctg gag cag ttg tgc gcc aac gcg<br>Phe Pro Ser Leu Ala Thr Arg Ile Leu Glu Gln Leu Cys Ala Asn Ala<br>80                   85                    90                95 | 287 |
| gtg gta gag acg cgg tac gcg gac gcc gcc ttc tac tac tat cag ctg<br>Val Val Glu Thr Arg Tyr Ala Asp Ala Ala Phe Tyr Tyr Tyr Gln Leu<br>                 100               105              110 | 335 |
| gcc atg gag gcg ctc aag agc atc aag aac ccg ccc tcc aac atg gcg<br>Ala Met Glu Ala Leu Lys Ser Ile Lys Asn Pro Pro Ser Asn Met Ala<br>              115               120              125 | 383 |
| ccc tcg gac cgc tcc gcg ctg gag cgc ttc acg gag ctg tac gac cgc<br>Pro Ser Asp Arg Ser Ala Leu Glu Arg Phe Thr Glu Leu Tyr Asp Arg<br>         130                 135               140 | 431 |
| gcc gag gtg tac tac gcc tac gaa gtg gtg cac aag tcc gtg cac tcg<br>Ala Glu Val Tyr Tyr Ala Tyr Glu Val Val His Lys Ser Val His Ser<br>        145                 150               155 | 479 |
| ccc ttc cgc acc acg cac ccc gac acg ctc ttc aac gcc tcg cgc ttc<br>Pro Phe Arg Thr Thr His Pro Asp Thr Leu Phe Asn Ala Ser Arg Phe<br>160                  165               170               175 | 527 |
| ctg ctc atg cgc ctg ctg ccg ccg cgc gag gtg ccg ctg ggc gtc agc<br>Leu Leu Met Arg Leu Leu Pro Pro Arg Glu Val Pro Leu Gly Val Ser<br>                 180               185              190 | 575 |
| gtg gtc aac gtg gtg tac gtg ctg gcc aag cag gct gtc gag gcg ggc<br>Val Val Asn Val Val Tyr Val Leu Ala Lys Gln Ala Val Glu Ala Gly<br>              195               200              205 | 623 |
| gcc ttc aag ctg gcg cgc ttc gcg tac aac aag ctg cag acg ctg gtg<br>Ala Phe Lys Leu Ala Arg Phe Ala Tyr Asn Lys Leu Gln Thr Leu Val<br>              210               215              220 | 671 |
| ctg ccg gcg gcc tgg cag gcg gag gtg gac ctg gca tcc gtg gtc atc<br>Leu Pro Ala Ala Trp Gln Ala Glu Val Asp Leu Ala Ser Val Val Ile<br>225                  230               235 | 719 |
| cgc tcc aag cct ttc tca gac aag gag gac ctg cta ccg gtg tgc tgg<br>Arg Ser Lys Pro Phe Ser Asp Lys Glu Asp Leu Leu Pro Val Cys Trp<br>240                  245               250               255 | 767 |
| cgc tgc tcc acc acc aac ccg ctc ctc aac acg cag ggc gac tac tgc<br>Arg Cys Ser Thr Thr Asn Pro Leu Leu Asn Thr Gln Gly Asp Tyr Cys<br>              260               265              270 | 815 |
| atc aac tgc ggc gcg ccc ttc atc cgc tcc ttc gtc acc ttc gag cac<br>Ile Asn Cys Gly Ala Pro Phe Ile Arg Ser Phe Val Thr Phe Glu His<br>            275               280              285 | 863 |
| ctg ccc gtg gtg gag ttt gag ctg gag ccg ggc gtg gac gac gag gag<br>Leu Pro Val Val Glu Phe Glu Leu Glu Pro Gly Val Asp Asp Glu Glu<br>         290                 295               300 | 911 |
| gcg ggc cgc ctg ctg ggc gag gac gcg ggc atg gag gcg gcg cgg cgc<br>Ala Gly Arg Leu Leu Gly Glu Asp Ala Gly Met Glu Ala Ala Arg Arg<br>        305               310               315 | 959 |
| gag cgc aag gcg gag cgg cag gcc aag gcg gcg gag gtg ggc ggc aac<br>Glu Arg Lys Ala Glu Arg Gln Ala Lys Ala Ala Glu Val Gly Gly Asn<br>320                  325               330              335 | 1007 |

```
atg ctg cgg ctg gac cag aac gag atc gac cgc atg gac gac gcc ttc      1055
Met Leu Arg Leu Asp Gln Asn Glu Ile Asp Arg Met Asp Asp Ala Phe
                340                 345                 350 gcg gcc cag atg atg gtg ccc aac acc acc atc cgc gtg gac cgg gcc      1103
Ala Ala Gln Met Met Val Pro Asn Thr Thr Ile Arg Val Asp Arg Ala
            355                 360                 365 atg ctg cgg cgg ctc aag acg gcc gag gtc atg gtg cgc acc tgg ccc      1151
Met Leu Arg Arg Leu Lys Thr Ala Glu Val Met Val Arg Thr Trp Pro
        370                 375                 380 aac ccc gtc atc ccc aag cag tac ttc cgc agt cat gga cca gga ggt      1199
Asn Pro Val Ile Pro Lys Gln Tyr Phe Arg Ser His Gly Pro Gly Gly
    385                 390                 395 gcc gct gtg ctg cag gac cct gcg gac act tct tcg agc agg atg agt      1247
Ala Ala Val Leu Gln Asp Pro Ala Asp Thr Ser Ser Ser Arg Met Ser
400                 405                 410                 415 tcg aga tgg cgg cgc tgg agc gtg gca cgg cgc cct tca gcc gca cca      1295
Ser Arg Trp Arg Arg Trp Ser Val Ala Arg Arg Pro Ser Ala Ala Pro
                420                 425                 430 ccg tgc gcg gcg agg gcc tgg cgc cgg gcg agg acg ccg agg atg agg      1343
Pro Cys Ala Ala Arg Ala Trp Arg Arg Ala Arg Thr Pro Arg Met Arg
            435                 440                 445 gtg ccg gcg gca aca agc tgg gcg ggc cgt tgg gca gcg cgc gtg ggc      1391
Val Pro Ala Ala Thr Ser Trp Ala Gly Arg Trp Ala Ala Arg Val Gly
        450                 455                 460 cca ttg ggg gcg cca gca agg cgc gca tgt ccg tgc cct tcc agc agg      1439
Pro Leu Gly Ala Pro Ala Arg Arg Ala Cys Pro Cys Pro Ser Ser Arg
    465                 470                 475 gcc ggc cgc tgg tgt gag cgg ggt cgc cta tcg ggc gct tac cgg gtg      1487
Ala Gly Arg Trp Cys Glu Arg Gly Arg Leu Ser Gly Ala Tyr Arg Val
480                 485                 490                 495 cgt ggg tgg att ccg gat gta ggc ggg gaa taggagctgc cggtagtggc        1537
Arg Gly Trp Ile Pro Asp Val Gly Gly Glu
                500                 505 gttgcagcag gccttcgtta cgcagcagag ggggcacgag gaggacgtga acgggtgtct    1597
tcatgctgct tgtggtctga cttggtagga cgggcgttgg tgccatcatt aggctgcccc    1657
tgccggtcca ccataggagc tgcgatgggc ctgaagcaag gcccatgcac ggtggccggg    1717
cacatgatgc atgacgggac agagcacggg acttgctgga accagtgtac atatgcccgc    1777
gcagagactg cgtgtctcga agcgggcaca aattgggaca tgtcggcgta cagacaaacg    1837
atgatgatga caggatgaca gttgttgtgc ggcagggggg ctcccaagcc cagttgaggc    1897
ccaggcaggt ttggttgaat ggggatgcac agtggcagtc taatgcgct ggcgctatga     1957 gcgtccatgg tgttggcggc ctcaagtaca agacaccta tagtagttca atctgccccg    2017
caaaaaaaaa aaaaaaaaa                                                 2036
```

<210> SEQ ID NO 18
<211> LENGTH: 505
<212> TYPE: PRT
<213> ORGANISM: Chlamydomonas reinhardtii

<400> SEQUENCE: 18

```
His Glu Gly His Phe Arg Arg Ala Pro His Phe Ala Tyr Ala Lys Glu
  1               5                  10                  15

Thr Leu Leu Lys Met Asp Asp Thr Lys Gly Leu Ile Thr Leu Tyr Val
                 20                  25                  30

Glu Ala Glu Lys Trp Asp Asp Ala Phe Leu Leu Leu His Ala His Pro
             35                  40                  45
```

-continued

```
Glu Cys Arg Gln Asp Val Tyr Leu Pro Tyr Ala Lys Trp Leu Ser Asn
     50                  55                  60
Gln Asp Arg Phe Asp Glu Ala Arg Leu Ala Tyr Gln Glu Gly Gly Phe
 65                  70                  75                  80
Pro Ser Leu Ala Thr Arg Ile Leu Glu Gln Leu Cys Ala Asn Ala Val
                 85                  90                  95
Val Glu Thr Arg Tyr Ala Asp Ala Ala Phe Tyr Tyr Gln Leu Ala
                100                 105                 110
Met Glu Ala Leu Lys Ser Ile Lys Asn Pro Ser Asn Met Ala Pro
            115                 120                 125
Ser Asp Arg Ser Ala Leu Glu Arg Phe Thr Glu Leu Tyr Asp Arg Ala
    130                 135                 140
Glu Val Tyr Tyr Ala Tyr Glu Val Val His Lys Ser Val His Ser Pro
145                 150                 155                 160
Phe Arg Thr Thr His Pro Asp Thr Leu Phe Asn Ala Ser Arg Phe Leu
                165                 170                 175
Leu Met Arg Leu Leu Pro Pro Arg Glu Val Pro Leu Gly Val Ser Val
            180                 185                 190
Val Asn Val Val Tyr Val Leu Ala Lys Gln Ala Val Glu Ala Gly Ala
    195                 200                 205
Phe Lys Leu Ala Arg Phe Ala Tyr Asn Lys Leu Gln Thr Leu Val Leu
    210                 215                 220
Pro Ala Ala Trp Gln Ala Glu Val Asp Leu Ala Ser Val Val Ile Arg
225                 230                 235                 240
Ser Lys Pro Phe Ser Asp Lys Glu Asp Leu Leu Pro Val Cys Trp Arg
                245                 250                 255
Cys Ser Thr Thr Asn Pro Leu Leu Asn Thr Gln Gly Asp Tyr Cys Ile
                260                 265                 270
Asn Cys Gly Ala Pro Phe Ile Arg Ser Phe Val Thr Phe Glu His Leu
            275                 280                 285
Pro Val Val Glu Phe Glu Leu Glu Pro Gly Val Asp Asp Glu Glu Ala
    290                 295                 300
Gly Arg Leu Leu Gly Glu Asp Ala Gly Met Glu Ala Ala Arg Arg Glu
305                 310                 315                 320
Arg Lys Ala Glu Arg Gln Ala Lys Ala Ala Glu Val Gly Gly Asn Met
                325                 330                 335
Leu Arg Leu Asp Gln Asn Glu Ile Asp Arg Met Asp Asp Ala Phe Ala
            340                 345                 350
Ala Gln Met Met Val Pro Asn Thr Thr Ile Arg Val Asp Arg Ala Met
    355                 360                 365
Leu Arg Arg Leu Lys Thr Ala Glu Val Met Val Arg Thr Trp Pro Asn
370                 375                 380
Pro Val Ile Pro Lys Gln Tyr Phe Arg Ser His Gly Pro Gly Gly Ala
385                 390                 395                 400
Ala Val Leu Gln Asp Pro Ala Asp Thr Ser Ser Ser Arg Met Ser Ser
                405                 410                 415
Arg Trp Arg Arg Trp Ser Val Ala Arg Arg Pro Ser Ala Ala Pro Pro
            420                 425                 430
Cys Ala Ala Arg Ala Trp Arg Arg Ala Arg Thr Pro Arg Met Arg Val
    435                 440                 445
Pro Ala Ala Thr Ser Trp Ala Gly Arg Trp Ala Ala Arg Val Gly Pro
    450                 455                 460
Leu Gly Ala Pro Ala Arg Arg Ala Cys Pro Cys Pro Ser Ser Arg Ala
465                 470                 475                 480
```

```
Gly Arg Trp Cys Glu Arg Gly Arg Leu Ser Gly Ala Tyr Arg Val Arg
                485                 490                 495

Gly Trp Ile Pro Asp Val Gly Gly Glu
            500                 505

<210> SEQ ID NO 19
<211> LENGTH: 2602
<212> TYPE: DNA
<213> ORGANISM: Chlamydomonas reinhardtii
<220> FEATURE:
<221> NAME/KEY: CDS
<222> LOCATION: (236)...(2602)

<400> SEQUENCE: 19
gggtagtcgt aacgtctcaa gtatcggacg cactatttgc aactgcttat tttcgcatgg      60
ctcccccatc aatgaacttg cttcgtccct atggcctccc atcgagcgtg caaggtatca     120
ccgtgtatac acatgctaaa tatacttcgt taaattggag ttcaccgcgg aggcctgaac     180
atttgccgaa ccgctcctga ggaagcagaa cgaatagcag tgcatacaaa tagcc atg     238
                                                               Met
                                                                 1 gcg gac agg gta ctt gcc ctg gtc cat tac tat gct cgc gag ggc tat     286
Ala Asp Arg Val Leu Ala Leu Val His Tyr Tyr Ala Arg Glu Gly Tyr
        5                  10                  15 ttt aga cat gtg cag acg gtg tgc aac gaa gtg ctc aag aag cgg ccg     334
Phe Arg His Val Gln Thr Val Cys Asn Glu Val Leu Lys Lys Arg Pro
 20                  25                  30 gga gat ggc gta ctc aca ttc tgg cgt gcc tat gga ctg ctc atg gag     382
Gly Asp Gly Val Leu Thr Phe Trp Arg Ala Tyr Gly Leu Leu Met Glu
 35                  40                  45 ggc aac acg gcg gac gcc atg cgt gac ctc tcc agc atc cag ggc aat     430
Gly Asn Thr Ala Asp Ala Met Arg Asp Leu Ser Ser Ile Gln Gly Asn
 50                  55                  60                  65 tct gac ctt gag ctg gcg gtc gca gcc gcg caa cta ctg ggt cac gaa     478
Ser Asp Leu Glu Leu Ala Val Ala Ala Ala Gln Leu Leu Gly His Glu
             70                  75                  80 tcc gcc aag gtg ccc gac cac gat gcc atc att gac ctc caa gcc aag     526
Ser Ala Lys Val Pro Asp His Asp Ala Ile Ile Asp Leu Gln Ala Lys
             85                  90                  95 ctg gag atc gag gag cgc acc gcc agc gac cag ccc tgc ctg cac ctg     574
Leu Glu Ile Glu Glu Arg Thr Ala Ser Asp Gln Pro Cys Leu His Leu
            100                 105                 110 gcc tcc ttc tac ctg tat acc aag tcc aag gag cgc gcc cgc ggt ctg     622
Ala Ser Phe Tyr Leu Tyr Thr Lys Ser Lys Glu Arg Ala Arg Gly Leu
        115                 120                 125 gtg gag cgc gtg ctg cgc aac cag ccc gac atg gtg ccg gcg cag gtt     670
Val Glu Arg Val Leu Arg Asn Gln Pro Asp Met Val Pro Ala Gln Val
130                 135                 140                 145 ctt ctg ggc tgg atc atc atc agc cag cag cag gac gac gag tac gac     718
Leu Leu Gly Trp Ile Ile Ile Ser Gln Gln Gln Asp Asp Glu Tyr Asp
                150                 155                 160 atg ctg ttt gac gag tcc gag ctg gac gac gcc ctc agc cac ttc gag     766
Met Leu Phe Asp Glu Ser Glu Leu Asp Asp Ala Leu Ser His Phe Glu
            165                 170                 175 cag gcg gtg gag cac gac cac aac gac ctg cag gcg ctg ctg ggc aaa     814
Gln Ala Val Glu His Asp His Asn Asp Leu Gln Ala Leu Leu Gly Lys
        180                 185                 190 gcc aag atc atg gag ctg aag aag cag ctg ggg ccc tgc ctg gac gtg     862
Ala Lys Ile Met Glu Leu Lys Lys Gln Leu Gly Pro Cys Leu Asp Val
    195                 200                 205
```

-continued

| | | |
|---|---|---|
| ctg acg gag atc aac gtg cgc ttc ggc tgg ttc gtg ccg gcg ctg gtg<br>Leu Thr Glu Ile Asn Val Arg Phe Gly Trp Phe Val Pro Ala Leu Val<br>210                          215                              220                        225 | 910 |
| gaa aag acg cgc atg ctc atg atg ctg ggc gac tgg gag cag gtg acg<br>Glu Lys Thr Arg Met Leu Met Met Leu Gly Asp Trp Glu Gln Val Thr<br>                    230                          235                          240 | 958 |
| gag acg ctg cag cgg gtg ctt gcg gcg gac caa cag aac atc atg gcg<br>Glu Thr Leu Gln Arg Val Leu Ala Ala Asp Gln Gln Asn Ile Met Ala<br>                    245                          250                          255 | 1006 |
| cag gcc tgg aac tgc atg atc tcc ctc act cgc gag ggc aac aac aag<br>Gln Ala Trp Asn Cys Met Ile Ser Leu Thr Arg Glu Gly Asn Asn Lys<br>260                          265                              270 | 1054 |
| cag gcg gcc aag cag ctg cag gac ctg ttc agc tca atg aac cgc cag<br>Gln Ala Ala Lys Gln Leu Gln Asp Leu Phe Ser Ser Met Asn Arg Gln<br>              275                          280                          285 | 1102 |
| gag ccc aag aac gcc gag ctc ttc ttc cgc gtc gcc cgg ccc ttc ggc<br>Glu Pro Lys Asn Ala Glu Leu Phe Phe Arg Val Ala Arg Pro Phe Gly<br>290                          295                              300                        305 | 1150 |
| cgc ctg gcc tgc agc gac ccc acg ctg ctg ggc atc acc tac ctc atg<br>Arg Leu Ala Cys Ser Asp Pro Thr Leu Leu Gly Ile Thr Tyr Leu Met<br>                    310                          315                          320 | 1198 |
| gcc gac cgc gcc gcg cag ctc agg ccg gag atg gcg gcc tac gtg gtg<br>Ala Asp Arg Ala Ala Gln Leu Arg Pro Glu Met Ala Ala Tyr Val Val<br>              325                          330                          335 | 1246 |
| gag gca gct gct cag aag ctg atg atg gac gag acc acc aac gcc acg<br>Glu Ala Ala Ala Gln Lys Leu Met Met Asp Glu Thr Thr Asn Ala Thr<br>                    340                          345                          350 | 1294 |
| gag cgc ttc acg cag gcg cta cag ctg gac gag ctg aac ctg gag gcc<br>Glu Arg Phe Thr Gln Ala Leu Gln Leu Asp Glu Leu Asn Leu Glu Ala<br>355                          360                              365 | 1342 |
| aac gcg ggc gcg ctg gag gcg cag atc atg gcg ggc gag ctg gag gag<br>Asn Ala Gly Ala Leu Glu Ala Gln Ile Met Ala Gly Glu Leu Glu Glu<br>370                          375                              380                        385 | 1390 |
| gcg gcg ggg cag atc atg ttc ctg gag gac atg ttc acc aac gcc gcg<br>Ala Ala Gly Gln Ile Met Phe Leu Glu Asp Met Phe Thr Asn Ala Ala<br>                    390                          395                          400 | 1438 |
| gcg gct ggc ggc ggc aag cgc aag ggc cgc ggc acc ggc gac atg gac<br>Ala Ala Gly Gly Gly Lys Arg Lys Gly Arg Gly Thr Gly Asp Met Asp<br>              405                          410                          415 | 1486 |
| gac gac ccc gat atg gcc gac ccc agt ctg ggc acc tcc tcc gac aac<br>Asp Asp Pro Asp Met Ala Asp Pro Ser Leu Gly Thr Ser Ser Asp Asn<br>                    420                          425                          430 | 1534 |
| ccc acg ctg ctc tac ctc aag ggt ctg ctg gcc tgg aag cag ggc atg<br>Pro Thr Leu Leu Tyr Leu Lys Gly Leu Leu Ala Trp Lys Gln Gly Met<br>435                          440                              445 | 1582 |
| ccg tcc gag ggc ctg ggt ctg ctg gag cgc tcc att gcc gcc ctg ttc<br>Pro Ser Glu Gly Leu Gly Leu Leu Glu Arg Ser Ile Ala Ala Leu Phe<br>450                          455                              460                        465 | 1630 |
| tcc gcc gcc gcc gac ttc cac ggc ccc agc ctg gag ctg tac gcg gcg<br>Ser Ala Ala Ala Asp Phe His Gly Pro Ser Leu Glu Leu Tyr Ala Ala<br>                    470                          475                          480 | 1678 |
| ctc aac ccg gcg cgc atc acc gca atg gtg cgg ctg ctg ctg cag agc<br>Leu Asn Pro Ala Arg Ile Thr Ala Met Val Arg Leu Leu Leu Gln Ser<br>              485                          490                          495 | 1726 |
| atc ggc ggt gag ccg cgc gct ccc act gag gcg ccg tct ccg ctc atc<br>Ile Gly Gly Glu Pro Arg Ala Pro Thr Glu Ala Pro Ser Pro Leu Ile<br>                  500                          505                          510 | 1774 |
| agc aag gtc acc cgc gcg ctg gac ctg ctg aac aag cag gcg ccg gcg<br>Ser Lys Val Thr Arg Ala Leu Asp Leu Leu Asn Lys Gln Ala Pro Ala<br>515                          520                          525 | 1822 |

```
ctg cag gag agc gcg ctg ctg cac gcg cgc gcg ctg tac ctg aac ggc    1870
Leu Gln Glu Ser Ala Leu Leu His Ala Arg Ala Leu Tyr Leu Asn Gly
530                 535                 540                 545 aac ctg gac ggc gcg ctg cgc aag gcg ggc gag atc ctg cgc atg aac    1918
Asn Leu Asp Gly Ala Leu Arg Lys Ala Gly Glu Ile Leu Arg Met Asn
                550                 555                 560 ccc gag gag agc tcc gcg cac ctg ctc atc tgt tcc gtg tac gtg gcg    1966
Pro Glu Glu Ser Ser Ala His Leu Leu Ile Cys Ser Val Tyr Val Ala
            565                 570                 575 cag gac aag ccc gag ctg gcc gtc agc gcg ctg gac cag gcc gtc agc    2014
Gln Asp Lys Pro Glu Leu Ala Val Ser Ala Leu Asp Gln Ala Val Ser
        580                 585                 590 agc aac ttc gcg atc cgc gag acg cct ctg tac cac gtg gtc cag gcc    2062
Ser Asn Phe Ala Ile Arg Glu Thr Pro Leu Tyr His Val Val Gln Ala
    595                 600                 605 aag gtg ctg gtg gcc aac aac aag ctg gac gac gcc aag cgc gtc ctg    2110
Lys Val Leu Val Ala Asn Asn Lys Leu Asp Asp Ala Lys Arg Val Leu
610                 615                 620                 625 gag tcc gcc atg aac ctg ccg ggc gtg cgc aca gcg ctc acc gtg cag    2158
Glu Ser Ala Met Asn Leu Pro Gly Val Arg Thr Ala Leu Thr Val Gln
                630                 635                 640 cag cgc gcg cga cta ggg cgc aag gtg gtc gag ccc acg ctg cac gag    2206
Gln Arg Ala Arg Leu Gly Arg Lys Val Val Glu Pro Thr Leu His Glu
            645                 650                 655 cgc gcc acc gtg tac ctg ctg ctg gcg gac gtg ctg gcg agg cag tcc    2254
Arg Ala Thr Val Tyr Leu Leu Leu Ala Asp Val Leu Ala Arg Gln Ser
        660                 665                 670 aag ata ccg gac gca cca gag gcc aag aag tac atc caa gac gcc atc    2302
Lys Ile Pro Asp Ala Pro Glu Ala Lys Lys Tyr Ile Gln Asp Ala Ile
    675                 680                 685 cgc gag ttc gag ggc acc agc gag gag gtg cgc gtc acg gtg gcg gac    2350
Arg Glu Phe Glu Gly Thr Ser Glu Glu Val Arg Val Thr Val Ala Asp
690                 695                 700                 705 tgc gag ctg gcc att gcg cgc ggc gac gtg gag ggc gcg ctc aag aag    2398
Cys Glu Leu Ala Ile Ala Arg Gly Asp Val Glu Gly Ala Leu Lys Lys
                710                 715                 720 ctg cgg cgc atc ccc aag gag tct ccg cac tac gtg aag gcg cgc atg    2446
Leu Arg Arg Ile Pro Lys Glu Ser Pro His Tyr Val Lys Ala Arg Met
            725                 730                 735 gcc atg gcc gac atc tac ctg cgc cac cgc aag gac aag gcc gcc tac    2494
Ala Met Ala Asp Ile Tyr Leu Arg His Arg Lys Asp Lys Ala Ala Tyr
        740                 745                 750 atc aag tgc tac atg gac ctg gtg gac cac acg ccc gac tac gac agc    2542
Ile Lys Cys Tyr Met Asp Leu Val Asp His Thr Pro Asp Tyr Asp Ser
    755                 760                 765 tac tgc atg ctg ggc gag gcg ttc atg cag atc cag gag ccg gag aag    2590
Tyr Cys Met Leu Gly Glu Ala Phe Met Gln Ile Gln Glu Pro Glu Lys
770                 775                 780                 785 gca gtg cgc gct                                                    2602
Ala Val Arg Ala <210> SEQ ID NO 20
<211> LENGTH: 789
<212> TYPE: PRT
<213> ORGANISM: Chlamydomonas reinhardtii

<400> SEQUENCE: 20

Met Ala Asp Arg Val Leu Ala Leu Val His Tyr Tyr Ala Arg Glu Gly
 1               5                  10                  15

Tyr Phe Arg His Val Gln Thr Val Cys Asn Glu Val Leu Lys Lys Arg
            20                  25                  30
```

-continued

Pro Gly Asp Gly Val Leu Thr Phe Trp Arg Ala Tyr Gly Leu Leu Met
         35                  40                  45

Glu Gly Asn Thr Ala Asp Ala Met Arg Asp Leu Ser Ser Ile Gln Gly
     50                  55                  60

Asn Ser Asp Leu Glu Leu Ala Val Ala Ala Gln Leu Leu Gly His
 65                  70                  75                  80

Glu Ser Ala Lys Val Pro Asp His Asp Ala Ile Ile Asp Leu Gln Ala
                 85                  90                  95

Lys Leu Glu Ile Glu Glu Arg Thr Ala Ser Asp Gln Pro Cys Leu His
             100                 105                 110

Leu Ala Ser Phe Tyr Leu Tyr Thr Lys Ser Lys Glu Arg Ala Arg Gly
         115                 120                 125

Leu Val Glu Arg Val Leu Arg Asn Gln Pro Asp Met Val Pro Ala Gln
     130                 135                 140

Val Leu Leu Gly Trp Ile Ile Ser Gln Gln Asp Asp Glu Tyr
145                 150                 155                 160

Asp Met Leu Phe Asp Glu Ser Glu Leu Asp Asp Ala Leu Ser His Phe
                 165                 170                 175

Glu Gln Ala Val Glu His Asp His Asn Asp Leu Gln Ala Leu Leu Gly
             180                 185                 190

Lys Ala Lys Ile Met Glu Leu Lys Lys Gln Leu Gly Pro Cys Leu Asp
         195                 200                 205

Val Leu Thr Glu Ile Asn Val Arg Phe Gly Trp Phe Val Pro Ala Leu
     210                 215                 220

Val Glu Lys Thr Arg Met Leu Met Met Leu Gly Asp Trp Glu Gln Val
225                 230                 235                 240

Thr Glu Thr Leu Gln Arg Val Leu Ala Ala Asp Gln Gln Asn Ile Met
                 245                 250                 255

Ala Gln Ala Trp Asn Cys Met Ile Ser Leu Thr Arg Glu Gly Asn Asn
             260                 265                 270

Lys Gln Ala Ala Lys Gln Leu Gln Asp Leu Phe Ser Ser Met Asn Arg
         275                 280                 285

Gln Glu Pro Lys Asn Ala Glu Leu Phe Phe Arg Val Ala Arg Pro Phe
     290                 295                 300

Gly Arg Leu Ala Cys Ser Asp Pro Thr Leu Leu Gly Ile Thr Tyr Leu
305                 310                 315                 320

Met Ala Asp Arg Ala Ala Gln Leu Arg Pro Glu Met Ala Ala Tyr Val
                 325                 330                 335

Val Glu Ala Ala Ala Gln Lys Leu Met Met Asp Glu Thr Thr Asn Ala
             340                 345                 350

Thr Glu Arg Phe Thr Gln Ala Leu Gln Leu Asp Glu Leu Asn Leu Glu
         355                 360                 365

Ala Asn Ala Gly Ala Leu Glu Ala Gln Ile Met Ala Gly Glu Leu Glu
     370                 375                 380

Glu Ala Ala Gly Gln Ile Met Phe Leu Glu Asp Met Phe Thr Asn Ala
385                 390                 395                 400

Ala Ala Ala Gly Gly Gly Lys Arg Lys Gly Arg Gly Thr Gly Asp Met
                 405                 410                 415

Asp Asp Asp Pro Asp Met Ala Pro Ser Leu Gly Thr Ser Ser Asp
             420                 425                 430

Asn Pro Thr Leu Leu Tyr Leu Lys Gly Leu Leu Ala Trp Lys Gln Gly
         435                 440                 445

Met Pro Ser Glu Gly Leu Gly Leu Leu Glu Arg Ser Ile Ala Ala Leu

```
          450                 455                 460
Phe Ser Ala Ala Ala Asp Phe His Gly Pro Ser Leu Glu Leu Tyr Ala
465                 470                 475                 480

Ala Leu Asn Pro Ala Arg Ile Thr Ala Met Val Arg Leu Leu Gln
                485                 490                 495

Ser Ile Gly Gly Glu Pro Arg Ala Pro Thr Glu Ala Pro Ser Pro Leu
                500                 505                 510

Ile Ser Lys Val Thr Arg Ala Leu Asp Leu Leu Asn Lys Gln Ala Pro
                515                 520                 525

Ala Leu Gln Glu Ser Ala Leu Leu His Ala Arg Ala Leu Tyr Leu Asn
                530                 535                 540

Gly Asn Leu Asp Gly Ala Leu Arg Lys Ala Gly Glu Ile Leu Arg Met
545                 550                 555                 560

Asn Pro Glu Glu Ser Ser Ala His Leu Leu Ile Cys Ser Val Tyr Val
                565                 570                 575

Ala Gln Asp Lys Pro Glu Leu Ala Val Ser Ala Leu Asp Gln Ala Val
                580                 585                 590

Ser Ser Asn Phe Ala Ile Arg Glu Thr Pro Leu Tyr His Val Val Gln
                595                 600                 605

Ala Lys Val Leu Val Ala Asn Asn Lys Leu Asp Asp Ala Lys Arg Val
                610                 615                 620

Leu Glu Ser Ala Met Asn Leu Pro Gly Val Arg Thr Ala Leu Thr Val
625                 630                 635                 640

Gln Gln Arg Ala Arg Leu Gly Arg Lys Val Val Glu Pro Thr Leu His
                645                 650                 655

Glu Arg Ala Thr Val Tyr Leu Leu Leu Ala Asp Val Leu Ala Arg Gln
                660                 665                 670

Ser Lys Ile Pro Asp Ala Pro Glu Ala Lys Lys Tyr Ile Gln Asp Ala
                675                 680                 685

Ile Arg Glu Phe Glu Gly Thr Ser Glu Glu Val Arg Val Thr Val Ala
                690                 695                 700

Asp Cys Glu Leu Ala Ile Ala Arg Gly Asp Val Glu Gly Ala Leu Lys
705                 710                 715                 720

Lys Leu Arg Arg Ile Pro Lys Glu Ser Pro His Tyr Val Lys Ala Arg
                725                 730                 735

Met Ala Met Ala Asp Ile Tyr Leu Arg His Arg Lys Asp Lys Ala Ala
                740                 745                 750

Tyr Ile Lys Cys Tyr Met Asp Leu Val Asp His Thr Pro Asp Tyr Asp
                755                 760                 765

Ser Tyr Cys Met Leu Gly Glu Ala Phe Met Gln Ile Gln Glu Pro Glu
770                 775                 780

Lys Ala Val Arg Ala
785
```

<210> SEQ ID NO 21
<211> LENGTH: 2298
<212> TYPE: DNA
<213> ORGANISM: Chlamydomonas reinhardtii
<220> FEATURE:
<221> NAME/KEY: CDS
<222> LOCATION: (1)...(2295)

<400> SEQUENCE: 21

```
atg cgt ctc aag gtc aag cag tcc agc gcg aat gtg cac agc gaa tta     48
Met Arg Leu Lys Val Lys Gln Ser Ser Ala Asn Val His Ser Glu Leu
 1               5                  10                  15
```

-continued

```
aca gca gct gtg ggc tgg aat gtc tgg aat gaa ctg ttc act tgt agc        96
Thr Ala Ala Val Gly Trp Asn Val Trp Asn Glu Leu Phe Thr Cys Ser
             20                  25                  30 gac gac cag act att cac aaa tgg aac atg ctg ggg gag cca gag cag       144
Asp Asp Gln Thr Ile His Lys Trp Asn Met Leu Gly Glu Pro Glu Gln
         35                  40                  45 aag gtc agc act ctg gac gca tac ttc acg gat atg cac tgg tac ccc       192
Lys Val Ser Thr Leu Asp Ala Tyr Phe Thr Asp Met His Trp Tyr Pro
     50                  55                  60 gtg agc tcg aag aag acg caa gca ggc ggg acg gac gta ttc gcg gtg       240
Val Ser Ser Lys Lys Thr Gln Ala Gly Gly Thr Asp Val Phe Ala Val
 65                  70                  75                  80 gcg tgc aca gac ggc tct gta aaa atc ctc agc cgc acg ggc cgc gtg       288
Ala Cys Thr Asp Gly Ser Val Lys Ile Leu Ser Arg Thr Gly Arg Val
                 85                  90                  95 gag aag tcc att gag ggg cac aag ggc gcg tgc atc tcg ctg cgc tgg       336
Glu Lys Ser Ile Glu Gly His Lys Gly Ala Cys Ile Ser Leu Arg Trp
             100                 105                 110 agc tat gac ggg acg gca ctg gcg acg gcg ggc gag gac ggg tcg gta       384
Ser Tyr Asp Gly Thr Ala Leu Ala Thr Ala Gly Glu Asp Gly Ser Val
         115                 120                 125 aag atc tgg tcg cgc aac ggc atg ctg cgc tcc acg cta gcg cag gcg       432
Lys Ile Trp Ser Arg Asn Gly Met Leu Arg Ser Thr Leu Ala Gln Ala
     130                 135                 140 gac agc ccc gtg tac tcg att gtg tgg gcc tac gac tgc gac cag ctg       480
Asp Ser Pro Val Tyr Ser Ile Val Trp Ala Tyr Asp Cys Asp Gln Leu
145                 150                 155                 160 tgc tac tgc acc ggc tcc aac gtg gtc atc aag tcg ctg tcc tcc aac       528
Cys Tyr Cys Thr Gly Ser Asn Val Val Ile Lys Ser Leu Ser Ser Asn
                 165                 170                 175 gcc aag cag aac gcg tgg aag gcg cac gac ggc gtg gtg ctc aag gtg       576
Ala Lys Gln Asn Ala Trp Lys Ala His Asp Gly Val Val Leu Lys Val
             180                 185                 190 gac tgg agc ccc atc aac cac ctc atc atc aca ggc ggc gag gac tgc       624
Asp Trp Ser Pro Ile Asn His Leu Ile Ile Thr Gly Gly Glu Asp Cys
         195                 200                 205 aag tac aag gtg tgg gac agc ttt ggg cgg ctg ctg ttc cag agc ggg       672
Lys Tyr Lys Val Trp Asp Ser Phe Gly Arg Leu Leu Phe Gln Ser Gly
     210                 215                 220 ctg ttc gac tac ccg gtc acg tcg gtg gcg tgg gcg ccc agc ggc gag       720
Leu Phe Asp Tyr Pro Val Thr Ser Val Ala Trp Ala Pro Ser Gly Glu
225                 230                 235                 240 ctg ttc gcg gtg ggc ggc ttc aac acg ctg cag ctg tgt gac cgc atg       768
Leu Phe Ala Val Gly Gly Phe Asn Thr Leu Gln Leu Cys Asp Arg Met
                 245                 250                 255 ggc tgg gcc tac tcc aag atc cac ctc aac gac acg ggc agc atc atg       816
Gly Trp Ala Tyr Ser Lys Ile His Leu Asn Asp Thr Gly Ser Ile Met
             260                 265                 270 act ctg agc tgg acg gcg gac agc acg cag ctg gcg ggc ggc ggc ggc       864
Thr Leu Ser Trp Thr Ala Asp Ser Thr Gln Leu Ala Gly Gly Gly Gly
         275                 280                 285 agc ggc ggc gtg gtg ttc ggc cag gtg gtg gac ctg gcg ctg gag gac       912
Ser Gly Gly Val Val Phe Gly Gln Val Val Asp Leu Ala Leu Glu Asp
     290                 295                 300 ggc aag atg cag gtg acg gtg gtg gac gac atg cgc att gtg gtg aac       960
Gly Lys Met Gln Val Thr Val Val Asp Asp Met Arg Ile Val Val Asn
305                 310                 315                 320 gac atc ttg aac gag aac gcg gac gag ctg ccc gag ttc cgt gac cgc      1008
Asp Ile Leu Asn Glu Asn Ala Asp Glu Leu Pro Glu Phe Arg Asp Arg
                 325                 330                 335
```

```
gtc atc aag gtg tcg cta ggg tac ggc tac ctg atc gtg gcc acc gcg    1056
Val Ile Lys Val Ser Leu Gly Tyr Gly Tyr Leu Ile Val Ala Thr Ala
        340                 345                 350 acg cag tgc cac gtg tac aac acc acc aac ctg ggc acg ccg cac atc    1104
Thr Gln Cys His Val Tyr Asn Thr Thr Asn Leu Gly Thr Pro His Ile
        355                 360                 365 ttt gac ctc aaa gac acg gtc acc ctg ctg ctg cag gct gag cgg cac    1152
Phe Asp Leu Lys Asp Thr Val Thr Leu Leu Leu Gln Ala Glu Arg His
        370                 375                 380 ttc ctg ctg ctg gac aac tcg gcg ggc atc cag atc tac acc tac gag    1200
Phe Leu Leu Leu Asp Asn Ser Ala Gly Ile Gln Ile Tyr Thr Tyr Glu
385                 390                 395                 400 ggc cgc cag atc tgc aac ccg cgc ttc cag ggc ctg cgc acc gag ctg    1248
Gly Arg Gln Ile Cys Asn Pro Arg Phe Gln Gly Leu Arg Thr Glu Leu
                405                 410                 415 ctg aac gcg cag atg atc acg ctg tcc aac gac acg ata gcg gtg ctg    1296
Leu Asn Ala Gln Met Ile Thr Leu Ser Asn Asp Thr Ile Ala Val Leu
        420                 425                 430 gac cag cag gcc agc ggc acc acc gtg cgc ttc ttc gac acg gcg cag    1344
Asp Gln Gln Ala Ser Gly Thr Thr Val Arg Phe Phe Asp Thr Ala Gln
        435                 440                 445 ggc cgg cca gtg ggc gag ccg tgg cag cac acg ttg gag gtg aag gag    1392
Gly Arg Pro Val Gly Glu Pro Trp Gln His Thr Leu Glu Val Lys Glu
        450                 455                 460 atc gcg ctg agc cag gcc ggc acc atc aac gac cgc cag ctc atc gtc    1440
Ile Ala Leu Ser Gln Ala Gly Thr Ile Asn Asp Arg Gln Leu Ile Val
465                 470                 475                 480 atc gac cgc aac cgc gac ctg tac ctg ctg ccc gtc atg aag cgc cac    1488
Ile Asp Arg Asn Arg Asp Leu Tyr Leu Leu Pro Val Met Lys Arg His
                485                 490                 495 gtg gcc aag ctg gcg gcc atg tgc gac tcg gcg cgc tgg cac gac agc    1536
Val Ala Lys Leu Ala Ala Met Cys Asp Ser Ala Arg Trp His Asp Ser
        500                 505                 510 acc gcc atg ctg tcc gcc atg gtg gac cag cgc ctg tgt gtg tgg tac    1584
Thr Ala Met Leu Ser Ala Met Val Asp Gln Arg Leu Cys Val Trp Tyr
        515                 520                 525 tac ccc agc gag gtg tac gtg gac aag gac ctg ctg gcc aag acg cgc    1632
Tyr Pro Ser Glu Val Tyr Val Asp Lys Asp Leu Leu Ala Lys Thr Arg
        530                 535                 540 tac acc aag tcc gac tcg gac ttt ggc aag tcg gcc cag atc cag ctc    1680
Tyr Thr Lys Ser Asp Ser Asp Phe Gly Lys Ser Ala Gln Ile Gln Leu
545                 550                 555                 560 ttc gcc ggc aac cgc tgc ctg gtg cgc cgc tcc gac ggc gtg ctg gtc    1728
Phe Ala Gly Asn Arg Cys Leu Val Arg Arg Ser Asp Gly Val Leu Val
                565                 570                 575 tcc gcc gcc acc tcg ccc tac cct gcc gta ctg tac gac atg atc cgc    1776
Ser Ala Ala Thr Ser Pro Tyr Pro Ala Val Leu Tyr Asp Met Ile Arg
        580                 585                 590 aag cag cag tgg gac aag gcc acg cgg ctg tgt cgc ttc atc aag gac    1824
Lys Gln Gln Trp Asp Lys Ala Thr Arg Leu Cys Arg Phe Ile Lys Asp
        595                 600                 605 ccc acc atg tgg gcc acg ctg gcg gcc atg gcc atg gcg gct aag gag    1872
Pro Thr Met Trp Ala Thr Leu Ala Ala Met Ala Met Ala Ala Lys Glu
        610                 615                 620 ctg aac acg gcg gag gtg gcg ttc gcg gcg att gac gag gtg gac aaa    1920
Leu Asn Thr Ala Glu Val Ala Phe Ala Ala Ile Asp Glu Val Asp Lys
625                 630                 635                 640 acg cac ttt gtg cgc aag gtg aag cag atc ccc acg gag gag ggc cgc    1968
Thr His Phe Val Arg Lys Val Lys Gln Ile Pro Thr Glu Glu Gly Arg
                645                 650                 655
```

```
aac gcc gag ctg gcg gtg tac cgg cgc aag ccc gag gag ggc gag tcc      2016
Asn Ala Glu Leu Ala Val Tyr Arg Arg Lys Pro Glu Glu Gly Glu Ser
            660                 665                 670 ata ctg ctg cag gcc ggc ctg gtc ttc cgc gcc atc aag ctg aac atc      2064
Ile Leu Leu Gln Ala Gly Leu Val Phe Arg Ala Ile Lys Leu Asn Ile
    675                 680                 685 aag ctg ttc aac tgg gag cgc gcg ctg sac ctg gcc acg cag cac aag      2112
Lys Leu Phe Asn Trp Glu Arg Ala Leu Xaa Leu Ala Thr Gln His Lys
690                 695                 700 cag cac cag gac acg gtg ctg tgg tac cgc cag cag ttc ctc aag aac      2160
Gln His Gln Asp Thr Val Leu Trp Tyr Arg Gln Gln Phe Leu Lys Asn
705                 710                 715                 720 gcc aag ctc gcc gag tcc atc acg cgc ttc atg cag atg aac gag tcg      2208
Ala Lys Leu Ala Glu Ser Ile Thr Arg Phe Met Gln Met Asn Glu Ser
            725                 730                 735 gtg gtt gtg gac cag gcg gcg gtg aag aag aag atc gag gag gag cgc      2256
Val Val Val Asp Gln Ala Ala Val Lys Lys Lys Ile Glu Glu Glu Arg
        740                 745                 750 atc aag gag tcg cag cgg cca ggc gcc aag cgc tac gtg taa              2298
Ile Lys Glu Ser Gln Arg Pro Gly Ala Lys Arg Tyr Val
        755                 760                 765

<210> SEQ ID NO 22
<211> LENGTH: 765
<212> TYPE: PRT
<213> ORGANISM: Chlamydomonas reinhardtii
<220> FEATURE:
<221> NAME/KEY: VARIANT
<222> LOCATION: (1)...(765)
<223> OTHER INFORMATION: Xaa = any amino acid

<400> SEQUENCE: 22

Met Arg Leu Lys Val Lys Gln Ser Ser Ala Asn Val His Ser Glu Leu
 1               5                  10                  15

Thr Ala Ala Val Gly Trp Asn Val Trp Asn Glu Leu Phe Thr Cys Ser
            20                  25                  30

Asp Asp Gln Thr Ile His Lys Trp Asn Met Leu Gly Glu Pro Glu Gln
        35                  40                  45

Lys Val Ser Thr Leu Asp Ala Tyr Phe Thr Asp Met His Trp Tyr Pro
    50                  55                  60

Val Ser Ser Lys Lys Thr Gln Ala Gly Gly Thr Asp Val Phe Ala Val
65                  70                  75                  80

Ala Cys Thr Asp Gly Ser Val Lys Ile Leu Ser Arg Thr Gly Arg Val
                85                  90                  95

Glu Lys Ser Ile Glu Gly His Lys Gly Ala Cys Ile Ser Leu Arg Trp
            100                 105                 110

Ser Tyr Asp Gly Thr Ala Leu Ala Thr Ala Gly Glu Asp Gly Ser Val
        115                 120                 125

Lys Ile Trp Ser Arg Asn Gly Met Leu Arg Ser Thr Leu Ala Gln Ala
    130                 135                 140

Asp Ser Pro Val Tyr Ser Ile Val Trp Ala Tyr Asp Cys Asp Gln Leu
145                 150                 155                 160

Cys Tyr Cys Thr Gly Ser Asn Val Val Ile Lys Ser Leu Ser Ser Asn
                165                 170                 175

Ala Lys Gln Asn Ala Trp Lys Ala His Asp Gly Val Val Leu Lys Val
            180                 185                 190

Asp Trp Ser Pro Ile Asn His Leu Ile Ile Thr Gly Gly Glu Asp Cys
        195                 200                 205

Lys Tyr Lys Val Trp Asp Ser Phe Gly Arg Leu Leu Phe Gln Ser Gly
```

```
              210                 215                 220
Leu Phe Asp Tyr Pro Val Thr Ser Val Ala Trp Ala Pro Ser Gly Glu
225                 230                 235                 240

Leu Phe Ala Val Gly Gly Phe Asn Thr Leu Gln Leu Cys Asp Arg Met
                245                 250                 255

Gly Trp Ala Tyr Ser Lys Ile His Leu Asn Asp Thr Gly Ser Ile Met
                260                 265                 270

Thr Leu Ser Trp Thr Ala Asp Ser Thr Gln Leu Ala Gly Gly Gly
            275                 280                 285

Ser Gly Gly Val Val Phe Gly Gln Val Val Asp Leu Ala Leu Glu Asp
        290                 295                 300

Gly Lys Met Gln Val Thr Val Val Asp Asp Met Arg Ile Val Val Asn
305                 310                 315                 320

Asp Ile Leu Asn Glu Asn Ala Asp Glu Leu Pro Glu Phe Arg Asp Arg
                325                 330                 335

Val Ile Lys Val Ser Leu Gly Tyr Gly Tyr Leu Ile Val Ala Thr Ala
                340                 345                 350

Thr Gln Cys His Val Tyr Asn Thr Thr Asn Leu Gly Thr Pro His Ile
            355                 360                 365

Phe Asp Leu Lys Asp Thr Val Thr Leu Leu Gln Ala Glu Arg His
    370                 375                 380

Phe Leu Leu Leu Asp Asn Ser Ala Gly Ile Gln Ile Tyr Thr Tyr Glu
385                 390                 395                 400

Gly Arg Gln Ile Cys Asn Pro Arg Phe Gln Gly Leu Arg Thr Glu Leu
                405                 410                 415

Leu Asn Ala Gln Met Ile Thr Leu Ser Asn Asp Thr Ile Ala Val Leu
                420                 425                 430

Asp Gln Gln Ala Ser Gly Thr Thr Val Arg Phe Phe Asp Thr Ala Gln
            435                 440                 445

Gly Arg Pro Val Gly Glu Pro Trp Gln His Thr Leu Glu Val Lys Glu
        450                 455                 460

Ile Ala Leu Ser Gln Ala Gly Thr Ile Asn Asp Arg Gln Leu Ile Val
465                 470                 475                 480

Ile Asp Arg Asn Arg Asp Leu Tyr Leu Leu Pro Val Met Lys Arg His
                485                 490                 495

Val Ala Lys Leu Ala Ala Met Cys Asp Ser Ala Arg Trp His Asp Ser
                500                 505                 510

Thr Ala Met Leu Ser Ala Met Val Asp Gln Arg Leu Cys Val Trp Tyr
            515                 520                 525

Tyr Pro Ser Glu Val Tyr Val Asp Lys Asp Leu Leu Ala Lys Thr Arg
        530                 535                 540

Tyr Thr Lys Ser Asp Ser Asp Phe Gly Lys Ser Ala Gln Ile Gln Leu
545                 550                 555                 560

Phe Ala Gly Asn Arg Cys Leu Val Arg Arg Ser Asp Gly Val Leu Val
                565                 570                 575

Ser Ala Ala Thr Ser Pro Tyr Pro Ala Val Leu Tyr Asp Met Ile Arg
                580                 585                 590

Lys Gln Gln Trp Asp Lys Ala Thr Arg Leu Cys Arg Phe Ile Lys Asp
            595                 600                 605

Pro Thr Met Trp Ala Thr Leu Ala Ala Met Ala Met Ala Ala Lys Glu
        610                 615                 620

Leu Asn Thr Ala Glu Val Ala Phe Ala Ala Ile Asp Glu Val Asp Lys
625                 630                 635                 640
```

```
Thr His Phe Val Arg Lys Val Lys Gln Ile Pro Thr Glu Glu Gly Arg
                645                 650                 655

Asn Ala Glu Leu Ala Val Tyr Arg Arg Lys Pro Glu Gly Glu Gly Ser
            660                 665                 670

Ile Leu Leu Gln Ala Gly Leu Val Phe Arg Ala Ile Lys Leu Asn Ile
        675                 680                 685

Lys Leu Phe Asn Trp Glu Arg Ala Leu Xaa Leu Ala Thr Gln His Lys
690                 695                 700

Gln His Gln Asp Thr Val Leu Trp Tyr Arg Gln Phe Leu Lys Asn
705                 710                 715                 720

Ala Lys Leu Ala Glu Ser Ile Thr Arg Phe Met Gln Met Asn Glu Ser
                725                 730                 735

Val Val Val Asp Gln Ala Ala Val Lys Lys Ile Glu Glu Arg
            740                 745                 750

Ile Lys Glu Ser Gln Arg Pro Gly Ala Lys Arg Tyr Val
        755                 760                 765

<210> SEQ ID NO 23
<211> LENGTH: 132
<212> TYPE: PRT
<213> ORGANISM: Homo sapiens

<400> SEQUENCE: 23

Met Ala Lys Asp Ile Leu Gly Glu Ala Gly Leu His Phe Asp Glu Leu
1               5                   10                  15

Asn Lys Leu Arg Val Leu Asp Pro Glu Val Thr Gln Gln Thr Ile Glu
            20                  25                  30

Leu Lys Glu Glu Cys Lys Asp Phe Val Asp Lys Ile Gly Gln Phe Gln
        35                  40                  45

Lys Ile Val Gly Gly Leu Ile Glu Leu Val Asp Gln Leu Ala Lys Glu
    50                  55                  60

Ala Glu Asn Glu Lys Met Lys Ala Ile Gly Ala Arg Asn Leu Leu Lys
65                  70                  75                  80

Ser Ile Ala Lys Gln Arg Glu Ala Gln Gln Gln Leu Gln Ala Leu
                85                  90                  95

Ile Ala Glu Lys Lys Met Gln Leu Glu Arg Tyr Arg Val Glu Tyr Glu
            100                 105                 110

Ala Leu Cys Lys Val Glu Ala Glu Gln Asn Glu Phe Ile Asp Gln Phe
        115                 120                 125

Ile Phe Gln Lys
    130

<210> SEQ ID NO 24
<211> LENGTH: 109
<212> TYPE: PRT
<213> ORGANISM: Homo sapiens
<220> FEATURE:
<221> NAME/KEY: VARIANT
<222> LOCATION: (1)...(109)
<223> OTHER INFORMATION: Xaa = any amino acid or absent

<400> SEQUENCE: 24

Gln Asp Ser Leu Gly Glu Ala Gly Leu Cys Phe Asp Glu Leu Ser Lys
1               5                   10                  15

Val Arg Asp Pro Glu Val Thr Xaa Gln Thr Arg Asp Pro Lys Glu Asp
            20                  25                  30

Cys Met Asp Phe Val Gly Lys Ile Ser Pro Phe Gln Lys Glu Ile Val
        35                  40                  45
```

```
Gly Gly Leu Ile Glu Pro Val Asp Gln Leu Ala Lys Ala Ala Glu Asn
 50                  55                  60

Glu Lys Arg Lys Val Val Gly Ala Trp Asn Leu Leu Gln Phe Met Ala
 65                  70                  75                  80

Lys His Arg Glu Ala Gln Gln Gln Leu Leu Ala Gln Thr Ala Glu
                 85                  90                  95

Glu Lys Met Trp Leu Lys Arg Trp Trp Ile Glu Tyr Glu
            100                 105

<210> SEQ ID NO 25
<211> LENGTH: 76
<212> TYPE: PRT
<213> ORGANISM: Homo sapiens
<220> FEATURE:
<221> NAME/KEY: VARIANT
<222> LOCATION: (1)...(76)
<223> OTHER INFORMATION: Xaa = any amino acid or absent

<400> SEQUENCE: 25

Met Val Lys Asp Ile Leu Ala Glu Glu Gly Leu His Phe Asp Glu Leu
  1               5                  10                  15

Asn Lys Leu Trp Val Leu Asp Ser Glu Val Thr Gln Gln Thr Thr Glu
             20                  25                  30

Leu Lys Glu Glu Cys Lys Asn Phe Ala Asp Lys Thr Gly Gln Phe Gln
         35                  40                  45

Lys Thr Val Gly Gly Leu Ile Glu Leu Val Asp Lys Leu Ala Lys Lys
     50                  55                  60

Ala Xaa Asn Ala Lys Met Arg Ala Met Val Leu Arg
 65                  70                  75

<210> SEQ ID NO 26
<211> LENGTH: 186
<212> TYPE: PRT
<213> ORGANISM: Homo sapiens

<400> SEQUENCE: 26

Met Val Lys Leu Ala Ala Lys Cys Ile Leu Ala Gly Asp Pro Ala Val
  1               5                  10                  15

Gly Lys Thr Ala Leu Ala Gln Ile Phe Arg Ser Asp Gly Ala His Phe
             20                  25                  30

Gln Lys Ser Tyr Thr Leu Thr Thr Gly Met Asp Leu Val Val Lys Thr
         35                  40                  45

Val Pro Val Pro Asp Thr Gly Asp Ser Val Glu Leu Phe Ile Phe Asp
     50                  55                  60

Ser Ala Gly Lys Glu Leu Phe Ser Glu Met Leu Asp Lys Leu Trp Glu
 65                  70                  75                  80

Ser Pro Asn Val Leu Cys Leu Val Tyr Asp Val Thr Asn Glu Glu Ser
                 85                  90                  95

Phe Asn Asn Cys Ser Lys Trp Leu Glu Lys Ala Arg Ser Gln Ala Pro
            100                 105                 110

Gly Ile Ser Leu Pro Gly Val Leu Val Gly Asn Lys Thr Asp Leu Ala
        115                 120                 125

Gly Arg Arg Ala Val Asp Ser Ala Glu Ala Arg Ala Trp Ala Leu Gly
    130                 135                 140

Gln Gly Leu Glu Cys Phe Glu Thr Ser Val Lys Glu Met Glu Asn Phe
145                 150                 155                 160

Glu Ala Pro Phe His Cys Leu Ala Lys Gln Phe His Gln Leu Tyr Arg
                165                 170                 175
```

Glu Lys Val Glu Val Phe Arg Ala Leu Ala
            180                 185

<210> SEQ ID NO 27
<211> LENGTH: 304
<212> TYPE: PRT
<213> ORGANISM: Homo sapiens

<400> SEQUENCE: 27

Met Ala Asp Asn Ser Ser Asp Glu Cys Glu Glu Asn Asn Lys Glu
 1               5                  10                  15

Lys Lys Lys Thr Ser Gln Leu Thr Pro Gln Arg Gly Phe Ser Glu Asn
                20                  25                  30

Glu Asp Asp Asp Asp Asp Asp Ser Ser Glu Thr Asp Ser Asp
                35                  40                  45

Ser Asp Asp Asp Glu Glu His Gly Ala Pro Leu Glu Gly Ala Tyr
        50                  55                  60

Asp Pro Ala Asp Tyr Glu His Leu Pro Val Ser Ala Glu Ile Lys Glu
 65                 70                  75                  80

Leu Phe Gln Tyr Ile Ser Arg Tyr Thr Pro Gln Leu Ile Asp Leu Asp
                85                  90                  95

His Lys Leu Lys Pro Phe Ile Pro Asp Phe Ile Pro Ala Val Gly Asp
            100                 105                 110

Ile Asp Ala Phe Leu Lys Val Pro Arg Pro Asp Gly Lys Pro Asp Asn
            115                 120                 125

Leu Gly Leu Leu Val Leu Asp Glu Pro Ser Thr Lys Gln Ser Asp Pro
        130                 135                 140

Thr Val Leu Ser Leu Trp Leu Thr Glu Asn Ser Lys Gln His Asn Ile
145                 150                 155                 160

Thr Gln His Met Lys Val Lys Ser Leu Glu Asp Ala Glu Lys Asn Pro
                165                 170                 175

Lys Ala Ile Asp Thr Trp Ile Glu Ser Ile Ser Glu Leu His Arg Ser
            180                 185                 190

Lys Pro Pro Ala Thr Val His Tyr Thr Arg Pro Met Pro Asp Ile Asp
        195                 200                 205

Thr Leu Met Gln Glu Trp Ser Pro Glu Phe Glu Glu Leu Leu Gly Lys
    210                 215                 220

Val Ser Leu Pro Thr Ala Glu Ile Asp Cys Ser Leu Ala Glu Tyr Ile
225                 230                 235                 240

Asp Met Ile Cys Ala Ile Leu Asp Ile Pro Val Tyr Lys Ser Arg Ile
                245                 250                 255

Gln Ser Leu His Leu Leu Phe Ser Leu Tyr Ser Glu Phe Lys Asn Ser
            260                 265                 270

Gln His Phe Lys Ala Leu Ala Glu Gly Lys Lys Ala Phe Thr Pro Ser
        275                 280                 285

Ser Asn Ser Thr Ser Gln Ala Gly Asp Met Glu Thr Leu Thr Phe Ser
    290                 295                 300

<210> SEQ ID NO 28
<211> LENGTH: 438
<212> TYPE: PRT
<213> ORGANISM: Homo sapiens

<400> SEQUENCE: 28

Met Glu Lys Glu Leu Arg Ser Thr Ile Leu Phe Asn Ala Tyr Lys Lys
 1               5                  10                  15

Glu Ile Phe Thr Thr Asn Asn Gly Tyr Lys Ser Met Gln Lys Lys Leu

```
                    20                  25                  30
Arg Ser Asn Trp Lys Ile Gln Ser Leu Lys Asp Glu Ile Thr Ser Glu
                35                  40                  45
Lys Leu Asn Gly Val Lys Leu Trp Ile Thr Ala Gly Pro Arg Glu Lys
            50                  55                  60
Phe Thr Ala Ala Glu Phe Glu Ile Leu Lys Lys Tyr Leu Asp Thr Gly
65                  70                  75                  80
Gly Asp Val Leu Val Met Leu Gly Glu Gly Glu Ser Arg Phe Asp
                85                  90                  95
Thr Asn Ile Asn Phe Leu Leu Glu Glu Tyr Gly Ile Met Val Asn Asn
                100                 105                 110
Asp Ala Val Val Arg Asn Val Tyr His Lys Tyr Phe His Pro Lys Glu
                115                 120                 125
Ala Leu Val Ser Ser Gly Val Leu Asn Arg Glu Ile Ser Arg Ala Ala
                130                 135                 140
Gly Lys Ala Val Leu Ala Ile Ile Asp Glu Ser Ser Gly Asn Asn
145                 150                 155                 160
Ala Gln Ala Leu Thr Phe Val Tyr Pro Phe Gly Ala Thr Leu Ser Val
                165                 170                 175
Met Lys Pro Ala Val Ala Val Leu Ser Thr Gly Ser Val Cys Phe Pro
                180                 185                 190
Leu Asn Arg Pro Ile Leu Ala Phe Tyr His Ser Lys Asn Gln Gly Gly
                195                 200                 205
Lys Leu Ala Val Leu Gly Ser Cys His Met Phe Ser Asp Gln Tyr Leu
                210                 215                 220
Asp Lys Glu Glu Asn Ser Lys Ile Met Asp Val Val Phe Gln Trp
225                 230                 235                 240
Leu Thr Thr Gly Asp Ile His Leu Asn Gln Ile Asp Ala Glu Asp Pro
                245                 250                 255
Glu Ile Ser Asp Tyr Met Met Leu Pro Tyr Thr Ala Thr Leu Ser Lys
                260                 265                 270
Arg Asn Arg Glu Cys Leu Gln Glu Ser Asp Glu Ile Pro Arg Asp Phe
                275                 280                 285
Thr Thr Leu Phe Asp Leu Ser Ile Phe Gln Leu Asp Thr Thr Ser Phe
                290                 295                 300
His Ser Val Ile Glu Ala His Glu Gln Leu Asn Val Lys His Glu Pro
305                 310                 315                 320
Leu Gln Leu Ile Gln Pro Gln Phe Glu Thr Pro Leu Pro Thr Leu Gln
                325                 330                 335
Pro Ala Val Phe Pro Pro Ser Phe Arg Glu Leu Pro Pro Pro Leu
                340                 345                 350
Glu Leu Phe Asp Leu Asp Glu Thr Phe Ser Ser Glu Lys Ala Arg Leu
                355                 360                 365
Ala Gln Ile Thr Asn Lys Cys Thr Glu Glu Asp Leu Glu Phe Tyr Val
                370                 375                 380
Arg Lys Cys Gly Asp Ile Leu Gly Val Thr Ser Lys Leu Pro Lys Asp
385                 390                 395                 400
Gln Gln Asp Ala Lys His Ile Leu Glu His Val Phe Gln Val Val
                405                 410                 415
Glu Phe Lys Lys Leu Asn Gln Glu His Asp Ile Asp Thr Ser Glu Thr
                420                 425                 430
Ala Phe Gln Asn Asn Phe
                435
```

<210> SEQ ID NO 29
<211> LENGTH: 472
<212> TYPE: PRT
<213> ORGANISM: Caenorhabditis elegans

<400> SEQUENCE: 29

```
Met Pro Pro Phe Ser Asp Glu Lys Met Thr Asn Arg Ser Ile Gly Arg
 1               5                  10                  15

Lys Val Leu Ile Asp Gln Ser Lys Gln Gln Ile Ser Leu Ile Ser
             20                  25                  30

Gly Phe Arg Gly Val Ala Arg His Leu Lys Ser Val Leu Thr Val Glu
         35                  40                  45

Ile Asn Thr Glu Pro Ile Asn Leu Asn Gly Leu Glu Asp Val Arg Met
     50                  55                  60

Leu Ile Ile Pro Gln Pro Lys Thr Ser Phe Gly Thr Gly Glu Ile Glu
 65                  70                  75                  80

Ala Ile Trp Lys Phe Val Glu Glu Gly Gly Ser Leu Met Ile Leu Ser
                 85                  90                  95

Gly Glu Gly Gly Glu Arg Gln Ser Leu Asn Glu Met Ile Ala Lys Tyr
            100                 105                 110

Gly Ile Thr Val Asn Lys Asp Ser Val Ile Arg Thr Val Phe Leu Lys
        115                 120                 125

Tyr Phe Asp Pro Lys Glu Ala Leu Val Ala Asn Gly Val Ile Asn Arg
    130                 135                 140

Ala Ile Ala Val Ala Ala Lys Lys Asn Val Ser Thr Glu Gln Lys His
145                 150                 155                 160

Asn Ser Gln Ala Leu Ser Phe Ile Tyr Pro Tyr Gly Cys Thr Leu Asp
                165                 170                 175

Val Asn Asn Arg Met Ser Asn Val Val Leu Ser Ser Gly Ser Thr Ser
            180                 185                 190

Phe Pro Thr Ser Arg Pro Val Ala Ala Phe His Glu Thr Lys Leu Asn
        195                 200                 205

Glu Met Lys Lys Lys Gly Arg Val Cys Val Val Gly Ser Val Ser Met
    210                 215                 220

Phe His Asp Thr Tyr Ile Asp Lys Glu Glu Asn Gly Lys Ile Phe Asp
225                 230                 235                 240

Thr Phe Val Glu Phe Leu Val Asn Gly Leu Glu Leu Asn Thr Ile Asp
                245                 250                 255

Ala Ala Glu Pro Glu Ile Asn Asp Tyr Thr Asn Ile Pro Asp His Ile
            260                 265                 270

His Met Ser Gln Gln Ile Lys Val Cys Met Tyr Glu Gly Glu Leu Asp
        275                 280                 285

Gln Ala Ile Ser Ser Asp Phe Met Lys Ile Met Asp Thr Ser Leu His
    290                 295                 300

Ser Phe Asn Leu Lys His Trp Pro Met Thr Ile Arg Leu Tyr Glu Ala
305                 310                 315                 320

Leu Asn Leu Ser Pro Pro Leu Thr Leu Val Glu Pro Gln Phe Glu
                325                 330                 335

Leu Pro Met Pro Pro Phe Gln Pro Ala Val Phe Pro Thr Phe Gln
            340                 345                 350

Glu Leu Pro Met Pro Pro Leu Glu Leu Phe Asp Leu Asp Glu Gln Phe
        355                 360                 365

Ser Ser Pro Glu Ile Gln Leu Ser Gln Leu Ala Asn Arg Ser Glu Glu
    370                 375                 380
```

```
Glu Asp Leu Ile Phe Phe Ile Glu Lys Ala Gly Ile Thr Gly Ile
385                 390                 395                 400

Ser Ala Glu Leu Thr Arg Ser Glu Arg Thr Pro Lys Lys Ile Ile Glu
                405                 410                 415

Leu Ala Val Ser Lys Leu Met Leu Phe Lys Arg Ser Met Met Asp Gly
                420                 425                 430

Glu Leu Glu Val Ala Ser Ala Phe Asp Ile Gly Glu His Asp Ala His
            435                 440                 445

His Gln Ser Phe Asn Gln Gly Glu Met Asp Glu Gln Leu Phe Ser
        450                 455                 460

Asp Ile Asp Glu Phe Asp Asp Leu
465                 470

<210> SEQ ID NO 30
<211> LENGTH: 429
<212> TYPE: PRT
<213> ORGANISM: Homo sapiens

<400> SEQUENCE: 30

Met Thr Ala Ala Leu Ala Val Val Thr Thr Ser Gly Leu Glu Asp Gly
1               5                   10                  15

Val Pro Arg Ser Arg Gly Glu Gly Thr Gly Glu Val Val Leu Glu Arg
                20                  25                  30

Gly Pro Gly Ala Ala Tyr His Met Phe Val Val Met Glu Asp Leu Val
            35                  40                  45

Glu Lys Leu Lys Leu Leu Arg Tyr Glu Glu Glu Phe Leu Arg Lys Ser
        50                  55                  60

Asn Leu Lys Ala Pro Ser Arg His Tyr Phe Ala Leu Pro Thr Asn Pro
65                  70                  75                  80

Gly Glu Gln Phe Tyr Met Phe Cys Thr Leu Ala Ala Trp Leu Ile Asn
                85                  90                  95

Lys Ala Gly Arg Pro Phe Glu Gln Pro Gln Glu Tyr Asp Asp Pro Asn
            100                 105                 110

Ala Thr Ile Ser Asn Ile Leu Ser Glu Leu Arg Ser Phe Gly Arg Thr
        115                 120                 125

Ala Asp Phe Pro Pro Ser Lys Leu Lys Ser Gly Tyr Gly Glu His Val
130                 135                 140

Cys Tyr Val Leu Asp Cys Phe Ala Glu Glu Ala Leu Lys Tyr Ile Gly
145                 150                 155                 160

Phe Thr Trp Lys Arg Pro Ile Tyr Pro Val Glu Glu Leu Glu Glu Glu
                165                 170                 175

Ser Val Ala Glu Asp Asp Ala Glu Leu Thr Leu Asn Lys Val Asp Glu
            180                 185                 190

Glu Phe Val Glu Glu Glu Thr Asp Asn Glu Glu Asn Phe Ile Asp Leu
        195                 200                 205

Asn Val Leu Lys Ala Gln Thr Tyr His Leu Asp Met Asn Glu Thr Ala
210                 215                 220

Lys Gln Glu Asp Ile Leu Glu Ser Thr Thr Asp Ala Ala Glu Trp Ser
225                 230                 235                 240

Leu Glu Val Glu Arg Val Leu Pro Gln Leu Lys Val Thr Ile Arg Thr
                245                 250                 255

Asp Asn Lys Asp Trp Arg Ile His Val Asp Gln Met His Gln His Arg
            260                 265                 270

Ser Gly Ile Glu Ser Ala Leu Lys Glu Thr Lys Gly Phe Leu Asp Lys
        275                 280                 285
```

```
Leu His Asn Glu Ile Thr Arg Thr Leu Glu Lys Ile Ser Ser Arg Glu
        290                 295                 300

Lys Tyr Ile Asn Asn Gln Leu Glu Asn Leu Val Gln Glu Tyr Arg Ala
305                 310                 315                 320

Ala Gln Ala Gln Leu Ser Glu Ala Lys Glu Arg Tyr Gln Gln Gly Asn
                325                 330                 335

Gly Gly Val Thr Glu Arg Thr Arg Leu Leu Ser Glu Val Met Glu Glu
                340                 345                 350

Leu Glu Lys Val Lys Gln Glu Met Glu Glu Lys Gly Ser Ser Met Thr
            355                 360                 365

Asp Gly Ala Pro Leu Val Lys Ile Lys Gln Ser Leu Thr Lys Leu Lys
        370                 375                 380

Gln Glu Thr Val Glu Met Asp Ile Arg Ile Gly Ile Val Glu His Thr
385                 390                 395                 400

Leu Leu Gln Ser Lys Leu Lys Glu Lys Ser Asn Met Thr Arg Asn Met
                405                 410                 415

His Ala Thr Val Ile Pro Glu Pro Ala Thr Gly Phe Tyr
                420                 425

<210> SEQ ID NO 31
<211> LENGTH: 141
<212> TYPE: PRT
<213> ORGANISM: Homo sapiens

<400> SEQUENCE: 31

Asp Gln Arg Ile His Val Asp Gln Met Tyr Gln His Lys Ser Gly Ile
1               5                   10                  15

Glu Ser Ser Leu Lys Glu Ser Lys Arg Phe Phe Asp Lys Leu His Asn
            20                  25                  30

Glu Ile Ser Lys Thr Leu Glu Lys Ile Ser His Cys Glu Lys Tyr Ile
        35                  40                  45

Asn His Gln Leu Glu His Arg Val Gln Glu Tyr Pro Ala Ala Gln Thr
    50                  55                  60

Gln Leu Ser Asp Val Arg Ser Gln Gln Gly Ser Gly Gly Val Ile Glu
65              70                  75                  80

Arg Thr Arg Leu Leu Ser Glu Ala Thr Glu Asp Thr Glu His Val Lys
                85                  90                  95

Leu Glu Met Glu Glu Lys Cys Ser Ser Met Thr Asp Gly Asp Ser Leu
            100                 105                 110

Val Lys Ile Lys Gln Ser Leu Thr Lys Leu Lys Gln Glu Thr Val Gln
        115                 120                 125

Met Asp Ile Arg Ile Gly Val Val Glu His Thr Leu Leu
    130                 135                 140

<210> SEQ ID NO 32
<211> LENGTH: 325
<212> TYPE: PRT
<213> ORGANISM: Caenorhabditis elegans

<400> SEQUENCE: 32

Met Leu His His Ile Lys Ser Leu Lys Ser Val Leu Ser Arg Gly Gln
1               5                   10                  15

Glu Gly Arg Phe Gly Lys Arg His Ser Asn Thr Thr Phe Ile Thr
            20                  25                  30

Gly Ile Ala Thr Asp Phe Thr Ala Ala Lys Leu Lys Ser Gly Ala Gly
        35                  40                  45

Glu Asn Val Ile Phe Ile Leu Asn Ser Leu Ala Asp Ala Ser Leu Val
```

```
                50                  55                  60
His Val Gly Phe Gln Trp Gln Lys Met Ile Pro Pro Lys Glu Glu Asp
             65                  70                  75                  80

Glu Asp Thr Ala Val Asp Glu Gln Asp Glu Asp Asp Asn Asp Asp
                         85                  90                  95

Ile Val Glu Glu Pro Met Asn Phe Leu Asp Asp Asp Asp Asp Asn
                100                 105                 110

Val Ile Glu Ile Asp Leu Lys Ala Gln Gly Leu Ala Thr Glu Ser Lys
                115                 120                 125

Asn Pro Leu Gln Ser Val Leu Gln Ser Asn Thr Asp Ala Ile Thr Trp
            130                 135                 140

Lys Gln Glu Val Glu Arg Val Ala Pro Gln Leu Lys Ile Thr Leu Lys
145                 150                 155                 160

Gln Asp Ala Lys Asp Trp Arg Leu His Leu Glu Gln Met Asn Ser Met
                    165                 170                 175

His Lys Asn Val Glu Gln Lys Val Gly Asn Val Gly Pro Tyr Leu Asp
                180                 185                 190

Asn Met Ser Lys Asp Ile Ala Lys Ala Leu Glu Arg Ile Ala Ser Arg
            195                 200                 205

Glu Lys Ser Leu Asn Ser Gln Leu Ala Ser Met Met Ser Lys Phe Arg
210                 215                 220

Arg Ala Thr Asp Thr Arg Ala Glu Leu Arg Lys Tyr Lys Ala Ala
225                 230                 235                 240

Ser Val Gly Val Ser Ser Arg Thr Glu Thr Leu Asp Arg Ile Ser Asp
                    245                 250                 255

Asp Ile Glu Gln Leu Lys Gln Gln Ile Glu Glu Gln Gly Ala Lys Ser
                260                 265                 270

Ser Asp Gly Ala Pro Leu Val Lys Ile Lys Gln Ala Val Ser Lys Leu
            275                 280                 285

Glu Glu Glu Leu Gln Thr Met Asn Val Gln Ile Gly Val Phe Glu Gln
                290                 295                 300

Ser Ile Leu Asn Thr Tyr Leu Arg Asp His Phe Asn Phe Ser Ala Asn
305                 310                 315                 320

Leu Leu Asn Ile Met
                325

<210> SEQ ID NO 33
<211> LENGTH: 435
<212> TYPE: PRT
<213> ORGANISM: Homo sapiens

<400> SEQUENCE: 33

Met Glu Glu Val Met Asn Gly Tyr Asn Met Leu Lys Ala Gln Asn Asp
  1               5                  10                  15

Arg Glu Thr Gln Ser Leu Asp Val Ile Phe Thr Glu Arg Gln Ala Lys
                 20                  25                  30

Glu Lys Gln Ile Arg Ser Val Glu Glu Ile Glu Gln Lys Gln
             35                  40                  45

Ala Thr Asp Asp Ile Ile Lys Asn Met Ser Leu Glu Asn Gln Val Lys
         50                  55                  60

Tyr Leu Glu Met Lys Thr Thr Asn Glu Lys Leu Leu Gln Glu Leu Asp
 65                  70                  75                  80

Thr Leu Gln Gln Gln Leu Asp Ser Gln Asn Met Lys Lys Glu Ser Leu
                 85                  90                  95

Glu Ala Glu Ile Ala His Ser Gln Val Lys Gln Glu Ala Val Leu Leu
```

```
                   100                 105                 110
His Glu Lys Leu Tyr Glu Leu Glu Ser His Arg Asp Gln Met Ile Ala
            115                 120                 125

Glu Asp Lys Ser Ile Gly Ser Pro Met Glu Arg Glu Lys Leu Leu
        130                 135                 140

Lys Gln Ile Lys Asp Asp Asn Gln Glu Ile Ala Ser Met Glu Arg Gln
145                 150                 155                 160

Leu Thr Asp Thr Lys Glu Lys Ile Asn Gln Phe Ile Glu Glu Ile Arg
                165                 170                 175

Gln Leu Asp Met Asp Leu Glu Glu His Gln Gly Glu Met Asn Gln Lys
            180                 185                 190

Tyr Lys Glu Leu Lys Lys Arg Glu Glu His Met Asp Thr Phe Ile Glu
        195                 200                 205

Thr Phe Glu Glu Thr Lys Asn Gln Glu Leu Lys Arg Lys Ala Gln Ile
    210                 215                 220

Glu Ala Asn Ile Val Ala Leu Leu Glu His Cys Ser Arg Asn Ile Asn
225                 230                 235                 240

Arg Ile Glu Gln Ile Ser Ser Ile Thr Asn Gln Glu Leu Lys Met Met
                245                 250                 255

Gln Asp Asp Leu Asn Phe Lys Ser Thr Glu Val Gln Lys Ser Gln Ser
            260                 265                 270

Thr Ala Gln Asn Leu Thr Ser Asp Ile Gln Arg Leu Gln Leu Asp Leu
        275                 280                 285

Gln Lys Met Glu Leu Leu Glu Ser Lys Met Thr Glu Glu Gln His Ser
    290                 295                 300

Leu Lys Ser Lys Ile Lys Gln Met Thr Thr Asp Leu Glu Ile Tyr Asn
305                 310                 315                 320

Asp Leu Pro Ala Leu Lys Ser Ser Gly Glu Glu Lys Ile Lys Lys Leu
                325                 330                 335

His Gln Glu Arg Met Ile Leu Ser Thr His Arg Asn Ala Phe Lys Lys
            340                 345                 350

Ile Met Glu Lys Gln Asn Ile Glu Tyr Glu Ala Leu Lys Thr Gln Leu
        355                 360                 365

Gln Glu Asn Glu Thr His Ser Gln Leu Thr Asn Leu Glu Arg Lys Trp
    370                 375                 380

Gln His Leu Glu Gln Asn Asn Phe Ala Met Lys Glu Phe Ile Ala Thr
385                 390                 395                 400

Lys Ser Gln Glu Ser Asp Tyr Gln Pro Ile Lys Lys Asn Val Thr Lys
                405                 410                 415

Gln Ile Ala Glu Tyr Asn Lys Thr Ile Val Asp Ala Leu His Ser Thr
            420                 425                 430

Ser Gly Asn
        435

<210> SEQ ID NO 34
<211> LENGTH: 824
<212> TYPE: PRT
<213> ORGANISM: Homo sapiens

<400> SEQUENCE: 34

Met Met Gln Asn Val His Leu Ala Pro Glu Thr Asp Glu Asp Asp Leu
1               5                   10                  15

Tyr Ser Gly Tyr Asn Asp Tyr Asn Pro Ile Tyr Asp Ile Glu Glu Leu
            20                  25                  30

Glu Asn Asp Ala Ala Phe Gln Gln Ala Val Arg Thr Ser His Gly Arg
```

-continued

```
                35                  40                  45
Arg Pro Pro Ile Thr Ala Lys Ile Ser Ser Thr Ala Val Thr Arg Pro
 50                  55                  60

Ile Ala Thr Gly Tyr Gly Ser Lys Thr Ser Leu Ala Ser Ser Ile Gly
 65                  70                  75                  80

Arg Pro Met Thr Gly Ala Ile Gln Asp Gly Val Thr Arg Pro Met Thr
                 85                  90                  95

Ala Val Arg Ala Ala Gly Phe Thr Lys Ala Ala Leu Arg Gly Ser Ala
            100                 105                 110

Phe Asp Pro Leu Ser Gln Ser Arg Gly Pro Ala Ser Pro Leu Glu Ala
        115                 120                 125

Lys Lys Lys Asp Ser Pro Glu Glu Lys Ile Lys Gln Leu Glu Lys Glu
130                 135                 140

Val Asn Glu Leu Val Glu Glu Ser Cys Ile Ala Asn Ser Cys Gly Asp
145                 150                 155                 160

Leu Lys Leu Ala Leu Glu Lys Ala Lys Asp Ala Gly Arg Lys Glu Arg
                165                 170                 175

Val Leu Val Arg Gln Arg Glu Gln Val Thr Thr Pro Glu Asn Ile Asn
            180                 185                 190

Leu Asp Leu Thr Tyr Ser Val Leu Ser Asn Leu Ala Ser Gln Tyr Ser
        195                 200                 205

Val Asn Glu Met Tyr Ala Glu Ala Leu Asn Thr Tyr Gln Val Ile Val
    210                 215                 220

Lys Asn Lys Met Phe Ser Asn Ala Gly Ile Leu Lys Met Asn Met Gly
225                 230                 235                 240

Asn Ile Tyr Leu Lys Gln Arg Asn Tyr Ser Lys Ala Ile Lys Phe Tyr
                245                 250                 255

Arg Met Ala Leu Asp Gln Val Pro Ser Val Asn Lys Gln Met Arg Ile
            260                 265                 270

Lys Ile Met Gln Asn Ile Gly Val Thr Phe Ile Gln Ala Gly Gln Tyr
        275                 280                 285

Ser Asp Ala Ile Asn Ser Tyr Glu His Ile Met Ser Met Ala Pro Asn
    290                 295                 300

Leu Lys Ala Gly Tyr Asn Leu Thr Ile Cys Tyr Phe Ala Ile Gly Asp
305                 310                 315                 320

Arg Glu Lys Met Lys Lys Ala Phe Gln Lys Leu Ile Thr Val Pro Leu
                325                 330                 335

Glu Ile Asp Glu Asp Lys Tyr Ile Ser Pro Ser Asp Pro His Thr
            340                 345                 350

Asn Leu Val Thr Glu Ala Ile Lys Asn Asp His Leu Arg Gln Met Glu
        355                 360                 365

Arg Glu Arg Lys Ala Met Ala Glu Lys Tyr Ile Thr Thr Ser Ala Lys
    370                 375                 380

Leu Ile Ala Pro Val Ile Glu Thr Ser Phe Ala Ala Gly Cys Asp Trp
385                 390                 395                 400

Cys Val Glu Val Val Lys Ala Ser Gln Tyr Val Glu Leu Ala Asn Asp
                405                 410                 415

Leu Glu Ile Asn Lys Ala Val Thr Tyr Leu Arg Gln Lys Asp Tyr Asn
            420                 425                 430

Gln Ala Val Glu Ile Leu Lys Val Leu Glu Lys Lys Asp Asn Arg Val
        435                 440                 445

Lys Ser Ala Ala Ala Thr Asn Leu Ser Ala Leu Tyr Tyr Met Gly Lys
450                 455                 460
```

Asp Phe Ala Gln Ala Ser Ser Tyr Ala Asp Ile Ala Val Asn Ser Asp
465                 470                 475                 480

Arg Tyr Asn Pro Ala Ala Leu Thr Asn Lys Gly Asn Thr Val Phe Ala
            485                 490                 495

Asn Gly Asp Tyr Glu Lys Ala Ala Glu Phe Tyr Lys Glu Ala Leu Arg
        500                 505                 510

Asn Asp Ser Ser Cys Thr Glu Ala Leu Tyr Asn Ile Gly Leu Thr Tyr
    515                 520                 525

Glu Lys Leu Asn Arg Leu Asp Glu Ala Leu Asp Cys Phe Leu Lys Leu
530                 535                 540

His Ala Ile Leu Arg Asn Ser Ala Glu Val Leu Tyr Gln Ile Ala Asn
545                 550                 555                 560

Ile Tyr Glu Leu Met Glu Asn Pro Ser Gln Ala Ile Glu Trp Leu Met
            565                 570                 575

Gln Val Val Ser Val Ile Pro Thr Asp Pro Gln Val Leu Ser Lys Leu
        580                 585                 590

Gly Glu Leu Tyr Asp Arg Glu Gly Asp Lys Ser Gln Ala Phe Gln Tyr
    595                 600                 605

Tyr Tyr Glu Ser Tyr Arg Tyr Phe Pro Cys Asn Ile Glu Val Ile Glu
610                 615                 620

Trp Leu Gly Ala Tyr Tyr Ile Asp Thr Gln Phe Trp Glu Lys Ala Ile
625                 630                 635                 640

Gln Tyr Phe Glu Arg Ala Ser Leu Ile Gln Pro Thr Gln Val Lys Trp
            645                 650                 655

Gln Leu Met Val Ala Ser Cys Phe Arg Arg Ser Gly Asn Tyr Gln Lys
        660                 665                 670

Ala Leu Asp Thr Tyr Lys Asp Thr His Arg Lys Phe Pro Glu Asn Val
    675                 680                 685

Glu Cys Leu Arg Phe Leu Val Arg Leu Cys Thr Asp Leu Gly Leu Lys
690                 695                 700

Asp Ala Gln Glu Tyr Ala Arg Lys Leu Lys Arg Leu Glu Lys Met Lys
705                 710                 715                 720

Glu Ile Arg Glu Gln Arg Ile Lys Ser Gly Arg Asp Gly Ser Gly Gly
            725                 730                 735

Ser Arg Gly Lys Arg Glu Gly Ser Ala Ser Gly Asp Ser Gly Gln Asn
        740                 745                 750

Tyr Ser Ala Ser Ser Lys Gly Glu Arg Leu Ser Ala Arg Leu Arg Ala
    755                 760                 765

Leu Pro Gly Thr Asn Glu Pro Tyr Glu Ser Ser Asn Lys Glu Ile
770                 775                 780

Asp Ala Ser Tyr Val Asp Pro Leu Gly Pro Gln Ile Glu Arg Pro Lys
785                 790                 795                 800

Thr Ala Ala Lys Lys Arg Ile Asp Glu Asp Phe Ala Asp Glu Glu
            805                 810                 815

Leu Gly Asp Asp Leu Leu Pro Glu
            820

<210> SEQ ID NO 35
<211> LENGTH: 820
<212> TYPE: PRT
<213> ORGANISM: Caenorhabditis elegans

<400> SEQUENCE: 35

Met Ala Asn Ser Thr Phe Arg Glu Asp Asp Asp Phe Tyr Gly Gly
1               5                   10                  15

-continued

```
Phe Asp Ser Tyr Asp Lys Ala Tyr Asp Ile Gln Asn Ile Thr Gln Asn
            20                  25                  30

Pro Gln Phe Gln Gln Ala Val Ala Arg Ser Ser His Gly Arg Arg Pro
        35                  40                  45

Thr Ala Ser Gln Met Gly Phe Arg Asp Ala Ser Ser Tyr Gly Lys
 50                  55                  60

Pro Pro Gly Thr Met Met Gly Asn Gln Ser Arg Met Gly Gly Arg Thr
 65                  70                  75                  80

Ala Met Ala Asn Asn Asn Glu Pro Ala Arg Pro Met Thr Ala Val Arg
                85                  90                  95

Gly Ala Gly Tyr Thr Ser Phe Ala Asn Lys Val Gln Ala Ala Glu Arg
            100                 105                 110

Pro Leu Ser Thr Glu Asn Ser Gly Glu Asn Gly Glu Glu Lys Cys Arg
        115                 120                 125

Gln Met Glu Asn Lys Val Met Glu Met Leu Arg Glu Ser Met Leu Ala
        130                 135                 140

Ser Glu Lys Lys Lys Phe Lys Glu Ala Leu Asp Lys Ala Lys Glu Ala
145                 150                 155                 160

Gly Arg Arg Glu Arg Ala Val Val Lys His Arg Glu Gln Gln Gly Leu
                165                 170                 175

Val Glu Met Met Asn Leu Asp Leu Thr Phe Thr Val Leu Phe Asn Leu
            180                 185                 190

Ala Gln Gln Tyr Glu Ala Asn Asp Met Thr Asn Glu Ala Leu Asn Thr
        195                 200                 205

Tyr Glu Ile Ile Val Arg Asn Lys Met Phe Pro Asn Ser Gly Arg Leu
210                 215                 220

Lys Val Asn Ile Gly Asn Ile His Phe Arg Lys Arg Glu Phe Thr Lys
225                 230                 235                 240

Ala Leu Lys Tyr Tyr Arg Met Ala Leu Asp Gln Val Pro Ser Ile Gln
                245                 250                 255

Lys Asp Thr Arg Ile Lys Ile Leu Asn Asn Ile Gly Val Thr Phe Val
            260                 265                 270

Arg Met Gly Ser Tyr Asp Asp Ala Ile Ser Thr Phe Asp His Cys Val
        275                 280                 285

Glu Glu Asn Pro Asn Phe Ile Thr Ala Leu Asn Leu Ile Leu Val Ala
290                 295                 300

Phe Cys Ile Gln Asp Ala Glu Lys Met Arg Glu Ala Phe Val Lys Met
305                 310                 315                 320

Ile Asp Ile Pro Gly Phe Pro Asp Asp Tyr Met Lys Glu Lys Asp
                325                 330                 335

Asp Asp Asp Val Leu Leu Asn Gln Thr Leu Asn Ser Asp Met Leu Lys
            340                 345                 350

Asn Trp Glu Lys Arg Asn Lys Ser Asp Ala Glu Lys Ala Ile Ile Thr
        355                 360                 365

Ala Val Lys Ile Ile Ser Pro Val Ile Ala Pro Asp Tyr Ala Ile Gly
        370                 375                 380

Tyr Glu Trp Cys Leu Glu Ser Leu Lys Gln Ser Val His Ala Pro Leu
385                 390                 395                 400

Ala Ile Glu Leu Glu Met Thr Lys Ala Gly Glu Leu Met Lys Asn Gly
                405                 410                 415

Asp Ile Glu Gly Ala Ile Glu Val Leu Lys Val Phe Asn Ser Gln Asp
            420                 425                 430

Ser Lys Thr Ala Ser Ala Ala Ala Asn Asn Leu Cys Met Leu Arg Phe
        435                 440                 445
```

```
Leu Gln Gly Gly Arg Arg Leu Val Asp Ala Gln Gln Tyr Ala Asp Gln
        450                 455                 460
Ala Leu Ser Ile Asp Arg Tyr Asn Ala His Ala Gln Val Asn Gln Gly
465                 470                 475                 480
Asn Ile Ala Tyr Met Asn Gly Asp Leu Asp Lys Ala Leu Asn Asn Tyr
                485                 490                 495
Arg Glu Ala Leu Asn Asn Asp Ala Ser Cys Val Gln Ala Leu Phe Asn
            500                 505                 510
Ile Gly Leu Thr Ala Lys Ala Gln Gly Asn Leu Glu Gln Ala Leu Glu
        515                 520                 525
Phe Phe Tyr Lys Leu His Gly Ile Leu Leu Asn Asn Val Gln Val Leu
    530                 535                 540
Val Gln Leu Ala Ser Ile Tyr Glu Ser Leu Glu Asp Ser Ala Gln Ala
545                 550                 555                 560
Ile Glu Leu Tyr Ser Gln Ala Asn Ser Leu Val Pro Asn Asp Pro Ala
                565                 570                 575
Ile Leu Ser Lys Leu Ala Asp Leu Tyr Asp Gln Glu Gly Asp Lys Ser
            580                 585                 590
Gln Ala Phe Gln Cys His Tyr Asp Ser Tyr Arg Tyr Phe Pro Ser Asn
        595                 600                 605
Leu Glu Thr Val Glu Trp Leu Ala Ser Tyr Tyr Leu Glu Thr Gln Phe
    610                 615                 620
Ser Glu Lys Ser Ile Asn Tyr Leu Glu Lys Ala Ala Leu Met Gln Pro
625                 630                 635                 640
Asn Val Ser Lys Trp Gln Met Met Ile Ala Ser Cys Leu Arg Arg Thr
                645                 650                 655
Gly Asn Tyr Gln Arg Ala Phe Glu Leu Tyr Arg Gln Ile His Arg Lys
            660                 665                 670
Phe Pro Gln Asp Leu Asp Cys Leu Lys Phe Leu Val Arg Ile Ala Gly
        675                 680                 685
Asp Leu Gly Met Thr Glu Tyr Lys Glu Tyr Lys Asp Lys Leu Glu Lys
    690                 695                 700
Ala Glu Lys Ile Asn Gln Leu Arg Leu Gln Arg Glu Ser Asp Ser Ser
705                 710                 715                 720
Gln Gly Lys Arg His Ser Ala Asn Ser Thr His Ser Leu Pro Pro Ser
                725                 730                 735
Gly Leu Thr Gly Leu Gly Ser Gly Ser Gly Ser Ser Gly Gly Gly
            740                 745                 750
Thr Arg Gln Tyr Ser Ala His Val Pro Leu Leu Asp Ser Gly Thr
    755                 760                 765
Pro Phe Thr Val Ala Gln Arg Asp Met Lys Ala Glu Asp Phe Ser Tyr
770                 775                 780
Asp Asp Pro Val Ala Ile Ser Ser Arg Pro Lys Thr Gly Thr Arg Lys
785                 790                 795                 800
Thr Thr Thr Asp Thr Asn Ile Asp Asp Phe Gly Asp Phe Asp Ser
                805                 810                 815
Leu Leu Pro Asp
        820

<210> SEQ ID NO 36
<211> LENGTH: 1198
<212> TYPE: PRT
<213> ORGANISM: Homo sapiens

<400> SEQUENCE: 36
```

```
Thr Leu Leu Gln Pro Leu Lys Gly His Lys Asp Thr Val Tyr Cys Val
  1               5                  10                  15

Ala Tyr Ala Lys Asp Gly Lys Arg Phe Ala Ser Gly Ser Ala Asp Lys
             20                  25                  30

Ser Val Ile Ile Trp Thr Ser Lys Leu Glu Gly Ile Leu Lys Tyr Thr
             35                  40                  45

His Asn Asp Ala Ile Gln Cys Val Ser Tyr Asn Pro Ile Thr His Gln
 50                  55                  60

Leu Ala Ser Cys Ser Ser Asp Phe Gly Leu Trp Ser Pro Glu Gln
 65                  70                  75                  80

Lys Ser Val Ser Lys His Lys Ser Ser Lys Ile Ile Cys Cys Ser
                 85                  90                  95

Trp Thr Asn Asp Gly Gln Tyr Leu Ala Leu Gly Met Phe Asn Gly Ile
             100                 105                 110

Ile Ser Ile Arg Asn Lys Asn Gly Glu Glu Lys Val Lys Ile Glu Arg
             115                 120                 125

Pro Gly Gly Ser Leu Ser Pro Ile Trp Ser Ile Cys Trp Asn Pro Ser
             130                 135                 140

Ser Arg Trp Glu Ser Phe Trp Met Asn Arg Glu Asn Glu Asp Ala Glu
145                 150                 155                 160

Asp Val Ile Val Asn Arg Tyr Ile Gln Glu Ile Pro Ser Thr Leu Lys
             165                 170                 175

Ser Ala Val Tyr Ser Ser Gln Gly Ser Glu Ala Glu Glu Glu Pro
             180                 185                 190

Glu Glu Glu Asp Asp Ser Pro Arg Asp Asp Asn Leu Glu Glu Arg Asn
             195                 200                 205

Asp Ile Leu Ala Val Ala Asp Trp Gly Gln Lys Val Ser Phe Tyr Gln
             210                 215                 220

Leu Ser Gly Lys Gln Ile Gly Lys Asp Arg Ala Leu Asn Phe Asp Pro
225                 230                 235                 240

Cys Cys Ile Ser Tyr Phe Thr Lys Gly Glu Tyr Ile Leu Leu Gly Gly
                 245                 250                 255

Ser Asp Lys Gln Val Ser Leu Phe Thr Lys Asp Gly Val Arg Leu Gly
             260                 265                 270

Thr Val Gly Glu Gln Asn Ser Trp Val Trp Thr Cys Gln Ala Lys Pro
             275                 280                 285

Asp Ser Asn Tyr Val Val Gly Cys Gln Asp Gly Thr Ile Ser Phe
             290                 295                 300

Tyr Gln Leu Ile Phe Ser Thr Val His Gly Leu Tyr Lys Asp Arg Tyr
305                 310                 315                 320

Ala Tyr Arg Asp Ser Met Thr Asp Val Ile Val Gln His Leu Ile Thr
                 325                 330                 335

Glu Gln Lys Val Arg Ile Lys Cys Lys Glu Leu Val Lys Lys Ile Ala
             340                 345                 350

Ile Tyr Arg Asn Arg Leu Ala Ile Gln Leu Pro Glu Lys Ile Leu Ile
             355                 360                 365

Tyr Glu Leu Tyr Ser Glu Asp Leu Ser Asp Met His Tyr Arg Val Lys
             370                 375                 380

Glu Lys Ile Ile Lys Lys Phe Glu Cys Asn Leu Leu Val Cys Ala
385                 390                 395                 400

Asn His Ile Ile Leu Cys Gln Glu Lys Arg Leu Gln Cys Leu Ser Phe
                 405                 410                 415

Ser Gly Val Lys Glu Arg Glu Trp Gln Met Glu Ser Leu Ile Arg Tyr
```

```
                 420              425              430
Ile Lys Val Ile Gly Pro Pro Gly Arg Glu Gly Leu Leu Val Gly
            435              440              445
Leu Lys Asn Gly Gln Ile Leu Lys Ile Phe Val Asp Asn Leu Phe Ala
    450              455              460
Ile Val Leu Leu Lys Gln Ala Thr Ala Val Arg Cys Leu Asp Met Ser
465              470              475              480
Ala Ser Arg Lys Lys Leu Ala Val Val Asp Glu Asn Asp Thr Cys Leu
            485              490              495
Val Tyr Asp Ile Asp Thr Lys Glu Leu Leu Phe Gln Glu Pro Asn Ala
            500              505              510
Asn Ser Val Ala Trp Asn Thr Gln Cys Glu Asp Met Leu Cys Phe Ser
            515              520              525
Gly Gly Gly Tyr Leu Asn Ile Lys Ala Ser Thr Phe Pro Val His Arg
            530              535              540
Gln Lys Leu Gln Gly Phe Val Val Gly Tyr Asn Gly Ser Lys Ile Phe
545              550              555              560
Cys Leu His Val Phe Ser Ile Ser Ala Val Glu Val Pro Gln Ser Ala
                565              570              575
Pro Met Tyr Gln Tyr Leu Asp Arg Lys Leu Phe Lys Glu Ala Tyr Gln
            580              585              590
Ile Ala Cys Leu Gly Val Thr Asp Thr Asp Trp Arg Glu Leu Ala Met
            595              600              605
Glu Ala Leu Glu Gly Leu Asp Phe Glu Thr Ala Lys Lys Ala Phe Ile
            610              615              620
Arg Val Gln Asp Leu Arg Tyr Leu Glu Leu Ile Ser Ser Ile Glu Glu
625              630              635              640
Arg Lys Lys Arg Gly Glu Thr Asn Asn Asp Leu Phe Leu Ala Asp Val
                645              650              655
Phe Ser Tyr Gln Gly Lys Phe His Glu Ala Ala Lys Leu Tyr Lys Arg
                660              665              670
Ser Gly His Glu Asn Leu Ala Leu Glu Met Tyr Thr Asp Leu Cys Met
            675              680              685
Phe Glu Tyr Ala Lys Asp Phe Leu Gly Ser Gly Asp Pro Lys Glu Thr
690              695              700
Lys Met Leu Ile Thr Lys Gln Ala Asp Trp Ala Arg Asn Ile Lys Glu
705              710              715              720
Pro Lys Ala Ala Val Glu Met Tyr Ile Ser Ala Gly Glu His Val Lys
                725              730              735
Ala Ile Glu Ile Cys Gly Asp His Gly Trp Val Asp Met Leu Ile Asp
            740              745              750
Ile Ala Arg Lys Leu Asp Lys Ala Glu Arg Glu Pro Leu Leu Leu Cys
            755              760              765
Ala Thr Tyr Leu Lys Lys Leu Asp Ser Pro Gly Tyr Ala Ala Glu Thr
            770              775              780
Tyr Leu Lys Met Gly Asp Leu Lys Ser Leu Val Gln Leu His Val Glu
785              790              795              800
Thr Gln Arg Trp Asp Glu Ala Phe Ala Leu Gly Glu Lys His Pro Glu
                805              810              815
Phe Lys Asp Asp Ile Tyr Met Pro Tyr Ala Gln Trp Leu Ala Glu Asn
                820              825              830
Asp Arg Phe Glu Glu Ala Gln Lys Ala Phe His Lys Ala Gly Arg Gln
            835              840              845
```

```
Arg Glu Ala Val Gln Val Leu Glu Gln Leu Thr Asn Asn Ala Val Ala
    850                 855                 860

Glu Ser Arg Phe Asn Asp Ala Ala Tyr Tyr Tyr Trp Met Leu Ser Met
865                 870                 875                 880

Gln Cys Leu Asp Ile Ala Gln Asp Pro Ala Gln Lys Asp Thr Met Leu
                885                 890                 895

Gly Lys Phe Tyr His Phe Gln Arg Leu Ala Glu Leu Tyr His Gly Tyr
            900                 905                 910

His Ala Ile His Arg His Thr Glu Asp Pro Phe Ser Val His Arg Pro
        915                 920                 925

Glu Thr Leu Phe Asn Ile Ser Arg Phe Leu Leu His Ser Leu Pro Lys
    930                 935                 940

Asp Thr Pro Ser Gly Ile Ser Lys Val Lys Ile Leu Phe Thr Leu Ala
945                 950                 955                 960

Lys Gln Ser Lys Ala Leu Gly Ala Tyr Arg Leu Ala Arg His Ala Tyr
                965                 970                 975

Asp Lys Leu Arg Gly Leu Tyr Ile Pro Ala Arg Phe Gln Lys Ser Ile
            980                 985                 990

Glu Leu Gly Thr Leu Thr Ile Arg Ala Lys Pro Phe His Asp Ser Glu
        995                 1000                1005

Glu Leu Val Pro Leu Cys Tyr Arg Cys Ser Thr Asn Asn Pro Leu Leu
    1010                1015                1020

Asn Asn Leu Gly Asn Val Cys Ile Asn Cys Arg Gln Pro Phe Ile Phe
1025                1030                1035                1040

Ser Ala Ser Ser Tyr Asp Val Leu His Leu Val Glu Phe Tyr Leu Glu
                1045                1050                1055

Glu Gly Ile Thr Asp Glu Glu Ala Ile Ser Leu Ile Asp Leu Glu Val
            1060                1065                1070

Leu Arg Pro Lys Arg Asp Asp Arg Gln Leu Glu Ile Ala Asn Asn Ser
        1075                1080                1085

Ser Gln Ile Leu Arg Leu Val Glu Thr Lys Asp Ser Ile Gly Asp Glu
    1090                1095                1100

Asp Pro Phe Thr Ala Lys Leu Ser Phe Glu Gln Gly Gly Ser Glu Phe
1105                1110                1115                1120

Val Pro Val Val Ser Arg Leu Val Leu Arg Ser Met Ser Arg Arg
                1125                1130                1135

Asp Val Leu Ile Lys Arg Trp Pro Pro Leu Arg Trp Gln Tyr Phe
            1140                1145                1150

Arg Ser Leu Leu Pro Asp Ala Ser Ile Thr Met Cys Pro Ser Cys Phe
        1155                1160                1165

Gln Met Phe His Ser Glu Asp Tyr Glu Leu Leu Val Leu Gln His Gly
    1170                1175                1180

Cys Cys Pro Tyr Cys Arg Arg Cys Lys Asp Asp Pro Gly Pro
1185                1190                1195

<210> SEQ ID NO 37
<211> LENGTH: 1047
<212> TYPE: PRT
<213> ORGANISM: Caenorhabditis elegans

<400> SEQUENCE: 37

Met Thr Met Lys Lys Ile Ser Arg Lys Leu Gly Phe His Gly Glu Gln
1               5                   10                  15

Val Cys Ile Tyr Asp Leu Ala Phe Lys Pro Asp Gly Ser Glu Leu Leu
            20                  25                  30
```

```
Leu Ala Ala Asp Asn Lys Val Tyr Leu Phe Asp Val Asn Glu Gly Gly
         35                  40                  45

Gln Met Gln Thr Leu Lys Gly His Lys Asp Leu Val Tyr Thr Val Ala
 50                  55                  60

Trp Ser His Asn Gly Glu Leu Phe Ala Ser Gly Ala Asp Lys Leu
 65                  70                  75                  80

Val Ile Leu Trp Asn Glu Lys His Glu Gly Thr Leu Arg Tyr Ser His
                     85                  90                  95

Thr Asp Val Ile Gln Cys Met Met Phe Asn Pro Cys Asn Gln Ile Leu
                 100                 105                 110

Leu Thr Cys Ala Leu Asn Glu Phe Gly Leu Trp Ser Thr Ala Asp Lys
             115                 120                 125

Asn Val Ile Lys Gln Arg Ser Val Val Arg Cys Cys Ser Cys Ala Trp
 130                 135                 140

Asn Thr Asp Gly Thr Ile Phe Ala Ile Gly His Gly Asp Gly Thr Ile
 145                 150                 155                 160

Thr Leu Arg Lys Gly Thr Asn Ala Thr Glu Glu Pro Ser Ile Ile
                 165                 170                 175

Gln Arg Asp Asn Glu Pro Ile Trp Gly Ile Ala Phe Ser Ser Asn Arg
                 180                 185                 190

Thr Phe Ala Ser Arg Asp Ser Gln Gly Asn Pro Met Gly Ile Asp Glu
                 195                 200                 205

Ile Met Ala Val Ile Asp Trp Asn Lys Thr Leu Ser Phe Tyr Ser Leu
 210                 215                 220

Asp Gly Thr Phe Ile Glu Ser Lys Asn Leu Glu Phe Glu Pro His Cys
225                 230                 235                 240

Ile Ser Tyr Cys Leu Asn Gly Glu Tyr Leu Leu Ile Gly Gly Ser Asp
                 245                 250                 255

Lys Ile Leu Lys Ile Tyr Thr Arg Lys Gly Val Leu Leu Gly Thr Val
                 260                 265                 270

Ala Gln Met Asp His Trp Ile Trp Ser Val Thr Val Arg Pro Asn Ser
                 275                 280                 285

Gln Thr Val Ala Met Gly Cys Val Asp Gly Thr Ile Ala Cys Tyr Asn
 290                 295                 300

Leu Val Phe Ser Thr Val His Cys Val Asp His Ala Arg Tyr Ala Asn
305                 310                 315                 320

Arg Lys Ser Met Thr Asp Val Phe Val Gln Asn Leu Glu Tyr Arg Thr
                 325                 330                 335

Ser Ser Asn Ile Cys Cys His Asp Leu Val Lys Met Ser Leu Tyr
                 340                 345                 350

Asp Thr Lys Leu Ala Val Gln Leu Ser Asp Lys Ile Gln Ile Tyr Lys
                 355                 360                 365

Gln Thr Gly Gly Val Ser Lys Asn Glu Arg Arg Lys Gln Leu Lys Tyr
 370                 375                 380

Thr Leu Gln Asp Thr Ile Arg Lys Asp Leu Ser Phe Ser Leu Met Val
385                 390                 395                 400

Val Thr His Gly His Leu Val Val Cys Asn Asp Glu Lys Leu Glu Cys
                 405                 410                 415

Tyr Asp Phe Lys Gly Ile Lys Lys Arg Ser Trp Asn Met Lys Ser Ile
                 420                 425                 430

Val Arg Tyr Leu Arg Val Leu Gly Gly Pro Ala His Arg Glu Thr Leu
                 435                 440                 445

Val Leu Gly Thr Thr Asp Gly Gly Val Tyr Lys Val Phe Ile Asp Asn
 450                 455                 460
```

```
Asp Tyr Pro Ile Leu Leu Asp Ser Arg Lys Thr Ala Ile Lys Cys Ile
465                 470                 475                 480

Asp Ile Asn Ala Asn Arg Thr Val Leu Ala Ser Ile Glu Asp Thr Leu
                485                 490                 495

Val Cys Lys Trp Ser Asp Ile Ala Thr Gly Glu Thr Leu Leu Gln Glu
                500                 505                 510

Pro Gly Cys Tyr Ser Val Val Phe Asn Thr Val Asn Glu Asn Leu Phe
                515                 520                 525

Ala Phe Thr Thr Asn Asn Met Leu His Val Arg Thr Leu Ala Ala Pro
530                 535                 540

Gly His Thr Thr Arg Gly Val Gly Tyr Val Leu Gly Phe Val Lys Asn
545                 550                 555                 560

Arg Thr Phe Cys Leu Val Gln Tyr Asn Leu Ile Pro Leu Glu Val Pro
                565                 570                 575

Tyr Thr Ile His Leu Tyr Gln Tyr Ile Glu Arg Gly Asp Phe Lys Glu
                580                 585                 590

Ala Leu Arg Ile Ala Cys Leu Gly Val Val Lys Asn Asp Trp Lys Tyr
                595                 600                 605

Leu Ala Asn Lys Ala Leu Asp Ala Leu Glu Phe Asp Val Ala Arg Lys
610                 615                 620

Ala Tyr Lys Arg Val Arg Asp Arg Lys Met Leu Arg Met Val Trp Glu
625                 630                 635                 640

Leu Lys Lys Met Lys Ser Asn Gly Glu Pro Asp Ala Ile Leu Arg Ala
                645                 650                 655

Thr Ile Leu Ala Tyr Thr Lys Lys Phe Arg Glu Ala Ala Lys Ile Phe
                660                 665                 670

Lys Glu Asn Gly Phe Glu Asn Arg Ala Met Glu Leu Phe Thr Asp Met
                675                 680                 685

Arg Met Phe Asp Asp Val Gln Glu Val Met Thr Thr Ala Ser Gly Glu
690                 695                 700

Thr Lys Lys Met Leu Met Arg Lys Arg Ala Ser Trp Ala Arg Asp Ala
705                 710                 715                 720

Asn Gln Pro Lys Ile Ala Ala Glu Met Leu Ile Ser Ser Gly Asp Leu
                725                 730                 735

Asp Lys Ala Ala Leu Leu Ile Ile Asp Asn Asp Trp Leu Glu Leu Ala
                740                 745                 750

Ile Glu Ile Ser His Lys Ile Asp Arg Ser Asp Leu Glu Thr Met Lys
                755                 760                 765

Lys Leu Ser Ala Tyr Phe Ile Arg Lys His Glu Phe Gly Leu Ala Ser
                770                 775                 780

Arg Ile Phe Gln Ser Ile Asn Asp Met Lys Ser Ile Val Asp Met His
785                 790                 795                 800

Val Asn Ala Gly His Trp Thr Asp Ala Phe Ala Ile Ala Asp Arg His
                805                 810                 815

Pro Lys Tyr Val Glu Asp Val Tyr Leu Pro Tyr Ala Arg Phe Leu Ala
                820                 825                 830

Glu Arg Asp Arg Phe Glu Glu Ala Gln Lys Ala Phe His Arg Ala Gly
                835                 840                 845

Lys Glu Gln Glu Ala Met His Val Leu Glu Gln Leu Thr Ser Asn Ser
                850                 855                 860

Val Asn Glu Asn Arg Phe Ala Asp Ala Gly Cys Gly Leu Asn Asn Pro
865                 870                 875                 880

Leu Leu Gly Gly Met Ser Cys Ile His Cys Glu Thr Pro Phe Ile Ile
```

```
                          885                 890                 895
Ser Phe Val Ser Phe Asp Ile Leu Pro Leu Ile Glu Phe Lys Ile Glu
                900                 905                 910

Asn Asp Ile Ser Phe Asp Glu Ala Lys Glu Leu Ile Glu Ser Glu Pro
            915                 920                 925

Pro Leu Ser Asp Asp Tyr Asn Pro Leu Arg Gly Leu Lys Lys Gly
        930                 935                 940

Ile Lys Glu Ile Ile Leu Asn Arg Glu Ser Leu Ser Lys Leu Glu Gln
945                 950                 955                 960

Gly His Val Ile Ile Gln Thr Phe Pro Pro Leu Ala Pro Lys Phe
                965                 970                 975

Leu Phe Asn Val Met Pro Ser Ile Thr Ile Ala Gln Cys Lys Gly Cys
                980                 985                 990

Asn Lys Val Phe Asp Leu Asp Asp Phe Glu Met Ala Cys Leu Arg Lys
            995                 1000                1005

Gly His Cys Pro Phe Cys Arg Thr Ser Tyr Asp Arg Asn Glu Ala Phe
        1010                1015                1020

Phe Val Asp Glu Glu Asp Glu Asp Asn Thr Asn Ile Pro Ser Phe
1025                1030                1035                1040

Gly Gln Phe Ser Arg Phe Ser
                1045

<210> SEQ ID NO 38
<211> LENGTH: 1386
<212> TYPE: PRT
<213> ORGANISM: Homo sapiens

<400> SEQUENCE: 38

Ser Phe Ile Gln Ala Gly Ile Ile Tyr Tyr Ser Gln Glu Lys Tyr Phe
1               5                   10                  15

His His Val Gln Ala Ala Ala Val Gly Leu Glu Lys Phe Ser Asn Asp
                20                  25                  30

Pro Val Leu Lys Phe Phe Lys Ala Tyr Gly Val Leu Lys Glu Asp Arg
            35                  40                  45

Glu Ala Ile Gln Glu Leu Glu Tyr Ser Leu Lys Glu Ile Arg Lys Thr
        50                  55                  60

Val Ser Gly Thr Ala Leu Tyr Tyr Ala Gly Leu Phe Leu Trp Leu Ile
65                  70                  75                  80

Gly Arg His Asp Lys Ala Lys Glu Tyr Ile Asp Arg Met Leu Lys Ile
                85                  90                  95

Ser Arg Gly Phe Arg Glu Ala Tyr Val Leu Arg Gly Trp Val Asp Leu
                100                 105                 110

Thr Ser Asp Lys Pro His Thr Ala Lys Lys Ala Ile Glu Tyr Leu Glu
            115                 120                 125

Gln Gly Ile Gln Asp Thr Lys Asp Val Leu Gly Leu Met Gly Lys Ala
        130                 135                 140

Met Tyr Phe Met Met Gln Gln Asn Tyr Ser Glu Ala Leu Glu Val Val
145                 150                 155                 160

Asn Gln Ile Thr Val Thr Ser Gly Ser Phe Leu Pro Ala Leu Val Leu
                165                 170                 175

Lys Met Gln Leu Phe Leu Ala Arg Gln Asp Trp Glu Gln Thr Val Glu
            180                 185                 190

Met Gly His Arg Arg Ile Leu Glu Lys Asp Glu Ser Asn Ile Asp Ala
        195                 200                 205

Cys Gln Ile Leu Thr Val His Glu Leu Ala Arg Glu Gly Asn Met Thr
```

-continued

```
              210                 215                 220
Thr Gln Ala Thr Asn His Val Arg Asn Leu Ile Lys Ala Leu Glu Thr
225                 230                 235                 240

Arg Glu Pro Glu Asn Pro Ser Leu His Leu Lys Lys Ile Ile Val Val
                245                 250                 255

Ser Arg Leu Val Cys Gly Ser His Gln Val Ile Leu Gly Leu Val Cys
                260                 265                 270

Ser Phe Ile Glu Arg Thr Phe Met Ala Thr Pro Ser Tyr Val His Val
            275                 280                 285

Ala Thr Glu Leu Gly Tyr Leu Phe Ile Leu Lys Asn Gln Val Lys Glu
        290                 295                 300

Ala Leu Leu Trp Tyr Ser Glu Ala Met Lys Leu Asp Lys Asp Gly Met
305                 310                 315                 320

Ala Gly Leu Thr Gly Ile Ile Leu Cys His Ile Leu Glu Gly His Leu
                325                 330                 335

Glu Glu Ala Glu Tyr Arg Leu Glu Phe Leu Lys Glu Val Gln Lys Ser
                340                 345                 350

Leu Gly Lys Ser Glu Val Arg Ala Pro Trp Gly Tyr Gly Leu Leu Gln
            355                 360                 365

Asp Asp Val Leu Cys Cys Pro Pro Thr Pro Thr Phe Gln Cys Lys Val
        370                 375                 380

Ala Trp Thr Phe Thr Leu Pro Leu Pro Thr Lys Ser Ala Gln Ala Asp
385                 390                 395                 400

Ile Gly Thr Glu Thr Arg Ser Ser Leu Pro Gln Val Leu Ile Phe Leu
                405                 410                 415

Gln Ala Leu Leu Met Ser Arg Lys His Lys Gly Glu Glu Thr Thr
                420                 425                 430

Ala Leu Leu Lys Glu Ala Val Glu Leu His Phe Ser Ser Met Gln Gly
            435                 440                 445

Ile Pro Leu Gly Ser Glu Tyr Phe Glu Lys Leu Asp Pro Tyr Phe Leu
        450                 455                 460

Val Cys Ile Ala Lys Glu Tyr Leu Leu Phe Cys Pro Lys Gln Pro Arg
465                 470                 475                 480

Leu Pro Gly Gln Ile Val Ser Pro Leu Leu Lys Gln Val Ala Val Ile
                485                 490                 495

Leu Asn Pro Val Val Lys Ala Ala Pro Ala Leu Ile Asp Pro Leu Tyr
            500                 505                 510

Leu Met Ala Gln Val Arg Tyr Tyr Ser Gly Glu Leu Glu Asn Ala Gln
        515                 520                 525

Ser Ile Leu Gln Arg Cys Leu Glu Leu Asp Pro Ala Ser Val Asp Ala
    530                 535                 540

His Leu Leu Met Cys Gln Ile Tyr Leu Ala Gln Gly Asn Phe Gly Met
545                 550                 555                 560

Cys Phe His Cys Leu Glu Leu Gly Val Ser His Asn Phe Gln Val Val
                565                 570                 575

Arg Asp His Pro Leu Tyr His Leu Ile Lys Ala Arg Ala Leu Asn Lys
            580                 585                 590

Ala Gly Asp Tyr Pro Glu Ala Ile Lys Thr Leu Lys Met Val Ile Lys
        595                 600                 605

Leu Pro Ala Leu Lys Lys Glu Glu Gly Arg Lys Phe Leu Arg Pro Ser
    610                 615                 620

Val Gln Pro Ser Gln Arg Ala Ser Ile Leu Leu Glu Leu Val Glu Ala
625                 630                 635                 640
```

```
Leu Arg Leu Asn Gly Glu Leu His Glu Ala Thr Lys Val Met Gln Asp
            645                 650                 655

Thr Ile Asn Glu Phe Gly Gly Thr Pro Glu Asn Arg Ile Thr Ile
        660                 665                 670

Ala Asn Val Asp Leu Val Leu Ser Lys Gly Asn Val Asp Val Ala Leu
            675                 680                 685

Asn Met Leu Arg Asn Ile Leu Pro Lys Gln Ser Cys Tyr Met Glu Ala
690                 695                 700

Arg Glu Lys Met Ala Asn Ile Tyr Leu Gln Thr Leu Arg Asp Arg Arg
705                 710                 715                 720

Leu Tyr Ile Arg Cys Tyr Glu Leu Cys Glu His Leu Pro Gly Pro His
                725                 730                 735

Thr Ser Leu Leu Leu Gly Asp Ala Leu Met Ser Ile Leu Glu Val Ser
            740                 745                 750

Glu Arg Pro His Ser Leu Ala Lys Trp Pro Ser Leu Pro Ser Pro
            755                 760                 765

Val Gly Glu Lys Arg Lys Thr Gln Arg His Phe Pro His Gln Pro Glu
    770                 775                 780

Lys Ala Leu Glu Val Tyr Asp Glu Ala Tyr Arg Gln Asn Pro His Asp
785                 790                 795                 800

Ala Ser Leu Ala Ser Arg Ile Gly His Ala Tyr Val Lys Ala His Gln
                805                 810                 815

Tyr Thr Lys Ala Ile Glu Tyr Tyr Glu Ala Ala Gln Lys Ile Asn Gly
            820                 825                 830

Gln Asp Phe Leu Cys Cys Asp Leu Gly Lys Leu Leu Leu Lys Leu Lys
        835                 840                 845

Lys Val Asn Lys Ala Glu Lys Val Leu Lys Gln Ala Leu Glu His Asp
850                 855                 860

Ile Gly Val Gln Asp Ile Pro Ser Met Met Asn Asp Val Lys Cys Leu
865                 870                 875                 880

Leu Leu Leu Ala Lys Val Tyr Lys Ser His Lys Lys Glu Ala Val Ile
                885                 890                 895

Glu Thr Leu Asn Lys Val Ile Asp Arg Trp Thr Gln Ala Leu Ala Leu
            900                 905                 910

Asp Leu Gln Ser Arg Ile Leu Lys Arg Val Pro Leu Glu Gln Pro Glu
        915                 920                 925

Met Ile Pro Ser Gln Lys Gln Leu Ala Ala Ser Ile Cys Ile Gln Phe
930                 935                 940

Ala Glu His Tyr Leu Ala Glu Lys Glu Tyr Asp Lys Ala Val Gln Ser
945                 950                 955                 960

Tyr Lys Asp Val Phe Ser Tyr Leu Pro Thr Asp Asn Lys Val Leu Met
                965                 970                 975

Ala Asp Leu Met Phe Arg Lys Gln Lys His Glu Ala Ala Ile Asn Leu
            980                 985                 990

Tyr His Gln Val Leu Glu Lys Ala Pro Gly Asp Asn Phe Leu Val Leu
        995                 1000                1005

His Lys Leu Ile Asp Leu Leu Arg Arg Ser Gly Lys Leu Glu Asp Ile
    1010                1015                1020

Pro Ala Phe Phe Glu Leu Ala Lys Lys Val Ser Ser Arg Val Pro Leu
1025                1030                1035                1040

Glu Pro Gly Phe Asn Tyr Cys Arg Gly Ile Tyr Cys Trp His Ile Gly
                1045                1050                1055

Gln Pro Asn Glu Ala Leu Lys Phe Leu Asn Lys Ala Arg Lys Asp Ser
            1060                1065                1070
```

```
Thr Trp Gly Gln Ser Ala Ile Tyr His Met Val Gln Ile Cys Leu Asn
        1075                1080                1085

Pro Asp Asn Glu Val Val Gly Gly Glu Ala Phe Glu Asn Leu Ile Pro
1090                1095                1100

Arg Ser Asn Thr Cys Ser Tyr Met Glu Lys Lys Glu Leu Glu Gln Gln
1105                1110                1115                1120

Gly Val Ser Thr Ala Glu Lys Leu Leu Arg Glu Phe Tyr Pro His Ser
        1125                1130                1135

Asp Ser Ser Gln Thr Gln Leu Arg Leu Leu Gln Gly Leu Cys Arg Leu
        1140                1145                1150

Ala Thr Arg Glu Lys Ala Asn Met Glu Ala Ala Leu Gly Ser Phe Ile
        1155                1160                1165

Gln Ile Ala Gln Ala Glu Lys Asp Ser Val Pro Ala Leu Leu Ala Leu
        1170                1175                1180

Ala Gln Ala Tyr Val Phe Leu Lys Gln Ile Pro Lys Ala Arg Met Gln
1185                1190                1195                1200

Leu Lys Arg Leu Ala Lys Thr Pro Trp Val Leu Ser Glu Ala Glu Asp
        1205                1210                1215

Leu Glu Lys Ser Trp Leu Leu Leu Ala Asp Ile Tyr Cys Gln Gly Ser
        1220                1225                1230

Lys Phe Asp Leu Ala Leu Glu Leu Leu Arg Arg Cys Val Gln Tyr Asn
        1235                1240                1245

Lys Ala Gln Ser Cys Tyr Lys Ala Tyr Glu Tyr Met Gly Phe Ile Met
        1250                1255                1260

Glu Lys Glu Gln Ser Tyr Lys Asp Ala Val Thr Asn Tyr Lys Leu Ala
1265                1270                1275                1280

Trp Lys Tyr Ser His His Ala Asn Pro Ala Ile Gly Lys Ala Thr Ser
        1285                1290                1295

Gln Gly Ala Arg Glu Thr Trp Glu Gly Gly Gln Glu Pro His His
        1300                1305                1310

Asp Pro Arg Thr Gln Gly Leu Tyr Pro Gly Cys Tyr Glu Asn Gln Arg
        1315                1320                1325

Gly Ser Gln Val Thr Arg Val Pro Pro Ser Leu Leu Ser Met Ser Pro
        1330                1335                1340

Val Gly Phe Lys Leu Ala Phe Asn Tyr Leu Lys Asp Lys Lys Phe Val
1345                1350                1355                1360

Glu Ala Ile Glu Ile Cys Asn Asp Val Ser Gln Gln Pro Trp Trp Gly
        1365                1370                1375

Gly Pro Gly Val Val Val Gly Asn Pro Ala
        1380                1385

<210> SEQ ID NO 39
<211> LENGTH: 1008
<212> TYPE: PRT
<213> ORGANISM: Homo sapiens

<400> SEQUENCE: 39

Ile Asn Tyr Tyr Cys Gln Glu Arg Tyr Phe His His Val Leu Leu Val
1               5                   10                  15

Ala Ser Glu Gly Ile Lys Arg Tyr Gly Ser Asp Pro Val Phe Arg Phe
            20                  25                  30

Tyr His Ala Tyr Gly Thr Leu Met Glu Gly Lys Thr Gln Glu Ala Leu
        35                  40                  45

Arg Glu Phe Glu Ala Ile Lys Asn Lys Gln Asp Val Ser Leu Cys Ser
    50                  55                  60
```

```
Leu Leu Ala Leu Ile Tyr Ala His Lys Asp Arg Glu Ala Ile Leu Glu
 65                  70                  75                  80

Ser Asp Ala Arg Val Lys Glu Gln Arg Lys Gly Ala Gly Glu Lys Ala
                 85                  90                  95

Leu Tyr His Ala Gly Leu Phe Leu Trp His Ile Gly Arg His Asp Lys
            100                 105                 110

Ala Arg Glu Tyr Ile Asp Arg Met Ile Lys Ile Ser Asp Gly Ser Lys
        115                 120                 125

Gln Gly His Val Leu Lys Ala Trp Leu Asp Ile Thr Arg Gly Lys Glu
    130                 135                 140

Pro Tyr Thr Lys Lys Ala Leu Lys Tyr Phe Glu Glu Gly Leu Gln Asp
145                 150                 155                 160

Gly Asn Asp Thr Phe Ala Leu Leu Gly Lys Val Ser Trp Arg Gln Asn
                165                 170                 175

Tyr Ser Gly Ala Leu Glu Thr Val Asn Gln Ile Ile Val Asn Phe Pro
            180                 185                 190

Ser Phe Leu Pro Ala Phe Val Lys Lys Met Lys Leu Gln Leu Ala Leu
        195                 200                 205

Gln Asp Trp Asp Gln Thr Val Glu Thr Ala Gln Arg Leu Ser Asn Lys
    210                 215                 220

Ile Ile Phe Phe Ser Phe Cys Gly Arg Ser Gln Leu Ile Leu Gln Lys
225                 230                 235                 240

Ile Gln Thr Leu Leu Glu Arg Ala Phe Ser Leu Asn Pro Gln Gln Ser
                245                 250                 255

Glu Phe Ala Thr Glu Leu Gly Tyr Gln Met Ile Leu Gln Gly Arg Val
            260                 265                 270

Lys Glu Ala Leu Lys Trp Tyr Lys Thr Ala Met Thr Leu Asp Glu Thr
        275                 280                 285

Ser Val Ser Ala Leu Val Gly Phe Ile Gln Cys Gln Leu Ile Glu Gly
    290                 295                 300

Gln Leu Gln Asp Ala Asp Gln Gln Leu Glu Phe Leu Asn Glu Ile Gln
305                 310                 315                 320

Gln Ser Ile Gly Lys Ser Ala Val Leu Ile Tyr Leu His Ala Val Leu
                325                 330                 335

Ala Met Lys Lys Asn Lys Arg Gln Glu Glu Val Ile Asn Leu Leu Asn
            340                 345                 350

Asp Val Leu Asp Thr His Phe Ser Gln Leu Glu Gly Leu Pro Leu Gly
        355                 360                 365

Ile Gln Tyr Phe Glu Lys Leu Asn Pro Asp Phe Leu Leu Glu Ile Val
    370                 375                 380

Met Glu Tyr Leu Ser Phe Cys Pro Met Gln Val Ser Asn Tyr Gly Phe
385                 390                 395                 400

Leu Leu Gly Asp Ile Glu Ala Ala Phe Asn Asn Leu Gln His Cys Leu
                405                 410                 415

Glu His Asn Pro Ser Tyr Ala Asp Ala His Leu Leu Leu Ala Gln Val
            420                 425                 430

Tyr Leu Ser Gln Glu Lys Val Lys Leu Cys Ser Gln Ser Leu Glu Leu
        435                 440                 445

Cys Leu Ser Tyr Asp Phe Lys Val Gln Val Arg Asp Tyr Pro Leu Tyr
    450                 455                 460

His Leu Ile Lys Ala Gln Ser Gln Lys Lys Met Gly Glu Ile Ala Asp
465                 470                 475                 480

Ala Ile Lys Thr Leu His Met Ala Met Ser Leu Pro Gly Met Lys Arg
```

-continued

```
                485                 490                 495
Ile Gly Ala Ser Thr Lys Ser Lys Asp Arg Lys Thr Glu Val Asp Thr
            500                 505                 510

Ser His Arg Leu Ser Ile Phe Leu Glu Leu Ile Asp Val His Arg Leu
            515                 520                 525

Asn Gly Glu His Glu Ala Thr Lys Val Leu Gln Asp Ala Ile His Glu
        530                 535                 540

Phe Ser Gly Thr Ser Glu Glu Val Arg Val Thr Ile Ala Asn Ala Asp
545                 550                 555                 560

Leu Ala Leu Ala Gln Gly Asp Ile Glu Arg Ala Leu Ser Ile Leu Gln
                565                 570                 575

Asn Val Thr Ala Glu Gln Pro Tyr Phe Ile Glu Ala Arg Glu Lys Met
            580                 585                 590

Ala Asp Ile Tyr Leu Lys His Arg Lys Asp Lys Met Leu Tyr Ile Thr
            595                 600                 605

Cys Phe Ala Ile Thr Tyr Tyr Glu Ala Ala Leu Lys Thr Gly Gln Lys
        610                 615                 620

Asn Tyr Leu Cys Tyr Asp Leu Ala Glu Leu Leu Leu Lys Leu Lys Trp
625                 630                 635                 640

Tyr Asp Lys Ala Glu Lys Val Leu Gln His Ala Leu Ala His Glu Pro
                645                 650                 655

Gly Met Lys Ala Arg Glu Leu Gln Ala Arg Val Leu Lys Arg Val Gln
            660                 665                 670

Met Glu Gln Pro Asp Ala Val Pro Ala Gln Lys His Leu Ala Ala Glu
            675                 680                 685

Ile Cys Ala Glu Ile Ala Lys His Ser Val Ala Gln Arg Asp Tyr Glu
        690                 695                 700

Lys Ala Ile Lys Phe Tyr Arg Glu Ala Leu Val His Cys Glu Thr Asp
705                 710                 715                 720

Asn Lys Val Asp Asn Tyr Met Thr Leu Ser Arg Leu Ile Asp Leu Leu
                725                 730                 735

Arg Arg Cys Gly Lys Leu Glu Asp Val Pro Arg Phe Phe Ser Met Ala
            740                 745                 750

Glu Lys Arg Asn Ser Arg Ala Lys Leu Glu Pro Gly Phe Gln Tyr Cys
            755                 760                 765

Lys Gly Leu Tyr Leu Trp Tyr Thr Gly Glu Pro Asn Asp Ala Leu Arg
        770                 775                 780

His Phe Asn Lys Ala Arg Lys Asp Arg Asp Trp Gly Gln Asn Ala Leu
785                 790                 795                 800

Tyr Asn Met Ile Glu Ile Cys Leu Asn Pro Asp Asn Glu Thr Val Gly
                805                 810                 815

Gly Glu Val Phe Glu Asn Leu Asp Gly Asp Ser Asn Ser Thr Glu Lys
            820                 825                 830

Gln Glu Ser Val Gln Leu Ala Val Arg Thr Ala Glu Lys Leu Leu Lys
            835                 840                 845

Glu Leu Lys Pro Gln Thr Val Gln Gly His Val Gln Leu Arg Ile Met
        850                 855                 860

Glu Asn Tyr Cys Leu Met Ala Thr Lys Gln Lys Ser Asn Val Glu Gln
865                 870                 875                 880

Ala Leu Asn Thr Phe Thr Glu Ile Ala Ala Ser Glu Lys Glu His Ile
                885                 890                 895

Pro Ala Leu Leu Gly Met Ala Thr Ala Tyr Met Ile Leu Lys Gln Thr
            900                 905                 910
```

```
Pro Arg Ala Arg Asn Gln Leu Lys Arg Ile Ala Lys Met Asn Trp Asn
            915                 920                 925

Ala Ile Asp Ala Glu Glu Phe Glu Lys Ser Trp Leu Leu Ala Asp
        930                 935                 940

Ile Tyr Ile Gln Ser Ala Lys Tyr Asp Met Ala Glu Asp Leu Leu Lys
945                 950                 955                 960

Arg Cys Leu Arg His Asn Arg Ser Cys Cys Lys Ala Tyr Glu Tyr Met
                965                 970                 975

Gly Tyr Ile Met Glu Lys Glu Gln Ala Tyr Thr Asp Ala Ala Leu Asn
                980                 985                 990

Tyr Glu Met Ala Trp Lys Tyr Ser Asn Arg Thr Asn Pro Ala Val Gly
                995                 1000                1005

<210> SEQ ID NO 40
<211> LENGTH: 1115
<212> TYPE: PRT
<213> ORGANISM: Caenorhabditis elegans

<400> SEQUENCE: 40

Met Lys Val Ala Ala Asn Glu Leu Ala Ile Ser Thr Ile His Phe Leu
1               5                   10                  15

Pro Gly His Ile Glu Lys Ala Lys Ala Ser Ile Met Met Lys Asp Trp
                20                  25                  30

Arg Gly Val Met Asp Cys Ile Met Asn Ala Asp Gln Pro Glu Gly Ser
            35                  40                  45

Asn Pro Tyr Ile Glu Val Leu Arg Thr Val His Gly Ile Cys Tyr Ala
        50                  55                  60

Gly Glu Val Ser Met Leu Lys Arg Thr Leu Gln Leu Leu Lys Ser
65                  70                  75              80

Leu Asp Glu Asn Glu Ala Thr Asn His Val Leu Tyr Ala Arg Ile Thr
                85                  90                  95

Lys Leu Leu Val Ser Ile Ser Gly Arg Asp Glu Lys Ile Leu Arg His
                100                 105                 110

Ala Arg Asp Phe Leu Thr Arg Ala Leu Lys Ile Ser Arg Lys Pro Asp
            115                 120                 125

Tyr Val Ala Leu Ser Met Arg Ile Ala Phe Gly Leu Gly Gly Ala Lys
        130                 135                 140

Glu Val Ser Thr Leu Ser Gln Glu Leu Val Ala Leu Asp Cys Glu Asp
145                 150                 155                 160

Ser Tyr Ala Val Leu Ser Ser Val Val Ser Met Leu Met Ile Ser Arg
                165                 170                 175

Val Ser Asp Ala Arg Ala Gln Phe Asp Ile Leu Pro Ser Ala His Pro
            180                 185                 190

Lys Leu Leu Glu Ser Pro Leu Tyr Tyr Leu Ile Ala Ser Val Leu Ala
        195                 200                 205

Lys Gln Ser Lys Asp Lys Ser Phe Glu Asn Phe Arg Gln His Ile Glu
    210                 215                 220

Asn Leu Val Glu Met Leu Arg Asn Gln Leu Gln Ser Phe Pro Phe Gly
225                 230                 235                 240

Leu Asp Tyr Leu Ser Leu Phe Ser Ser Asp Leu Leu Tyr Ser Ala Val
                245                 250                 255

Glu Gln Cys Phe Asp Phe Tyr Pro Leu Val Pro Ile Lys Ala Pro Asp
            260                 265                 270

Asp Cys Met Lys Leu Thr Ala Lys Thr Leu Gln Met Ile Tyr Asp Val
        275                 280                 285
```

```
Ala Pro Gly Leu Ala His Cys Thr Leu Gln Leu Ala Arg Asn Ser Tyr
    290                 295                 300

Leu Cys Ser Asn Thr Asn Ala Ala Glu Lys Trp Ile Glu Lys Val Leu
305                 310                 315                 320

Asp Lys Asp Asp Ser Leu Ala Asp Ala His Ile Leu Arg Ala Glu Leu
                325                 330                 335

Ile Leu Asp Arg Gly Lys Ile Thr Asp Ala Asp Asp Ala Leu Val
            340                 345                 350

Thr Gly Leu Asn Phe Asn Phe Lys Leu Arg Glu Thr Ser Leu Tyr His
        355                 360                 365

Leu Ile Lys Ser Lys Thr Phe Lys Arg Asn Glu Asn Asp Glu Ala
370                 375                 380

Ile Lys Thr Leu Lys Met Ala Leu Gln Ile Pro Arg Lys Glu Pro Ser
385                 390                 395                 400

Lys Asn Leu Phe Gln Pro Lys Glu Ser Ala Asp Thr His Lys Ile Ser
                405                 410                 415

Val Gln Leu Glu Leu Ile Asp Thr Leu Gln His Met Lys Arg Ile Gln
                420                 425                 430

Glu Ala Glu Thr Thr Met Thr Asp Ala Leu Ala Glu Trp Ala Gly Gln
            435                 440                 445

Pro Glu Gln Asp Gln Leu Val Ile Ala Gln Ala Gln Leu Tyr Leu Thr
        450                 455                 460

Lys Gly His Val Glu Arg Ala Leu Gly Ile Leu Lys Lys Ile Gln Pro
465                 470                 475                 480

Gly Gln Ser Asn Phe His Leu Ser Arg Ile Lys Met Ala Glu Ile Tyr
                485                 490                 495

Leu Glu Glu Lys Lys Asp Lys Arg Met Phe Ala Ala Cys Tyr Arg Glu
                500                 505                 510

Leu Leu Lys Val Glu Ala Thr Pro Gly Ser Tyr Ser Leu Leu Gly Asp
            515                 520                 525

Ala Phe Met Lys Val Gln Glu Pro Glu Asp Ala Ile Asn Phe Tyr Glu
        530                 535                 540

Gln Ala Leu Lys Met Gln Ser Lys Asp Val Gln Leu Ala Glu Lys Ile
545                 550                 555                 560

Gly Glu Ala Tyr Val Met Ala His Leu Tyr Ser Lys Ala Val Asn Phe
                565                 570                 575

Tyr Glu Ser Ser Met Asn Ile Tyr Lys Asp Lys Asn Met Arg Leu Lys
                580                 585                 590

Leu Ala Asn Leu Leu Leu Lys Leu Arg Asn Phe Glu Lys Cys Glu Lys
            595                 600                 605

Val Leu Arg Ala Pro Phe Glu Arg Asp Pro Glu Pro Val Gly Thr Glu
        610                 615                 620

Thr Ile Gln Thr Tyr Ile Gln Phe Leu Leu Leu Leu Ala Glu Cys His
625                 630                 635                 640

Glu Met Met Asp Asn Val Pro Glu Ala Met Asn Asp Phe Glu Lys Ala
                645                 650                 655

Lys Ser Leu His Ser Arg Ile Gln Asp Lys Thr Leu Thr Ala Ala Leu
                660                 665                 670

Lys Lys Glu Gly Ala Arg Ile Cys Asn Leu Gln Ala Glu Leu Leu Tyr
            675                 680                 685

Arg Arg Arg Glu Phe Ser Gln Ala Val Asp Ile Cys Lys Gln Ala Leu
        690                 695                 700

Ala Tyr His Glu Thr Asp Leu Lys Ala Asn Leu Leu Leu Ser Lys Ile
705                 710                 715                 720
```

-continued

```
Phe Lys Glu Glu Asn Lys Trp Thr Leu Val Leu Gln Pro Cys Gln Thr
            725                 730                 735

Val Ile Gln Val Asp Pro His Asn Asp Glu Ala Asn Ser Ile Leu Ala
        740                 745                 750

Asp Phe Tyr Tyr Ile Arg Ser Glu Ala Ala His Ala Ser Thr Ser Tyr
    755                 760                 765

Thr Thr Leu Leu Asn Thr Asn Pro Gln His Trp His Ala Leu Ser Arg
770                 775                 780

Val Val Glu Leu Phe Cys Arg Asn Gly Glu Gln Asn Ala Ala Glu Lys
785                 790                 795                 800

His Leu Asp Arg Ala Lys Glu Val Asn Pro Arg Cys Val Thr Glu Ser
                805                 810                 815

Gly Tyr Asn Val Cys Arg Gly Arg Phe Glu Trp Tyr Thr Gly Asp Gln
            820                 825                 830

Asn Glu Ala Leu Arg Tyr Tyr Ser Arg Thr Lys Asp Ser Ala Ala Gly
        835                 840                 845

Trp Arg Glu Lys Ala Leu Tyr Tyr Met Ile Asp Ile Cys Leu Asn Pro
    850                 855                 860

Asp Asn Glu Ile Ile Ile Asp Glu Asn Ser Val Glu Asn Pro Glu Thr
865                 870                 875                 880

Thr Lys Ile Ile Tyr Leu Val Ser Glu Leu Trp Lys Lys Leu Val Asn
                885                 890                 895

Ser Lys Asn Leu Pro Asn Ile Thr Ser Ile Tyr Ser Glu Asn Phe Gln
            900                 905                 910

Ser Thr Asp Arg Phe Leu Leu Ala Gln Asn Phe Ile Arg Met His Thr
        915                 920                 925

Thr Asp Lys Ser Ala Ile Gln Ala Ala Leu Asp Glu Phe Asn Arg Met
    930                 935                 940

Ala Phe Asn Ala Asp Arg Ser Gln Val Thr Asn Val Gly Ala Val Phe
945                 950                 955                 960

Gly Val Ala Arg Gly His Val Leu Leu Lys Gln Val Gln Lys Ala Lys
                965                 970                 975

Thr Val Leu Lys Met Val Asn Gly Arg Val Trp Asn Phe Asp Asp Ser
            980                 985                 990

Asp Tyr Leu Glu Lys Cys Trp Leu Met Leu Ala Asp Ile Tyr Ile Asn
        995                 1000                1005

Gln Asn Lys Asn Asp Gln Ala Val Thr Phe Leu Asp Leu Val Phe Lys
    1010                1015                1020

Tyr Asn Cys Asn Cys Leu Lys Ala Phe Glu Leu Tyr Gly Tyr Met Arg
1025                1030                1035                1040

Glu Lys Glu Gln Lys Tyr Val Glu Ala Tyr Lys Met Tyr Glu Lys Ala
                1045                1050                1055

Phe Met Ala Thr Lys Glu Arg Asn Pro Gly Phe Gly Tyr Lys Leu Ala
            1060                1065                1070

Phe Thr Tyr Leu Lys Ala Lys Arg Leu Phe Ala Cys Ile Glu Thr Cys
        1075                1080                1085

Gln Lys Val Leu Asp Leu Asn Pro Gln Tyr Pro Lys Ile Lys Lys Glu
    1090                1095                1100

Ile Met Asp Lys Ala Lys Ala Leu Ile Arg Thr
1105                1110                1115

<210> SEQ ID NO 41
<211> LENGTH: 764
<212> TYPE: PRT
<213> ORGANISM: Homo sapiens
```

<400> SEQUENCE: 41

```
Ile Glu Leu Val Ser Cys Val Gly Trp Thr Thr Ala Glu Glu Leu Tyr
  1               5                  10                  15

Ser Cys Ser Asp Asp His Gln Ile Val Lys Trp Asn Leu Leu Thr Ser
             20                  25                  30

Glu Thr Thr Gln Ile Val Lys Leu Pro Asp Asp Ile Tyr Pro Ile Asp
         35                  40                  45

Phe His Trp Phe Pro Lys Ser Leu Gly Val Lys Gln Thr Gln Ala
     50                  55                  60

Glu Ser Phe Val Leu Thr Ser Ser Asp Gly Lys Phe His Leu Ile Ser
 65                  70                  75                  80

Lys Leu Gly Arg Val Glu Lys Ser Val Glu Ala His Cys Gly Ala Val
                 85                  90                  95

Leu Ala Gly Arg Trp Asn Tyr Glu Gly Thr Ala Leu Val Thr Val Gly
             100                 105                 110

Glu Asp Gly Gln Ile Lys Ile Trp Ser Lys Thr Gly Met Leu Arg Ser
         115                 120                 125

Thr Leu Ala Gln Gln Gly Thr Pro Val Tyr Ser Val Ala Trp Gly Pro
130                 135                 140

Asp Ser Glu Lys Val Leu Tyr Thr Ala Gly Lys Gln Leu Ile Ile Lys
145                 150                 155                 160

Pro Leu Gln Pro Asn Ala Lys Val Leu Gln Trp Lys Ala His Asp Gly
                 165                 170                 175

Ile Ile Leu Lys Val Asp Trp Asn Ser Val Asn Asp Leu Ile Leu Ser
             180                 185                 190

Ala Gly Glu Asp Cys Lys Tyr Lys Val Trp Asp Ser Tyr Gly Arg Pro
         195                 200                 205

Leu Tyr Asn Ser Gln Pro His Glu His Pro Ile Thr Ser Val Ala Trp
210                 215                 220

Ala Pro Asp Gly Glu Leu Phe Ala Val Gly Ser Phe His Thr Leu Arg
225                 230                 235                 240

Leu Cys Asp Lys Thr Gly Trp Ser Tyr Ala Leu Glu Lys Pro Asn Thr
                 245                 250                 255

Gly Ser Ile Phe Asn Ile Ala Trp Ser Ile Asp Gly Thr Gln Ile Ala
             260                 265                 270

Gly Ala Cys Gly Asn Gly His Val Phe Ala His Val Val Glu Gln
         275                 280                 285

His Trp Glu Trp Lys Asn Phe Gln Val Thr Leu Thr Lys Arg Arg Ala
290                 295                 300

Met Gln Val Arg Asn Val Leu Asn Asp Ala Val Asp Leu Leu Glu Phe
305                 310                 315                 320

Arg Asp Arg Val Ile Lys Ala Ser Leu Asn Tyr Ala His Leu Val Val
                 325                 330                 335

Ser Thr Ser Leu Gln Cys Tyr Val Phe Ser Thr Lys Asn Trp Asn Thr
             340                 345                 350

Pro Ile Ile Phe Asp Leu Lys Glu Gly Thr Val Ser Leu Ile Leu Gln
         355                 360                 365

Ala Glu Arg His Phe Leu Leu Val Asp Gly Ser Ser Ile Tyr Leu Tyr
370                 375                 380

Ser Tyr Glu Gly Arg Phe Ile Ser Ser Pro Lys Phe Pro Gly Met Arg
385                 390                 395                 400

Thr Asp Ile Leu Asn Ala Gln Thr Val Ser Leu Ser Asn Asp Thr Ile
                 405                 410                 415
```

```
Ala Ile Arg Asp Lys Ala Asp Glu Lys Ile Ile Phe Leu Phe Glu Ala
            420                 425                 430

Ser Thr Gly Lys Pro Leu Gly Asp Gly Lys Phe Leu Ser His Lys Asn
        435                 440                 445

Glu Ile Leu Glu Ile Ala Leu Asp Gln Lys Gly Leu Thr Asn Asp Arg
    450                 455                 460

Lys Ile Ala Phe Ile Asp Lys Asn Arg Asp Leu Cys Ile Thr Ser Val
465                 470                 475                 480

Lys Arg Phe Gly Lys Glu Gln Ile Ile Lys Leu Gly Thr Met Val
                485                 490                 495

His Thr Leu Ala Trp Asn Asp Thr Cys Asn Ile Leu Cys Gly Leu Gln
            500                 505                 510

Asp Thr Arg Phe Ile Val Trp Tyr Tyr Pro Asn Thr Val Tyr Val Asp
        515                 520                 525

Arg Asp Ile Leu Pro Lys Thr Leu Tyr Glu Arg Asp Ala Ser Glu Phe
    530                 535                 540

Ser Lys Asn Pro His Ile Val Ser Phe Val Gly Asn Gln Val Thr Ile
545                 550                 555                 560

Arg Arg Ala Asp Gly Ser Leu Val His Ile Ser Ile Thr Pro Tyr Pro
                565                 570                 575

Ala Ile Leu His Glu Tyr Val Ser Ser Ser Lys Trp Glu Asp Ala Val
            580                 585                 590

Arg Leu Cys Arg Phe Val Lys Glu Gln Thr Met Trp Ala Cys Leu Ala
        595                 600                 605

Ala Met Ala Val Ala Asn Arg Asp Met Thr Thr Ala Glu Ile Ala Tyr
    610                 615                 620

Ala Ala Ile Gly Glu Ile Asp Lys Val Gln Tyr Ile Asn Ser Ile Lys
625                 630                 635                 640

Asn Leu Pro Ser Lys Glu Ser Lys Met Ala His Ile Leu Leu Phe Ser
                645                 650                 655

Gly Asn Ile Gln Glu Ala Glu Ile Val Leu Leu Gln Ala Gly Leu Val
            660                 665                 670

Tyr Gln Ala Ile Gln Ile Asn Ile Asn Leu Tyr Asn Trp Glu Arg Ala
        675                 680                 685

Leu Glu Leu Ala Val Lys Tyr Lys Thr His Val Asp Thr Val Leu Ala
    690                 695                 700

Tyr Arg Gln Lys Phe Leu Glu Thr Phe Gly Lys Gln Glu Thr Asn Lys
705                 710                 715                 720

Arg Tyr Leu His Tyr Ala Glu Gly Leu Gln Ile Asp Trp Glu Lys Ile
                725                 730                 735

Lys Ala Lys Ile Glu Met Glu Ile Thr Lys Glu Arg Gly Gln Ser Ser
            740                 745                 750

Ser Ser Gln Ser Ser Lys Ser Ile Gly Leu Lys Pro
        755                 760

<210> SEQ ID NO 42
<211> LENGTH: 760
<212> TYPE: PRT
<213> ORGANISM: Caenorhabditis elegans

<400> SEQUENCE: 42

Met Lys Leu Lys Leu Ser Ala Ser Arg Lys Thr Arg His Thr Glu Met
  1               5                  10                  15

Val Cys Gly Val Gly Trp Ile Gly Thr Glu Ala Ile Leu Ser Ala Ala
             20                  25                  30
```

-continued

```
Asp Asp His Val Phe Leu Leu Thr Asn Thr Ala Thr Asn Glu Ser Gln
        35                  40                  45

Gln Ile Leu Asn Met Pro Glu Thr Phe Phe Pro Thr Ser Leu His Ile
    50                  55                  60

Phe Pro Arg Ser Gln Thr Lys Gly Gly Gln Asn Asp Val Phe Ala Val
65                  70                  75                  80

Ser Thr Ser Asp Gly Lys Ile Asn Ile Leu Ser Arg Asn Gly Lys Val
                85                  90                  95

Glu Asn Met Val Asp Ala His Asn Gly Ala Ala Leu Cys Ala Arg Trp
            100                 105                 110

Asn Ser Asp Gly Thr Gly Leu Leu Ser Ser Gly Glu Asp Gly Phe Val
        115                 120                 125

Lys Met Trp Ser Arg Ser Gly Met Leu Arg Ser Val Leu Ala Gln Phe
    130                 135                 140

Ala Thr Ala Val Tyr Cys Val Ala Trp Asp Ser Thr Ser Asn Val
145                 150                 155                 160

Leu Tyr Cys Asn Ala Asp His Cys Tyr Ile Lys Ser Leu Lys Met Gln
                165                 170                 175

Val Ala Pro Ile Lys Trp Lys Ala His Asp Gly Ile Ile Leu Cys Cys
            180                 185                 190

Asp Trp Asn Pro Thr Ser Asp Leu Ile Val Thr Gly Gly Glu Asp Leu
        195                 200                 205

Lys Phe Lys Val Trp Asp Gly Phe Gly Gln Ile Leu Phe Asn Ser Ser
210                 215                 220

Val His Asp Tyr Pro Ile Thr Ser Ile Ser Trp Asn Thr Asp Gly Thr
225                 230                 235                 240

Leu Phe Ala Val Gly Ser His Asn Ile Leu Arg Leu Cys Asp Lys Ser
                245                 250                 255

Gly Trp Ser His Ser Leu Glu Lys Met Asn Ala Gly Ser Val Met Ala
            260                 265                 270

Leu Ser Trp Ser Pro Asp Gly Thr Gln Leu Ala Val Gly Thr Ala Ala
        275                 280                 285

Gly Leu Val Phe His Ala His Ile Ile Asp Lys Arg Leu Thr Tyr Glu
    290                 295                 300

Glu Phe Glu Ile Val Gln Thr Gln Lys Thr Val Ile Glu Val Arg Asp
305                 310                 315                 320

Val Ser Ser Glu Val Ser Arg Glu Thr Leu Glu Thr Lys Glu Arg Ile
                325                 330                 335

Ser Lys Ile Ala Ile Leu Tyr Lys Tyr Leu Ile Val Val Thr Ser Ser
            340                 345                 350

His Ile Tyr Ile Tyr Ser Ser Lys Asn Trp Asn Thr Pro Thr Met Ile
        355                 360                 365

Glu Tyr Asn Glu Arg Thr Val Asn Ile Val Gln Cys Glu Lys Ile
    370                 375                 380

Phe Leu Val Ser Asp Gly Met Thr Ile Thr Ile Phe Thr Tyr Glu Gly
385                 390                 395                 400

Arg Lys Leu Ile Asn Leu Asn Pro Pro Gly Gln Val Met Ala Leu Leu
                405                 410                 415

Asp Glu Arg Lys Ile Asp Leu Ala Asn Asp Thr Leu Val Val Arg Asp
            420                 425                 430

Arg Ala Asp Asn Lys Val Leu His Phe Phe Asp Pro Thr Thr Gly Lys
        435                 440                 445

Ala Gln Gly Asp Gly Asn Leu Lys His Glu His Asp Ile Val Glu Leu
    450                 455                 460
```

```
Thr Val Asn Gln Cys Gly Pro Leu Asn Asp Arg Asn Val Ala Phe Arg
465                 470                 475                 480

Asp Gln Ile Gly Ala Val His Ile Ala Met Val Lys Thr Phe Gly Val
            485                 490                 495

Ser Gln Arg Met Val Lys Ile Gly Ser Leu Val Glu Gln Leu Val Phe
        500                 505                 510

Asn Asp Val Thr Asn Met Leu Cys Gly Ile Ser Glu Gly Lys Ile Ala
            515                 520                 525

Val Trp Pro Leu Pro Asn Val Ala Phe His Asp Arg Asn Leu Leu Gln
530                 535                 540

Lys Ser Leu Ile Gln Lys Asn Ile Gly Ser Val Gly Lys Phe Pro Gln
545                 550                 555                 560

Leu Ala Asn Phe Ala Gly Asn Thr Ile Val Ile Arg Lys Ser Asp Gly
            565                 570                 575

Cys Leu Leu Pro Thr Gly Ile Leu Pro Phe Tyr Gly Thr Leu Ile Thr
            580                 585                 590

Met Ala Ser Gln Ser Lys Trp Asp Gln Ala Ile Arg Leu Cys Arg Ser
        595                 600                 605

Ile Gly Asn Asp Thr Met Trp Ala Thr Phe Ala Gly Leu Ala Val Leu
610                 615                 620

His Lys Asn Met Ile Val Met Glu Ile Ala Tyr Ala Ala Leu Glu Asp
625                 630                 635                 640

Asp Glu Lys Val Ser Leu Ile Asn Glu Ile Lys Asp Lys Thr Asp Lys
            645                 650                 655

Glu Thr Arg Gln Ala Met Gln Val Val Leu Thr Gly Lys Leu Ala Asp
        660                 665                 670

Ala Asp Val Leu Leu Glu Arg Ser Gly Leu Ser Phe Arg Ser Leu Met
            675                 680                 685

Leu Asn Ile Gln Met Phe Lys Trp Lys Arg Ala Leu Glu Leu Gly Leu
690                 695                 700

Lys Asn Lys Gln Trp Leu Glu Ile Val Met Gly Tyr Arg Glu Lys Tyr
705                 710                 715                 720

Leu Lys Asn Cys Gly Gln Lys Glu Thr Asp Pro Leu Phe Leu Lys His
            725                 730                 735

Met Ser Glu Val Glu Ile Asp Trp Val His Ile Arg Glu Leu Ile Ala
        740                 745                 750

Ala Glu Lys Ala Lys Gly Asn Asn
            755                 760

<210> SEQ ID NO 43
<211> LENGTH: 8
<212> TYPE: PRT
<213> ORGANISM: Chlamydomonas reinhardtii

<400> SEQUENCE: 43

Leu Glu Gly Glu Thr Asp Gln Ala
  1               5

<210> SEQ ID NO 44
<211> LENGTH: 8
<212> TYPE: PRT
<213> ORGANISM: Chlamydomonas reinhardtii
```

```
<400> SEQUENCE: 44

Gly Ile Asp Pro Tyr Cys Val Glu
  1               5

<210> SEQ ID NO 45
<211> LENGTH: 23
<212> TYPE: DNA
<213> ORGANISM: Artificial Sequence
<220> FEATURE:
<223> OTHER INFORMATION: primer for PCR

<400> SEQUENCE: 45
garacbgayc argcbgayaa rta                                              23

<210> SEQ ID NO 46
<211> LENGTH: 23
<212> TYPE: DNA
<213> ORGANISM: Artificial Sequence
<220> FEATURE:
<223> OTHER INFORMATION: primer for PCR

<400> SEQUENCE: 46
gcytcvacrc artavggrtc rat                                              23

<210> SEQ ID NO 47
<211> LENGTH: 27
<212> TYPE: PRT
<213> ORGANISM: Chlamydomonas reinhardtii

<400> SEQUENCE: 47

Ala Ala Thr Asn Leu Ala Phe Leu Tyr Phe Leu Glu Gly Glu Thr Asp
  1               5                  10                  15

Gln Ala Asp Lys Tyr Ser Glu Met Ala Leu Lys
             20                  25

<210> SEQ ID NO 48
<211> LENGTH: 26
<212> TYPE: PRT
<213> ORGANISM: Chlamydomonas reinhardtii

<400> SEQUENCE: 48

Ser Leu Phe Asn Glu Ala Ala Gly Ile Asp Pro Tyr Cys Val Glu Ala
  1               5                  10                  15

Ile Tyr Asn Leu Gly Leu Val Ser Gln Arg
             20                  25

<210> SEQ ID NO 49
<211> LENGTH: 11
<212> TYPE: PRT
<213> ORGANISM: Chlamydomonas reinhardtii

<400> SEQUENCE: 49

Gly Val Tyr Phe Asp Glu Asp Phe His Val Arg
  1               5                  10

<210> SEQ ID NO 50
<211> LENGTH: 11
<212> TYPE: PRT
<213> ORGANISM: Chlamydomonas reinhardtii

<400> SEQUENCE: 50

Tyr Val Ser Ala Ile Asp Gln Gln Val Glu Arg
  1               5                  10
```

CHLAMYDOMONAS INTRAFLAGELLAR TRANSPORT 88 (IFT-88)

CROSS REFERENCE TO RELATED APPLICATIONS

This application is a divisional of U.S. application Ser. No. 12/481,536, filed Jun. 9, 2009, now U.S. Pat. No. 7,985,583, which is a divisional of U.S. application Ser. No. 10/839,016, filed May 5, 2004, now U.S. Pat. No. 7,553,674, which is a continuation of U.S. application Ser. No. 09/866,582, filed May 24, 2001, now abandoned, which claims the benefit of U.S. Provisional Application No. 60/206,923, filed May 24, 2000, all of which are incorporated herein by reference in their entireties.

STATEMENT AS TO FEDERALLY SPONSORED RESEARCH

This invention was made with government support under grant no. GM030626 awarded by the National Institutes of Health. The government has certain rights in the invention.

TECHNICAL FIELD

This invention relates to intraflagellar transport proteins.

BACKGROUND

Cilia are tiny cellular structures that protrude from cells. They are about 0.25 micrometers in diameter and contain a bundle of microtubules. They are widespread among living organisms, occurring in most animals, many single-celled eukaryotes, and in some lower plants.

Cilia tend to function in one of two ways. They may move fluid across the surface of the cell or they may propel cells through a fluid. They may also serve to gather food. In humans, cilia on the surfaces of respiratory epithelia function to push mucus and trapped particles and dead cells out of the lungs. Cilia also function to carry eggs through the oviduct. Cilia function in myriad ways in different kinds of cells.

Flagella are structures related to cilia. They are similar in internal structure but tend to be much longer than cilia. Sperm cells are propelled by flagella, as are many other single-celled eukaryotes.

Groups of cilia tend to move together in coordinated unidirectional waves. The motion made by each individual cilium is whiplike. This motion includes two phases. First, the cilium extends forward, pushing against the surrounding liquid as it goes. At the end of its forward stroke, the cilium bends, reducing viscous drag as it pulls itself back to its original position. By contrast, flagella tend to propagate quasi-sinusoidal waves. Despite the differences in their external motions, the molecular basis of movement in both cilia and flagella appear to be the same.

Cilia and flagella move by bending their core—the axoneme. The axoneme is composed of microtubules and associated proteins. The pattern of microtubules is distinctive: nine pairs of microtubules that form a ring around two single microtubules. This arrangement is typically referred to as "9+2". The pairs are composed of one complete and one partial microtubule. These microtubules extend the full length of the axoneme, which can range in length from 10-200 micrometers.

Intraflagellar transport (IFT) is a dynein and kinesin-based motility process in which non-membrane-bound particles move along flagellar microtubules, just beneath the flagellar membrane, from the base to the tip of the flagellum and back. IFT is essential for the assembly and maintenance of all cilia and flagella, including non-motile primary cilia and sensory cilia. Recent results indicate that defects in IFT are a primary cause of several human diseases.

SUMMARY

The invention is based on the discovery of various new IFT particle polypeptides and the genes that encode them.

In general, the invention features, an isolated nucleic acid molecule selected from the group consisting of: a) a nucleic acid molecule having a nucleotide sequence which is at least 90% identical to the nucleotide sequence of *Chlamydomonas* intraflagellar transport (IFT) particle protein gene 20, 27, 46, 52, 57, 72, 88, 122, 139, or Che-2, or a complement thereof; b) a nucleic acid molecule comprising at least 15 nucleotide residues and having a nucleotide sequence identical to at least 15 consecutive nucleotide residues of the nucleotide sequence of *Chlamydomonas* IFT particle protein gene 20, 27, 46, 52, 57, 72, 88, 122, or 139, or Che-2, or a complement thereof; c) a nucleic acid molecule which encodes a polypeptide comprising the amino acid sequence of *Chlamydomonas* IFT particle protein 20, 27, 46, 52, 57, 72, 88, 122, 139, or Che-2; or d) a nucleic acid molecule which encodes a polypeptide comprising at least 10 amino acids and having an amino acid sequence identical to at least 10 consecutive amino acids of the amino acid sequence of *Chlamydomonas* IFT particle protein 20, 27, 46, 52, 57, 72, 88, 122, 139, or Che-2.

The nucleic acid molecules can further include nucleic acid sequences encoding a heterologous polypeptide. The invention also features a vector including the nucleic acid molecules and host cells including the new nucleic acid molecules, such as non-human mammalian host cells.

The invention also features an isolated polypeptide selected from the group consisting of: a) a polypeptide comprising at least 10 amino acids and having an amino acid sequence identical to at least 10 consecutive amino acids of the amino acid sequence of *Chlamydomonas* intraflagellar transport (IFT) particle protein 20, 27, 46, 52, 57, 72, 88, 122, 139, or Che-2; b) a polypeptide comprising the amino acid sequence of *Chlamydomonas* IFT particle protein 20, 27, 46, 52, 57, 72, 88, 122, 139, or Che-2, wherein the polypeptide comprises one or more conservative amino acid substitutions that do not inhibit the biological activity of the polypeptide relative to a corresponding native *Chlamydomonas* IFT particle protein; and c) a polypeptide which is encoded by a nucleic acid molecule comprising a nucleotide sequence which is at least 90% identical to a nucleic acid consisting of the nucleotide sequence of *Chlamydomonas* IFT particle protein gene 20, 27, 46, 52, 57, 72, 88, 122, 139, or Che-2, or a complement thereof.

In another aspect, the invention features an antibody that selectively binds to the new polypeptides.

Yet other nucleic acid molecules of the invention include those having sequences that (1) are at least 90% identical to the nucleotide sequence of mouse intraflagellar transport (IFT) particle protein gene 57 (or are complements thereof); (2) are at least 15 nucleotide residues long and have a sequence identical to at least 15 consecutive nucleotide residues of the nucleotide sequence of mouse IFT particle protein gene 57 (or complements thereof); (3) encode a polypeptide that is or that includes the amino acid sequence of mouse IFT particle protein 57; or (4) encode a polypeptide having at least 10 amino acids and an amino acid sequence identical to at least 10 consecutive amino acids of the amino acid sequence of mouse IFT particle protein 57. For example, a nucleic acid molecule of the invention can be a nucleic acid having the nucleotide sequence of mouse IFT particle protein gene 57 (or a complement thereof) or a nucleic acid molecule that encodes a polypeptide having the amino acid sequence of mouse IFT particle protein 57.

Yet other polypeptides of the invention include those having sequences that (1) include at least 10 amino acid residues and have an amino acid sequence identical to at least 10 consecutive amino acids of the amino acid sequence of mouse intraflagellar transport (IFT) particle protein 57; (2) include the amino acid sequence of mouse IFT particle protein 57; or (3) are encoded by a nucleic acid molecule having a nucleotide sequence that is at least 90% identical to a nucleic acid consisting of the nucleotide sequence of mouse IFT particle protein gene 57 (or a complement thereof). For example, a polypeptide of the invention can include the amino acid sequence of mouse IFT particle protein 57. Any of the polypeptides described herein can include one or more conservative amino acid substitutions that do not inhibit the biological activity of the polypeptide relative to native mouse IFT particle protein 57 (e.g., polypeptides that retain at least 50% (e.g. 60%, 75%, 80%, 90%, or 95% or more) of one or more of the biological activities of a native IFT polypeptide (e.g. particle protein 57)).

Various methods are also within the scope of the invention. For example, the invention features a method for identifying a candidate compound that modulates (e.g., inhibits or stimulates) the activity of mouse intraflagellar transport (IFT) particle protein 57. The method can be carried out, for example, by contacting a test compound with an isolated IFT particle polypeptide and determining whether the test compound interacts with the polypeptide. Interaction indicates that the test compound is a candidate modulator of mouse IFT particle protein 57. Similarly, one can carry out methods to identify a candidate compound that modulates (e.g., inhibits or stimulates) the activity of a human intraflagellar transport (IFT) particle protein. These methods can be carried out, for example, by contacting a test compound with an isolated IFT particle polypeptide and determining whether the test compound interacts with the polypeptide. Here again, interaction indicates that the test compound is a candidate modulator of a human IFT particle protein. The isolated human IFT particle polypeptide can be human IFT particle polypeptide 20-1, 20-2, 20-3, 27, 46, 52, 57-1, 57-2, 72, 88, 122, 139-1, 139-2 or Che-2.

The methods described above can include additional steps. For example, one can contact that candidate modulator with one or more cells (e.g. cultured cells) that have functional cilia and determine whether the modulator modulates (e.g. inhibits or stimulates) cilia function. In the event cilia function is inhibited, the candidate modulate is an IFT particle protein inhibitory agent. In other embodiments, the candidate modulator can be contacted with one or more cells (e.g. cultured cells) that have non-functional or functionally impaired cilia (e.g. a cell or cells lacking a specific IFT particle protein). Restoration (partial or complete) of cilia function indicates that the candidate modulator is an IFT particle protein restorative agent.

Other methods of the invention can be used to identify a candidate compound that restores the activity of a defective or absent human intraflagellar transport (IFT) particle protein. These methods can be carried out by, for example, obtaining a mixture of isolated IFT particle polypeptides that include (i) all but one of the IFT particle polypeptides required to form the IFT particle, and (ii) a medium that enables the IFT particle polypeptides to form the IFT particle when all normal IFT particle polypeptides that constitute that IFT particle are present. The mixture is then contacted with a test compound, after which one determines whether the test compound enables the IFT particle to be formed. IFT particle formation indicates that the test compound is a candidate compound that restores the activity of a defective or absent human IFT particle protein. These methods can be carried out by contacting the candidate compound with one or more cells (e.g., cultured cells) that have non-functional (or impaired) cilia and that lack a specific IFT particle protein. One can then determine whether the candidate compound restores cilia function, which would indicate that the candidate compound is an IFT particle protein restorative agent. These methods (and others of the invention) can be carried out with a human IFT particle polypeptide (e.g., human IFT particle polypeptides 20-1, 20-2, 20-3, 27, 46, 52, 57-1, 57-2, 72, 88, 122, 139-1, 139-2 or Che-2; or combinations thereof).

Diagnostic methods are also within the scope of the invention. For example, the invention features a method of diagnosing a disorder in a tissue in a subject that is associated with (e.g. caused by, in whole or in part) a defective or absent human intraflagellar transport (IFT) particle protein. The method can be carried out, for example, by disrupting cells from a tissue sample, contacting the disrupted cells with an antibody that specifically binds to a normal human IFT particle protein, and detecting binding of the antibody to any IFT particle protein in the sample. An absence of specific binding indicates that the tissue is one in which IFT particle protein is defective or absent. Disorders (or diseases or conditions) associated with this tissue defect include, but are not limited to, kidney disease, retinal disorders, thyroid disorders, chondrocyte disease, olfactory disease, azoospermia, and primary ciliary dyskinesia.

In other embodiments, the methods are methods of treatment. For example, the invention features a method of treating a disorder in a subject (e.g. a disorder associated with a defective or absent intraflagellar transport (IFT) protein) by administering to the subject a human IFT particle polypeptide. The amount of the polypeptide is an amount that is effective to compensate for the defective or absent IFT particle protein. Rather than administering a polypeptide of the invention, one can administer a nucleic acid molecule that encodes it. For example, one can administer a human IFT particle polypeptide (e.g., human IFT particle polypeptides 20-1, 20-2, 20-3, 27, 46, 52, 57-1, 57-2, 72, 88, 122, 139-1, 139-2 or Che-2) or a nucleic acid molecule encoding such a polypeptide. The polypeptides or nucleic acid molecules can be delivered with a pharmaceutically acceptable carrier, excipient, or diluent.

The methods of the invention can also be carried out to treat an infection in a subject that is caused by a pathogen (e.g. a nematode, bacteria, protozoa or insect) that has an intraflagellar transport (IFT) particle protein. The subjects are treated by administering to them an effective amount of an agent that inhibits the function of the IFT particle protein (e.g., an antibody that binds specifically to the IFT particle protein). The diagnostic and therapeutic methods of the invention can be used to diagnose or treat mammals (e.g. humans or other primates, or domesticated or farm animals) as well as plants.

Another suitable method for identifying compounds that inhibit or restore IFT function involves screening for small molecules that specifically bind to IFT proteins. A variety of suitable binding assays are known in the art as described, for example, in U.S. Pat. Nos. 5,585,277 and 5,679,582, incorporated herein by reference. For example, in various conventional assays, test compounds can be assayed for their ability to bind to a polypeptide by measuring the ability of the small molecule to stabilize the polypeptide in its folded, rather than unfolded, state. More specifically, one can measure the degree of protection against unfolding that is afforded by the test compound. Test compounds that bind to an IFT protein with high affinity cause, for example, a significant shift in the temperature at which the polypeptide is denatured. Test compounds that stabilize the polypeptide in a folded state can be further tested for IFT inhibitive or restorative activity in a standard susceptibility assay.

The IFT polypeptides also can be used in assays to identify test compounds that bind to the polypeptides. Test compounds that bind to IFT polypeptides then can be tested, in conventional assays, for their ability to inhibit or restore IFT function. Test compounds that bind to IFT polypeptides are candidate IFT inhibitive or restorative agents, in contrast to compounds that do not bind to IFT polypeptides. As described herein, any of a variety of art-known methods can be used to assay for binding of test compounds to IFT polypeptides. If desired, the test compound can be immobilized on a substrate, and binding of the test compound to an IFT polypeptide is detected as immobilization of an IFT polypeptide on the immobilized test compound. Immobilization of an IFT polypeptide on the test compound can be detected in an immunoassay with an antibody that specifically binds to an IFT polypeptide.

Also included in the invention is a method for identifying a candidate IFT restorative agent useful for treating abnormal IFT function by: (a) contacting a polypeptide encoded by an IFT nucleic acid with a test compound; and (b) detecting binding of the test compound to the polypeptide, wherein a compound that binds to the IFT polypeptide indicates that the compound is a candidate IFT function restorative agent, and wherein the polypeptide is encoded by a gene selected from the group consisting of a first nucleic acid molecule which encodes a polypeptide containing the amino acid sequence of a polypeptide of the invention or a naturally occurring allelic variant of a polypeptide of the invention, wherein the first nucleic acid molecule hybridizes to a second nucleic acid molecule under stringent conditions. The method can further include a step of determining whether the candidate compound that binds to the IFT polypeptide inhibits growth of cells or organisms, relative to growth of cells or organisms grown in the absence of the test compound, wherein inhibition of growth indicates that the candidate compound is an anti-IFT agent.

In one example, the test compound is immobilized on a substrate, and binding of the test compound to the IFT polypeptide is detected as immobilization of the IFT polypeptide on the immobilized test compound. Immobilization of the IFT polypeptide on the test compound can be detected in an immunoassay with an antibody that specifically binds to the IFT polypeptide.

In one example, the test compound is selected from the group consisting of polypeptides, ribonucleic acids, small molecules (e.g., organic or inorganic), aptamers, peptidomimetics, carbohydrates, and deoxyribonucleic acids.

By "operably linked" is meant that a gene and a regulatory sequence(s) are connected in such a way as to permit gene expression when the appropriate molecules (e.g., transcriptional activator proteins) are bound to the regulatory sequence(s).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

A. Intraflagellar Transport

Figure 1:
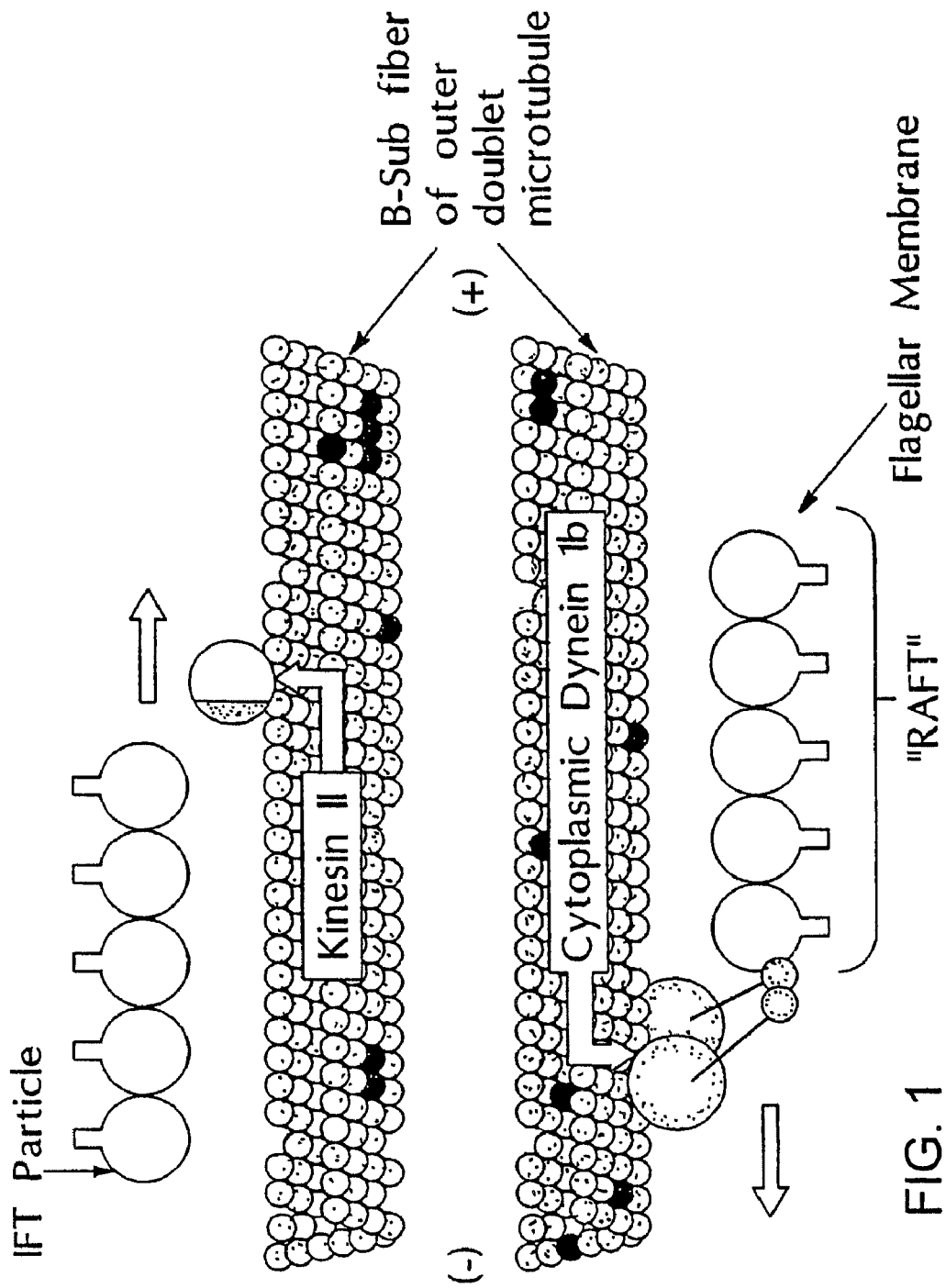
FIG. 1 is a representation of a model of the IFT particles involved in intraflagellar transport towards and away from the tip of a flagellum.

Intraflagellar transport (IFT) is a dynein and kinesin-based motility process in which non-membrane-bound particles move along flagellar microtubules, just beneath the flagellar membrane, from the base to the tip of the flagellum and back (see FIG. 1). IFT is essential for the assembly and maintenance of all cilia and flagella, including non-motile primary cilia and sensory cilia. Recent results indicate that defects in IFT are a primary cause of several human diseases.

Much of our knowledge of the protein machinery and basic biology of IFT has come from studies of the bi-flagellate alga *Chlamydomonas*, which is an excellent model system for biochemical and molecular genetic analyses of proteins and processes occurring in the flagellum.

IFT was first observed in *Chlamydomonas* using Differential Interference Contrast (DIC) microscopy (Kozminski et al., Proc. Nat. Acad. Sci. U.S.A., 90:5519-5523, 1993), where particles were seen to move anterogradely (i.e., from base to tip) along the flagellum at ~2.5 mm/s without pause, while apparently smaller particles moved retrogradely at ~4 mm/s Correlative light and electron microscopy revealed that the particles being moved during IFT were organized into linear arrays termed "rafts" (Kozminski et al., Proc. Nat. Acad. Sci. U.S.A., 90:5519-5523, 1993). Electron microscopy of the arrays showed that they were connected by periodic links to both the flagellar membrane and the B-tubule of the outer doublet microtubule (Kozminski et al., Proc. Nat. Acad. Sci. U.S.A., 90:5519-5523, 1993; Kozminski et al., J. Cell Biol., 131:1517-1527, 1995; Pazour et al., J. Cell Biol, 141:979-992, 1998). Biochemical characterization of the *Chlamydomonas* IFT particles revealed that they are composed of at least 16 different polypeptides (Piperno and Mead, Proc. Natl. Acad. Sci., 94:4457-4462, 1997; Cole et al., J. Cell Biol., 141:993-1008, 1998); many of these are now known to have homologues in higher organisms, including humans. More recently, IFT has been visualized in the ciliated sensory neurons of *C. elegans* (Orozco et al., Nature, 398:674, 1999; Signor et al., J. Cell Biol., 147:519-530, 1999; Qin et al., Cur. Bio., 11:1-20, 2001) and in the primary cilia of mouse kidney cells (Pazour, manuscript in preparation) using GFP-tagged IFT proteins. Defects in IFT motors and particle proteins lead to defects in assembly of motile flagella in *Chlamydomonas* (Kozminski et al., J. Cell. Biol., 131:1517-1527, 1995; Pazour et al., J. Cell Biol., 144:473-481, 1999; Pazour et al., J. Cell Biol., 151:709-718, 2000), of ciliated sensory neurons in *C. elegans* (Perkins et al., Dev. Biol., 117:456-487, 1986; Cole et al., J. Cell Biol., 141:993-1008, 1998; Collet et al., Genetics, 148:187-200, 1998; Signor et al., J. Cell Biol., 147:519-530, 1999; Wicks et al., Dev. Biol., 221:295-307, 2000; Qin et al., Cur. Bio., 11:1-20, 2001), and of nodal cilia (Nonaka et al., Cell, 95:829-837, 1998; Marszalek et al., Proc. Natl. Acad. Sci. U.S.A., 96:5043-5048, 1999; Takeda et al., J. Cell Biol., 145:825-836, 1999; Murcia et al., Development, 127:2347-2355, 2000), kidney primary cilia (Pazour et al., J. Cell Biol., 151:709-718, 2000), and rod outer segments in mice (Pazour et al., manuscript in preparation). IFT functions in the transport of flagellar precursors to the tip of the flagellum, where they are needed for both flagellar assembly and maintenance. In cilia and flagella with a sensory function, IFT can also be involved in signal transduction between the cilium or flagellum and the cell body.

The Motors Powering IFT

The motors moving the IFT particles were defined by means of *Chlamydomonas* flagellar mutants defective in either kinesin-II or cytoplasmic dynein 1b.

The anterograde motor. Studies of flagellar assembly (fla) mutants in *Chlamydomonas* first identified the gene FLA10, which encodes a kinesin-II motor subunit (termed Fla10) present in the flagellum. IFT and Fla10 were essential for both the assembly and maintenance of the flagella. Inasmuch as kinesin-II moves towards the + ends of microtubules (Scholey, J. Cell Biol., 133:1-4, 1996), it was proposed that anterograde IFT was powered by kinesin-II (Kozminski et al., J. Cell Biol., 131:1517-1527, 1995). The flagellar Fla10-kinesin-II was purified to homogeneity and shown to be a typical heterotrimeric kinesin-II, composed of two motor subunits of 85 and 95 kD (also called Kif 3a and 3b [Scholey, J. Cell Biol., 133:1-4, 1996]), and a non-motor subunit of 115 kD, called KAP (kinesin-associated protein, [Scholey, J. Cell Biol., 133:1-4, 1996]).

The retrograde motor. Cytoplasmic dynein was first implicated in IFT when it was found that a mutation in *Chlamydomonas* LC8, a cytoplasmic dynein light chain, had short flagella that initially grew out to about one-half to three-quarters normal length, and then gradually shortened (Pazour et al., 1998). These flagella exhibited normal levels of anterograde IFT, but had greatly reduced levels of retrograde IFT.

The *Chlamydomonas* dynein heavy chain isoform DHC1b forms the retrograde motor. In *C. elegans*, the homologue of DHC1b is Che-3, and mutations in Che-3 result in a phenotype very similar to that seen in DHC mutants in *Chlamydomonas*: the sensory cilia are very short and filled with IFT particles (Collet et al., 1998; Wicks et al., 2000). Therefore, DHC1b (also known as DHC2 in mammals) is likely to be the retrograde IFT motor in all cilia and flagella.

IFT and the Tip of the Flagellum

Figure 2:
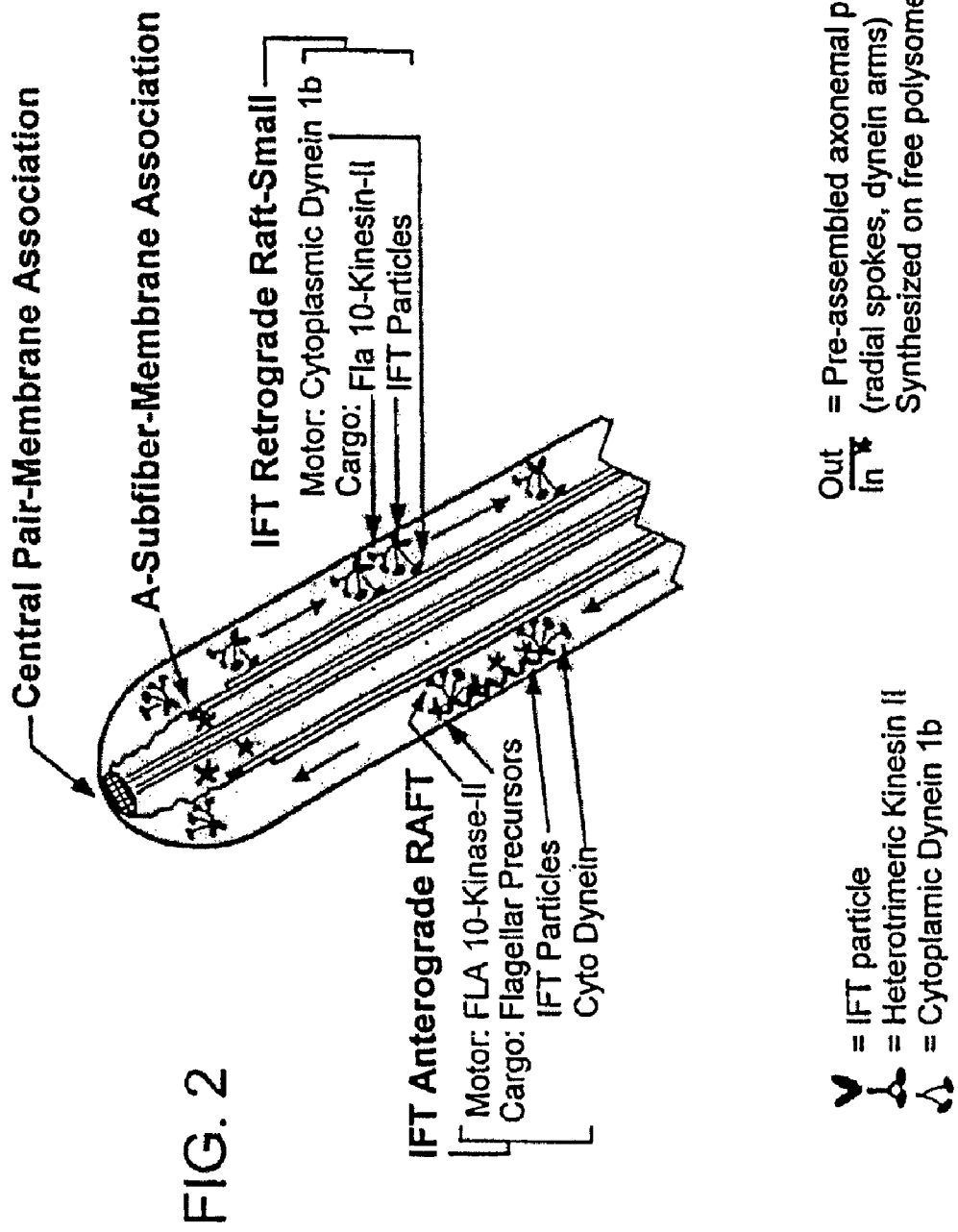
FIG. 2 is a representation of a large scale model of the IFT particles involved in intraflagellar transport towards and away from the tip of the flagellum.

IFT particles move all the way to the tip or base of the flagellum without pause; particles moving to the tip appear by DIC microscopy to have more contrast than those moving to the base (Kozminski et al., 1993; Piperno et al., 1998). FIG. 2 shows a model of this process. Analysis of *Chlamydomonas* IFT motor mutants indicates that kinesin-II is carried as IFT cargo from the flagellar tip to the base (Pazour et al., 1998, 1999); conversely, because dyneins are minus-end directed motors, it can be inferred that cytoplasmic dynein 1b is carried as IFT cargo to the tip. There is evidence that flagellar precursor proteins also are transported by IFT particles to the site of axonemal assembly at the flagellar tip, and released there (Piperno et al., 1996). At the tip, the apparent size of the particles is reduced (possibly due to unloading of axonemal precursors), the kinesin motor becomes cargo, and the cytoplasmic dynein 1b motor takes over to transport the particles back to the peri-basal body region.

The mechanisms by which IFT particle turnaround, cargo-release, and motor exchange occur at the tip are unknown, but by analogy with other bi-directional particle movement systems, e.g. melanophore movement (Reese and Haimo, 2000), it may involve phosphorylation and dephosphorylation of motors and/or their associated proteins. Because the IFT particles move unidirectionally without stopping or reversing, the proteins that control the IFT motors must be highly localized at the tip and base of the flagellum. At the base of the flagellum, the regulatory proteins may be anchored to the transition fibers (Deane et al., manuscript in preparation). The tip of the flagellum also contains specialized structures that may serve as anchors for the proteins that turn kinesin off and dynein on: each of the A-subfibers of the outer doublets is terminated by a plug which is connected to the flagellar membrane by a thin filament (Dentler and Rosenbaum, 1977; Dentler, 1989). The central pair of microtubules likewise is connected to the tip by a specific structure (Dentler and Rosenbaum, 1977), but this probably is not involved in the turnaround process because *Chlamydomonas* mutants lacking the central pair have normal IFT (Kozminski et al., 1993).

Characterization of *Chlamydomonas* IFT Particles

When fla10ts mutant cells are shifted to restrictive temperature, the number of IFT particles in the flagella decreases substantially before the flagella are resorbed (Kozminski et al., 1995). By comparing these fla10 mutant flagella to those of wild-type cells, it was possible to determine which flagellar polypeptides make up the IFT particles. In this way, the IFT particles were found to sediment at ~16 S in sucrose gradients and to be composed of at least 16 polypeptides (Piperno and Mead, 1997; Cole et al., 1998), occurring in two complexes, termed A and B. Complex A contains 4 polypeptides of relatively high molecular weight (Mr 122K-144K), whereas Complex B contains 11-12 mostly lower MW polypeptides (Mr<100K) (Cole et al. 1998). The identity of the proteins was confirmed by analysis of LC8 mutant flagella, which accumulated both the IFT polypeptides and IFT particles (Pazour et al., 1998).

Separation of the IFT particle polypeptides on two-dimensional gels permitted microsequencing of individual proteins to obtain short internal amino-acid sequences (Cole et al., 1998). The peptide sequences were in turn used to generate PCR primers for amplification of cDNAs encoding several of the IFT particle polypeptides (see below). To date, the predicted sequences are novel. The sequences have permitted the identification of *Chlamydomonas* insertional mutants lacking the genes encoding two of the IFT particle proteins, IFT57 and IFT88 (Pazour et al., 1999b; Pazour et al., 2000). These mutants grow and divide normally, demonstrating that these IFT particle proteins are not involved in any essential processes. However, the IFT88 mutant fails to assemble flagella, whereas the IFT57 mutant assembles only very short flagella. Thus, these specific IFT particle proteins are required for flagellar formation, although the difference in phenotypes suggests that the two proteins differ in their importance. In contrast to the DHC1b mutant, the IFT57 and IFT88 mutants do not accumulate IFT particles in their flagella.

Localization of IFT Particle Proteins

Isolation of the IFT particles permitted the production of both monoclonal and polyclonal antibodies recognizing specific IFT particle proteins. Immunofluorescence microscopy using these antibodies and those prepared against the IFT motors revealed punctate staining along the flagella, presumably representing IFT particles in transit. However, the principal localization of both the IFT particle polypeptides and the kinesin and dynein motors was in a circular pattern around the two basal bodies/centrioles (Cole et al., 1998; Pazour et al., 1999). This was somewhat surprising, because moving IFT particles had been observed only in the flagella by DIC microscopy, and the linear arrays of IFT particles had been observed only in the flagella by electron microscopy. This notwithstanding, the immunofluorescence localization pattern indicated that there is a large pool of IFT particle proteins and motors at the base of the flagellum.

To learn more about this peri-basal body distribution of IFT particle proteins, studies were carried out using gold-labeled antibodies and thin-sectioned material (Deane et al., manuscript in preparation). These higher resolution studies revealed that the IFT proteins were localized at the "flagellar" end of the basal bodies, specifically on the membrane-associated ends of the transition fibers that connect the basal body to the cell membrane (Ringo, 1967; Weiss et al., 1977). These fibers demarcate the boundary between the cytoplasmic and flagellar "compartments." Although the flagellum is ostensibly "open" to the cytoplasm, it appears that only a subset of cytoplasmic proteins (the "flagellar" proteins) gain admission to the flagellar compartment. Thus, the transition fibers may be structural components of a filter or "flagellar pore" that controls movement of molecules and particles between the cytoplasmic and flagellar compartments, much as the nuclear pore controls movement between the cytoplasmic and nuclear compartments. If access to the flagellar compartment is controlled, then one would predict that pre-assembled flagellar structures, such as radial spokes (Diener et al., 1996) and dyneins arms (Fowkes and Mitchell, 1998), either have flagellar localization signals on one or more of their constituent polypeptides, or that they are escorted through the pore by a carrier—perhaps the IFT particles—with which they associate. Therefore, the flagellar pore, where non-membrane bound polypeptides dock prior to gaining entrance to the flagellar compartment, would be functionally similar to the nuclear pore.

A Flagellar Pore Complex?

Figure 3:
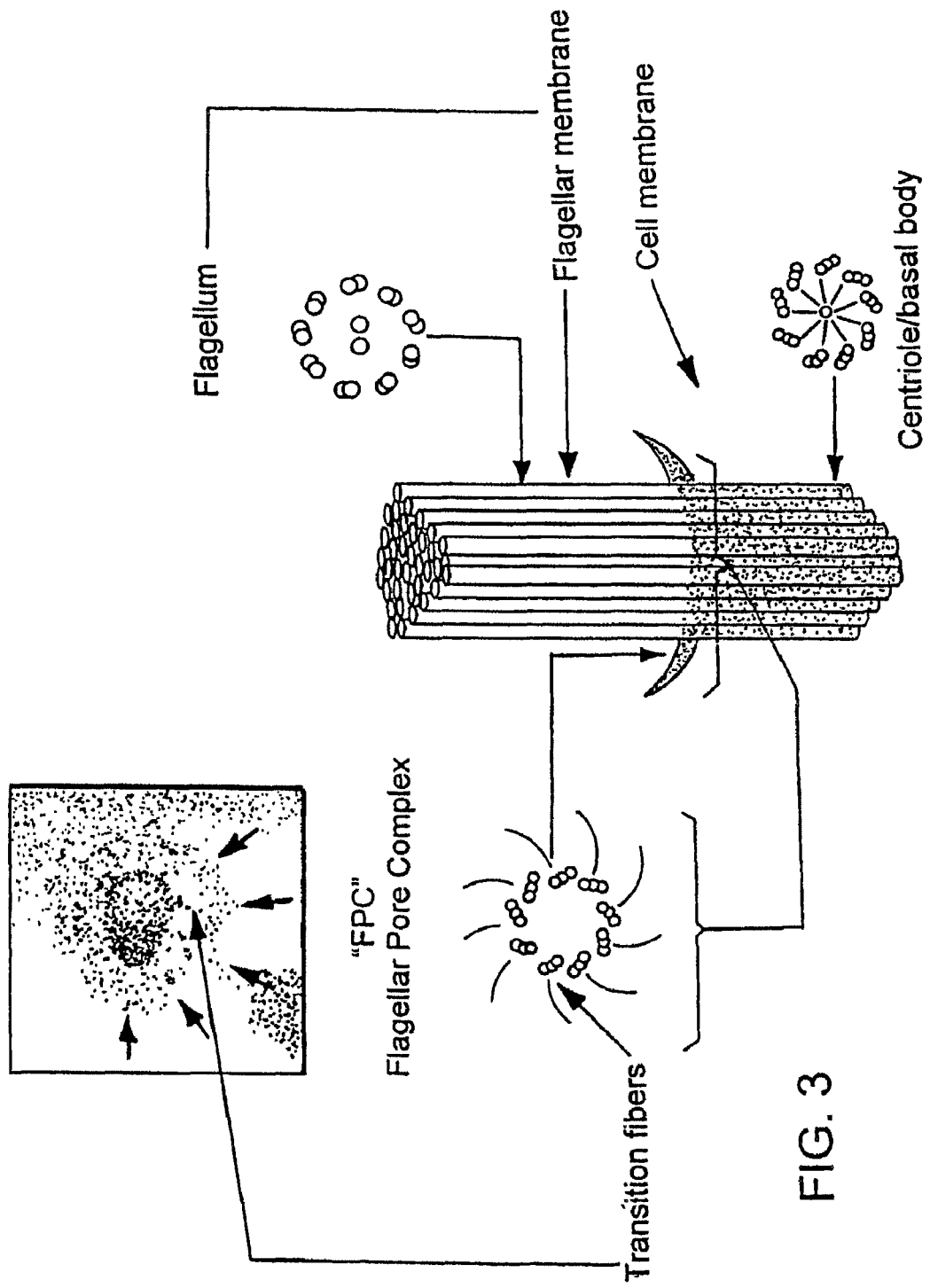
FIG. 3 is a representation of the flagellar pore complex.
Figure 4:
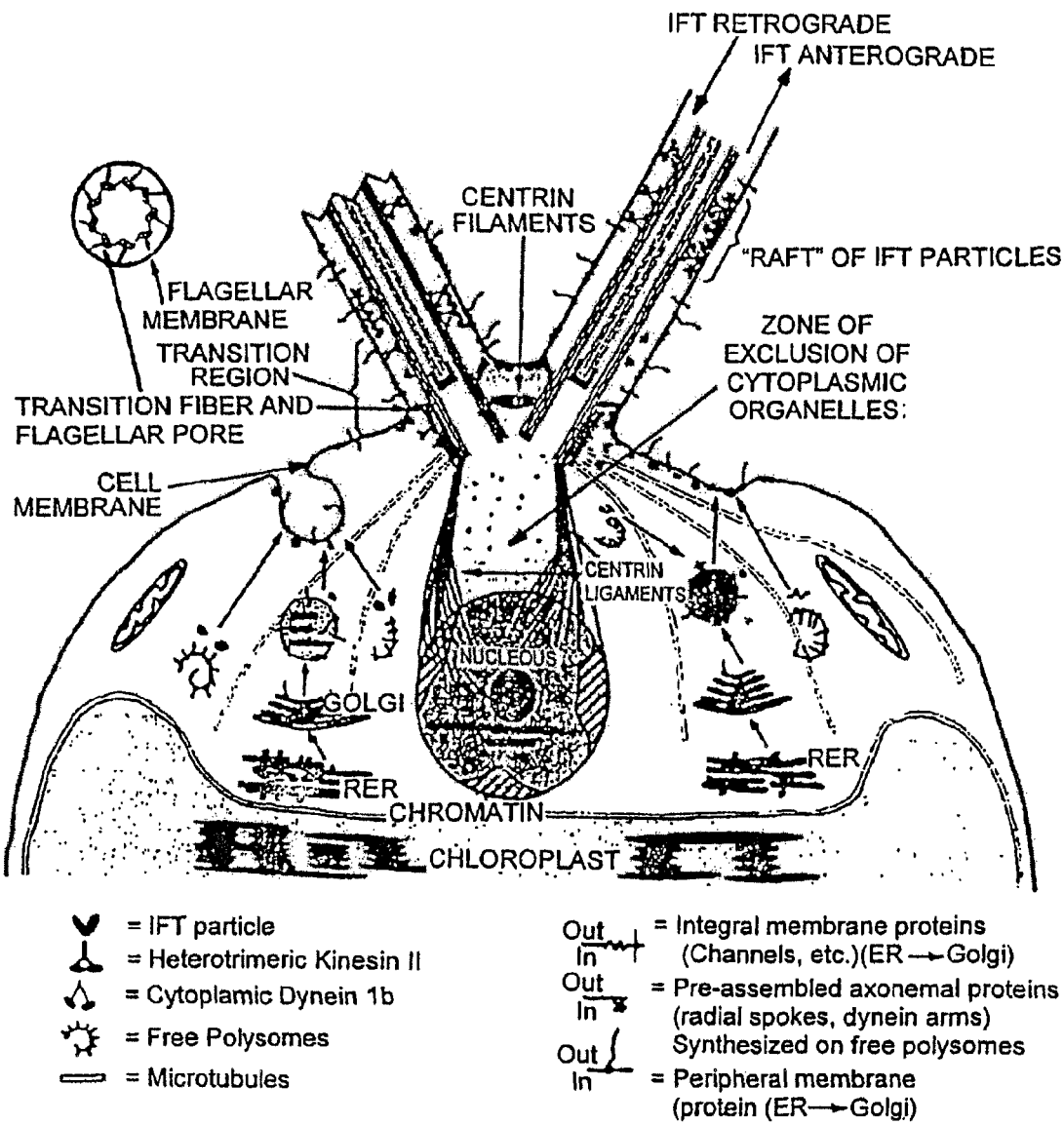
FIG. 4 is a representation of a model of how flagellar proteins are targeted to the flagellum.

Immunofluorescence microscopy indicates that IFT particle proteins are localized primarily to the base of the *Chlamydomonas* flagellum, with only a few particles in the flagellum that must represent IFT rafts in transit. Immunoelectron microscopy reveals that the IFT particle proteins are docked at the ends of "transition fibers" that extend from the distal end of the basal body to the plasma membrane at the base of the flagellum. These fibers, which connect each of the nine basal body triplet microtubules to the flagellar membrane, demarcate the boundary between the cytoplasmic and flagellar compartments. The transition fibers thus may be the structural basis for a "flagellar pore complex" (FPC) that limits access to the flagellar compartment (see FIG. 3). We propose that flagellar membrane and axonemal proteins synthesized in the cytoplasm are transported to the base of the flagellum, where they are recognized by IFT particle proteins and ushered through the FPC into the flagellar compartment. Transition fibers are present in association with all basal bodies, so it is expected that all cilia and flagella have an FPC that serves as a gateway for admission of specific proteins to the cilium or flagellum.

IFT Particle Polypeptides in *C. elegans*

Database searching using the *Chlamydomonas* IFT particle protein sequences revealed a large number of homologues in the nematode *C. elegans* for which there are known mutations. Interestingly, the mutations are in the Che, Daf, and Osm genes that are required for formation and function of the worm sensory cilia. For example, Osm-1, Osm-5, and Osm-6 encode homologues of the *Chlamydomonas* IFT172, IFT88 and IFT52 IFT particle proteins (Collet et al., 1998; Wicks et al., 2000; Qin et al., 2001). Therefore, IFT is essential for the assembly of non-motile sensory cilia in *C. elegans*. These findings, as well as those on Che-3, which encodes the retrograde IFT motor DHC1b (see above), indicated that the process of IFT has been highly conserved throughout evolution and is likely to be necessary for the assembly of all flagella and cilia, including structures derived from these organelles.

It was presumed that, like the *Chlamydomonas* IFT particles, the IFT polypeptides initially localized in *C. elegans* sensory cilia move anterogradely and retrogradely in the cilia. This has now been elegantly demonstrated by fusing sequences encoding GFP to either the kinesin-II non-motor subunit (KAP) gene or to IFT particle polypeptide genes, transforming the constructs into *C. elegans*, and observing the motility of their products in vivo (Orozco et al., 1999; Signor et al., 1999). The rates of movement of IFT polypeptides and motors were similar to each other, and were likewise similar to those of IFT particles in *Chlamydomonas* flagella. Recently, several additional *C. elegans* IFT particle polypeptides, contained in both IFT Complexes A and B, have been tagged with GFP and their motility observed in vivo. Complexes A and B, and the motors that move them, were all shown to translocate at the same rates in neuronal sensory cilia (Qin et al., 2001).

IFT and Polycystic Kidney Disease

Searching the databases with the sequences of the *Chlamydomonas* IFT particle proteins also revealed close homologues in higher organisms, including mice and humans. The homologue of *Chlamydomonas* IFT88, termed Tg737 in mouse and man, was of particular interest, because an insertional mutation in this gene causes autosomal recessive polycystic kidney disease (ARPKD) in the mouse (Moyer et al., 1994). In both the mouse and humans, ARPKD involves the formation of numerous cysts in the proximal and collecting tubules of the kidney (Grantham et al., 1996; Moyer et al., 1994). In humans, ARPKD affects up to 1 in 10,000 newborns; most die within a few weeks of birth (Blythe and Ockenden, 1971; Cole et al., 1987). ARPKD also may be responsible for ~1 in 3000 prenatal deaths and still births.

Although the kidney lacks motile cilia, many of the epithelial cells of the kidney collecting ducts and tubules have a single, non-motile '9+0' cilium, called the primary cilium. Primary cilia are in fact present on most cells in the body (see the World Wide Web at members.global2000.net/bowser/cilialist.html for a comprehensive list of cells having primary cilia), but in the kidney they are particularly well developed. The fact that IFT88 is essential for flagellar formation in *Chlamydomonas* (see above) suggested that its mammalian homologue, Tg737, might be important for formation of the primary cilia in the kidney. Indeed, when kidneys of mice homozygous for the Tg737 insertional mutation were examined by scanning electron microscopy, they were found to be defective in ciliary assembly (Pazour et al., 2000). Whereas wild-type mice had cilia extending several microns into the lumens of the collecting ducts and tubules, the mutant had only short stubs of cilia, just as in the case of the *Chlamydomonas* IFT88 deletion mutant. These results indicated that the primary cause of ARPKD in the mutant mouse is failure to assemble the primary cilium due to a defect in an IFT particle protein. Subsequent studies have shown that the Tg737 protein is concentrated at the base of the kidney cilia (Taulman et al., 2001), just as IFT particle proteins are located at the base of the flagellum of *Chlamydomonas*, and that GFP-tagged Tg737 moves anterogradely and retrogradely in the cilia of wild-type kidney cells in culture (Pazour, unpublished results).

The function of the primary cilium is unknown (Alberts et al., 1994). In the kidney, the primary cilium may function as a flowmeter (Schwartz et al., 1997), as an osmometer, or as a chemodetector. Whatever its specific function, the results with the Tg737 mutant mice provide the first evidence that it has a very important role in kidney physiology (Pazour et al., 2000).

A related renal disease, autosomal dominant polycystic kidney disease (ADPKD), which affects up to 1 in 500 individuals, similarly results in the formation of renal cysts, although the symptoms may not be clinically apparent until the patient reaches middle age (Grantham et al., 199_). The primary defects in the most common forms of ADPKD are in genes coding for polycystin 1 (PKD1) and polycystin 2 (PKD2). PKD1 is an integral membrane protein that directly interacts with PKD2 to form a calcium-sensitive cation channel probably acting in a sensory signaling pathway (Emmons and Somlo, 1999; Murcia et al., 1999; Somlo and Ehrlich, 2001). How are the ADPKD polycystins and the defect in kidney cilia assembly in ARPKD related? A clue to this was a report showing that the *C. elegans* homologues of the vertebrate polycystins are located on the worm's sensory cilia (Barr and Sternberg, 1999), where they also appear to be involved in signal transduction. More recent work indicates that the human polycystins likewise are displayed principally on the ciliary membrane (Pazour et al., manuscript in preparation), suggesting that a defect in one of the polycystins impairs normal functioning of the kidney primary cilium and lead to ADPKD.

IFT Reveals a Role for Primary Cilia in Polycystic Kidney Disease

The cells of the proximal and distal collecting tubules of the vertebrate kidney each have a single nonmotile "9+0" primary cilium extending from the apical cell surface into the lumen of the tubule. The function of these primary cilia is unknown, but if their assembly is disrupted in the mouse by a defect in a homologue of one of the *Chlamydomonas* IFT particle polypeptides, autosomal recessive polycystic kidney disease (ARPKD) results and the mice die during gestation or soon after birth (Pazour et al., 2000). Therefore, vertebrate ARPKD occurs when the kidney tubule primary cilia are missing or defective.

In humans the most common genetic deficiencies in a related disorder, autosomal dominant polycystic kidney disease (ADPKD), are in the genes PKD1 and PKD2, which encode polycystin 1 and 2, respectively (Somlo and Ehrlich, 2001). The two polycystins interact to form a calcium-activated cation channel involved in signal transduction (Gonzalez-Perrett et al., 2001).

The reason why either lack of the primary cilia or mutations in the polycystins cause the polycystic kidney phenotype is likely to be because the polycystins on the cell surface are concentrated on the membranes of the kidney primary cilia (Pazour et al., manuscript in preparation). This suggests that a defect in a polycystin impairs functioning of the primary cilium. Therefore, polycystic kidney disease can result either from mutations in the polycystins that are targeted to the primary cilia, or from an inability to form the primary cilia themselves.

IFT and Retinal Degenerative Disease

Primary cilia, or structures derived from primary cilia, also are involved in the development and function of several sensory structures in the vertebrate body, e.g., in the retina, the inner ear, and the nasal epithelium Inasmuch as IFT probably occurs in all cilia and flagella, it is likely to be important for the assembly and maintenance of these sensory structures/tissues as well. The role of IFT has been most closely examined in retinal rod and cone outer segments. These light sensory dendritic processes, containing the photopigments and light-transducing machinery, initially form from primary cilia (De Robertis, 1956; Tokuyasu and Yamada, 1959); a short '9+0' "connecting cilium" remains in the adult as the only path of communication between the outer segment and the inner segment, where protein synthesis occurs (Young, 1976; Besharse, 1986). Following its formation, the rod outer segment turns over continuously at a high rate; it is estimated that ~2000 opsin molecules per minute are required to maintain the mammalian rod outer segment (Besharse, 1986), and all of this newly synthesized protein is likely to be transported to the outer segment through the connecting cilium. A possible role for IFT in this process was first indicated by the discovery that the IFT motor kinesin-II is present in the connecting cilia of fish rods and cones (Beech et al., 1996). Subsequently, Cre-loxP mutagenesis was used to remove the kinesin-II motor subunit, KIF3A, specifically from photoreceptor cells (Marszalek et al., 2000). In the absence of KIF3A, large quantities of opsin, arrestin and membranes accumulated in the inner segment, and the photoreceptor cells eventually underwent apoptotic cell death. These results implied that kinesin-II, present in the connecting cilium, was powering IFT there and was required for the assembly and continued maintenance of the rod outer segment.

Figure 5:
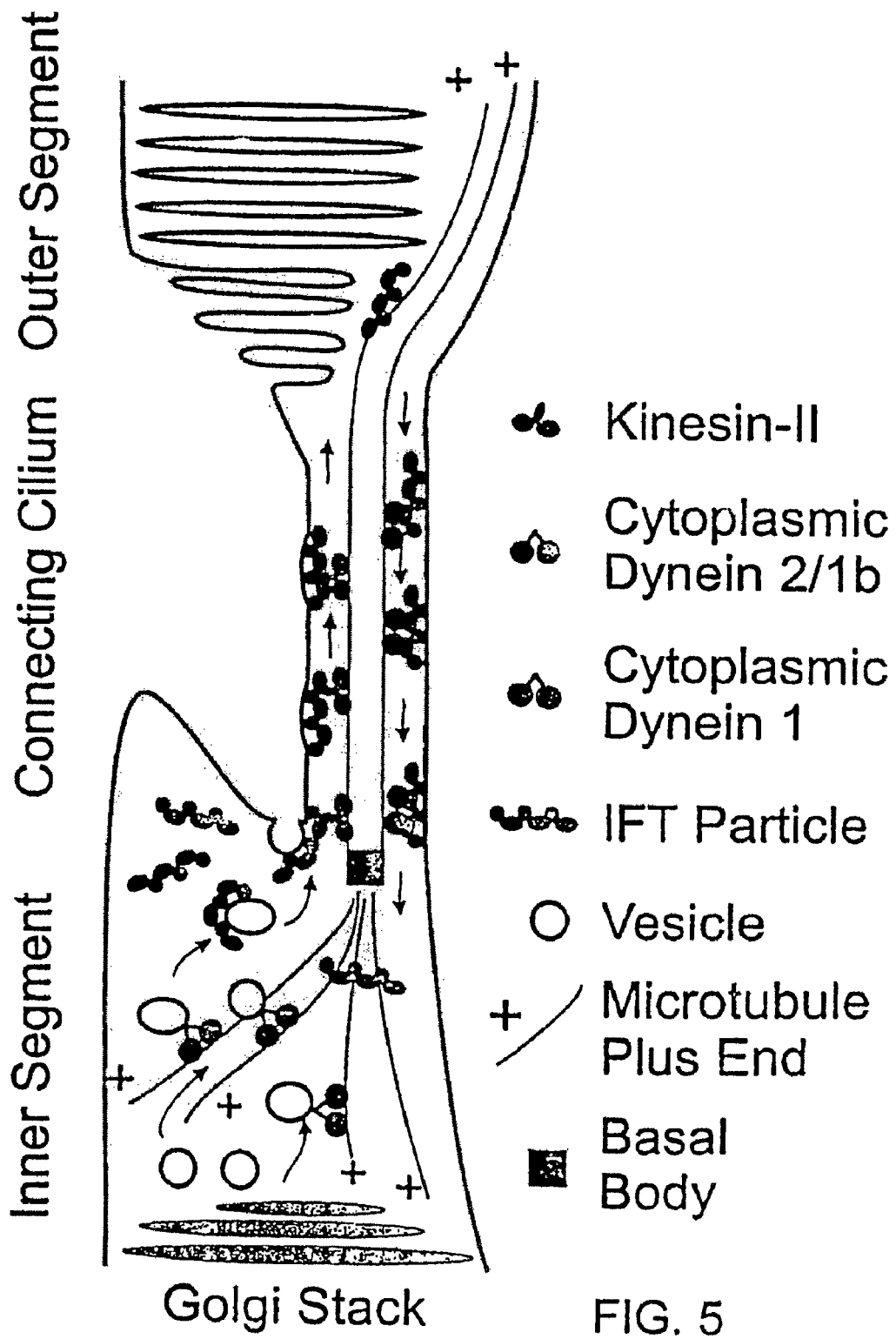
FIG. 5 is a representation of a model of the photoreceptor cell IFT.

More recently, immunofluorescence microscopy has revealed that several IFT particle proteins are concentrated at the proximal ends, and to a lesser extent the distal ends, of mouse rod connecting cilia (Pazour et al., 2000b), a distribution remarkably similar to that seen for IFT particle proteins in *Chlamydomonas*. Moreover, in mice homozygous for the insertional mutation in the IFT particle protein Tg737, the rod outer segments develop abnormally, and eventually degenerate, leading to complete disappearance of the rod cells (Pazour et al., manuscript in preparation). These latter results provide very strong independent evidence that IFT occurs in the connecting cilium and has an important role in assembling and maintaining the rod outer segment, presumably by transporting essential proteins from the inner segment to the outer segment (see FIG. 5). The degeneration of rod cells resulting from defects in IFT motors and particle proteins is very similar to that observed in retinitis pigmentosa and other human diseases causing progressive blindness (Sung and Tai, 2000; Traboulsi, 1998). Therefore, the genes encoding IFT proteins must now be considered candidate genes for these diseases.

IFT and Rod Outer Segments

Vertebrate rod outer segments are derived from '9+0' primary cilia during embryogenesis of the retina. The distal portion of the cilium differentiates into folds that contain the visual pigments and the phototransduction machinery. The proximal portion of the primary cilium remains as the "connecting cilium." The connecting cilium is the only connection between the rod inner segment, which contains all the cytoplasmic organelles, and the outer segment. In the adult, the outer segment turns over very rapidly due to shedding of membranous disks from its distal tip. Both the initial development of the outer segment and its continued maintenance are dependent on the movement of precursors from their site of synthesis in the inner segment, through the connecting cilium to the outer segment.

Membrane proteins such as rhodopsin that are destined for the outer segment are synthesized in the endoplasmic reticulum, processed through the Golgi apparatus, and then transported in vesicles by cytoplasmic dynein 1 along microtubules that converge at the base of the connecting cilium. There the vesicles fuse with the plasma membrane at a specialized structure termed the periciliary ridge complex (Peters et al., 1983). Immunofluorescence microscopy has revealed a high concentration of IFT particle proteins at the base of the connecting cilium, just as in *Chlamydomonas* (Pazour et al., 2000b). It is hypothesized that the rhodopsin and other outer segment precursors become associated with IFT particles at the base of the connecting cilium, and are transported by kinesin II through the flagellar pore complex and up the cilium to the base of the outer segment, where they are released. The IFT particles are then transported by cytoplasmic dynein 2/1b back down the connecting cilium to the peri-basal body region. Mutations in the carboxyl-terminal portion of rhodopsin cause abnormal transport and/or localization of rhodopsin, resulting in retinal degeneration (Sung and Tai, 2000; Tam et al., 2000). Similarly, mutations in kinesin-II or an IFT particle protein in the mouse result in abnormal localization of rhodopsin and retinal degeneration (Marszalek et al., 2000; Pazour et al., manuscript in preparation). Thus, defects in IFT may be one cause of retinal degeneration in humans.

IFT is Required for Assembly of Nodal Cilia

As noted above, deletion of the IFT88 gene in *Chlamydomonas* completely blocks flagellar assembly. Why, then, are connecting cilia formed at all in rod cells of the mouse homozygous for an insertional mutation in the IFT88 homologue, Tg737? The Tg737 insertional allele used in the above studies results in expression of a smaller-than-normal Tg737 protein, probably due to a defect in mRNA splicing (Taulman et al., 2001; G. Pazour, unpublished result). Apparently, this small product is sufficient to support the assembly of the connecting cilium, but not adequate for full development and long-term maintenance of the outer segment. Interestingly, complete knockout of the mouse Tg737 gene is embryonic lethal (Murcia et al., 2000); the embryos lack nodal cilia and are defective in left-right axis determination, a hallmark of defects in the nodal cilia (see "Defects in IFT reveal a role for nodal cilia in the development of left-right axis determination"). Therefore, Tg737 in the mouse, like its homologue IFT88 in *Chlamydomonas*, is essential for cilia formation. As in the case of the connecting cilium, the abnormal Tg737 protein in the original insertional mutant mouse must be sufficient to allow nodal cilia formation and normal embryogenesis. One also can infer that some cilia or structures derived from cilia—viz., kidney primary cilia, rod outer segments—are more sensitive to defects in IFT than other cilia— viz. nodal cilia and respiratory cilia (the latter are relatively unaffected in the original Tg737 insertional mutant mouse.

Defects in IFT Reveal a Role for Embryonic Nodal Cilia in Left-Right Axis Determination Because IFT is required for the formation of all cilia and flagella, animals lacking IFT should be defective in all processes that depend on these organelles. Knockouts of IFT motors and particle proteins in the mouse reveal that one of the earliest roles for cilia in the mammalian embryo is the development of left-right asymmetry. This process appears to depend on the motility of nodal cilia, which resemble primary cilia but are unique in that they exhibit an unusual twirling movement not seen in other primary cilia. In the absence of the IFT motor kinesin-II (Nonaka et al., 1998; Marzalek et al., 1999; Takeda et al., 1999) or the IFT particle protein Tg737 (Murcia et al., 2000), nodal cilia fail to develop. In these embryos, the earliest molecular markers of left-right asymmetry, which normally are expressed only in the left lateral plate mesoderm shortly after development of the nodal cilia, are expressed bilaterally (Nonaka et al., 1998; Marszalek et al., 1999). Subsequently, the embryos undergo random laterality of heart looping, so that in half of the embryos the heart is on the wrong side of the midline, a condition known as situs inversus and frequently observed in humans with defects in cilia function (Afzelius and Mossberg, 1995). It has been proposed that the twirling movement of the nodal cilia sets up a gradient of a morphogen in the extraembryonic fluid across the node, resulting in left-right axis determination (Okada et al., 1999; Supp et al., 1999). In support of such a role, embryos of mice with a defect in left-right dynein, which may be the motor powering nodal cilia movement, have non-motile nodal cilia and situs inversus (Okada et al., 1999; Supp et al., 1999). (Modified from Supp et al., 2000).

Further Examples of IFT Function

Intraflagellar Transport (IFT) is essential for both the initial assembly and subsequent maintenance of all motile (9+2) and sensory (9+0) cilia/flagella. The research shows that IFT is required for the movement of structural proteins, which form the microtubular axoneme, to the flagellar tip, where assembly occurs. For those 9+2 cilia and flagella where motility is the principal function, e.g. flagella of sperm, and cilia of the respiratory tract, oviduct, fimbriae, efferent ducts of the testis, and ependymal cells lining the cavities of the spinal cord and brain, the motility function is dependent on proper assembly and maintenance of the microtubule-containing axoneme. When the nodal cilia cannot form in the embryo, developmental diseases such as situs inversus result. IFT also is important for movement and maintenance of proteins in the flagellar and ciliary membranes. For example, the membrane-associated proteins involved in phototransduction in the vertebrate retina are in the rod and cone outer segments, which are modified cilia. Finally, IFT is important in the movement of signals from the cilium to the cell body, as in the case of 9+0 primary cilia and sensory cilia which monitor the environment and relay that information to the cell or nervous system.

II. DNA and Polypeptide Sequences

The present invention is based, at least in part, on the discovery or characterization of a variety of cDNA and polypeptide molecules, and sequences inferred from or homologous to them, which encode proteins which are herein designated IFT 20, 27, 46, 52, 57, 72, 88, 122, and 139, and Che-2. Sequences from *Chlamydomonas, Caenorhabditis elegans*, mouse, and human are included in the invention. These proteins exhibit a variety of physiological activities, and are included in a single application for the sake of convenience. It is understood that the allowability or non-allowability of claims directed to one of these proteins has no bearing on the allowability of claims directed to the others. The characteristics of each of these proteins and the cDNAs encoding them are described separately in the ensuing sections. In addition to the full length mature and immature human proteins described in the following sections, the invention includes fragments, derivatives, and variants of these proteins, as described herein. These proteins, fragments, derivatives, and variants are collectively referred to herein as polypeptides of the invention or proteins of the invention.

IFT27 is a member of the Rab family of small GTPases. Rab GTPases and their effectors are generally involved in membrane vesicle formation, vesicle and organelle motility and transport, and tethering of vesicles to their target compartment (Zerial and McBride, *Nature Reviews Molecular Cell Biology*, 2:107-119, 2001). Known Rabs cycle between an "active" state in which GTP is bound, and an "inactive" state in which GDP is bound. Thus they serve as molecular "switches."

An "isolated nucleic acid molecule" is a nucleic acid molecule that is separated from the 5' and 3' coding sequences with which it is immediately contiguous in the naturally occurring genome of an organism. Isolated nucleic acid molecules include nucleic acid molecules that are not naturally occurring, e.g., nucleic acid molecules created by recombinant DNA techniques. Nucleic acid molecules include both RNA and DNA, including cDNA, genomic DNA, and synthetic (e.g., chemically synthesized) DNA. Where single-stranded, the nucleic acid molecule may be a sense strand or an antisense strand.

As used herein, a "signal sequence" includes a peptide of at least about 15 or 20 amino acid residues in length which occurs at the N-terminus of secretory and membrane-bound proteins and which contains at least about 70% hydrophobic amino acid residues such as alanine, leucine, isoleucine, phenylalanine, proline, tyrosine, tryptophan, or valine. In a preferred embodiment, a signal sequence contains at least about 10 to 40 amino acid residues, preferably about 19-34 amino acid residues, and has at least about 60-80%, more preferably at least about 65-75%, and more preferably at least about 70% hydrophobic residues. A signal sequence serves to direct a protein containing such a sequence to a lipid bilayer. A signal sequence is usually cleaved during processing of the mature protein.

The term "purified" as used herein refers to a nucleic acid or peptide that is substantially free of cellular material, viral material, or culture medium when produced by recombinant DNA techniques, or chemical precursors or other chemicals when chemically synthesized.

Polypeptides or other compounds of interest are said to be "substantially pure" when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

Where a particular polypeptide or nucleic acid molecule is said to have a specific percent identity to a reference polypeptide or nucleic acid molecule of a defined length, the percent identity is relative to the reference polypeptide or nucleic acid molecule. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Of course, many other polypeptides will meet the same criteria. The same rule applies for nucleic acid molecules.

For polypeptides, the length of the reference polypeptide sequence will generally be at least 16 amino acids, preferably at least 20 amino acids, more preferably at least 25 amino acids, and most preferably 35 amino acids, 50 amino acids, or 100 amino acids. For nucleic acids, the length of the reference nucleic acid sequence will generally be at least 50 nucleotides, preferably at least 60 nucleotides, more preferably at least 75 nucleotides, and most preferably 100 nucleotides or 300 nucleotides.

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). Preferably, the two sequences are the same length.

The determination of percent homology between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to IFT 20, 27, 46, 52, 57, 72, 88, 122, or 139, or Che-2 nucleic acid molecules of the invention. BLAST protein searches can be performed with the XBLAST program, score=50, wordlength=3 to obtain amino acid sequences homologous to IFT 20, 27, 46, 52, 57, 72, 88, 122, or 139, or Che-2 protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search that detects distant relationships between molecules. Id. When utilizing BLAST, Gapped BLAST, and PSI-Blast programs, the default parameters of the respective programs (e.g., XBLAST and NBLAST) can be used. See the World Wide Web at ncbi.nlm.nih.gov. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Another preferred, non-limiting example of a mathematical algorithm utilized for the comparison of sequences is the local homology algorithm of Smith and Waterman (Advances in Applied Mathematics 2: 482-489 (1981)). Such an algorithm is incorporated into the BestFit program, which is part of the Wisconsin™ package, and is used to find the best segment of similarity between two sequences. BestFit reads a scoring matrix that contains values for every possible GCG symbol match. The program uses these values to construct a path matrix that represents the entire surface of comparison with a score at every position for the best possible alignment to that point. The quality score for the best alignment to any point is equal to the sum of the scoring matrix values of the matches in that alignment, less the gap creation penalty multiplied by the number of gaps in that alignment, less the gap extension penalty multiplied by the total length of all gaps in that alignment. The gap creation and gap extension penalties are set by the user. If the best path to any point has a negative value, a zero is put in that position.

After the path matrix is complete, the highest value on the surface of comparison represents the end of the best region of similarity between the sequences. The best path from this highest value backwards to the point where the values revert to zero is the alignment shown by BestFit. This alignment is the best segment of similarity between the two sequences. Further documentation can be found on the World Wide Web at ir.ucdavis.edu/GCGhelp/bestfit.html#algorithm.

Additional algorithms for sequence analysis are known in the art and include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined Ktup can be set to 2 or 1 for protein sequences, or from 1 to 6 for DNA sequences. The default if ktup is not specified is 2 for proteins and 6 for DNA. For a further description of FASTA parameters, see the world wide web at bioweb.pasteur.fr/docs/man/man/fasta.1.html#sect2, the contents of which are incorporated herein by reference.

The percent identity between two sequences can be determined using techniques similar to those described above, with or without allowing gaps. In calculating percent identity, typically exact matches are counted.

As used herein, the phrase "allelic variant" refers to a nucleotide sequence that occurs at a given locus or to a polypeptide encoded by the nucleotide sequence. Allelic variants of any of these genes can be identified by sequencing the corresponding chromosomal portion at the indication location in multiple individuals.

Nucleic Acids Encoding IFT Particle Proteins

The invention encompasses nucleic acids that have a sequence that is substantially identical to the nucleic acid sequence of *Chlamydomonas* IFT particle protein genes 20, 27, 46, 52, 57, 72, 88, 122, or 139, or Che-2, as well as homologous mouse and human sequences. A nucleic acid sequence which is substantially identical to a given reference nucleic acid sequence is hereby defined as a nucleic acid having a sequence that has at least 85%, preferably 90%, and more preferably 95%, 98%, 99% or more identity to the sequence of the given reference nucleic acid sequence.

The IFT 20, 27, 46, 52, 57, 72, 88, 122, or 139, or Che-2 nucleic acid molecules of the invention can be cDNA, genomic DNA, synthetic DNA, or RNA, and can be double-stranded or single-stranded (i.e., either a sense or an antisense strand). Fragments of these molecules are also considered within the scope of the invention, and can be produced, for example, by the polymerase chain reaction (PCR) or generated by treatment with one or more restriction endonucleases. A ribonucleic acid (RNA) molecule can be produced by in vitro transcription.

The nucleic acid molecules of the invention can contain naturally occurring sequences, or sequences that differ from those that occur naturally, but, due to the degeneracy of the genetic code, encode the same polypeptide. In addition, these nucleic acid molecules are not limited to sequences that only encode polypeptides, and thus, can include some or all of the non-coding sequences that lie upstream or downstream from a coding sequence.

The nucleic acid molecules of the invention can be synthesized (for example, by phosphoramidite-based synthesis) or obtained from a biological cell, such as the cell of a mammal. Thus, the nucleic acids can be those of a human, mouse, rat, guinea pig, cow, sheep, horse, pig, rabbit, monkey, dog, or cat. Combinations or modifications of the nucleotides within these types of nucleic acids are also encompassed.

In addition, the isolated nucleic acid molecules of the invention encompass fragments that are not found as such in the natural state. Thus, the invention encompasses recombinant molecules, such as those in which a nucleic acid molecule (for example, an isolated nucleic acid molecule encoding IFT 20, 27, 46, 52, 57, 72, 88, 122, or 139, or Che-2) is incorporated into a vector (for example, a plasmid or viral vector) or into the genome of a heterologous cell (or the genome of a homologous cell, at a position other than the natural chromosomal location). Recombinant nucleic acid molecules and uses therefor are discussed further below.

In the event the nucleic acid molecules of the invention encode or act as antisense molecules, they can be used for example, to regulate translation of mRNA of the invention. Techniques associated with detection or regulation of expression of nucleic acids or polypeptides of the invention are well known to skilled artisans and can be used to diagnose and/or treat disorders associated with aberrant expression of nucleic acids or polypeptides of the invention.

The invention also encompasses nucleic acid molecules that hybridize under stringent conditions to a nucleic acid molecule encoding a polypeptide of the invention. The cDNA sequences described herein can be used to identify these hybridizing nucleic acids, which include, for example, nucleic acids that encode homologous polypeptides in other species, and splice variants of the genes of the invention in humans or other mammals. Accordingly, the invention features methods of detecting and isolating these nucleic acid molecules. Using these methods, a sample (for example, a nucleic acid library, such as a cDNA or genomic library) is contacted (or "screened") with a probe specific to a nucleotide of the invention. The probe will selectively hybridize to nucleic acids encoding related polypeptides (or to complementary sequences thereof). The probe, which can contain at least 25 (for example, 25, 50, 100, or 200 nucleotides) can be produced using any of several standard methods (see, for example, Ausubel et al., "Current Protocols in Molecular Biology, Vol. I," Green Publishing Associates, Inc., and John Wiley & Sons, Inc., NY, 1989). For example, the probe can be generated using PCR amplification methods in which oligonucleotide primers are used to amplify a nucleic acid sequence specific to a nucleic acid of the invention that can be used as a probe to screen a nucleic acid library and thereby detect nucleic acid molecules (within the library) that hybridize to the probe.

One single-stranded nucleic acid is said to hybridize to another if a duplex forms between them. This occurs when one nucleic acid contains a sequence that is the reverse and complement of the other (this same arrangement gives rise to the natural interaction between the sense and antisense strands of DNA in the genome and underlies the configuration of the "double helix"). Complete complementarity between the hybridizing regions is not required in order for a duplex to form; it is only necessary that the number of paired bases is sufficient to maintain the duplex under the hybridization conditions used.

Typically, hybridization conditions are of low to moderate stringency. These conditions favor specific interactions between completely complementary sequences, but allow some non-specific interaction between less than perfectly matched sequences to occur as well. After hybridization, the nucleic acids can be "washed" under moderate or high conditions of stringency to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature, the higher the stringency. Washing can be initiated at a low temperature (for example, room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary. There is not one set of conditions, for example, that will allow duplexes to form between all nucleic acids that are 85% identical to one another; hybridization also depends on unique features of each nucleic acid. The length of the sequence, the composition of the sequence (for example, the content of purine-like nucleotides versus the content of pyrimidine-like nucleotides) and the type of nucleic acid (for example, DNA or RNA) affect hybridization. An additional consideration is whether one of the nucleic acids is immobilized (for example, on a filter).

An example of a progression from lower to higher stringency conditions is the following, where the salt content is given as the relative abundance of SSC (a salt solution containing sodium chloride and sodium citrate; 2×SSC is 10-fold more concentrated than 0.2×SSC). Nucleic acids are hybridized at 42 EC in 2×SSC/0.1% SDS (sodium dodecylsulfate; a detergent) and then washed in 0.2×SSC/0.1% SDS at room temperature (for conditions of low stringency); 0.2×SSC/0.1% SDS at 42 EC (for conditions of moderate stringency); and 0.1×SSC at 68 EC (for conditions of high stringency). Washing can be carried out using only one of the conditions given, or each of the conditions can be used (for example, washing for 10-15 minutes each in the order listed above). Any or all of the washes can be repeated. As mentioned above, optimal conditions will vary and can be determined empirically.

A second set of conditions that are considered "stringent conditions" are those in which hybridization is carried out at 50 EC in Church buffer (7% SDS, 0.5% NaHPO$_4$, 1 M EDTA, 1% BSA) and washing is carried out at 50 EC in 2×SSC.

Once detected, the nucleic acid molecules can be isolated by any of a number of standard techniques (see, for example, Sambrook et al., "Molecular Cloning, A Laboratory Manual," 2nd Ed. Cold Spring Harbor Laboratory Press, Cold Spring Harbor, N.Y., 1989).

The invention also encompasses: (a) expression vectors that contain any of the foregoing coding sequences (related to a polypeptide of the invention) and/or their complements (that is, "antisense" sequence); (b) expression vectors that contain any of the foregoing coding sequences (related to a polypeptide of the invention) operatively associated with a regulatory element (examples of which are given below) that directs the expression of the coding sequences; (c) expression vectors containing, in addition to sequences encoding a polypeptide of the invention, nucleic acid sequences that are unrelated to nucleic acid sequences encoding a polypeptide of the invention, such as molecules encoding a reporter or marker; and (d) genetically engineered host cells that contain any of the foregoing expression vectors and thereby express the nucleic acid molecules of the invention in the host cell.

Recombinant nucleic acid molecules can contain a sequence encoding a soluble polypeptide of the invention; mature polypeptide of the invention; or polypeptide of the invention having an added or endogenous signal sequence. A full length polypeptide of the invention; a domain of a polypeptide of the invention; or a fragment thereof may be fused to additional polypeptides, as described below. Similarly, the nucleic acid molecules of the invention can encode the mature form of a polypeptide of the invention or a form that encodes a polypeptide that facilitates secretion. In the latter instance, the polypeptide is typically referred to as a proprotein, which can be converted into an active form by removal of the signal sequence, for example, within the host cell. Proproteins can be converted into the active form of the protein by removal of the inactivating sequence.

The regulatory elements referred to above include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, sequences that function as a marker or reporter. Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XG-PRT). As with many of the standard procedures associated with the practice of the invention, skilled artisans will be aware of additional useful reagents, for example, of additional sequences that can serve the function of a marker or reporter. Generally, the hybrid polypeptide will include a first portion and a second portion; the first portion being a polypeptide of the invention and the second portion being, for example, the reporter described above or an immunoglobulin constant region.

The expression systems that may be used for purposes of the invention include, but are not limited to, microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, *Saccharomyces* and *Pichia*) transformed with recombinant yeast expression vectors containing the nucleic acid molecules of the invention (preferably containing the nucleic acid sequence encoding a polypeptide of the invention); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing nucleotide sequences of nucleic acids of the invention; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter).

In bacterial systems, a number of expression vectors may be advantageously selected depending upon the use intended for the gene product being expressed. For example, when a large quantity of such a protein is to be produced, for the generation of pharmaceutical compositions containing polypeptides of the invention or for raising antibodies to those polypeptides, vectors that are capable of directing the expression of high levels of fusion protein products that are readily purified may be desirable. Such vectors include, but are not limited to, the *E. coli* expression vector pUR278 (Ruther et al., *EMBO J.* 2:1791, 1983), in which the coding sequence of the insert may be ligated individually into the vector in frame with the lacZ coding region so that a fusion protein is produced; pIN vectors (Inouye and Inouye, *Nucleic Acids Res.* 13:3101-3109, 1985; Van Heeke and Schuster, *J. Biol. Chem.* 264:5503-5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) can be used as a vector to express foreign genes. The virus grows in *Spodoptera frugiperda* cells. The coding sequence of the insert may be cloned individually into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (for example, see Smith et al., *J. Virol.* 46:584, 1983; Smith, U.S. Pat. No. 4,215,051).

In mammalian host cells, a number of viral-based expression systems may be utilized. In cases where an adenovirus is used as an expression vector, the nucleic acid molecule of the invention may be ligated to an adenovirus transcription/translation control complex, for example, the late promoter and tripartite leader sequence. This chimeric gene may then be inserted in the adenovirus genome by in vitro or in vivo recombination. Insertion in a non-essential region of the viral genome (for example, region E1 or E3) will result in a recombinant virus that is viable and capable of expressing a gene product of the invention in infected hosts (for example, see Logan and Shenk, *Proc. Natl. Acad. Sci. USA* 81:3655-3659, 1984). Specific initiation signals may also be required for efficient translation of inserted nucleic acid molecules. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516-544, 1987).

In addition, a host cell strain may be chosen which modulates the expression of the inserted sequences, or modifies and processes the gene product in the specific fashion desired. Such modifications (for example, glycosylation) and processing (for example, cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. The mammalian cell types listed above are among those that can serve as suitable host cells.

For long-term, high-yield production of recombinant proteins, stable expression is preferred. For example, cell lines that stably express the sequences of nucleic acids or polypeptides of the invention described above may be engineered. Rather than using expression vectors that contain viral origins of replication, host cells can be transformed with DNA controlled by appropriate expression control elements (for example, promoter, enhancer sequences, transcription terminators, polyadenylation sites, etc.), and a selectable marker. Following the introduction of the foreign DNA, engineered cells may be allowed to grow for 1-2 days in an enriched media, and then switched to a selective media. The selectable marker in the recombinant plasmid confers resistance to the selection and allows cells to stably integrate the plasmid into their chromosomes and grow to form foci that in turn can be cloned and expanded into cell lines. This method can advantageously be used to engineer cell lines that express nucleic acids or polypeptides of the invention. Such engineered cell lines may be particularly useful in screening and evaluation of compounds that affect the endogenous activity of the gene product.

A number of selection systems can be used. For example, the herpes simplex virus thymidine kinase (Wigler et al., *Cell* 11:223, 1977), hypoxanthine-guanine phosphoribosyltransferase (Szybalska and Szybalski, *Proc. Natl. Acad. Sci. USA* 48:2026, 1962), and adenine phosphoribosyltransferase (Lowy, et al., *Cell* 22:817, 1980) genes can be employed in tk⁻, hgprt⁻ or aprt⁻ cells, respectively. Also, anti-metabolite resistance can be used as the basis of selection for the following genes: dhfr, which confers resistance to methotrexate (Wigler et al., *Proc. Natl. Acad. Sci. USA* 77:3567, 1980; O'Hare et al., *Proc. Natl. Acad. Sci. USA* 78:1527, 1981); gpt, which confers resistance to mycophenolic acid (Mulligan and Berg, *Proc. Natl. Acad. Sci. USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al., *Gene* 30:147, 1984).

The nucleic acid molecules of the invention are useful for diagnosis of disorders associated with aberrant expression of nucleic acid molecules of the invention are also useful in genetic mapping and chromosome identification.

IFT Particle Polypeptides

The invention also includes polypeptides that have a sequence that is substantially identical to the amino acid sequence of *Chlamydomonas* IFT particle polypeptides 20, 27, 46, 52, 57, 72, 88, 122, or 139, or Che-2. A polypeptide which is "substantially identical" to a given reference polypeptide is a polypeptide having a sequence that has at least 85%, preferably 90%, and more preferably 95%, 98%, 99% or more identity to the sequence of the given reference polypeptide sequence.

The terms "protein" and "polypeptide" are used herein interchangeably to describe any chain of amino acids, regardless of length or post-translational modification (for example, glycosylation or phosphorylation). Thus, the term "IFT 20, 27, 46, 52, 57, 72, 88, 122, or 139, or Che-2 polypeptide" includes: full-length, naturally occurring protein of the invention; recombinantly or synthetically produced polypeptide that corresponds to a full-length naturally occurring protein of the invention; or particular domains or portions of the naturally occurring protein. The term also encompasses a mature polypeptide of the invention that has an added amino-terminal methionine (useful for expression in prokaryotic cells).

The polypeptides of the invention described herein are those encoded by any of the nucleic acid molecules described above and include fragments, mutants, truncated forms, and fusion proteins of polypeptides of the invention. These polypeptides can be prepared for a variety of uses, including but not limited to, the generation of antibodies, as reagents in diagnostic assays, for the identification of other cellular gene products or compounds that can modulate the activity or expression of nucleic acids or polypeptides of the invention, and as pharmaceutical reagents useful for the treatment of disorders associated with aberrant expression or activity of nucleic acids or polypeptides of the invention.

Preferred polypeptides are substantially pure polypeptides of the invention, including those that correspond to the polypeptide with an intact signal sequence, and the secreted form of the polypeptide. Especially preferred are polypeptides that are soluble under normal physiological conditions.

The invention also encompasses polypeptides that are functionally equivalent to polypeptides of the invention. These polypeptides are equivalent to polypeptides of the invention in that they are capable of carrying out one or more of the functions of polypeptides of the invention in a biological system. Preferred polypeptides of the invention have 20%, 40%, 50%, 75%, 80%, or even 90% of one or more of the biological activities of the full-length, mature human form of polypeptides of the invention. Such comparisons are generally based on an assay of biological activity in which equal concentrations of the polypeptides are used and compared. The comparison can also be based on the amount of the polypeptide required to reach 50% of the maximal stimulation obtainable.

Functionally equivalent proteins can be those, for example, that contain additional or substituted amino acid residues. Substitutions may be made on the basis of similarity in polarity, charge, solubility, hydrophobicity, hydrophilicity, and/or the amphipathic nature of the residues involved. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Polypeptides that are functionally equivalent to polypeptides of the invention can be made using random mutagenesis techniques well known to those skilled in the art. It is more likely, however, that such polypeptides will be generated by site-directed mutagenesis (again using techniques well known to those skilled in the art). These polypeptides may have increased functionality or decreased functionality.

To design functionally equivalent polypeptides, it is useful to distinguish between conserved positions and variable positions. This can be done by aligning the amino acid sequence of a protein of the invention from one species with its homolog from another species. Skilled artisans will recognize that conserved amino acid residues are more likely to be necessary for preservation of function. Thus, it is preferable that conserved residues are not altered.

Mutations within the coding sequence of nucleic acid molecules of the invention can be made to generate variant genes that are better suited for expression in a selected host cell. For example, N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur, and/or an amino acid deletion at the second position of any one or more of such recognition sequences, will prevent glycosylation at the modified tripeptide sequence (see, for example, Miyajima et al., *EMBO J.* 5:1193, 1986).

The polypeptides of the invention can be expressed fused to another polypeptide, for example, a marker polypeptide or fusion partner. For example, the polypeptide can be fused to a hexa-histidine tag to facilitate purification of bacterially expressed protein or a hemagglutinin tag to facilitate purification of protein expressed in eukaryotic cells.

A fusion protein may be readily purified by utilizing an antibody specific for the fusion protein being expressed. For example, a system described by Janknecht et al. allows for the ready purification of non-denatured fusion proteins expressed in human cell lines (*Proc. Natl. Acad. Sci. USA* 88: 8972-8976, 1991). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$□nitriloacetic acid-agarose columns and histidine-tagged proteins are selectively eluted with imidazole-containing buffers.

The polypeptides of the invention can be chemically synthesized (for example, see Creighton, "Proteins: Structures and Molecular Principles," W.H. Freeman & Co., NY, 1983), or, perhaps more advantageously, produced by recombinant DNA technology as described herein. For additional guidance, skilled artisans may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis Gait, M. J. Ed. ("Oligonucleotide Synthesis," IRL Press, Oxford, 1984).

The invention also features polypeptides that interact with nucleic acids or polypeptides of the invention (and the genes that encode them) and thereby alter the function of nucleic acids or polypeptides of the invention. Interacting polypeptides can be identified using methods known to those skilled in the art. One suitable method is the "two-hybrid system," which detects protein interactions in vivo (Chien et al., *Proc. Natl. Acad. Sci. USA*, 88:9578, 1991). A kit for practicing this method is available from Clontech (Palo Alto, Calif.).

Transgenic Animals

Polypeptides of the invention can also be expressed in transgenic animals. These animals represent a model system for the study of disorders that are caused by or exacerbated by overexpression or underexpression of nucleic acids or polypeptides of the invention, and for the development of therapeutic agents that modulate the expression or activity of nucleic acids or polypeptides of the invention.

Transgenic animals can be farm animals (pigs, goats, sheep, cows, horses, rabbits, and the like), rodents (such as rats, guinea pigs, and mice), non-human primates (for example, baboons, monkeys, and chimpanzees), and domestic animals (for example, dogs and cats). Transgenic mice are especially preferred.

Any technique known in the art can be used to introduce an IFT 20, 27, 46, 52, 57, 72, 88, 122, or 139, or Che-2 transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA* 82:6148, 1985); gene targeting into embryonic stem cells (Thompson et al., Cell 56:313, 1989); and electroporation of embryos (Lo, *Mol. Cell. Biol.* 3:1803, 1983).

The present invention provides for transgenic animals that carry a transgene of the invention in all their cells, as well as animals that carry a transgene in some, but not all of their cells. That is, the invention provides for mosaic animals. The transgene can be integrated as a single transgene or in concatamers, e.g., head-to-head tandems or head-to-tail tandems. The transgene can also be selectively introduced into and activated in a particular cell type (Lasko et al., *Proc. Natl. Acad. Sci. USA* 89:6232, 1992). The regulatory sequences required for such a cell-type specific activation will depend upon the particular cell type of interest, and will be apparent to those of skill in the art.

When it is desired that the transgene of the invention be integrated into the chromosomal site of the endogenous gene, gene targeting is preferred. Briefly, when such a technique is to be used, vectors containing some nucleotide sequences homologous to an endogenous gene of the invention are designed for the purpose of integrating, via homologous recombination with chromosomal sequences, into and disrupting the function of the nucleotide sequence of the endogenous gene. The transgene also can be selectively introduced into a particular cell type, thus inactivating the endogenous gene of the invention in only that cell type (Gu et al., *Science* 265:103, 1984). The regulatory sequences required for such a cell-type specific inactivation will depend upon the particular cell type of interest, and will be apparent to those of skill in the art. These techniques are useful for preparing "knock outs" lacking a functional gene.

Once transgenic animals have been generated, the expression of the recombinant gene of the invention can be assayed utilizing standard techniques. Initial screening may be accomplished by Southern blot analysis or PCR techniques to determine whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Biological samples can also be evaluated immunocytochemically using antibodies specific for the product of the transgene of the invention. Samples of tissue expressing the gene of the invention can also be evaluated immunocytochemically using antibodies specific for the product of the transgene of the invention.

For a review of techniques that can be used to generate and assess transgenic animals, skilled artisans can consult Gordon (*Intl. Rev. Cytol.* 115:171-229, 1989), and may obtain additional guidance from, for example: Hogan et al. "Manipulating the Mouse Embryo" (Cold Spring Harbor Press, Cold Spring Harbor, N.Y., 1986; Krimpenfort et al., *Bio/Technology* 9:86, 1991; Palmiter et al., *Cell* 41:343, 1985; Kraemer et al., "Genetic Manipulation of the Early Mammalian Embryo," Cold Spring Harbor Press, Cold Spring Harbor, N.Y., 1985; Hammer et al., *Nature* 315:680, 1985; Purcel et al., *Science*, 244:1281, 1986; Wagner et al., U.S. Pat. No. 5,175,385; and Krimpenfort et al., U.S. Pat. No. 5,175,384 (the latter two publications are hereby incorporated by reference).

Anti-IFT 20, 27, 46, 52, 57, 72, 88, 122, or 139, or Che-2 Antibodies

Human polypeptides of the invention (or immunogenic fragments or analogs) can be used to raise antibodies useful in the invention; such polypeptides can be produced by recombinant techniques or synthesized (see, for example, "Solid Phase Peptide Synthesis," supra; Ausubel et al., supra). In general, the peptides can be coupled to a carrier protein, such as KLH, as described in Ausubel et al., supra, mixed with an adjuvant, and injected into a host mammal. Antibodies can be purified by peptide antigen affinity chromatography.

In particular, various host animals can be immunized by injection with a polypeptide of the invention. Host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Potentially useful human adjuvants include BCG (bacille Calmette-Guerin) and *Corynebacterium parvum*. Polyclonal antibodies are heterogeneous populations of antibody molecules that are contained in the sera of the immunized animals.

Antibodies within the invention therefore include polyclonal antibodies and, in addition, monoclonal antibodies, humanized or chimeric antibodies, single chain antibodies, Fab fragments, $F(ab')_2$ fragments, and molecules produced using a Fab expression library.

Monoclonal antibodies, which are homogeneous populations of antibodies to a particular antigen, can be prepared using the polypeptides of the invention described above and standard hybridoma technology (see, for example, Kohler et al., *Nature* 256:495, 1975; Kohler et al., *Eur. J. Immunol.* 6:511, 1976; Kohler et al., *Eur. J. Immunol.* 6:292, 1976; Hammerling et al., "Monoclonal Antibodies and T Cell Hybridomas," Elsevier, N.Y., 1981; Ausubel et al., supra).

In particular, monoclonal antibodies can be obtained by any technique that provides for the production of antibody molecules by continuous cell lines in culture such as described in Kohler et al., *Nature* 256:495, 1975, and U.S. Pat. No. 4,376,110; the human B-cell hybridoma technique (Kosbor et al., *Immunology Today* 4:72, 1983; Cole et al., *Proc. Natl. Acad. Sci. USA* 80:2026, 1983), and the EBV-hybridoma technique (Cole et al., "Monoclonal Antibodies and Cancer Therapy," Alan R. Liss, Inc., pp. 77-96, 1983). Such antibodies can be of any immunoglobulin class including IgG, IgM, IgE, IgA, IgD and any subclass thereof. The hybridoma producing the mAb of this invention may be cultivated in vitro or in vivo. The ability to produce high titers of mAbs in vivo makes this a particularly useful method of production.

Once produced, polyclonal or monoclonal antibodies are tested for specific recognition of polypeptides of the invention by Western blot or immunoprecipitation analysis by standard methods, e.g., as described in Ausubel et al., supra. Antibodies that specifically recognize and bind to polypeptides of the invention are useful in the invention. For example, such antibodies can be used in an immunoassay to monitor the level of a polypeptide of the invention produced by a mammal (for example, to determine the amount or subcellular location of a polypeptide of the invention).

Preferably, antibodies of the invention are produced using fragments of the protein of the invention that lie outside highly conserved regions and appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections.

Antisera may also be checked for its ability to immunoprecipitate recombinant proteins of the invention or control proteins, such as glucocorticoid receptor, CAT, or luciferase.

The antibodies can be used, for example, in the detection of the polypeptide of the invention in a biological sample as part of a diagnostic assay. Antibodies also can be used in a screening assay to measure the effect of a candidate compound on expression or localization of a polypeptide of the invention. Additionally, such antibodies can be used in conjunction with the gene therapy techniques described to, for example, evaluate normal and/or genetically engineered cells that express nucleic acids or polypeptides of the invention prior to their introduction into the patient. Such antibodies additionally can be used in a method for inhibiting abnormal activity of nucleic acids or polypeptides of the invention.

In addition, techniques developed for the production of "chimeric antibodies" (Morrison et al., *Proc. Natl. Acad. Sci. USA*, 81:6851, 1984; Neuberger et al., *Nature*, 312:604, 1984; Takeda et al., *Nature*, 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Generally, partially human antibodies and fully human antibodies have a longer half-life within the human body than other antibodies. Accordingly, lower dosages and less frequent administration are often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

Alternatively, techniques described for the production of single chain antibodies (U.S. Pat. Nos. 4,946,778, 4,946,778, and 4,704,692) can be adapted to produce single chain antibodies against polypeptides of the invention. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., *Science*, 246:1275, 1989) to allow rapid and easy identification of monoclonal Fab fragments with the desired specificity.

Antibodies to polypeptides of the invention can, in turn, be used to generate anti-idiotype antibodies that resemble a portion of the protein of the invention using techniques well known to those skilled in the art (see, e.g., Greenspan et al., *FASEB J.* 7:437, 1993; Nissinoff, *J. Immunol.* 147:2429, 1991). For example, antibodies that bind to the protein of the invention and competitively inhibit the binding of a binding partner of the protein can be used to generate anti-idiotypes that resemble a binding partner binding domain of the protein and, therefore, bind and neutralize a binding partner of the protein. Such neutralizing anti-idiotypic antibodies or Fab fragments of such anti-idiotypic antibodies can be used in therapeutic regimens.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., *Nature Genetics* 7:13-21, 1994; see also U.S. Pat. Nos. 5,545,806 and 5,569,825, both of which are hereby incorporated by reference).

The methods described herein in which anti-polypeptide-of-the-invention antibodies are employed may be performed, for example, by utilizing pre-packaged diagnostic kits comprising at least one specific polypeptide-of-the-invention antibody reagent described herein, which may be conveniently used, for example, in clinical settings, to diagnose patients exhibiting symptoms of disorders associated with aberrant expression of nucleic acids or polypeptides of the invention.

An antibody (or fragment thereof) can be conjugated to a therapeutic moiety such as a cytotoxin, a therapeutic agent, or a radioactive agent (e.g., a radioactive metal ion). Cytotoxins and cytotoxic agents include any agent that is detrimental to cells. Examples of such agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, and 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin {formerly designated daunomycin} and doxorubicin), antibiotics (e.g., dactinomycin {formerly designated actinomycin}, bleomycin, mithramycin, and anthramycin), and antimitotic agents (e.g., vincristine and vinblastine).

Conjugated antibodies of the invention can be used for modifying a given biological response, the drug moiety not being limited to classical chemical therapeutic agents. For example, the drug moiety can be a protein or polypeptide possessing a desired biological activity. Such proteins include, for example, toxins such as abrin, ricin A, *Pseudomonas* exotoxin, or diphtheria toxin; proteins such as tumor necrosis factor, alpha-interferon, beta-interferon, nerve growth factor, platelet derived growth factor, tissue plasminogen activator; and biological response modifiers such as lymphokines, interleukin-1, interleukin-2, interleukin-6, granulocyte macrophage colony stimulating factor, granulocyte colony stimulating factor, or other growth factors.

Techniques for conjugating a therapeutic moiety to an antibody are well known (see, e.g., Amon et al., 1985, "Monoclonal Antibodies For Immunotargeting Of Drugs In Cancer Therapy," in Monoclonal Antibodies And Cancer Therapy, Reisfeld et al., Eds., Alan R. Liss, Inc. pp. 243-256; Hellstrom et al., 1987, "Antibodies For Drug Delivery," in Controlled Drug Delivery, 2nd ed., Robinson et al., Eds., Marcel Dekker, Inc., pp. 623-653; Thorpe, 1985, "Antibody Carriers Of Cytotoxic Agents In Cancer Therapy: A Review", in Monoclonal Antibodies '84: Biological And Clinical Applications, Pinchera et al., Eds., pp. 475-506; "Analysis, Results, And Future Prospective Of The Therapeutic Use Of Radiolabeled Antibody In Cancer Therapy," in Monoclonal Antibodies For Cancer Detection And Therapy, Baldwin et al., Eds., Academic Press, pp. 303-316, 1985; and Thorpe et al., 1982, Immunol. Rev., 62:119-158). Alternatively, an antibody can be conjugated to a second antibody to form an antibody heteroconjugate as described by Segal in U.S. Pat. No. 4,676,980.

Antisense Nucleic Acids

Treatment regimes based on an "antisense" approach involve the design of oligonucleotides (either DNA or RNA) that are complementary to mRNA of the invention. These oligonucleotides bind to the complementary mRNA transcripts of the invention and prevent translation. Absolute complementarity, although preferred, is not required. A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs recently have been shown to be effective at inhibiting translation of mRNAs as well (Wagner, *Nature* 372:333, 1984). Thus, oligonucleotides complementary to either the 5' or 3' non-translated, non-coding regions of the gene or mRNA can be used in an antisense approach to inhibit translation of endogenous mRNA. Oligonucleotides complementary to the 5' untranslated region of the mRNA should include the complement of the AUG start codon.

Antisense oligonucleotides complementary to mRNA coding regions are less efficient inhibitors of translation but can be used in accordance with the invention. Whether designed to hybridize to the 5', 3', or coding region of an mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides, or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (as described, e.g., in Letsinger et al., *Proc. Natl. Acad. Sci. USA* 86:6553, 1989; Lemaitre et al., *Proc. Natl. Acad. Sci. USA* 84:648, 1987; PCT Publication No. WO 88/09810) or the blood-brain barrier (see, for example, PCT Publication No. WO 89/10134), or hybridization-triggered cleavage agents (see, for example, Krol et al., *BioTechniques* 6:958, 1988), or intercalating agents (see, for example, Zon, *Pharm. Res.* 5:539, 1988). To this end, the oligonucleotide can be conjugated to another molecule, e.g., a peptide, hybridization triggered cross-linking agent, transport agent, or hybridization-triggered cleavage agent.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids. Res.* 15:6625, 1987). The oligonucleotide is a 2'-0-methylribonucleotide (Inoue et al., *Nucl. Acids Res.* 15:6131, 1987), or a chimeric RNA-DNA analog (Inoue et al., *FEBS Lett.* 215:327, 1987).

Antisense oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (*Nucl. Acids Res.* 16:3209, 1988), and methylphosphonate oligonucleotides can be prepared by use of controlled pore glass polymer supports (Sarin et al., *Proc. Natl. Acad. Sci. USA* 85:7448, 1988).

The antisense molecules should be delivered to cells that express nucleic acids or polypeptides of the invention in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense molecule sufficient to suppress translation of endogenous mRNAs. Therefore, a preferred approach uses a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous transcripts of nucleic acids of the invention and thereby prevent translation of the endogenous mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include, but are not limited to: the SV40 early promoter region (Bernoist et al., *Nature* 290:304, 1981); the promoter contained in the 3' long terminal repeat of Rous sarcoma virus (Yamamoto et al., *Cell* 22:787-797, 1988); the herpes thymidine kinase promoter (Wagner et al., *Proc. Natl. Acad. Sci. USA* 78:1441, 1981); or the regulatory sequences of the metallothionein gene (Brinster et al., *Nature* 296:39, 1988).

Ribozymes

Ribozyme molecules designed to catalytically cleave mRNA transcripts of nucleic acids of the invention can be used to prevent translation and expression of mRNA of the invention. (see, e.g., PCT Publication WO 90/11364; Saraver et al., *Science* 247:1222, 1990). While various ribozymes that cleave mRNA at site-specific recognition sequences can be used to destroy mRNAs of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art (Haseloff et al., *Nature* 334:585, 1988). There are numerous examples of potential hammerhead ribozyme cleavage sites within the nucleotide sequence of human cDNA of the invention. Preferably, the ribozyme is engineered so that the cleavage recognition site is located near the 5' end of the mRNA, i.e., to increase efficiency and minimize the intracellular accumulation of non-functional mRNA transcripts.

The ribozymes of the present invention also include RNA endoribonucleases (hereinafter "Cech-type ribozymes"), such as the one that occurs naturally in *Tetrahymena thermophila* (known as the IVS or L-19 IVS RNA), and which has been extensively described by Cech and his collaborators (Zaug et al., *Science* 224:574, 1984; Zaug et al., *Science*, 231:470, 1986; Zug et al., *Nature* 324:429, 1986; PCT Application No. WO 88/04300; and Been et al., *Cell* 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in nucleic acids of the invention.

As in the antisense approach, the ribozymes can be composed of modified oligonucleotides (e.g., for improved stability, targeting, etc.), and should be delivered to cells which express nucleic acids or polypeptides of the invention in vivo. A preferred method of delivery involves using a DNA construct "encoding" the ribozyme under the control of a strong constitutive pol III or pol II promoter, so that transfected cells will produce sufficient quantities of the ribozyme to destroy endogenous messages and inhibit translation. Because ribozymes, unlike antisense molecules, are catalytic, a lower intracellular concentration is required for efficiency.

Other Methods for Modulating IFT 20, 27, 46, 52, 57, 72, 88, 122, and 139, and Che-2 Expression Endogenous expression of a gene of the invention can also be modulated by inactivating the endogenous gene or its promoter using targeted homologous recombination (see, e.g., U.S. Pat. No. 5,464,764). For example, a mutant, non-functional gene of the invention (or a completely unrelated DNA sequence) flanked by DNA homologous to the endogenous gene of the invention (either the coding regions or regulatory regions of the gene of the invention) can be used, with or without a selectable marker and/or a negative selectable marker, to transfect cells that express the endogenous gene of the invention in vivo. Insertion of the DNA construct, via targeted homologous recombination, results in inactivation of the gene of the invention. Such approaches are particularly suited for use in the agricultural field where modifications to ES (embryonic stem) cells can be used to generate animal offspring with an inactive gene of the invention. However, this approach can be adapted for use in humans, provided the recombinant DNA constructs are directly administered or targeted to the required site in vivo using appropriate viral vectors.

Alternatively, endogenous expression of a gene of the invention can be modulated by targeting deoxyribonucleotide sequences complementary to the regulatory region of the gene of the invention (i.e., the promoter and/or enhancers of a gene of the invention) to form triple helical structures that prevent transcription of the gene of the invention in target cells in the body (Helene, *Anticancer Drug Res.* 6:569, 1981; Helene et al., *Ann. N.Y. Acad. Sci.* 660:27, 1992; and Maher, *Bioassays* 14:807, 1992).

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent that modulates expression or activity of a polypeptide or nucleic acid of the invention and one or more additional active compounds.

The agent that modulates expression or activity can, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents and protein or polypeptide agents depends upon a number of factors within the ken of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the nucleic acid or polypeptide of the invention. Examples of doses of a small molecule include milligram or microgram amounts per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). Examples of doses of a protein or polypeptide include gram, milligram or microgram amounts per kilogram of subject or sample weight (e.g., about 1 microgram per kilogram to about 5 grams per kilogram, about 100 micrograms per kilogram to about 500 milligrams per kilogram, or about 1 milligram per kilogram to about 50 milligrams per kilogram). For antibodies, examples of dosages are from about 0.1 milligram per kilogram to 100 milligrams per kilogram of body weight (generally 10 milligrams per kilogram to 20 milligrams per kilogram). If the antibody is to act in the brain, a dosage of 50 milligrams per kilogram to 100 milligrams per kilogram is usually appropriate. It is furthermore understood that appropriate doses of one of these agents depend upon the potency of the agent with respect to the expression or activity to be modulated. Such appropriate doses can be determined using the assays described herein. When one or more of these agents is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

As an alternative to making determinations based on the absolute expression level of selected genes, determinations may be based on the normalized expression levels of these genes. Expression levels are normalized by correcting the absolute expression level of a gene encoding a polypeptide of the invention by comparing its expression to the expression of a different gene, e.g., a housekeeping gene that is constitutively expressed. Suitable genes for normalization include housekeeping genes such as the actin gene. This normalization allows the comparison of the expression level in one sample (e.g., a patient sample), to another sample, or between samples from different sources.

Alternatively, the expression level can be provided as a relative expression level. To determine a relative expression level of a gene, the level of expression of the gene is determined for 10 or more samples of different endothelial (e.g. intestinal endothelium, airway endothelium, or other mucosal epithelium) cell isolates, preferably 50 or more samples, prior to the determination of the expression level for the sample in question. The mean expression level of each of the genes assayed in the larger number of samples is determined and this is used as a baseline expression level for the gene(s) in question. The expression level of the gene determined for the test sample (absolute level of expression) is then divided by the mean expression value obtained for that gene. This provides a relative expression level and aids in identifying extreme cases of disorders associated with aberrant expression of a gene encoding a polypeptide of the invention protein or with aberrant expression of a ligand thereof.

Preferably, the samples used in the baseline determination will be from either or both of cells which aberrantly express a gene encoding a polypeptide of the invention or a ligand thereof (i.e. 'diseased cells') and cells which express a gene encoding a polypeptide of the invention at a normal level or a ligand thereof (i.e. 'normal' cells). The choice of the cell source is dependent on the use of the relative expression level. Using expression found in normal tissues as a mean expression score aids in validating whether aberrance in expression of a gene encoding a polypeptide of the invention occurs specifically in diseased cells. Such a use is particularly important in identifying whether a gene encoding a polypeptide of the invention can serve as a target gene. In addition, as more data is accumulated, the mean expression value can be revised, providing improved relative expression values based on accumulated data. Expression data from endothelial cells (e.g. mucosal endothelial cells) provides a means for grading the severity of the disorder.

Detecting Proteins Associated with IFT 20, 27, 46, 52, 57, 72, 88, 122, or 139, or Che-2

The invention also features polypeptides that interact with (e.g., bind directly or indirectly) IFT 20, 27, 46, 52, 57, 72, 88, 122, or 139, or Che-2. Any method suitable for detecting protein-protein interactions may be employed for identifying transmembrane proteins, intracellular, or extracellular proteins that interact with polypeptides of the invention. Among the traditional methods which may be employed are co-immunoprecipitation, cross-linking and co-purification through gradients or chromatographic columns of cell lysates or proteins obtained from cell lysates and the use of polypeptides of the invention to identify proteins in the lysate that interact with polypeptides of the invention. For these assays, the polypeptide of the invention can be full length polypeptide of the invention, a soluble extracellular domain of a polypeptide of the invention, or some other suitable polypeptide of the invention. Once isolated, such an interacting protein can be identified and cloned and then used, in conjunction with standard techniques, to identify proteins with which it interacts. For example, at least a portion of the amino acid sequence of a protein which interacts with the polypeptide of the invention can be ascertained using techniques well known to those of skill in the art, such as via the Edman degradation technique. The amino acid sequence obtained may be used as a guide for the generation of oligonucleotide mixtures that can be used to screen for gene sequences encoding the interacting protein. Screening may be accomplished, for example, by standard hybridization or PCR techniques. Techniques for the generation of oligonucleotide mixtures and the screening are well-known. (Ausubel, supra; and "PCR Protocols: A Guide to Methods and Applications," Innis et al., eds. Academic Press, Inc., NY, 1990).

Additionally, methods may be employed which result directly in the identification of genes which encode proteins which interact with polypeptides of the invention. These methods include, for example, screening expression libraries, in a manner similar to the well known technique of antibody probing of $\lambda$gt11 libraries, using labeled polypeptide of the invention or a fusion protein of the invention, e.g., a polypeptide of the invention or domain thereof fused to a marker such as an enzyme, fluorescent dye, a luminescent protein, or to an IgFc domain.

There are also methods capable of detecting protein interaction. A method that detects protein interactions in vivo is the two-hybrid system (Chien et al., *Proc. Natl. Acad. Sci. USA*, 88:9578, 1991). A kit for practicing this method is available from Clontech (Palo Alto, Calif.).

III. Uses

A. Human and Animal Therapeutic Uses

Inhibition of IFT Particle Protein Function (Spermiogenesis and Contraception)

The sperm flagellum consists of a 9+2 axoneme which generates sperm movement. In addition, the flagellum of the mammalian sperm contains accessory structures, viz. the fibrous sheath and the outer dense fibers, which are believed to stiffen the flagellum and enable it to function in the viscous environment of the female reproductive tract (Witman, Introduction to cilia and flagella. *In: Ciliary and Flagellar Membranes* (ed. R. A. Bloodgood). Plenum Press, NY. pp. 1-30, 1990). During spermiogenesis in the mammalian testis, a 9+2 axoneme is formed within a flagellar membrane; as in other flagella, proper assembly of this axoneme must require IFT to move the axonemal precursors to the tip of the flagellum, where they are assembled. After assembly of the axoneme, the accessory structures are assembled beginning at the distal tip of the flagellum and progressing toward its base (Oko and Clermont, Mammalian spermatozoa: structure and assembly of the tail. *In: Controls of Sperm Motility: Biological and Clinical Aspects*. (ed. C. Gagnon), CRC Press, Boca Raton, Fla., pp. 3-27, 1990). Concomitant with this assembly, accessory structure proteins, previously present in the cytoplasm of the spermiogenic cells, are mobilized from the cytoplasm to the flagellum. This transport of outer dense fiber and fibrous sheath precursors from the cytoplasm to the tip of the forming flagellum also must be dependent on IFT. Indeed, in the Tg737 insertional mutant mouse, which has a defect in IFT, the sperm flagellum is not formed, and accessory structure precursors remain in the cell body (J. San Agustin, G. Pazour and G. Witman, unpublished results). Therefore, in humans, a defect in IFT would be expected to result in azoospermia and oligozoospermia. Azoospermia and oligospermia are among the most common reasons for infertility in men. It is likely that a genetic defect in an IFT protein is responsible for at least some cases of azoospermia and oligozoospermia.

Because IFT is essential for sperm flagella formation, a drug that inhibits IFT would block spermiogenesis and prevent fertility. Ideally, this drug would 1) target an IFT protein or isoform expressed specifically in the testis, and 2) be able to cross the blood/testis barrier. Such a drug, which can be administered to men orally or by any other preferred route, would be specific for IFT in the testis and can serve as a male contraceptive.

Human and Animal Parasites

Many human and animal eukaryotic parasites have cilia or flagella that are critical for their ability to infect and survive in their hosts. Therefore, these parasites are likely to be susceptible to anti-IFT drugs that would block formation and function of their cilia or flagella. Ideally, anti-IFT drugs would be tailored to bind specifically to the parasite's IFT proteins in order to avoid undesirable effects on the host's cilia and flagella. However, because short-term drug-induced inhibition of IFT in humans and animals is unlikely to cause long-lasting side effects, the host most likely can tolerate treatment with non-host specific anti-IFT drugs for the short time periods necessary to eliminate a parasite. Some examples of ciliated or flagellated parasites that would be amenable to treatment by anti-IFT drugs are given below.

Parasitic Protozoa

Parasitic protozoa cause numerous human and animal diseases, including malaria, African sleeping sickness, trypanosomosis, leishmanioses, trichomonosis, and giardiosis. All of these parasites have stages of their life cycles that are dependent on cilia or flagella, and in many cases cilia or flagella are present during those life-cycle stages that occur in the human or animal host, making the parasites vulnerable to drugs which would block IFT and hence inhibit cilia or flagella assembly or function.

One example is *Giardia* sp., an intestinal parasite which causes debilitating diarrhea and other symptoms in humans. *Giardia* live primarily in the upper portion of the lumen of the small intestine, where they attach to the enterocytes of the intestinal wall (Marquardt et al., *Parasitology and Vector Biology*, 2nd ed., Academic Press, San Diego, 2000). Each *Giardia* cell has 8 motile flagella, which presumably are used to stay in the upper portion of the small intestine and to reach the site of attachment. An anti-IFT drug, taken orally, would inhibit assembly of flagella in newly divided *Giardia* and cause disassembly of previously formed flagella in non-dividing *Giardia*. As a result, the *Giardia* would not be able to move up the lumen of the small intestine, or reach the wall of the small intestine to attach to its surface. In the absence of motility and anchorage, the *Giardia* would be passed out of the intestine and the infection would be eliminated.

An anti-IFT drug also would be effective against trypanosomes, which are responsible for diseases such as African sleeping sickness and Chagas' disease in humans, and nagana in cattle. Trypanosomes circulate in the blood where they reproduce by asexual division. These parasites are characterized by the presence of a single motile flagellum that arises from a flagellar pocket and is enclosed by a sheath called the undulating membrane. An anti-IFT drug would block assembly of the flagellum and the flagellar sheath and affect the trypanosome's life cycle and host-parasite interactions in at least three ways. First, by blocking flagellar assembly, it would affect those normal life processes that are dependent upon flagellar motility. Second, the ability of the trypanosome to evade the human or animal host's defense mechanisms in the bloodstream is dependent on its production of a protective glycoprotein coat that covers both the cell body and the flagellar sheath (Marquandt et al., 1999). Movement of these proteins onto the flagellar sheath is dependent upon IFT (Rosenbaum and Witman, 2001; Bloodgood, 2000). In the absence of IFT, the protective coating would not be present on the flagellar sheath and the parasite would be susceptible to attack by the host immune system. Third, the flagellum is essential for the trypanosome's attachment to, and infection of, the insect vector (e.g., tsetse fly, kissing bugs) which take up the parasite from the human or animal bloodstream and then spread the disease to other humans or animals (Vickerman and Tetley, Flagellar surfaces of parasitic protozoa and their role in attachment, *In: Ciliary and Flagellar Membranes* (ed. R. A. Bloodgood), Plenum Press, N.Y., 1989; Marquardt et al., *Parasitology and Vector Biology*, 2nd ed., Academic Press, San Diego, 2000). By eliminating the trypanosome's flagellum prior to uptake of the parasite by the insect vector, the trypanosome's life cycle would be interrupted and transmission of the parasite to new hosts would be prevented. Because trypanosomes live in the bloodstream, they would be very susceptible to anti-IFT drugs administered by intravenous injection.

Trichomonads are flagellated parasitic protozoans that likewise can be treated with an anti-IFT drug. *Tritrichomonas foetus* causes trichomonad abortion in cattle and other bovines. In the United States alone, it is estimated that there is an annual loss of $650 million to the cattle industry from trichomonosis (Marquardt et al., *Parasitology and Vector Biology*, 2nd ed., Academic Press, San Diego, 2000). *T. foetus* infects the reproductive tracts of both cows and bulls. It reproduces by asexual division, and is spread by sexual intercourse. Upon introduction into the reproductive tract of a cow during sexual intercourse, the trichomonads reproduce in the vagina. If the animal becomes pregnant, the organisms may invade the uterus and infect the developing fetus, causing abortion (Marquardt et al., *Parasitology and Vector Biology*, 2nd ed., Academic Press, San Diego, 2000). Trichomonads have three or more motile anterior flagella, and a motile recurrent flagellum usually attached to the body by an undulating membrane. These flagella presumably are essential for movement of the parasite up the reproductive tract. Treatment of infected cows with an anti-IFT drug delivered orally or by intravagina suppository would prevent assembly of the flagella of newly divided cells, and result in loss of flagella of non-dividing cells. In the absence of the flagellum, the trichomonads would be immotile and would be unable to move up the female reproductive tract and cause abortion. Moreover, rendering the parasites immotile and paralyzed would decrease their ability to withstand the host's own immune defenses, so that the infection can be completely eliminated. Similarly, treatment of bulls with anti-IFT drugs administered orally would render the trichomonads immotile, so they can be eliminated by the bull's own immune system.

*Trichomonas vaginalis* causes trichomonas vaginitis in humans and can be similarly treated to eliminate infection.

Parasitic Platyhelminthes

Many human and animal parasites are members of the phylum Platyhelminthes. Parasitic Platyhelminthes include liver flukes, intestinal flukes, lung flukes and other trematodes, and cestodes or tapeworms. In humans, these parasites cause severe illnesses such as schistosomosis, dicrocoeliosis, clonorchiasis, opisthorchosis, echinostomatiasis, heterophyidosis, swimmer's itch, taeniosis, and cysticercosis. Infection of livestock by these parasites results in huge economic losses in cattle- and sheep-raising areas. All Platyhelminthes have an excretory system based on the flame cell or protonephridium, in which currents are created by a tuft of vigorously beating cilia (Bogitsh and Cheng, *Human Parisitology*, Academic Press, San Diego, 1979; Marquardt et al., *Parasitology and Vector Biology*, 2nd ed., Academic Press, San Diego, 2000). The flame cell cilia may have additional sensory or osmoregulatory functions. In addition, some parasitic Platyhelminthes, such as flatworms, have external cilia that are believed to have a sensory role (Marquardt et al., *Parasitology and Vector Biology*, 2nd ed., Academic Press, San Diego, 2000). Because all cilia and flagella appear to be dependent upon IFT for their assembly and maintenance, one would expect that a drug that inhibited IFT would prevent assembly of the cilia, or result in disassembly of previously formed cilia, in these parasites, causing malfunction of the parasite's osmoregulatory and/or nervous systems. Thus, treatment of infected humans or animals with an anti-IFT drug would control or cure infections by these Platyhelminthes. The anti-IFT drug would be administered orally or intravenously, depending on the site of infection.

Parasitic Nematodes

Over half of the world's population is estimated to be infected by at least one or more species of parasitic nematodes. Animal parasitic nematodes are also widespread and exhibit a wide diversity. Nematodes sense their environment with a set of sensory neurons in which the dendrites are ciliated. These sensory cilia extend outside of the tough nematode cuticle and are exposed to the outer environment where they are responsible for detecting various chemical signals as well as monitor osmotic conditions. Nematodes, for example, will move away from high salt conditions so as to protect themselves from osmotic stress. In nematode mutants where the sensory cilia are structurally defective, the organism is unable to identify dangerous levels of salt; these mutants are also defective in chemosensation (Perkins et al., *Dev. Biol.*, 117:456-487, 1986). Since IFT is required for the formation and maintenance of these sensory cilia, blocking IFT with various anti-IFT agents should result in nematodes that have lost their ability to sense their environment. This will adversely affect the organism's ability to determine where it is going and in finding sexual partners. As described in detail under Combating phytopathogenic nematodes, nematode-specific RNA interference should also work in combating human and animal nematode parasites.

*Ascariasis*, caused by *Ascaris lumbricoides* is globally distributed with more than 1.4 billion persons infected throughout the world (Khuroo, *Gastroenterol Clin North Am*, 25:553-577 1996). *Ascaris* infection begins with the ingestion of infective eggs. Once in the small intestine, the eggs hatch and the resulting juveniles pass through the intestinal wall and enter the bloodstream and eventually end up in the lungs. After entering the airspace, *Ascaris* move up into the pharynx where they are swallowed and reappear in the small intestine. The adult female can lay as many as 200,000 eggs a day in the small intestine. Potentially fatal pathologies includes *ascariasis* pneumonia due to pulmonary hemorrhaging and inflammation and physical blockage of the gastrointestinal tract due to a large mass of the *Ascaris* nematodes. *Ascaris suum* is a common pig parasite that also infects humans but the juvenile gets no farther than the lungs; pathology includes *ascariasis* pneumonia. In the intestine, *Ascaris* spp can be susceptible to orally administered anti-IFT agents. Anti-IFT agents can also be administered by intra-venous injection to treat juvenile nematodes in the bloodstream.

The nematodes known as hookworms infect over a billion people. Most of these infections are caused by either *Ancylostoma duodenale* or *Necator americanus*. The life cycle of hookworms is similar to that of *Ascaris* and suggests that anti-IFT treatments that are successful in treating *ascariasis* should also be successful in treating hookworm infections.

The nematodes known as whipworms are also estimated to infect over a billion people. These infections, caused by *Trichuris trichiura*, are typically confined to the large intestine. Anti-IFT agents can be administered either orally or by suppository.

Animals are infected at a high rate by a large and diverse group of nematodes. In all cases, however, the nematodes may be susceptible to anti-IFT treatments described above. These include nematode-specific RNA interference directed against expression of IFT subunits. The appropriate IFT-derived double stranded RNA can be administered directly to the infected animals or used as a preventive treatment prior to ingestion of the infective eggs. Alternatively, transgenic animal strains can be developed that contain stable transformed DNA that encodes double stranded RNA derived from nematode-specific sequences that encode IFT proteins. In this way, entire populations of livestock can be produced that will no longer support infection by one or more species of parasitic nematode. Two obvious benefits of this approach are (1) that animals will not have to be periodically treated to reduce or remove infection and (2) it may be possible to eradicate specific infectious species by making all hosts resistant.

Restoration of IFT Particle Protein Function

Gene Therapy

The gene constructs of the invention can also be used as a part of a gene therapy protocol to deliver nucleic acids encoding either an agonistic or antagonistic form of a polypeptide of the invention. The invention features expression vectors for in vivo transfection and expression of a polypeptide of the invention in particular cell types so as to reconstitute the function of, or alternatively, antagonize the function of a polypeptide of the invention in a cell in which that polypeptide is misexpressed. Expression constructs of polypeptides of the invention, may be administered in any biologically effective carrier, e.g. any formulation or composition capable of effectively delivering a gene of the invention to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA, encoding a polypeptide of the invention. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) *Blood* 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include yCrip, yCre, y2 and yAm. Retroviruses have been used to introduce a variety of genes into many different cell types, including epithelial cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150: 4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) *Curr.*

*Topics in Micro. and Immunol.* 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

In addition to viral transfer methods, such as those illustrated above, non-viral methods can also be employed to cause expression of a polypeptide of the invention in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject gene of the invention by the targeted cell. Exemplary gene delivery systems of this type include liposomal derived systems, poly-lysine conjugates, and artificial viral envelopes. Other embodiments include plasmid injection systems such as are described in Meuli et al. (2001) *J Invest Dermatol.* 116(1):131-135; Cohen et al. (2000) *Gene Ther* 7(22):1896-905; or Tam et al. (2000) *Gene Ther* 7(21): 1867-74.

In a representative embodiment, a gene encoding a polypeptide of the invention can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547-551; PCT publication WO91/06309; Japanese patent application 1047381; and European patent publication EP-A-43075).

In clinical settings, the gene delivery systems for the therapeutic gene of the invention can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054-3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Compounds that Affect the Activity of IFT

Drugs that stop IFT can have important anti-fertility, anti-parasitic, and anti-pesticide activities while drugs that enhance IFT can be used to improve ciliary function in patients with diseases caused by reduced IFT. In vitro binding assays can be used to identify compounds that bind with high affinity to IFT particle proteins. The identified compounds can then be used in in vivo assays to determine if they affect ciliary assembly. Compounds may include small organic or inorganic molecules, peptides, peptidomimetics, nucleic acids, or carbohydrates.

Genes encoding IFT particle proteins from humans or other species can be expressed in bacterial, mammalian, insect, or other cells and purified. These proteins can then be used in high-throughput screens of chemical compounds to identify those that bind, e.g., with high affinity. The identified compounds can then be screened to determine if they affect ciliary assembly.

The effect of the drugs on ciliary assembly can be determined by adding them to cultures of ciliated organisms and observing how this affects the cilia. For example, the effect on trypanosome ciliary assembly can be determined by adding the compounds to axenic cultures and observing the cells by light microscopy to see if ciliary assembly is affected (Tyler and Engman, *Cell Motil Cytoskeleton*, 46(4):269-78, 2000). The effect on nemotode sensory cilia can be determined by assaying the ability of treated worms to take up membrane-soluble fluorescent dyes. Nematodes that lack cilia do not take up the dyes (Starich et al, *Genetics*, 139:171-188, 1995). The effect on mammalian primary cilia assembly can be determined by adding the compounds to cultured mammalian cells and assaying ciliary assembly by immunofluorescence microscopy (Wheatley et al., *Cell Biol. Int.*, 20:73-81, 1996).

Compounds that bind to IFT particle proteins can also be screened to determine if they enhance IFT. This can be done using cultured cells derived from the Tg737 mutant mouse (Taulman et al., *Mol Biol Cell*, 12(3):589-99, 2001). This mouse has a reduced amount of the Tg737/IFT88 protein (Taulman et al., *Mol Biol Cell*, 12(3):589-99, 2001; Pazour unpublished observation) and shows defects in assembly of kidney primary cilia (Pazour et al., *Mol. Biol. Cell*, 151:709-718, 2000). Presumably the cells derived from this mouse will also show defects in ciliary assembly and can be used to screen for compounds that enhance IFT to compensate for the reduced amount of protein.

Assays for Compounds Capable of Restoring or Inhibiting IFT Function

Even after a particular intracellular target is selected, the means by which new IFT protein function restoration agents are identified pose certain challenges. Despite the increased use of rational drug design, a preferred method continues to be the mass screening of compound "libraries" for active agents by exposing cultures of cells with cilia or flagella to the test compounds and assaying for inhibition or restoration of normal IFT protein activity. In testing thousands or tens of thousands of compounds, however, a correspondingly large number of cell cultures of interest must be grown over time periods which are relatively long. Moreover, a compound that is found to inhibit or restore normal IFT protein function in culture may be acting not on the desired target but on a different, less unique component of the IFT system, with the result that the compound may act against host cells as well and thereby produce unacceptable side effects. Consequently, there is a need for an assay or screening method that more specifically identifies those agents that are active against a certain intracellular target. Additionally, there is a need for assay methods having greater throughput, that is, assay methods that reduce the time and materials needed to test each compound of interest.

The invention provides methods for identifying agents capable of modululating, e.g., restoring or inhibiting, IFT function. In some methods, screening for potential or candidate IFT function restorative or inhibitory agents is accomplished by identifying those compounds (e.g., small organic molecules) that interact with, e.g., bind directly or indirectly, to an IFT polypeptide and/or inhibit the activity of a IFT polypeptide or the expression of an IFT gene. For example, screens can be performed that identify those compounds that inhibit an IFT activity described herein.

In various suitable methods, screening for anti-IFT agents can be accomplished by (i) identifying those compounds that bind to IFT (and are thus candidate anti-IFT compounds) and (ii) further testing such candidate compounds for their ability to inhibit intraflagellar transport in vitro or in vivo, in which case they are anti-IFT agents.

Specific binding of a test compound to a polypeptide can be detected, for example, in vitro by reversibly or irreversibly immobilizing the test compound(s) on a substrate, e.g., the surface of a well of a 96-well polystyrene microtitre plate. Methods for immobilizing polypeptides and other small molecules are well known in the art. For example, the microtitre plates can be coated with a IFT polypeptide by adding the polypeptide in a solution (typically, at a concentration of 0.05 to 1 mg/ml in a volume of 1-100 ml) to each well, and incubating the plates at room temperature to 37° C. for 0.1 to 36 hours. Polypeptides that are not bound to the plate can be removed by shaking the excess solution from the plate, and then washing the plate (once or repeatedly) with water or a buffer. Typically, the polypeptide is in water or a buffer. The plate is then washed with a buffer that lacks the bound polypeptide. To block the free protein-binding sites on the plates, the plates are blocked with a protein that is unrelated to the bound polypeptide. For example, 300 ml of bovine serum albumin (BSA) at a concentration of 2 mg/ml in Tris-HCl is suitable. Suitable substrates include those substrates that contain a defined cross-linking chemistry (e.g., plastic substrates, such as polystyrene, styrene, or polypropylene substrates from Corning Costar Corp., Cambridge, Mass., for example). If desired, a beaded particle, e.g., beaded agarose or beaded Sepharose, can be used as the substrate. The IFT is then added to the coated plate and allowed to bind to the test compound (e.g., at 37° C. for 0.5-12 hours). The plate then is rinsed as described above.

Binding of the test compound to the IFT can be detected by any of a variety of known methods. For example, an antibody that specifically binds to a IFT polypeptide can be used in an immunoassay. If desired, the antibody can be labeled (e.g., fluorescently or with a radioisotope) and detected directly (see, e.g., West and McMahon, J. Cell Biol. 74:264, 1977). Alternatively, a second antibody can be used for detection (e.g., a labeled antibody that binds to the Fc portion of an anti-YphC antibody). In an alternative detection method, the IFT polypeptide is labeled, and the label is detected (e.g., by labeling a IFT polypeptide with a radioisotope, fluorophore, chromophore, or the like). In still another method, the IFT polypeptide is produced as a fusion protein with a protein that can be detected optically, e.g., using green fluorescent protein (which can be detected under UV light). In an alternative method, the polypeptide can be produced as a fusion protein with an enzyme having a detectable enzymatic activity, such as horseradish peroxidase, alkaline phosphatase, J-galactosidase, or glucose oxidase. Genes encoding all of these enzymes have been cloned and are available for use by those of skill in the art. If desired, the fusion protein can include an antigen, and such an antigen can be detected and measured with a polyclonal or monoclonal antibody using conventional methods. Suitable antigens include enzymes (e.g., horseradish peroxidase, alkaline phosphatase, and J-galactosidase) and non-enzymatic polypeptides (e.g., serum proteins, such as BSA and globulins, and milk proteins, such as caseins).

In various in vivo methods for identifying polypeptides that bind to IFT, the conventional two-hybrid assays of protein/protein interactions can be used (see e.g., Chien et al., Proc. Natl. Acad. Sci. USA, 88:9578, 1991; Fields et al., U.S. Pat. No. 5,283,173; Fields and Song, Nature, 340:245, 1989; Le Douarin et al., Nucleic Acids Research, 23:876, 1995; Vidal et al., Proc. Natl. Acad. Sci. USA, 93:10315-10320, 1996; and White, Proc. Natl. Acad. Sci. USA, 93:10001-10003, 1996). Generally, the two-hybrid methods involve in vivo reconstitution of two separable domains of a transcription factor. One fusion protein contains the IFT polypeptide fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the IFT polypeptide to the test polypeptide (i.e., candidate anti-IFT agent) reconstitutes the transcription factor. Reconstitution of the transcription factor can be detected by detecting expression of a gene (i.e., a reporter gene) that is operably linked to a DNA sequence that is bound by the DNA binding domain of the transcription factor. Kits for practicing various two-hybrid methods are commercially available (e.g., from Clontech; Palo Alto, Calif.).

The methods described above can be used for high throughput screening of numerous test compounds to identify candidate compounds that modulate the function or activity of IFT particle proteins. Having identified a test compound as a candidate compound, the candidate compound can be further tested for inhibition of intraflagellar transport in vitro or in vivo (e.g., using a cell, animal, e.g., rodent, model) if desired.

In vitro, further testing can be accomplished by means known to those in the art such as an enzyme inhibition assay or a whole-cell growth inhibition assay. For example, an agar dilution assay identifies a substance that inhibits cell growth. Microtiter plates are prepared with serial dilutions of the test compound, adding to the preparation a given amount of growth substrate, and providing a preparation of cells Inhibition of cell growth is determined, for example, by observing changes in optical densities of the cell cultures.

Inhibition of cell growth is demonstrated, for example, by comparing (in the presence and absence of a test compound) the rate of growth or the absolute growth of cells Inhibition includes a reduction in the rate of growth or absolute growth by at least 20%. Particularly potent test compounds can further reduce the growth rate (e.g., by at least 25%, 30%, 40%, 50%, 75%, 80%, or 90%).

Animal (e.g., rodent such as murine) models of intraflagellar transport are known to those of skill in the art, and such animal model systems are acceptable for screening potential compounds capable of restoring intraflagellar transport function as an indication of their therapeutic efficacy in human patients. In a typical in vivo assay, an animal is treated with a compound that is capable of restoring IFT function, and conventional methods and criteria are used to diagnose the mammal as having impaired intraflagellar transport. The candidate IFT restorative agent then is administered to the mammal at a dosage of 1-100 mg/kg of body weight, and the mammal is monitored for signs of IFT function restoration. Of course, the results obtained in the presence of the test compound should be compared with results in control animals, which are not treated with the test compound. Administration of candidate IFT function restorative agents to the mammal can be carried out as described below, for example.

IFT function restorative agents can be identified with high throughput assays to detect IFT activity, e.g., the ability to grow cilia or flagella. For example, this restoration can be effected by small molecules binding directly to the IFT particle protein, or by binding of small molecules to other essential polypeptides in a biochemical pathway in which IFT participates.

The invention also provides methods of identifying agents (such as compounds, other substances, or compositions) that affect, or selectively affect, (such as inhibit, restore or otherwise modify) the activity of and/or expression of IFT particle polypeptides (or the IFT particle itself), by contacting an IFT polypeptide or the nucleotide sequence encoding the same with the agent and then measuring the activity of IFT, e.g., intraflagellar transport. In a related aspect, the invention features a method of identifying agents (such as compounds, other substances or compositions comprising same) that affect (such as inhibit, restore, or otherwise modify) the activity of and/or expression of nucleic acids encoding IFT particle polypeptides, by measuring the activity of and/or expression of IFT in the presence of the agent or after the addition of the agent in: (a) a cell line into which has been incorporated a recombinant construct including the nucleotide sequence of the nucleic acid encoding an IFT polypeptide or an allelic variation thereof or (b) a cell population or cell line that naturally selectively expresses IFT polypeptides, and then measuring the activity of IFT polypeptides (or intraflagellar transport as a whole) and/or the expression thereof.

Since the IFT nucleic acids described herein have been identified, they can be cloned into various host cells (e.g., fungi, *E. coli*, or yeast) for carrying out such assays in whole cells.

To identify compounds that modulate expression of the IFT gene the test compound(s) can be added at varying concentrations to the culture medium of cells. Such test compounds can include small molecules (typically, non-protein, non-polysaccharide chemical entities), polypeptides, and nucleic acids. The expression of IFT nucleic acid is then measured, for example, by Northern blot PCR analysis or RNAse protection analyses using a nucleic acid molecule of the invention as a probe. The level of expression in the presence of the test molecule, compared with the level of expression in its absence, will indicate whether or not the test molecule alters the expression of IFT. Because IFT is essential for survival of many organisms (e.g., mammals), test compounds that inhibit the expression and/or function of IFT nucleic acids are expected inhibit growth of, or kill, the cells that express IFT.

Some specific embodiments of the present invention relate to assay methods for the identification of anti-IFT agents using assays for anti-IFT agents which may be carried out both in whole cell preparations and in ex vivo cell-free systems. In each instance, the assay target is the IFT nucleotide sequence and/or the IFT polypeptide. Test compounds which are found to inhibit the IFT nucleotide sequence and/or IFT polypeptide in any assay method of the present invention are thus identified as potential or candidate anti-IFT agents. It is expected that the assay methods of the present invention will be suitable for both small and large-scale screening of test compounds as well as in quantitative assays such as serial dilution studies where the target IFT nucleotide sequence or the IFT polypeptide are exposed to a range of test compound concentrations.

A variety of protocols for detecting and measuring the expression of IFT, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on IFT polypeptides is suitable; alternatively, a competitive binding assay may be employed. These and other assays are described, among other places, in Hampton, R et al. (1990, Serological Methods, A Laboratory Manual, APS Press, St Paul, Minn.) and Maddox, D E et al. (1983, J. Exp. Med. 158:121).

Pharmaceutical Formulations

The present invention also provides a pharmaceutical composition for treating an individual in need of such treatment of a disease caused by abnormal functioning of at least one IFT protein (or that can be treated by inhibiting abnormal IFT protein activity); the treatment method entails administering a therapeutically effective amount of an agent that affects (such as inhibits) the activity and a pharmaceutically acceptable carrier, diluent, excipient, or adjuvant.

The pharmaceutical compositions can be used for humans or animals and will typically include any one or more of a pharmaceutically acceptable diluent, carrier, excipient, or adjuvant. The choice of pharmaceutical carrier, excipient, and diluent can be selected with regard to the intended route of administration and standard pharmaceutical practice. The pharmaceutical compositions can include as (or in addition to) the carrier, excipient, or diluent, any suitable binder(s), lubricant(s), suspending agent(s), coating agent(s), or solubilizing agent(s).

The invention includes pharmaceutical formulations that include a pharmaceutically acceptable excipient and an anti-IFT agent identified using the methods described herein. In particular, the invention includes pharmaceutical formulations that restore normal function to at least one IFT protein. Such pharmaceutical formulations can be used in a method of treating abnormal function of at least one IFT protein in an organism. Such a method entails administering to the organism a therapeutically effective amount of the pharmaceutical formulation, i.e., an amount sufficient to ameliorate signs and/or symptoms of abnormal IFT protein function. In particular, such pharmaceutical formulations can be used to treat abnormal IFT protein function in mammals such as humans and domesticated mammals (e.g., cows, pigs, dogs, and cats), and in plants. The efficacy of such IFT protein function restoration agents in humans can be estimated in an animal model system well known to those of skill in the art (e.g., mouse systems of abnormal IFT protein function).

Treatment includes administering a pharmaceutically effective amount of a composition containing IFT protein function restoration agent to a subject in need of such treatment, thereby restoring normal IFT protein function in the subject. Such a composition typically contains from about 0.1 to 90% by weight (such as 1 to 20% or 1 to 10%) of a IFT protein function restoration agent of the invention in a pharmaceutically acceptable carrier.

Solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, micro-crystalline cellulose, corn starch, sodium starch glycolate and alginic acid. Tablet binders that can be used include acacia, methylcellulose, sodium carboxymethylcellulose, polyvinylpyrrolidone (Povidone®), hydroxypropyl methylcellulose, sucrose, starch, and ethylcellulose. Lubricants that can be used include magnesium stearates, stearic acid, silicone fluid, talc, waxes, oils, and colloidal silica.

Liquid formulations of the compositions for oral administration prepared in water or other aqueous vehicles can contain various suspending agents such as methylcellulose, alginates, tragacanth, pectin, kelgin, carageenan, acacia, polyvinylpyrrolidone, and polyvinyl alcohol. The liquid formulations can also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds can be administered by the drip method, whereby a pharmaceutical formulation containing the anti-IFT agent and a physiologically acceptable excipient is infused. Physiologically acceptable excipients can include, for example, 5% dextrose, 0.9% saline, Ringer's solution, or other suitable excipients. For intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound can be prepared and administered as a suspension in an aqueous base or a pharmaceutically acceptable oil base, such as an ester of a long chain fatty acid, (e.g., ethyl oleate).

A topical semi-solid ointment formulation typically contains a concentration of the active ingredient from about 1 to 20%, e.g., 5 to 10% in a carrier such as a pharmaceutical cream base. Various formulations for topical use include drops, tinctures, lotions, creams, solutions, and ointments containing the active ingredient and various supports and vehicles.

The optimal percentage of the IFT protein function restoration agents in each pharmaceutical formulation varies according to the formulation itself and the therapeutic effect desired in the specific pathologies and correlated therapeutic regimens. Appropriate dosages of the IFT protein function restoration agents can be determined by those of ordinary skill in the art of medicine by monitoring the mammal for signs of disease amelioration or inhibition, and increasing or decreasing the dosage and/or frequency of treatment as desired. The optimal amount of the IFT protein function restoration agent used for treatment of conditions caused by or contributed to by abnormal IFT protein function depends upon the manner of administration, the age and the body weight of the subject, and the condition of the subject to be treated. Generally, the IFT protein function restoration compound is administered at a dosage of 1 to 100 mg/kg body weight, and typically at a dosage of 1 to 10 mg/kg body weight.

B. Diagnostic Uses

Diagnosis of Defective or Absent IFT Particle Proteins

PCR to Detect Missing or Defective IFT Particle Protein Genes

RNA is extracted from patient biopsy material, e.g. nasal scrapings, and reverse transcribed into cDNA. PCR reactions are carried out on this cDNA using pairs of PCR primers designed from the sequence of the human homologue of each of the IFT particle protein genes. If the patient lacked mRNA for any of the genes, then no product would be amplified. The PCR products can also be analyzed by sequencing or other standard methods to identify nucleotide changes. The Tg737 mutant mouse has reduced levels of the mRNA derived from the mouse Tg737/IFT88 gene (Moyer et al., 1994).

Alternatively, PCR can be used to amplify exons of genes encoding IFT particle proteins from genomic DNA purified from patient blood. These amplified products can then be sequenced or analyzed by other standard methods to identify nucleotide changes.

Antibody Assays to Identify Missing IFT Proteins

Protein extracts would be prepared from patient biopsy material, e.g. nasal scrapings, and analyzed by enzyme-linked immunosorbent assay (ELISA) or by western blot analysis using antibodies to the IFT particle proteins. The amount of protein in the patient sample would be compared to normal controls to determine if the patient lacks a particular IFT particle protein. *Chlamydomonas* cells with a mutation in the IFT88 gene lack the IFT88 protein and IFT57 protein (Pazour et al., 2000) and the Tg737 mutant mouse has reduced amounts of full length Tg737/IFT88 protein (Pazour unpublished; Taulman et al., 2001).

C. Use in Agriculture

Combating Phytopathogenic Nematodes

Phytopathogenic nematodes are responsible for tens of billions of dollars lost each year for farmers throughout the world (Williamson, *Curr Opin Plant Biol*, 2:327-331, 1999). A new way to combat these parasites is the use of internalizable agents that interfere with the nematode's ability to sense its environment by disrupting the structure and function of nematode sensory cilia. Nematodes largely sense their environment by chemosensation, a process that occurs at the sensory cilia of sensory neurons (Troemel, *Bioessays*, 21:1011-1020, 1999). Loss of function of these cilia will have multiple effects, including the loss of ability to locate the host plant as well as reproductive mates.

Small Molecule Inhibitors of Intraflagellar Transport

Intraflagellar Transport (IFT) is necessary for both the construction and continued maintenance of cilia and flagella in diverse organisms, including nematodes (Rosenbaum and Witman, unpublished manuscript, 2001). If IFT is interrupted, cilia shorten and become dysfunctional. We propose to block IFT with one or more small molecules. Large numbers of small molecules will be screened for their ability to disrupt IFT and thus, sensory cilia function. The IFT motors, kinesin-II and cytoplasmic dynein 1b would be likely targets but other IFT machinery might also be involved. There is already precedence for this strategy. Monastrol is a small organic molecule that was found via screening to selectively inhibit a subgroup of kinesins known as Eg5 or bimC (Mayer et al, *Science*, 286:971-974, 1999). Eg5 inhibition by monastrol is specific and does not affect the behavior of other kinesins.

The screening process would identify the loss of sensory cilia function. Normal nematode sensory cilia are exposed to the environment and have the unique ability to take up membrane-soluble fluorescent dyes such as DiO and DiI (Molecular Probes, Inc). The cilia-dependent uptake of these dyes into the sensory neurons allows for easy and fast screening using fluorescence microscopy and has been used to identify a relatively large number of sensory cilia mutants (Starich et al, *Genetics*, 139:171-188, 1995). In mutants where the sensory cilia are structurally defective and fail to extend out into the environment, no dye is taken up into the sensory neurons. This same screen can be used to identify agents that cause normal, full-length sensory cilia to shorten to the point at which they are no longer exposed to the environment. As for the anti-IFT agents, many possible small molecules can be screened. Since monastrol binds and specifically inhibits Eg5 kinesin, it would be logical to try variations of this molecule since slight changes in chemical structure can result in a molecule that binds and inhibits kinesin-II. Molecules that affect nematode IFT would likely be added topically to the plant or the soil. Another, more specific approach involves identification of small peptide(s) that block IFT.

Identification of one or more small peptides that block nematode IFT is particularly attractive because host plants can be transformed with the appropriate vector so that the host plant makes the inhibitory peptide(s). Transformation would be mediated by *Agrobacterium tumefaciens* with a standard vector such as pCAMBIA1380 or pCAMBIA1390 (Center for the Application of Molecular Biology to International Agriculture) encoding the inhibitory peptide. Different promoters can be chosen which would result in either constitutive expression or tissue-specific expression of the peptide gene. For example, many nematodes attack their host plant at the roots. Root-specific expression, therefore, is desirable.

RNA Interference of Nematode IFT

Known as RNA interference or RNAi, the introduction of gene-specific sequences of double-stranded RNA (dsRNA) result in a specific gene silencing event which can block the ability of that specific gene to generate protein. In the nematode, this specific dsRNA can be introduced simply by ingestion (Timmons and Fire, *Nature*, 395:854, 1998; Court and Fire, *Gene*, 263:103-112, 2001). IFT genes are specifically targeted in the nematode by transforming plant hosts so that they produce dsRNA derived from portions of genes encoding nematode IFT machinery, including kinesin-II and dynein 1b subunits as well as the IFT raft proteins. This strategy allows for very specific targeting of nematodes that attack and ingest part of the host plant. DNA/RNA sequences of portions of the IFT machinery will be chosen which do not have high homology to the homologous genes in other classes of organisms so as to protect various animals and humans from potential RNAi. Indeed, noncoding introns may be particularly useful for this purpose.

Generating dsRNA via plant transformation with a stable vector has already been achieved in *Arabidopsis* (Chuang and Meyerowitz, *Proc Natl Acad Sci*, 97:4985-4990, 2000). For transformation, suitable vectors such as pCAMBIA vectors can be used. To generate the dsRNA, as little as 100 base pairs of coding or noncoding sequence would be linked to double-stranded complementary sequence so that when the RNA is generated, the two matching RNA sequences would base pair with one another and form double stranded RNA. Attacking nematodes would ingest this dsRNA which would lead to RNA silencing of IFT genes which would result in the loss of the sensory cilia. We would likely want to use a strong promoter so that the concentration of dsRNA in the plant cells would be relatively high. The actual dose needed to affect loss of ciliary function would be measured in a laboratory setting. One positive aspect of RNAi technology is that small amounts of RNA appear to be amplified within the nematode and transmitted adjacently (Fire et al., *Nature*, 391:806-811, 1998).

IFT and Insect Pests

All insect pests utilize sensory cilia for important life functions, including location of mates and identification of food sources. Sensory cilia (ciliated sensory neurons) are the organelles for smell, taste and hearing in insects. A compound that inhibited IFT would block sensory cilia function and/or assembly, leaving an insect unable to smell, unable to taste, and unable to hear. Insects deprived of these senses would be unable to locate mates; as a result, their populations would be controlled. Many insects deprived of these senses also would be unable to sense food, and thus would not eat, or would eat plants that would be harmful to them; this would both reduce insect populations and reduce damage to crop plants. Therefore, a compound that blocked IFT would be a very effective pesticide. Such a compound can be applied by spraying of fields, plants, insect habitats, etc., or by any other preferred method.

For example, the male cabbage looper moth (*Trichoplusia ni*) uses ciliated sensory neurons, called sensilla, which are located on its antennae, to find a female moth (Borroni and O'Connell, *J. Comp. Physiol.*, 170:691-700, 1992). The female moth releases a specific pheromone, which the male then detects by means of its sensilla and follows upwind until it locates the female, with which it then mates. By disrupting the assembly and/or function of the male's sensilla, an anti-IFT compound would render the male moth unable to find the female, and the thus control the population of this major pest.

In another example, mosquitoes use olfactory receptors located on sensory cilia to detect $CO_2$ and other attractants, and thus find their prey (Grant et al., *J. Comp. Physiol.*, 177:389-396, 1995). Spraying mosquitoes with an anti-IFT compound, which would block sensory cilia assembly/function, would render the insect unable to locate its prey and obtain a blood meal.

Combating Insects

The approaches described above regarding nematodes can be adapted to combat insects. Insects that attack and consume plants are good targets for plant transformants that generate either anti-IFT peptides or double stranded RNA that is derived from insect genes encoding IFT proteins. Blocking IFT in the insect should result in at least two desirable effects. First, the chordotonal organ, also known as Johnston's organ, contains a ciliated structure that is necessary for sound transduction. Second, insect sperm is flagellated and motile. Interruption of IFT should result in (1) deaf insects, which will affect communication with other insects, including potential mates and (2) immotile sperm, which will make the males of the species infertile. Both of these effects can dramatically reduce the population of an insect species. Additional cells/tissues that can be affected by blocking IFT include the mechanosensory bristles. Many mutations that affect sound transduction by the chordotonal organ also affect touch transduction by these tactile bristles (Eberl, Hardy, and Kernan, *J. Neurosci.*, 20:5981-5988, 2000); these results suggest that IFT, or portions of the IFT machinery, is involved with touch transduction in insects. Losing the sense of touch as a result of anti-IFT agent(s) would result in an obvious disadvantage for the organism.

EXAMPLES

The invention will be further described in the following examples, which do not limit the scope of the invention described in the claims.

Example 1

Identification of the Genes Encoding *Chlamydomonas* IFT Particle Proteins and Homologous Proteins in Other Species Purification and Microsequencing of *Chlamydomonas* IFT Particle Proteins 16S IFT particles were purified from *Chlamydomonas* flagella as described in Cole et al. (1998), further purified by two-dimensional gel electrophoresis and transferred to Immobilon$P^{SQ}$ (Millipore Corp., Bedford, Mass.). The spots corresponding to each of the IFT particle proteins were excised and digested with trypsin. Tryptic peptides were eluted from the membrane and fractionated by high performance liquid chromatography. Pure peptides, identified by mass spectrometry, were subjected to microsequence analysis in the UMMS Protein Sequencing Facility.

Cloning Genes Encoding *Chlamydomonas* IFT Particle Proteins

The peptide sequences from the purified IFT particle proteins were used to design PCR primers that were then used to amplify portions of the genes from *Chlamydomonas* genomic DNA or cDNA. These fragments of DNA were then used to obtain the rest of the genes by screening cDNA libraries by DNA hybridization, or the fragments sequenced and the sequences used to design additional primers that were used in 5' and 3' RACE (rapid amplification of cDNA ends) reactions to PCR amplify the remainder of the genes.

Obtaining Mouse IFT57 Sequence

The predicted peptide from *Chlamydomonas* IFT57 was used to search the ESTS portion of Genbank. One positive ESTS clone (Accession #AA763980) was purchased from ATCC and sequenced.

Identifying Homologous Genes

The predicted peptide sequences of the *Chlamydomonas* IFT particle proteins were used to search the protein and ESTS portions of Genbank with BLAST to identify homologous proteins. Typically human and *Chlamydomonas* homologues were 30-50% identical at the protein sequence level. If a human homologue was not present in either the protein or ESTS portion of Genbank, then the *Chlamydomonas* sequences (and any mammalian homologues found above) were used to search the draft human genome sequence to identify homologous loci. The proteins predicted to be encoded at these loci were compiled using the homology to the *Chlamydomonas* (or non-human mammalian) homologue as a guide. Similar methods were used to identify *Caenorhabditis elegans* homologues and can also be used to identify genes encoding IFT particle proteins in any organism (e.g. *Giardia, Plasmodium, Drosophilia*) for which extensive DNA sequence data has been obtained.

Example 2

Correction of IFT Defects in Retinal Cells by Gene Therapy

Defects in IFT particle proteins cause retinal degeneration in mice (Pazour et al., 2001) and are likely to be a cause of degenerative retinal disease leading to blindness in humans (Rosenbaum and Witman, 2001). In such cases vision may be corrected by gene therapy methods in which a vector containing the wild-type gene for the defective IFT particle protein is injected subretinally and the IFT particle protein gene thereby transfected into the photoreceptor cells and expressed.

The vector can be any non-viral or viral vector, e.g., recombinant adeno-associated virus (rAAV) vector (Ackland et al., 2001), which has the ability to transfect the target retinal cells. Expression of the IFT gene would be driven by its endogenous promoter, or by a photoreceptor cell-specific promoter, e.g., the opsin promoter, or by another promoter, such as the immediate-early cytomegalovirus (CMV) enhancer-promoter, which would be placed upstream of the IFT gene in the construct. Plasmid DNA containing this construct would be packaged into the vector.

In the case of rAAV, this can be achieved by inserting the gene into a basic rAAV vector plasmid, e.g., pTR-UF5, and transfecting the plasmid into a suitable human host cell in culture, e.g., human 293 cells, together with helper plasmid required for productive AAV infection and packaging of the rAAV DNA. After harvesting cells, the virus is extracted by a standard procedure, e.g., by freezing and thawing the cells, and then purified by iodixanol density gradient centrifugation followed by heparin-Sepharose agarose column chromatography (Hauswirth et al., 2000 Meth. Enzymol. 316: 743-761). Alternatively, any other procedure which results in efficient recovery of high quality virus may be used.

The purified vector would then be injected into the subretinal space underlying the central retina by means of an anterior chamber cannula inserted through a sclerotomy and monitored by microscopy (Bennett et al., 1999). Related protocols have been demonstrated to give stable, long-term expression of the transgene in non-human primate photoreceptor cells (Bennett, J. et al., 1999. PNAS 96: 9920-9925), without toxicity, and to restore vision in a large animal model—the dog—in which retinal degeneration occurs as a result of a defect in the RPE65 gene (Acland et al., 2001).

Example 3

Correction of IFT Defects in Airway Epithelial Cells by Gene Therapy

Because IFT particle proteins are necessary for the formation and maintenance of all cilia and flagella, defects in IFT particle proteins are expected to prevent normal assembly and functioning of respiratory tract cilia. Defects in assembly and functioning of respiratory tract cilia lead to human disorders such as primary ciliary dyskinesia (Afzelius and Mossberg, 1995), which are characterized by bronchiectasis, chronic bronchitis, and chronic sinusitis. Respiratory tract cilia arise from epithelial cells, which are exposed on the surface of the airway. Thus, these cells should be ideal targets for gene therapy to correct pulmonary disease due to a defect in an IFT particle protein. In this case, viral or nonviral vectors containing the IFT gene can be delivered topically to the airways via direct liquid instillation (Yonemitsu et al., 2000) or via an aerosol, such as can be produced by a nebulizer (Gautam et al., 2001).

The wild-type IFT particle protein gene to be transfected into the target cells can be contained in a plasmid ("IFT gene plasmid") and can be under the control of its endogenous promoter or another promoter, e.g., the human CMV early promoter/enhancer element. In one approach, the purified plasmid can be inserted into a rAAV vector plasmid for production of rAAV in a suitable human host cell, followed by purification of the rAAV as described above for gene therapy methods to correct a defect in the retina. The purified rAAV can then be delivered to the airway epithelial cells by instillation of a solution containing the rAAV, or by aspiration of an aerosol containing the rAAV. Related approaches might use recombinant lentiviral vectors (Kobinger et al., 2001) or recombinant Sendai virus vectors (Yonemitsu et al., 2000) to transfer the IFT gene to the airway epithelial cells. Both of these vectors have been shown to efficiently transduce airway epithelial cells (Kobinger et al., 2001; Yonemitsu et al., 2000).

Alternatively, the IFT gene plasmid can be complexed with other components to create a nonviral vector that can fuse with the airway epithelial cell membrane and deliver the plasmid DNA to the cytosol, from where it would then move to the nucleus. For example, the IFT gene plasmid DNA can be mixed with cationic lipids to produce a DNA-cationic lipid complex or "liposome" that can be delivered as an aerosol or via liquid instillation. Additional components, such as protamine or proteins, may be added to increase efficiency of delivery of the vector to the target cell (e.g., Sorgi, F L et al., 1997. Gene Therapy 4:961-968). Gene transfer efficiency is 10-200 times higher using liposomes containing specific peptides—e.g., an integrin-binding motif—than using liposomes alone (Scott et al., 2001. J. Gene Med. 3:125-134). In another approach, the DNA can be complexed with polyethylenimine (PEI) to create a PEI-DNA complex. PEI-DNA complexes have been demonstrated to be effective for the aerosol delivery of reporter genes to the lungs of mice, and may be more effective than liposomes (A. Gautam et al., 2000. Mol. Therapy 3:551-556).

With either viral or nonviral vectors, the efficiency of delivery of the DNA to the target cells may be enhanced by directing the vector to a specific target, e.g., the extracellular ATP/UTP receptor, termed P2Y2-R, which internalizes into the cell via clathrin-coated pits upon agonist stimulation (Boucher, R C. 1999. J. Clin Invest. 103:441-445).

Example 4

Determining the Role of IFT88 for Assembly of Cilia and Flagella

Introduction

Defects in the Tg737 gene cause kidney and liver defects in mice that are very similar to those seen in humans with autosomal recessive polycystic kidney disease (ARPKD) (Moyer et al., 1994). This disease affects ~1 in 10,000 children born each year and may be responsible for a much higher proportion of stillbirths and prenatal deaths (Blyth and Ockenden, 1971; Cole et al., 1987). The function of the Tg737 protein is unknown. Here we identify a protein in *Chlamydomonas* that is homologous to Tg737 and show that it is required for assembly of flagella.

The epithelial cells lining the collecting tubules of the kidney have very well developed primary cilia (Andrews and Porter, 1974). The role of these cilia is unknown; however they extend into the lumen of the tubule and may serve as sensory appendages. Precedence for primary cilia serving a sensory role is well established in vision and olfaction, as the outer segments of the rod and cone cells of the eye and the olfactory cilia of the nose have evolved from cilia and have retained primary cilia characteristics, e.g., the 9+0 microtubule arrangement. Primary cilia in other organisms such as *Caenorhabditis elegans* also serve a sensory role (Perkins et al., *Dev. Biol.*, 117:456-487, 1986; White et. al., *Phil. Trans. R. Soc. Lond.*, 275:327-348, 1976).

Eukaryotic cilia and flagella are built and maintained by a process called intraflagellar transport (IFT) (Rosenbaum et al., 1999). Most well characterized in *Chlamydomonas*, IFT is a rapid movement of particles along the axonemal microtubules of cilia and flagella. The outward movement of these particles from the cell body to the tip of the flagellum is driven by FLA10 kinesin-II (Kozminski et al., 1993; 1995), whereas the transport of the particles from the tip back to the cell body is driven by DHC1b/DHC2 cytoplasmic dynein (Pazour et al., 1998, 1999; Porter et al., 1999). The particles that are transported by IFT are composed of at least 17 protein subunits (Piperno et al., 1997; Cole et al., 1998). The functions of the individual subunits are not known but the proteins are conserved between green algae, nematodes, and vertebrates (Cole et al., 1998; Rosenbaum et al. 1999). In this manuscript, we describe the cloning of the IFT88 subunit of the *Chlamydomonas* IFT particle and show that cells missing this gene do not assemble flagella. We further show that IFT88 is homologous to the polycystic kidney disease gene Tg737 and that mice with mutations in this gene have shorter than normal primary cilia in their kidney.

Materials And Methods

Purification and Microsequencing of *Chlamydomonas* IFT88

16S IFT particles were purified from *Chlamydomonas* flagella as described in Cole et al. (1998). The IFT88 subunit was further purified by two-dimensional gel electrophoresis and transferred to ImmobilonP$^{SQ}$ (Millipore Corp., Bedford, Mass.) as described previously (Cole et al., 1998). The spot corresponding to IFT88 was excised and digested with trypsin. Tryptic peptides were eluted from the membrane and fractionated by high performance liquid chromatography. Pure peptides, identified by mass spectrometry, were subjected to microsequence analysis in the UMMS Protein Sequencing Facility.

Cloning IFT88

Portions of the IFT88 peptide sequence (LEGETDQA and GIDPYCVE) were used to design two degenerate oligonucleotide PCR primers (GA[A/G] AC[C/G/T] GA[C/T] CA[A/G] GC[C/G/T] GA[C/T] AA[A/G] TA and GC [C/T]TC [A/C/G]AC [A/G]CA [A/G]TA [A/C/G]GG [A/G]TC [A/G]AT). These primers amplified a 365-bp fragment of genomic DNA that contained parts of two exons and a 132-bp intron. This fragment of genomic DNA was used to screen a *Chlamydomonas* cDNA library made from cells undergoing division (Pazour and Witman, unpublished). Two positive clones were identified and sequenced by primer walking. These two clones were similar except for the sequences at their 5'-ends. IFT88cDNA-1 was longer than IFT88cDNA-2 and appeared to have a short region of poly-A inappropriately fused to the 5'-end, probably the result of a cloning artifact. One *Chlamydomonas* IFT88 EST clone is in Genbank (accession number AV395576). This EST sequence, which is from the 5' end of the gene and overlaps the cDNA clones, was used to define the 5'-end of the cDNA sequence.

Four independent BAC clones (40-B3, 11-O21, 24-F2, and 27-M3) were found in the Genome Systems (St Louis, Mich., USA) *Chlamydomonas* BAC library by Southern hybridization using the 365-bp fragment of IFT88 genomic DNA as a probe. These four BAC clones were purchased from Genome Systems. The presence of the IFT88 gene in the clones was confirmed by Southern blotting.

Identification and Rescue of an IFT88 Mutant

DNA from each of the ~400 transformants in our insertional mutant collection (Pazour et al., 1995; 1998; Pazour and Witman, 2000) was cut with PstI and analyzed by Southern blotting with the 365-bp fragment IFT88 genomic DNA fragment. This probe detected an ~2.5-kb band in wild-type cells and all of the mutants except strain V79.

The motility/flagellar defect in V79 was rescued by transforming with BAC clones carrying the IFT88 gene. Transformation was performed by the glass bead method of Kindle (1990), and rescued cell lines were identified by restoration of their ability to swim. One rescued cell line was crossed to wild-type CC124 cells. Tetrads from this cross were dissected and analyzed by standard procedures (Levine and Ebersold, 1960; Harris, 1989) as described in Pazour et al. (1998). The flagellar phenotype was scored by light microscopy when the cells were in the early log phase of growth.

Electron Microscopy

*Chlamydomonas* cells were fixed in glutaraldehyde for EM (Hoops and Witman, 1983) and processed as described in Wilkerson et al. (1995). Tissues of anesthetized mice were fixed in situ by brief cardiac perfusion with 2.5% gluteraldehyde in 100 mM cacodylate buffer. The kidneys were removed and a small amount of additional fixative was injected under the capsule of the kidney. The kidneys were placed in additional fixative for 1 hour. At that time, the kidneys were sliced in half and further fixed for 2 days. The tissue was freeze fractured and metal impregnated as described in McManus et al. (1993).

Western Blotting

Whole cell extracts of wild-type and mutant cells were made by resuspending log-phase cells in SDS-sample buffer, heating at 50° C. for 10 min, and repeatedly drawing the sample through a 26-gauge needle to shear the DNA. Proteins were separated by SDS-PAGE, blotted onto polyvinylidene difluoride membranes, and probed with antibodies as described in Pazour et al. (1998). Antibodies used included mAb57.1, mAb81.1, mAb139.1, and mAb172.1, which are monoclonal antibodies against IFT particle proteins (Cole et al., 1998); FLA10N, which is specific for a kinesin-II motor subunit (Cole et al., 1998); DHC1b, which is specific for the heavy chain of DHC1b/DHC2 cytoplasmic dynein; and B-5-1-2, which is specific for alpha tubulin (Piperno et al., 1985).

Chlamydomonas Culture

Chlamydomonas strains used in this work included: g1 (nit1, agg1, mt+) (Pazour et al., 1995), CC124 (nit1, nit2, mt−), and CC1390 (fla2, mt−). The latter two strains are available from the Chlamydomonas Genetics Center (Duke University, Durham, N.C.). Strains generated in the course of this work included: V79 (ift88-1::NIT1, mt+), which was generated by random insertional mutagenesis of g1, V79/40-B3#2.5 (ift88-1::NIT1, IFT88, mt+) generated by transformation of V79 with BAC clone 40-B3, and 3276.2 (ift88-1::NIT1) which is a progeny from a cross between V79/40-B3#2.5 and CC124.

Mouse Genotyping

DNA was purified by digesting mouse tails with proteinase K, extracting once with 50% phenol/50% chloroform, once with chloroform and then precipitating the DNA with ethanol. The genomic DNA was amplified using the RW450, RW451, and RW452 primer set described by Yoder et al. (1997). These primers amplified a 270-bp fragment from the wild-type locus and a 340-bp fragment from the mutant locus.

Digital Image Processing

Western and Southern blots were scanned from negative x-ray film with a Linotype-Hell Saphir Ultra 2 flatbed scanner and brought into Photoshop for cropping and contrast adjustment. Scanning EM micrographs were scanned from positive Polaroid film in the same way. Transmission EM negatives were scanned with a Polaroid Sprint Scan 45 and brought into Photoshop for cropping, contrast adjustment and inversion from a negative to a positive image.

Results

Cloning and Sequencing of Chlamydomonas IFT88

In order to learn more about the structure and function of the proteins that make up the IFT particle, we cloned and sequenced the IFT88 protein, formerly known as p88 (Cole et al., 1998). To do this, Chlamydomonas IFT particles were purified from the matrix of isolated flagella by sucrose density gradient centrifugation and two-dimensional gel electrophoresis. IFT88 was cleaved by trypsin and two internal peptides were microsequenced (Cole et al., 1998), yielding the sequences AATNLAFLYFLEGETDQADKYSEMALK and SLFNEAAGIDPYCVEAIYNLGLVSQR. Degenerate PCR primers were designed from these sequences and used to amplify a fragment of genomic DNA. A cDNA library was screened with the genomic fragment and the resulting clones were sequenced by primer walking. Southern blots indicated that there is only one copy of the IFT88 gene in the Chlamydomonas genome.

Sequence analysis showed that the IFT88 cDNA contains a 2346-nt open reading frame that is predicted to encode an 86.3-kD protein with a pI of 5.87. Perfect matches to both IFT88 tryptic peptides are found in the open reading frame of this cDNA, rigorously confirming that these clones encode the Chlamydomonas IFT88 protein. No discernable motifs were identified within the sequence except for the presence of 10 tetratricopeptide repeats (TPR). TPRs are degenerate 34-amino acid repeats (Lamb et al., 1995), present in tandem arrays of 3-16 units that are predicted to form amphipathic helices (Hirano et al., 1990). The first three TPR motifs are found closely spaced between amino-acid residues 185-294. The other seven TPR motifs occur without spacing between amino-acid residues 441-676.

Chlamydomonas IFT88 is Homologous to a Mouse Polycystic Kidney Disease Gene

Blast searches with the Chlamydomonas IFT88 protein sequence indicate that it is very similar to the mouse (41% identical; BLAST E=e-148) and human Tg737 (40% identical; BLAST E=e-146) proteins. Mice with defects in Tg737 have severe polycystic kidney disease and die within a few weeks of birth. The protein also is homologous to proteins predicted by ESTs from zebra fish and swine and fragments of preliminary C. elegans and D. melanogaster genomic sequence. IFT88 and Tg737 are likely to be functionally equivalent orthologues as the similarity between the Chlamydomonas and mammalian proteins is robust and distributed over the entire coding region and not just within the TPR domains. 40% identity is very typical of the amount of similarity seen between other Chlamydomonas and mammalian orthologues that encode flagellar proteins (Pazour, Dickert and Witman, manuscript in preparation).

IFT88 is Required for Flagellar Assembly

To learn more about the function of IFT88 in cells, we searched our collection of Chlamydomonas insertional mutants (Pazour et al., 1995, 1998; Pazour and Witman, 2000) for a cell line with a defect in this gene. The insertional mutants were made by transforming cells with DNA carrying a selectable marker. In Chlamydomonas, transforming DNA is integrated randomly throughout the genome and disrupts genes at the site of integration. DNA was isolated from ~400 insertional mutants having behavioral or motility defects, and was screened by Southern blotting using a fragment of IFT88 genomic DNA as probe. One cell line (V79) was identified that had an insertion in the IFT88 gene. The fact that the single hybridizing band in wild-type cells was split into two bands in the mutant indicated that the selectable marker integrated into the gene within the region covered by the probe and did not result in a large deletion of the genome at the site of integration. The mutant allele was termed ift88-1.

The ift88-1 cells grew at the same rate as wild-type cells, indicating that IFT88 is not required for processes essential for growth or cell division. However, in contrast to wild-type cells that normally have two ~10-μm flagella extending from the anterior end of the cell body, the ift88-1 cells completely lack flagella. Electron microscopic analysis of these cells showed that the basal bodies were structurally normal but the flagella did not extend beyond the transition zone. In some cells, the membrane covering the flagellar tips was tightly apposed to the microtubules with no material between them and the membrane. In other cells, the flagellar stubs were slightly swollen and contained fragments of microtubules in random orientations. However, in contrast to the IFT mutants fla14 (Pazour et al., 1998) and dhc1b (Pazour et al., 1999), no accumulation of IFT particles was observed in any of the flagellar stubs.

To determine the effect of the lack of IFT88 on the IFT particle and the IFT motors, we examined whole cell extracts by western blotting. The IFT particle is made up of two large complexes. Complex A is composed of four to five proteins and includes IFT139. Complex B is composed of IFT88 and ten other proteins including IFT172, IFT81 and IFT57. The complex A protein IFT139 is enriched in the mutant suggesting that the gene may be upregulated in the mutant cells. The mutation has little or no effect on the levels of complex B proteins IFT172 and IFT81, but causes a significant decrease in IFT57, another complex B protein. The cellular levels of the IFT motors FLA10 kinesin-II and DHC1b are not affected by the ift88 mutation.

To be certain that the flagellar assembly defect is caused by the mutation in IFT88 and is not the result of another mutation elsewhere in the genome, we transformed the mutant cells with BAC clones carrying the IFT88 gene. Three independent BAC clones (40-B3, 24-F2, and 27-M3) complemented the flagellar defect. The complemented cell lines swam like wild-type cells and had IFT. One of the rescued cell lines was crossed to a wild-type cell line and 26 tetrads were dissected. All four products of one tetrad and a single product of the remaining 25 tetrads were analyzed by Southern blotting. Because the transformed copy of the IFT88 gene inserted at a site unlinked to the original locus, the inserted DNA segregated independently from the original gene, allowing offspring to carry zero, one, or two copies of the wild-type gene. Cells that carry at least one copy of wild-type IFT88 have normal flagella and motility, whereas those that carry no copies of wild-type IFT88 lack flagella and are non-motile. These data indicate that the flagellar defect is tightly linked to the ift88 mutation and is almost certainly the result of it.

Primary Cilia in the Kidney of Tg737 Mice are Shorter than Normal

Primary cilia are present on many cells in the mammalian body (Wheatley, 1995; Wheatley et al., 1996), and are particularly well developed in the kidney (Andrews and Porter, 1974). Inasmuch as *Chlamydomonas* IFT88 is necessary for assembly of flagella and is homologous to mammalian Tg737, and because a defect in mouse Tg737 leads to kidney disease, it was of great interest to determine if the defect in Tg737 affected formation of the primary cilia in the kidney. In wild-type rats, the cilia are ~2.5 μm long and are found in the proximal tubule, the loop of Henle, the distal tubules, and the collecting ducts (Andrews and Porter, 1974). In wild-type mice these cilia are less than 5 μm long and similarly distributed (Flood and Totland, 1977).

We obtained the hypomorphic Tg737-mutant mice from Oak Ridge National Laboratory and examined the kidneys of 4-day and 7-day old pups by scanning electron microscopy. Numerous monociliated cells were observed in the kidneys of both wild-type (+/+) and homozygous mutant (−/−) mice, but the cilia in the mutant kidneys were much shorter. To quantify this difference, the cilia lengths were measured from scanning electron micrographs taken from the tubules distal to the proximal tubule. The proximal tubule was avoided because it contains a thick brush border that can obscure a micron or more of cilia length. The tubules distal to the proximal tubule have only sparse microvilli that do not obscure cilia, and the cilia in these regions are uniform in length (Andrews and Porter, 1974). These cilia in wild-type mice were 3.1+/−1.4 μm and 3.5+/−1.7 μm long at 4 and 7 days respectively, whereas these cilia in the mutant mice were 1.0+/−0.6 μm and 1.3+/−0.6 μm at 4 and 7 days respectively. These values represent minimum lengths as it is difficult to accurately measure cilia that are lying at different angles in the tubules. However, the differences are quite large and are significant at the >99% level. Thus, Tg737, like its IFT88 homologue in *Chlamydomonas*, plays an essential role in assembly of the primary cilium in the mouse.

The IFT88 Gene is Required for Flagellar Assembly in *Chlamydomonas*

*Chlamydomonas* cells lacking the IFT88 gene do not assemble flagella, indicating that the IFT88 protein is required for flagellar assembly. This is the first *Chlamydomonas* IFT particle subunit to be shown to be required for ciliary assembly. Loss of IFT88 causes a substantial decrease in the amount of IFT57 relative to other IFT particle proteins in the cytoplasm, suggesting that IFT88 is important for assembly of at least a portion of the IFT particle. Thus, IFT may be blocked at a very early stage in the ift88-1 mutant. Consistent with this, IFT particles do not accumulate in the flagellar stubs of the ift88 mutant, in sharp contrast to the dramatic accumulation of apparently intact IFT particles in the flagella of mutants with defects in cytoplasmic dynein DHC1b/DHC2 (Pazour et al., 1999) or the dynein light chain LC8 (Pazour et al., 1998). Alternatively, IFT88 may have a vital role in the attachment of the IFT particle to its cargo or to the anterograde IFT motor FLA10-kinesin-II; in either case, loss of IFT88 would preclude flagellar assembly. It is also possible that IFT88 is essential for transduction of a signal that is necessary for flagellar assembly.

Tg737, the Mouse IFT88 Homologue, is Required for Assembly of the Primary Cilia in Kidney.

We have shown that IFT88 is highly similar to the mouse and human Tg737 proteins and that mice with defects in Tg737 have defective cilia in their kidneys. Tg737 was identified at Oak Ridge National Laboratory by random insertional mutagenesis of mice. Hypomorphic mutations in Tg737 cause kidney disease and death within a few weeks of birth. The phenotype of this mutation closely resembles human ARPKD in that the mice develop cystic kidneys and have hepatic biliary disease which is also common in human patients with ARPKD (Moyer et al., 1994). The mice develop large cysts in their collecting ducts and are unable to concentrate urine (Yoder et al., 1996; 1997). Null alleles of Tg737 have a more severe phenotype and cause the mice to die during mid-gestation (Murcia et al., 2000). The phenotype caused by the null Tg737 mutation closely resembles the phenotype of kinesin-II knockout mice (Nonaka et al., 1998; Marszalek et al., 1999, Takeda et al., 1999). Both the kinesin-II and Tg737 null mice have left-right asymmetry defects, lack cilia on the embryonic node, and die during mid gestation. Our finding that IFT88 is required for ciliary assembly provides the first evidence that the lack of nodal cilia on embryos of Tg737 null mutant mice is a direct result of a defect in IFT.

Primary cilia are extremely widely dispersed throughout the mammalian body. The only cells that are known NOT to contain primary cilia are hepatocytes, and differentiated cells of myeloid or lymphoid origin (Wheatley, 1995; Wheatley et al., 1996). The primary cilia in kidney tubules and ducts (Andrews and Porter, 1974) and hepatic biliary ducts (Motta and Fumagalli, 1974) are unusually long and project into the lumens of these structures. The role of the primary cilia in the kidney or hepatic ducts is not known but has been suggested to be sensory (Roth et al., 1988). The most studied primary cilia are the outer segments of rod and cone photoreceptor cells and the olfactory cilia in the nasal cavity. In these examples, the role of the primary cilia is clearly to serve as an appendage to concentrate sensory machinery. *C. elegans* also makes extensive use of primary cilia to detect osmolarity gradients and chemical signals (White et. al., *Phil. Trans. R. Soc. Lond.*, 275:327-348, 1976; Lewis and Hodgkin, *Comp. Neur.*, 172:489-510, 1977). Primary cilia on other cells may similarly have a sensory role. Supporting this idea, the somatostatin 3 receptor has recently been localized to primary cilia in the brain (Handel et al., 1999). Kidney epithelial cells sense multiple extracellular signals including peptide hormones like angiotensin and ions like chloride (reviewed in Gunning et al., 1996). Whether any of these sensory receptors are localized to the primary cilia of the vertebrate kidney remains to be determined.

*C. elegans* homologues of the human polycystic kidney disease genes, PKD1 and PKD2, are localized to sensory cilia (Barr and Sternberg, 1999). Humans with mutations in PKD1 and PKD2 develop kidney disease similar to that caused by Tg737 mutations in mice. PKD1 and PKD2 are transmembrane proteins that interact with each other (Qian et al., 1997; Tsiokas et al., 1997). PKD1 has a large extracellular domain that is thought to bind an unknown ligand (Hughes et al., 1995; The International Polycystic Kidney Disease Consortium, 1995). PKD2 is homologous to calcium-regulated cation channels, suggesting that PKD2 also is a cation channel (Chen et al., 1999). Further work will be necessary to determine if PKD1 or PKD2 are ever found on mammalian primary cilia.

TPR Repeats in IFT88 and Tg737 Suggest that these Proteins are Involved in Protein-Protein Interactions TPR repeats are degenerate 34-amino acid motifs (Lamb et al., 1995) that are present in tandem arrays in proteins. These arrays are predicted to form super-helices (Hirano et al., 1990) with amphipathic grooves responsible for binding specific target proteins (Das et al., 1998). TPR domains have been found to mediate multiple simultaneous protein-protein interactions in such multiprotein complexes as molecular chaperones and the anaphase-promoting complex (reviewed in Blatch and Lassle, 1999). In IFT88 and Tg737, there are three closely spaced TPR repeats in the amino-terminal half of the protein and another seven TPR repeats in the carboxyl-terminal half of the protein. These two separate TPR domains can serve to bind simultaneously to two separate target proteins. These target proteins can be axonemal subunits that are transported via IFT to the flagellar tip where they are assembled (Piperno et al., 1996). The targets also could be membrane proteins such as receptors and channels, as IFT particles are tightly associated with the flagellar membrane (Kozminski et al., 1995; Pazour et al., 1998). Alternatively, IFT88 can be binding to other subunits of the IFT particle and holding it together. IFT57 is likely to be an interacting protein because it is destabilized in the absence of IFT88.

IFT is a Conserved Mechanism in the Assembly and Maintenance of Cilia and Flagella A strong body of evidence indicates that IFT is necessary for assembly and maintenance of all eukaryotic motile and sensory cilia. Previous work has shown that the anterograde motor, kinesin-II, is necessary for assembly and maintenance of cilia and flagella in diverse organisms that include green algae, ciliated protozoa, nematodes, echinoderms, and vertebrates (reviewed in Cole, 1999; Marszalek and Goldstein, 2000). The retrograde motor, cytoplasmic dynein DHC1b/DHC2, also has been shown to be required for assembly of *Chlamydomonas* flagella (Pazour et al., 1999; Porter et al., 1999) and *Caenorhabditis* sensory cilia (Signor et al., 1999; Wicks et al., 2000). Our initial report on the composition of the *Chlamydomonas* IFT particle proteins showed that IFT52 was homologous to *C. elegans* OSM-6 and that IFT172 was homologous to *C. elegans* OSM-1 (Cole et al., 1998). OSM-1 and OSM-6 are required for assembly of sensory cilia in worms (Collet et al., 1998; Perkins et al., *Dev. Biol.*, 117:456-487, 1986). The involvement of these two nematode proteins in IFT was recently confirmed when GFP-labeled OSM-6 and USM-1 were both shown to undergo IFT in transformed *C. elegans* (Orozco et al., 1999; Signor et al., 1999). The work in this paper shows that the IFT particle protein IFT88 is required for ciliary assembly in *Chlamydomonas* and that the IFT88 homologue, Tg737, is required for assembly of primary cilia in the kidney of mice. Thus, evidence from a diverse group of eukaryotes shows that both the IFT motors and the IFT particle proteins are required for assembly and maintenance of cilia and flagella. This indicates that IFT is an ancient and conserved mechanism by which eukaryotic cilia and flagella are built and maintained.

IFT is Likely to Play Important Roles in Many Disease States

In addition to PKD discussed above, there are many other diseases that involve IFT. This includes retinitis pigmentosa (RP), which is a genetic disorder that causes destruction of photoreceptor cells resulting in progressive vision loss. Transport of opsin and other components of the rod outer segment is very important in photoreceptor cells, as ~10% of the outer segment is turned over each day. Transport from the inner segment to the outer segment occurs through the connecting cilium (reviewed in Besharse and Horst, 1990). Kinesin-II and several IFT particle proteins are located in the connecting cilium of photoreceptor cells (Beech et al., 1996, Whitehead et al., 1999; Pazour et al., submitted). Moreover, Marszalek et al. (2000) recently showed that photoreceptor cells lacking kinesin-II accumulate opsin and arrestin in the inner segment, indicating that kinesin-II is involved in transport in photoreceptor cells. Therefore IFT is likely to be an important transport mechanism in vertebrate photoreceptor cells, and mutations in IFT particle proteins are likely to cause vision defects.

Defects in IFT also are likely to affect motile cilia and flagella and be a cause of primary ciliary dyskinesia (PCD). PCD is a syndrome caused by defects in motile cilia and is characterized by male infertility, respiratory disease and situs inversus. It is well known that defects in axonemal components cause PCD (Afzelius, 1979; Pennarun et al., 1999). However, IFT particle proteins are highly expressed in the testis and lung, suggesting that they are involved in the assembly of motile sperm flagella and respiratory tract cilia (Pazour, unpublished). Thus, a mutation in an IFT particle protein can lead to defects in sperm flagellar assembly and result in sperm with short disorganized tails as have been described in some infertile human males (Baccetti et al., 1993). It is possible that mutations that prevent assembly of both motile and sensory cilia are so severe that the embryos terminate during gestation, as has been observed with mutations in the mouse kinesin-II motor subunits kif3a (Marszalek et al., 1999; Takeda et al., 1999) and kif3b (Nonaka et al., 1998).

Example 5

IFT Proteins in Vertebrate Photoreceptor Connecting Cilium

Introduction

Vertebrate photoreceptors are polarized sensory neurons consisting of a photosensitive outer segment, and an inner segment that supports synthesis of proteins destined for all cellular compartments. Transport of the visual pigment, opsin, and other components of the phototransduction machinery from the inner segment to the outer segment is very important in photoreceptor cells, as ~10% of the outer segment is turned over each day (Young, *J. Cell Biol.* 33:61-72 (1967). Although disruption of this process of intersegmental transport results in photoreceptor degeneration and blindness, the mechanisms involved have not been identified. Outer segments develop from a primary cilium which remains as the sole connecting link and presumably the major transport corridor between inner and outer segments (Besharse and Horst, In *Ciliary and Flagellar Membranes* (ed Bloodgood, R. A.) pp. 389-417, Plenum Publishing Corp, New York, 1990). Recently, a process called intraflagellar transport (IFT) has been found to be essential for the assembly and maintenance of sensory cilia in *Caenorhabditis* and the motile cilia of the green alga, *Chlamydomonas*, and sea urchins (Kozminski et al., *J. Cell Biol.* 131:1517-1527, 1995; Collet et al., *Genetics*, 148:187-200, 1998; Morris et al., *J. Cell Biol.*, 138:1009-1022, 1997). During IFT, kinesin-II transports a large protein complex from the cell body to the tip of the flagellum (Piperno and Mead, *Proc. Natl. Acad. Sci. USA*, 94:4457-4462, 1997; Cole et al., *J. Cell Biol.*, 141:993-1008, 1998; Orozco et al., *Nature*, 398:674, 1999; Signor et al, *Mol. Biol. Cell*, 10:345-360, 1999). These particles are then returned to the cell body by the DHC1b/DHC2 form of cytoplasmic dynein (Pazour et al., *J. Cell Biol.*, 141:979-992, 1998; Pazour et al., *J. Cell Biol.*, 144:473-481, 1999; Porter et al., *Mol. Biol. Cell*, 10:693-712, 1999; Signor et al., *J. Cell Biol.*, 147:519-530, 1999).). IFT particles are composed of ~17 proteins and are thought to carry components needed for assembly and maintenance of cilia and flagella. They also transport signals between cilia and the cell body (Rosenbaum et al., *J. Cell Biol.*, 144:385-388, 1999). The functions of individual IFT particle proteins are not known but mutations in genes encoding IFT particle proteins in *Chlamydomonas* and *Caenorhabditis* prevent ciliary assembly (Pazour et al., manuscript in preparation). IFT particle proteins are conserved among green algae, nematodes, and vertebrates. To investigate the possibility that IFT functions in sensory cilia of vertebrates, we have identified mouse homologues of three *Chlamydomonas* IFT particle proteins, have generated antibodies against the mouse proteins, and localized the proteins within the retina.

Cloning IFT20: *Chlamydomonas* IFT20 was purified and the sequence of two tryptic peptides was obtained (GVYFD-EDFHVR and YVSAIDQQVER) (Cole et al., *J. Cell Biol.* 141:993-1008, 1998). A degenerate PCR primer designed from the first peptide sequence was used in combination with an oligo-dT primer to amplify most of the coding sequence from reverse-transcribed cDNA. The remainder of the gene was amplified from a *Chlamydomonas* cDNA library in lambda ZapII (Stratagene) with a vector primer (M13Rev) and a IFT20-specific primer designed from the sequence of the first PCR product. The open reading frame contained within these clones encodes a 15.6-kD peptide containing both tryptic peptides.

Bioinformatics: Mouse and human homologues of the *Chlamydomonas* IFT particle proteins were identified by BLAST searches of Genbank. The human genetic map positions were determined using publicly available data by the following method. First, a mapped sequence tagged site (STS) from the gene itself (e.g. IFT20-1 and IFT52) or encoded within a genomic clone that also encodes the IFT gene was identified in the STS portion of Genbank. This allowed all the genes to be placed on the human radiation hybrid map. The approximate cytogenetic positions were then predicted using the data of Bray-Ward et al. (Bray-Ward et al., *Genomics* 15:1-14, 1996).

Antibody production: The antibodies were produced in rabbits by injecting bacterially expressed maltose-binding fusion proteins made by cloning the open reading frames of mouse NDG5 (IFT52), IFT57, and IFT20 into the pMalc expression vector (New England Biolabs, MA). The sera were affinity purified using immobilized glutathione S-transferase fusion proteins. The latter fusion proteins were made by cloning the open reading frames of the IFT genes into the pGEX-6p-1 (Amersham Pharmacia Biotech, NJ) expression vector.

Preparation of the detergent extracted photoreceptor cytoskeleton (DEPC) and western blotting: The DEPC was prepared as described in Horst et al (Horst et al., *J. Cell Biol.* 105:2973-2987, 1987). Briefly, rod outer segments shaken from 50 dark-adapted, frozen bovine retinas in Buffer A (10 mM PIPES, pH 7.0, 1 mM EDTA, 5 mM $MgCl_2$, 0.02% $NaN_3$), supplemented with a protease inhibitor cocktail (1 ug/ml pepstatin, 1 ug/ml leupeptin, 4 ug/ml aprotinin, 1 mM benamidine, 1 mM PMSF) were purified by sucrose density centrifugation. Outer segments were then extracted in Buffer A containing 2% Triton X-100. Ciliary axonemes were separated from detergent-soluble material by centrifugation over a 45%-60% linear sucrose gradient. Equal aliquots were separated on a 12% denaturing polyacrylamide gel and transferred to Immobilon membranes for antibody labeling and detection using the SuperSignal West Femto chemiluminescent system (Pierce Chemical Co., IL).

Immunocytochemistry: Fresh mouse or bovine retinal tissue was placed in Tissue Freezing Medium™ (Triangle Biomedical Sciences, NC) and quickly frozen in liquid nitrogen with or without prior fixation in 4% paraformadehyde; *Xenopus* retina was prepared in the same way except that fixation was in cold methanol (Whitehead et al., *Exp. Eye Res.* 69:491-503, 1999). Fish inner segment-outer segment preparations were made using procedures described in Beech et al. (Beech et al., *J. Cell Sci.*, 109:889-897, 1996). Primary antibodies were detected with goat anti-rabbit or goat anti-mouse IgG conjugated with Cy3 (Jackson Laboratories), Texas Red™, fluoroscein, Alexa 488, or Alexa 568 (Molecular Probes, Eugene Oreg.). In double-label experiments, discrimination of signals for K26 versus IFT proteins involved use of conjugated anti-mouse and anti-rabbit antibodies respectively. For discrimination of two monoclonal antibodies (K26 versus tubulin or opsin), we labeled with one monoclonal antibody and a fluorescent anti-mouse antibody, and then repeated the procedure for the second monoclonal antibody using a different fluorophore. Images of cells labeled with more than one fluorophore were pseudocolored and merged using NIH Image 1.62 or Adobe Photoshop.

Identification of Vertebrate Homologues of *Chlamydomonas* IFT Particle Proteins The *Chlamydomonas* IFT20, IFT52, and IFT57 particle proteins were purified, partially sequenced, and the peptides compared to sequences in GenBank. Three peptides from IFT52 closely matched a rodent protein of ~52 kDa called NGD5, and a *C. elegans* protein called OSM-6. The function of NGD5 is unknown, but its expression is down-regulated by exposing cultured cells to opioids (Wick et al., *Mol. Brain Res.*, 32:171-175, 1995). OSM-6 is required for assembly of sensory cilia in nematodes. The sequence of the *Chlamydomonas* peptides from IFT57 and IFT20 did not show strong similarity to any proteins in the databases. Consequently, degenerate PCR was used to clone these two genes from *Chlamydomonas*. The full-length cDNA sequence of *Chlamydomonas* IFT57 strongly matched a number of human and mouse EST sequences. To determine the extent of homology between the *Chlamydomonas* and mouse proteins, a mouse IFT57 cDNA clone was completely sequenced. The *Chlamydomonas* and mouse proteins are 38% identical and have a BLAST p-value of 3e-67, indicating that the proteins are very likely to have related functions (Pazour et al., manuscript in preparation). The *Chlamydomonas* IFT20 sequence strongly matched a small protein in mouse as well as EST sequences from humans, cattle and a large number of other vertebrate and invertebrate species. The *Chlamydomonas* and mouse proteins are 32% identical and have a BLAST p-value of 4e-15. Bovine, mouse and human IFT20 proteins are nearly identical to each other.

We have obtained data indicating the chromosome locations of the three human IFT protein homologues. Although none map to a region currently associated with retinal degeneration[s], these data will prove useful in future studies of photoreceptor disease or diseases resulting from defects in ciliary development. Analysis of genomic sequence data indicated that in addition to the IFT20 sequence (IFT20-1) most similar to *Chlamydomonas* IFT20, at least two additional related genes are present in man; all three map to different chromosomes. All but one of the IFT20 EST sequences identified corresponded to IFT20-1. The EST corresponding to IFT20-2 has a stop codon within the region of homology, suggesting that it contains a sequencing error or does not encode a functional protein.

Localization of IFT Particle Proteins to the Vertebrate Photoreceptor:

Initial evidence for association of IFT particle proteins with photoreceptor cilia came from western blot analysis. Bovine retinal tissue was used for this analysis in order to take advantage of a connecting cilium-specific monoclonal antibody (K26) for immunocytochemistry (Horst et al., *Cell Motil. Cytoskeleton* 17:329-344, 1990) and a procedure for production of a detergent-extracted photoreceptor cytoskeletal (DEPC) fraction from bovine retina (Horst et al., *J. Cell Biol.* 105:2973-2987, 1987). Affinity-purified antibodies to IFT20, IFT52 and IFT57 did not readily detect proteins in whole cell extracts of bovine retina, but strongly detected single bands of ~16, 52 and 57 kDa respectively in the DEPC fraction. Because this fraction is highly enriched in ciliary axonemes from photoreceptors, it seemed very likely that the IFT proteins were associated with the photoreceptor cilia.

Immunocytochemical analysis revealed that IFT20, IFT52, and IFT57 were most abundant in the inner segments (IS) of mouse (not shown) and bovine photoreceptors, with distinctly less labeling over the outer segments and other regions of the photoreceptor cells. The signal in the inner segment was distinctly granular in appearance, particularly at the junction between the inner and outer segments where the connecting cilia are located. The outer nuclear layer (ONL) containing photoreceptor nuclei exhibited perinuclear staining. The inner nuclear layer (INL) was also labeled; the latter was most easily seen with antibodies to IFT52. All three antibodies labeled the outer plexiform layer which contains the synaptic terminals of photoreceptors. This and the presence of kinesin II in these synapses (Muresan et al., *J. Neurosci.*, 19:1027-1037, 1999) suggests that IFT proteins have functions in photoreceptor synaptic terminals.

Double-label immunocytochemistry with a monoclonal antibody (K26) that recognizes a connecting cilium specific epitope demonstrated that all three IFT proteins are associated with the ciliary axoneme in situ. The K26 antibody uniquely stained the connecting cilium at the base of photoreceptor outer segments, which were identified with antibodies to rod opsin. In contrast, antibodies to acetylated alpha-tubulin labeled microtubules of the inner segment and the ciliary axoneme. Labeling by both K26 (red) and acetylated alpha tubulin (green) antibodies in the connecting cilium resulted in a yellow to orange color due to overlap in the connecting cilium, and demonstrated that axonemal microtubules extend distally beyond the connecting cilium into the outer segment. Antibodies to IFT20, IFT52 and IFT57 labeled structures both on the proximal (inner segment) and distal (outer segment) side of the connecting cilium in a large proportion of the photoreceptors. Frequent yellow to orange coloration of the connecting cilium was indicative of overlap of the two labels (red, K26 and green, anti-IFT antibody) within the connecting cilium. Triple-labeled images revealed a similar pattern in which IFT57 (blue) is found in association with microtubules (acetylated α-tubulin) at both ends of the connecting cilium (K26) in most but not all photoreceptors.

Association of IFT proteins with ciliary axonemes was also detected in the large rod photoreceptors of the frog, *Xenopus laevis*, and the fish, *Lepomis macrochirus*. Confocal analysis of *Xenopus* tissue sections double labeled with antibodies to acetylated α-tubulin and IFT57 revealed a single area of intense immunoreactivity in each cell corresponding to the base of the ciliary axoneme, in the region of the basal body. A similar pattern was seen in whole-mounted, isolated cells of *Lepomis*, although the zone of staining at the base of the axoneme was broader than in *Xenopus*. IFT57 staining of the distal axoneme within the outer segment was sometimes seen as punctate spots in both *Xenopus* and *Lepomis*. These staining patterns are similar to those seen in *Chlamydomonas*. In *Chlamydomonas*, the IFT particle proteins are located primarily in a cytoplasmic pool at the base of the cilia with only a small number of punctate spots found along the length of the cilia. The punctate staining is thought to be due to IFT particles that were in transit when the cells were fixed.

Discussion:

Macromolecules of the photoreceptor outer segment are synthesized in the inner segment and transported into the outer segment. This process occurs at a prodigious rate. It has been estimated that turnover in each mammalian photoreceptor outer segment requires delivery of as many as 2000 photopigment molecules per minute throughout the life of the cell. In the larger photoreceptors of amphibians, this rate is increased by more than an order of magnitude. In addition to the photopigment molecules, proteins of the phototransduction machinery (Philp et al., *FEBS Lett.*, 225:127-132, 1987; Whelan et al., *J. Neurosci. Res.* 20:263-270, 1988) and phospholipid components of the discs (Anderson et al., *Biochim. Biophys. Acta*, 620:212-226, 1980) turn over rapidly. Although transport between the inner and outer segment is crucial to polarized organization of the cell, the underlying mechanism has remained elusive.

The presence of IFT proteins in photoreceptor cilia strongly suggests that IFT is an important transport mechanism in these cells. Although the transported cargo has not been identified, our data allow us to propose the following model based on the idea that membrane components, including rhodopsin and phospholipid, and many soluble proteins are normally targeted to the photoreceptor outer segment. Membrane proteins are synthesized on the endoplasmic reticulum and modified during passage through the Golgi network. The polarity of inner segment microtubules with their minus ends associated with the base of the cilium suggests that these membrane proteins and phospholipids are transported from the Golgi stack to the base of the connecting cilium by dynein complexes containing the DHC1 heavy chain. DHC1 is a well established vesicle transporter and has been shown to interact with the cytoplasmic tail of rhodopsin (Tai et al., *Cell* 97:877-887, 1999). Cytoplasmic proteins destined for the outer segment such as components of the transduction machinery (transducin and arrestin) and the ciliary axoneme are also synthesized in the inner segment and can be transported in association with IFT particles. At the base of the connecting cilium where IFT proteins are normally most concentrated, they associate with the surface of these vesicles and with other outer segment proteins. Once the vesicles fuse with the plasma membrane adjacent to the cilium, transport of the complex with attached cargo along the connecting cilium would occur by the kinesin-II motor. Kinesin-II is thought to be the anterograde IFT motor in *Chlamydomonas* and *Caenorhabditis* and has been localized to the connecting cilium in vertebrates (Beech et al., *J. Cell Sci.*, 109:889-897, 1996; Whitehead et al., *Exp. Eye Res.*, 69:491-503, 1999). In the outer segment, the IFT particles disengage from their cargo, and the membrane is organized into disks and pinched off by myosin VIIA. Myosin VII is required for phagocytosis in *Dictyostelium* (Titus, *Curr. Biol.*, 9:1297-1303, 1999), and mice with defects in the myosin VIIA gene accumulate opsin in the connecting cilium (Liu et al., *J. Neurosci.* 19:6267-6274, 1999). Soluble proteins of the transduction machinery and cytoskeleton would be expected to associate with appropriate protein complexes within the outer segment, while IFT particles at the distal end of the connecting cilium would be returned to the base of the cilium by a dynein complex containing the DHC1b/DHC2 heavy chain. DHC1b/DHC2 is the retrograde IFT motor in *Chlamydomonas*[10-12] and *Caenorhabditis* (Signor, *J. Cell Biol.*, 147:519-530, 1999) and has been localized to the connecting cilium of vertebrate photoreceptors (Besharse et al., in preparation). At the base of the connecting cilium the IFT particles re-enter a peri-basal body pool of IFT particle proteins and begin the cycle again. The IFT particles also move components of the transduction machinery from the outer segment to the inner segment. For example, both transducin and arrestin have been shown to rapidly move between the segments during light and dark adaptation.

In conclusion, we have shown that three different IFT particle proteins are localized to the connecting cilium of vertebrate photoreceptor cells. Since IFT is essential for assembly and maintenance of motile and sensory cilia of *Chlamydomonas* and *Caenorhabditis*, it is likely that it also is important in vertebrate photoreceptors. The availability of mouse mutations in the genes encoding kinesin-II (Nonaka, *Cell* 95:829-837, 1998; Bray-Ward et al., *Genomics*, 15:1-14, 1996) and an IFT particle protein (Pazour et al., manuscript in preparation) will allow us to directly test this hypothesis.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

LITERATURE CITED

Afzelius et al., Immotile-cilia syndrome (primary ciliary dyskinesia), including Kargagener syndrome. In: The Metabolic and Molecular Bases of Inherited Disease, Vol. III. Ed: Scriver, C. R. et al. McGraw-Hill, Inc., NY. pp. 3943-3954 (1995).
Alberts, B. et al. Molecular Biology of the Cell. Third Ed. Garland Publishing Inc. (1994) p. 820.
Barr et al., *Nature* 401, 386-389 (1999).
Beech et al., *J. Cell Sci.* 109, 889-897 (1996).
Bergman et al., *J. Cell Biol.* 3, 606-622 (1975).
Besharse, J. C. Photosensitive membrane turnover: Differentiated membrane domains and cell-cell interaction, in: *The Retina: A Model for Cell Biological Studies*, Part 1 (R. Adler and D. Farber, eds.), Academic Press, New York, pp. 297-352 (1986).
Bloodgood, *Exp. Cell Res.* 150, 488-493 (1984).
Bloodgood, *Cell Biol. Int.* 24, 857-862 (2000).
Bouck, *J. Cell Biol.* 50, 362-384 (1971).
Blyth et al., *J. Med. Genet.* 8, 257-284 (1971).
Cole et al., *J. Pediatr.* 111, 693-699 (1987).
Cole, D. G. et al., *J. Cell Biol.* 141, 993-1008 (1998).
Collet et al., *Genetics* 148, 187-200 (1998).
Dentler, W. L. Linkages between microtubules and membranes in cilia and flagella. In: Ciliary and Flagellar Membranes. Ed: Bloodgood, R. A. Plenum Press, NY. pp. 31-64 (1990).
Dentler et al., *J. Cell Biol.* 74, 747-759 (1977).
De Robertis, E., *J. Biophys. Biochem. Cytol. Suppl.* 2, 209-216.
Diener et al., *Mol. Biol. Cell* 7, 47a (1996).
Emmons et al., *Nature* 401, 339-340 (1999).
Espindola et al., *Cell Motil. Cytoskeleton* 47, 269-281 (2000).
Fowkes et al., *Mol. Biol. Cell* 9, 2337-2347 (1998).
Godsel et al., *EMBO Journal* 18, 2057-2065 (1999).
Gonzalez-Perret, S., et al., *Proc. Natl. Acad. Sci. U.S.A.* 98, 1182-1187 (2001).
Handel, M., et al., *Neuroscience* 89, 909-926 (1999).
Johnson et al., *J. Cell Biol.* 119, 1605-1611 (1992).
King, S. M., et al., *J. Biol. Chem.* 271, 19358-19366 (1996).
Kozminski et al., *Proc. Nat. Acad. Sci. U.S.A.* 90, 5519-5523 (1993).
Kozminski et al., *J. Cell Biol.* 131, 1517-1527 (1995).
Marshall, W. F. & Rosenbaum, J. L., Mol. Biol. Cell 11, 368a. (2000c).
Marszalek et al., *Proc. Natl. Acad. Sci. U.S.A.* 96, 5043-5048 (1999).
Marszalek, J. R. et al., *Cell* 102, 175-187 (2000).
Morris, R. L. & Scholey, J. M., J. Cell Biol. 138, 1009-1022 (1997).
Moyer, J. H., et al., *Science* 264, 1329-1333 (1994).
Murcia et al., *Kidney Intl.* 55, 1187-1197 (1999).
Orozco et al., *Nature* 398, 674 (1999).
Pan, J. & Snell, W. J., *Curr. Opin. Microbiol.* 6, 596-602 (2000b).
Pan, J. & Snell, W. J., *Mol. Biol. Cell* 11, 368a (2000c).
Pazour et al., *J. Cell Biol.* 141, 979-992 (1998).
Pazour et al., *J. Cell Biol.* 144, 473-481 (1999).
Pazour et al., *Mol. Biol. Cell* 10, 369a (1999b).
Pazour et al., *Mol. Biol. Cell* 10, 388a. (1999c).
Pazour, G. J., et al., *J. Cell Biol.* 151, 709-718 (2000).
Pazour, G. J., et al., *Mol. Biol. Cell* 11, 540a (2000b).
Perkins et al., *Dev. Biol.* 117, 456-487 (1986).
Piperno et al., *J. Cell Biol.* 133, 371-379 (1996).
Piperno et al., *Proc. Natl. Acad. Sci. U.S.A.* 94, 4457-4462 (1997).
Piperno et al., *J. Cell Biol.* 143, 1591-1601 (1998).
Qin et al., *Cur. Bio.* 11, 1-20 (2001).
Scholey, J. M., *J. Cell Biol.* 133, 1-4 (1996).
Signor et al., *J. Cell Biol.* 147, 519-530 (1999).
Snapp et al., *J. Cell Biol.* 139, 1775-1783 (1997).
Snapp et al., *J. Biol Chem.* 274, 29543-29548 (1999).
Somlo, S. & Ehrlich, B., *Current Biol.* 11, R356-R360 (2001).
Sung, C—H. & Tai, A. W., *Internat. Rev. Cytology* 195, 0074-7696 (2000).
Supp et al., *Trends Cell Biol.* 10, 41-45 (2000).
Wheatley et al., *Cell Biol. Int.* 20, 73-81 (1996).
Wicks et al., *Dev. Biol.* 221, 295-307 (2000).
Young, R. W. *Invest. Opthalmol.* 15, 700-725 (1976).
Afzelius, B. A. 1979, *Int. Rev. Exp. Pathol.* 19:1-43.
Baccetti et al., 1993, *Andrologia* 25:331-335.
Cole, D. G. 1999. Kinesin-II, coming and going. *J. Cell Biol.* 147:463-466.
Flood, P. R. and G. K. Totland. 1977, *Cell Tiss. Res.* 183:281-290.
Hughes, et al., 1995, *Nat. Genet.* 10:151-160.
Motta et al., 1974, *Z. Anat. Entwickl.-Gesch.* 145:223-226.
Pazour et al., 1999, *Mol. Biol. Cell* 10:3507-3520.
Pazour et al., 1995, *J. Cell Biol.* 131:427-440.
Richards et al., 1997, *Am. J. Path.* 150:1189-1197.
Rosenbaum et al., 1999, *J. Cell Biol.* 144:385-388.

The International Polycystic Kidney Disease Consortium. 1995. Polycystic kidney disease: The complete structure of the PKD1 gene and its protein. *Cell* 81:289-298.

Wheatley, D. N. 1995, *Pathobiology* 63:222-238.
Whitehead et al., 1999, *Exp. Eye Res.* 69:491-503.
Yoder et al., 1996, *Kid. Int.* 50:1240-1248.

What is claimed is:

1. An isolated antibody that binds specifically to a polypeptide consisting of the amino acid sequence of SEQ ID NO:16.

2. The antibody of claim 1, wherein the antibody is a monoclonal antibody.

3. The antibody of claim 1, wherein the antibody is a polyclonal antibody.

4. The antibody of claim 1, wherein the antibody is a chimeric antibody.

5. The antibody of claim 1, wherein the antibody is a humanized antibody.

6. The antibody of claim 1, wherein the antibody is a single chain antibody.

7. The antibody of claim 1, wherein the antibody is an antibody fragment.

8. The antibody of claim 7, wherein the antibody is a Fab fragment.

9. The antibody of claim 7, wherein the antibody is a F(ab')$_2$ fragment.

* * * * *